(12) United States Patent
Wender et al.

(10) Patent No.: US 7,256,286 B2
(45) Date of Patent: *Aug. 14, 2007

(54) BRYOSTATIN ANALOGUES, SYNTHETIC METHODS AND USES

(75) Inventors: Paul A. Wender, Menlo Park, CA (US); Blaise Lippa, Stonington, CT (US); Cheol-Min Park, Gurnee, IL (US); Kevin W. Hinkle, Chapel Hill, NC (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 204 days.

This patent is subject to a terminal disclaimer.

(21) Appl. No.: 10/366,776

(22) Filed: Feb. 14, 2003

(65) Prior Publication Data

US 2003/0220334 A1    Nov. 27, 2003

Related U.S. Application Data

(63) Continuation-in-part of application No. 09/728,929, filed on Nov. 30, 2000, now Pat. No. 6,624,189.

(60) Provisional application No. 60/357,177, filed on Feb. 15, 2002, provisional application No. 60/168,181, filed on Nov. 30, 1999.

(51) Int. Cl.
*C07D 267/22* (2006.01)
*C07D 323/00* (2006.01)

(52) U.S. Cl. .................................. 540/456; 549/267
(58) Field of Classification Search ............... 540/456; 549/267
See application file for complete search history.

(56) References Cited

U.S. PATENT DOCUMENTS

| | | | | |
|---|---|---|---|---|
| 4,560,774 | A | 12/1985 | Pettit et al. | 549/267 |
| 4,611,066 | A | 9/1986 | Pettit et al. | 549/267 |
| 4,833,257 | A | 5/1989 | Pettit et al. | 549/267 |
| 5,072,004 | A | 12/1991 | Pettit | 549/267 |
| 5,328,929 | A | 7/1994 | Pettit et al. | 514/462 |
| 5,358,711 | A | 10/1994 | May et al. | 424/93.7 |
| 5,891,870 | A | 4/1999 | Dreidger et al. | 514/183 |
| 6,043,270 | A | 3/2000 | Driedger et al. | 514/450 |
| 6,060,505 | A | 5/2000 | Blumberg et al. | 514/449 |
| 6,624,189 | B2 | 9/2003 | Wender et al. | 514/450 |
| 2003/0199469 | A1 | 10/2003 | Schwartz et al. | 514/44 |
| 2003/0233000 | A1 | 12/2003 | Lindquist et al. | 549/267 |

FOREIGN PATENT DOCUMENTS

| | | |
|---|---|---|
| EP | 0264173 | 4/1988 |
| EP | 0324574 B1 | 11/1993 |
| WO | WO 01/11024 A2 | 2/2001 |

OTHER PUBLICATIONS

Wender et al., Selective Binding of Bryostatin Analogues to the Cysteine Rich Domains of Protein Kinase C Isozymes, Bioorganic & Medicinal Chemistry Letters, vol. 9, No. 12, pp. 1687-1690, Jun. 1999.*

Wender et al., Synthesis and Biological Evaluation of a New Class of Bryostatin Analogues: the Role of the C20 Substituent in Protein Kinase C Binding, Tetrahedron Letters, vol. 41, No. 35, pp. 6725-6729, Aug. 2000.*

Pettit, G.R., "The bryostatins," *Fortschritte der Chemie Organischer Naturstoffe—Progress in the Chemistry of Natural Products*, 57:153-195 (1991).

Registry printout of Bryostatin 4, 5, 10 and 15, 2003.

Baryza, J.L.; Brenner, S.E.; Craske, M.L.; Meyer, T.; Wender, P.A., "Simplified Analogs of Bryostatin with Anticancer Activity Display Greater Potency for Translocation of PKCδ-GFP", *Chemistry & Biology*, vol. 11; pp. 1261-1267 (2004).

Evans, D.A.; Carter, P.H.; Carreira, E.M.; Prunet, J.A.; Charette, A.B.; Lautens, M., "Asymmetric Synthesis of Bryostatin 2", *Angew. Chem. Int. Ed. Engl.*, vol. 37 (17); pp. 2354-2359 (1998).

Evans, D.A.; Carter, P.H.; Carreira, E.M.; Charette, A.B.; Prunet, J.A.; Lautens, M., "Total Synthesis of Bryostatin 2", *J. Am. Chem. Soc.*, vol. 121; pp. 7540-7552 (1999).

Hale, K.J.; Hummersone, M.G.; Bhatia, G.S., "Control of Olefin Geometry in the Bryostatin B-Ring through Exploitation of a $C_2$-Symmetry Breaking Tactic and a Smith-Tietze Coupling Reaction", *Organic Letters*, vol. 2; pp. 2189-2192 (2000).

Hale, K.J.; Frigerio, M.; Manaviazar, S.; Hummersone, M.G.; Fillingham, I.J.; Barsukov, I.G.; Damblon, C.F.; Gescher, A.; Roberts, G.C.K., "Synthesis of a Simplified Bryostatin C-Ring Analogue That Binds to the CRD2 of Human PKC-α and Construction of a Novel BC-Analogue by an Unusual Julia Olefination Process", *Organic Letters*, vol. 5; pp. 499-502 (2003).

Hale, K.J.; Frigerio, M.; Manaviazar, S., "New, Abridged Pathway to Masamune's "Southern Hemisphere" Intermediate for the Total Synthesis of Bryostatin 7", *Organic Letters*, vol. 5; pp. 503-505 (2003).

Harada, T.; Inoue, A.; Wada, I.; Uchimura, J-J.; Tanaka, S.; Oku, A., "Stereoselective Acetilization of 1,3-Alkanediols Controlled by Intramolecular van der Waals Attractive Interactions and Its Application to an Enantiodifferentiating Transformation of σ-Symmetric 1,3,5-Pentanetriols", *J. Am. Chem. Soc.*, vol. 115; pp. 7665-7674 (1993).

Kageyama, M.; Tamura, T., "Synthesis of Bryostatin 7", *J. Am. Chem. Soc.*, vol. 112; pp. 7407-7408 (1990).

López-Pelegrin, J.A.; Wentworth, P.; Sieber, F.; Metz, W.A.; Janda, K.D., "Soluble Polymer-Supported Chemoenzymatic Synthesis of the C21-C27 Fragment of the Bryostatins", *J. Org. Chem.*, vol. 65; pp. 8527-8531 (2000).

(Continued)

*Primary Examiner*—Brenda Coleman
(74) *Attorney, Agent, or Firm*—King & Spalding

(57) ABSTRACT

Biologically active compounds related to the bryostatin family of compounds, having simplified spacer domains and/or improved recognition domains are disclosed, including methods of preparing and utilizing the same.

19 Claims, No Drawings

OTHER PUBLICATIONS

O'Brian, M.; Taylor, N.H.; Thomas, E.J., "Synthesis of the C(1)-C(16) Fragment of Bryostatins", *Tetrahedron Letters*, vol. 43: pp. 5491-5494 (2002).

Ohmori, K.; Ogawa, Y.; Obitsu, T.; Ishikawa, Y.; Nishiyama, S.; Yamamura, S., "Total Synthesis of Bryostatin 3", *Angew. Chem. Int. Ed. Engl.*, vol. 39: pp. 2290-2294 (2000).

Pettit, G.R.; Herald, C.L.; Doubek, D.L.; Herald, D.L., "Isolation and Structure of Bryostatin 1", *J. Am. Chem. Soc.*, vol. 104: pp. 6846-6848 (1982).

Pettit, G.R., "Progress in the Discovery of Biosynthetic Anticancer Drugs", *J. Natural Products*, vol. 59: pp. 812-821 (1996).

Theisen, P.D.; Heathcock, C.H., "Improved Procedure for Preparation of Optically Active 3-Hydroxyglutarate Monoesters and 3-Hydroxy-5-oxoalkanoic Acids", *J. Org. Chem.*, Vol. 53: pp. 2374-2378 (1988).

Vakalopoulos, A.; Lampe, T.F.J.; Hoffmann, H.M.R., "Asymmetric Synthesis of the Northern Half $C_1$-$C_{16}$ of the Bryostatins", *Organic Letters*, vol.3: pp. 929-932 (2001).

Voight, E.A.; Roethle, P.A.; Burke, S.D., "Concise Formal Synthesis of the Bryostatin Southern Hemisphere (C17-C27)", *J. Org. Chem.*, vol. 69: pp. 4534-4537 (2004).

Voight, E.A.; Seradj, H.; Roethle, P.A.; Burke, S.D., "Synthesis of the Bryostatin 1 Northern Hemisphere (C1-C16) via Desymmetrization by Ketalization/Ring-Closing Metathesis", *Organic Letters*, vol. 6: pp. 4045-4048 (2004).

Wender, P.A.; Cribbs, C.M.; Koehler, K.F.; Sharkey, N.A.; Herald, C.L.; Kamano, Y.; Pettit, G.R.; Blumberg, P.M., "Modeling of the Bryostatins to the Phorbol Ester Pharmacophore on Protein Kinase C", *Proc. Natl. Acad. Sci., USA*, vol. 85: pp. 7197-7201 (1988).

Wender, P.A.; Irie, K.; Miller, B., "Identification, Activity, and Structural Studies of Peptides Incorporating the Phorbol Ester-Binding Domain of Protein Kinase C", *Proc. Natl. Acad. Sci., USA*, vol. 92: pp. 239-243 (1995).

Wender, P.A.; Brabander, J.D.; Harran, P.G.; Jimenez, J-M.; Koehler, M.F.T.; Lippa, B.; Park, C.-M.; Shiozaki, M., "Synthesis of the First Members of a New Class of Biologically Active Bryostatin Analogues", *J. Am. Chem. Soc.*, vol. 120: pp. 4534-4535 (1998).

Wender, P.A.; DeBrabander, J.; Harran, P.G.; Jimenez, J.-M.; Koehler, M.F.T.; Lippa, B.; Park, C.-M.; Siedenbiedel, C.; Pettit, G.R., "The Design, Computer Modeling, Solution Structure, and Biological Evaluation of Synthetic Analogues of Bryostatin 1", *Proc. Natl. Acad. Sci., USA*, vol. 95: pp. 6624-6629 (1998).

Wender, P.A.; DeBrabander, J.; Harran, P.G.; Hinkle, K.W.; Lippa, B.; Pettit, G.R., "Synthesis and Biological Evaluation of Fully Synthetic Bryostatin Analogues", *Tetrahedron Letters*, vol. 39: pp. 8625-8628 (1998).

Wender, P.A.; Lippa, B., "Synthesis and Biological Evaluation of Bryostatin Analogues: The Role of the A-Ring", *Tetrahedron Letters*, vol. 41: pp. 1007-1011 (2000).

Wender, P.A.; Baryza, J.L.; Bennett, C.E.; Bi, F.C.; Brenner, S.E.; Clarke, M.O.; Horan, J.C.; Kan, C.; Lacote, E.; Lippa, B.; Nell, P.G.; Turner, T.M., "The Practical Synthesis of a Novel and Highly Potent Analogue of Bryostatin", *J. Am. Chem. Soc.*, vol. 124: pp. 13648-13649 (2002).

Wender, P.A.; Maywey, A.V.W.; VanDeusen, C.L., "A Concise, Selective Synthesis of the Polyketide Spacer Domain of a Potent Bryostatin Analogue", *Organic Letters*, vol. 5: pp. 277-279 (2003).

Wender, P.A.; Koehler, M.F.T.; Sendzik, M., "A New Synthetic Approach to the C Ring of Known as Well as Novel Bryostatin Analogues", *Organic Letters*, vol. 5: pp. 4549-4552 (2003).

* cited by examiner

BRYOSTATIN ANALOGUES, SYNTHETIC METHODS AND USES

CROSS-REFERENCE TO RELATED APPLICATIONS

This application claims the benefit of co-pending provisional application U.S. Ser. No. 60/357,177, filed Feb. 15, 2002, incorporated herein by reference. This application is also a continuation-in-part of U.S. application Ser. No. 09/728,929, filed Nov. 30, 2000, now U.S. Pat. No. 6,624,189 which claims the benefit of provisional application U.S. Ser. No. 60/168,181, filed Nov. 30, 1999, both incorporated herein by reference.

GOVERNMENT INTEREST

This invention was made with the support of NIH grant number CA31845. Accordingly, the U.S. Government may have certain rights in this invention.

BACKGROUND OF THE INVENTION

1. Field of the Invention

The present invention concerns biologically active compounds related to the bryostatin family of compounds, and to methods of preparing and utilizing the same.

2. Introduction

Cancer is a major cause of death in the developed countries, with more than 500,000 human fatalities occurring annually in the United States. Cancers are generally the result of the transformation of normal cells into modified cells that proliferate excessively, leading to the formation of abnormal tissues or cell populations. In many cancers, cell proliferation is accompanied by dissemination (metastasis) of malignant cells to other parts of the body, which spawn new cancerous growths. Cancers can significantly impair normal physiological processes, ultimately leading to patient mortality. Cancers have been observed for many different tissue and cell types, with cancers of the lung, breast, and colorectal system accounting for about half of all cases.

Currently, about one-third of cancer patients can be cured by surgical or radiation techniques. However, these approaches are most effective with cancerous lesions that have not yet metastasized to other regions of the body. Chemotherapeutic techniques currently cure another 17% of cancer patients. Combined chemotherapeutic and non-chemotherapeutic protocols can further enhance prospects for full recovery. Even for incurable cancer conditions, therapeutic treatments can be useful to achieve remission or at least extend patient longevity.

Numerous anticancer compounds have been developed over the past several decades (e.g., Katzung, 1998; Wilson et al., 1991; Hardman et al., 1996). While these compounds comprise many different classes that act by a variety of mechanisms, one general approach has been to block the proliferation of cancerous cells by interfering with cell division. For example, anthracyclines, such as doxorubicin and daunorubicin, have been found to intercalate DNA, blocking DNA and RNA synthesis and causing strand scission by interacting with topoisomerase II. The taxanes, such as Taxol™ and Taxotere™, disrupt mitosis by promoting tubulin polymerization in microtubule assembly. Cis-platin forms interstrand crosslinks in DNA and is effective to kill cells in all stages of the cell cycle. As another example, cyclophosphamide and related alkylating agents contain di-(2-chloroethyl)-amino groups that bind covalently to cellular components such as DNA.

The bryostatins (Formula A) are a family of naturally occurring macrocyclic compounds originally isolated from marine bryozoa. Currently, there are about 20 known natural bryostatins which share three six-membered rings designated A, B and C, and which differ mainly in the nature of their substituents at C7 ($OR^A$) and C20 ($R^B$) (Pettit, 1996).

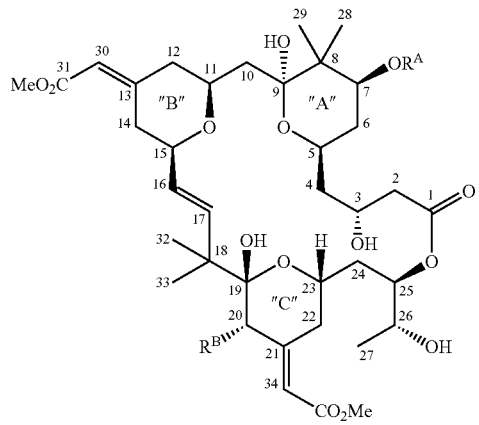

Formula A

The bryostatins exhibit potent activity against a broad range of human cancer cell lines and provide significant in vivo life extensions in murine xenograft tumor models (Pettit et al., 1982; Homung et al., 1992; Schuchter et al., 1991; Mohammad et al., 1998). Doses that are effective in vivo are extremely low, with activities demonstrated for concentrations as low as 1 μg/kg (Schuchter et al., 1991). Among additional therapeutic responses, the bryostatins have been found to promote the normal growth of bone marrow progenitor cells (Scheid, 1994; Kraft, 1996), provide cellular protection against normally lethal doses of ionizing radiation (Szallasi, 1996), and stimulate immune system responses that result in the production of T cells, tumor necrosis factors, interleukins and interferons (Kraft, 1996; Lind, 1993). Bryostatins are also effective in inducing transformation of chronic lymphocytic leukemia cells to a hairy cell type (Alkatib, 1993), increasing the expression of p53 while decreasing the expression of bcl-2 in inducing apoptosis in cancer cells (Maki, 1995; Mohammad, 1995) or at least pre-disposing a cell towards apoptosis, and reversing multidrug resistance (MDR) (Spitaler, 1998).

At the molecular level, bryostatins have been shown to competitively inhibit the binding of plant-derived phorbol esters and endogenous diacyl glycerols to protein kinase C (PKC) at nanomolar to picomolar drug concentrations (DeVries, 1998), and to stimulate comparable kinase activity (Kraft, 1986; Berkow, 1985; Ramsdell, 1986). Unlike the phorbol esters, however, the bryostatins do not act as tumor promoters. Thus, the bryostatins appear to operate through a mode of action different from, and complementary to, the modes of action of established anticancer agents; human clinical trials are presently evaluating bryostatin combination therapy with cisplatin or taxol.

Various studies have demonstrated good affinity for bryostatins in which $R^A$ is hydroxyl, acetyl, pivaloyl, or n-butanoate, and $R^B$ is H, acetyl, n-butanoate, or 2,4-unsaturated octanoate, as measured by PKC binding assay (Wender et al., 1988). The double bond between C13 and C30 can be hydrogenated or epoxidized without significant loss of binding affinity. Hydrogenation of the C21–C34 alkene or acetylation of the C26 hydroxyl, on the other hand, can significantly reduce binding affinity. Inversion of the stereoconfiguration at C26 leads to modest loss of activity (approx. 30-fold) and the suggestion that the methyl group may limit rotation of bonds proximate to the methyl group and contribute to the apparent high binding affinity observed for the bryostatins. Elimination of the hydroxyl at C19 (with concomitant omission of the C20 $R^B$ group) causes an approximately 100-fold to 200-fold decrease in binding. Likewise, impairing the accessibility of the C26 hydroxymethyl moiety by replacement of the C26 hydroxyl, or by replacing the methyl or hydrogen substituents of C26 with a tert-butyl or similar bulky substituent, has been proposed for diminishing toxicity (Blumberg et al., 1997).

Although the bryostatins have been known for some time, their low natural abundance, difficulties in isolation and severely limited availability through total synthesis have impeded efforts to elucidate their mode of action and to advance their clinical development. Recently, synthetic analogues of bryostatin were reported wherein the C4–C14 spacer domain was replaced with simplified spacer segments using a highly efficient esterification-macrotransacetalization (Wender et al., 1998a, 1998b). The reported analogues retained orientation of the C1-, C19-, C26-oxygen recognition domain as determined by NMR spectroscopic comparison with bryostatin and varying degrees of PKC-binding affinity. The one analogue tested for in vitro inhibition in human tumor cell lines was reported to possess significant activity. It has remained, however, desired to provide new, simplified, and more readily accessible synthetic agents based on the bryostatin structure to further elucidate the molecular basis of bryostatin's activity and develop improved and more readily available clinical candidates, especially for anticancer applications.

SUMMARY OF THE INVENTION

One aspect of the present invention concerns simplified bryostatin analogues, i.e., the compounds represented by Formula I:

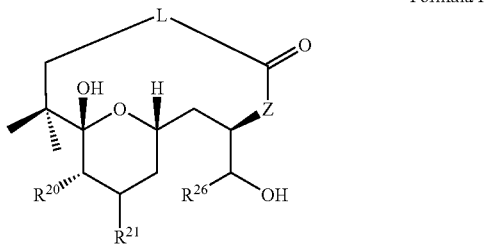

Formula I wherein:
$R^{20}$ is H, OH, or -T-U—V—R' where:
  T is selected from —O—, —S—, —N(H)— or —N(Me)—;
  U is absent or is selected from —C(O)—, —C(S)—, —S(O)— or —S(O)$_2$—; and
  V is absent or is selected from —O—, —S—, —N(H)— or —N(Me)—, provided that V is absent when U is absent;
$R^{21}$ is =CR$^a$R$^b$ or $R^{21}$ represents independent moieties R$^c$ and R$^d$ where:
  R$^a$ and R$^b$ are independently H, CO$_2$R', CONR$^c$R$^d$ or R';

R$^c$ and R$^d$ are independently H, alkyl, alkenyl or alkynyl, or (CH$_2$)$_n$CO$_2$R' where n is 1, 2 or 3;
$R^{26}$ is H, OH or R';
R' (each instance) being independently selected from the group: H, alkyl, alkenyl or alkynyl, or aryl, heteroaryl, aralkyl or heteroaralkyl;
L is a straight or branched linear, cyclic or polycyclic moiety, containing a continuous chain of preferably from 6 to 14 chain atoms, which substantially maintains the relative distance between the C1 and C17 atoms and the directionality of the C1C2 and C16C17 bonds of naturally-occurring bryostatin; and
Z is —O— or —N(H)—;

and the pharmaceutically acceptable salt thereof.

In a preferred aspect of the recognition domain in this embodiment $R^{26}$ is H or methyl, particularly when $R^{21}$ is =C(H)CO$_2$R' and/or where $R^{20}$ is —O$_2$CR'. Especially preferred are the compounds where $R^{26}$ is H. A preferred upper limit on carbon atoms in any of R$^d$, R$^e$ and R' is about 20, more preferably about 10 (except as otherwise specifically noted, for example, with reference to the embodiment of the invention where a preferred $R^{20}$ substituent has about 9 to 20 carbon atoms). In certain embodiments, R' is a straight-chain alkyl, alkenyl (having from 1 to 6, preferably 1 to 4 double bonds, preferably trans double bonds) or alkynyl group. In a preferred aspect of the spacer domain of this embodiment, L contains a terminal carbon atom that, together with the carbon atom corresponding to C17 in the native bryostatin structure, forms a trans olefin. It is further preferred that L contain a hydroxyl on the carbon atom corresponding to C3 in the native bryostatin structure.

Another aspect of the invention concerns the simplified bryostatin analogues represented by Formulae II–V:

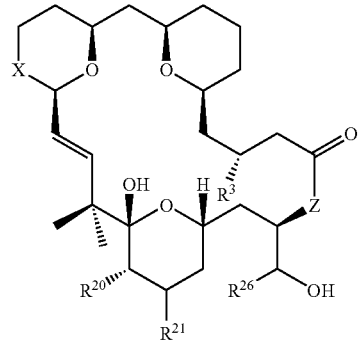

Formula II

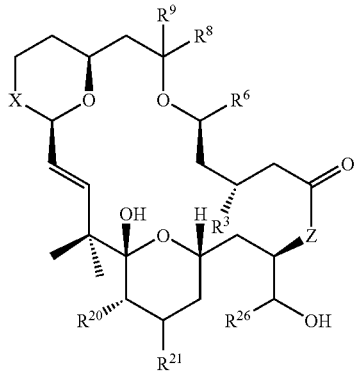

Formula III

-continued

Formula IV

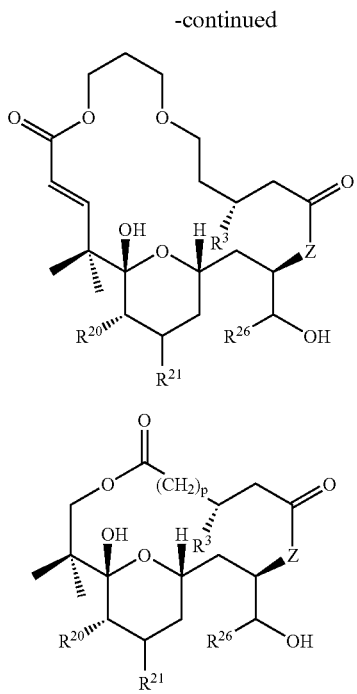

Formula V

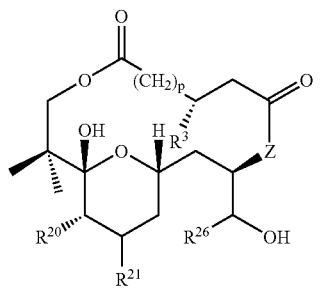

wherein:
- $R^3$ is H, OH or a protecting group;
- $R^6$ is H, H or =O;
- $R^8$ is selected from the group: H, OH, =O, R', —(CH$_2$)$_n$O(O)CR' or (CH$_2$)$_n$CO$_2$-haloalkyl where n is 0, 1, 2, 3, 4 or 5, provided that $R^6$ and $R^8$ are not both =O;
- $R^9$ is H, OH or is absent;
- $R^{20}$, $R^{21}$, $R^{26}$, R' and Z are as defined above with respect to Formula I;
- p is 1, 2 or 3; and
- X is —CH$_2$—, —O—, —S— or —N(R$^e$)— where R$^e$ is COH, CO$_2$R' or SO$_2$R', X preferably being —O—, and the pharmaceutically acceptable salts thereof.

Still another aspect of the invention concerns the simplified bryostatin analogues represented by Formulae II-A to V-A:

Formula II-A

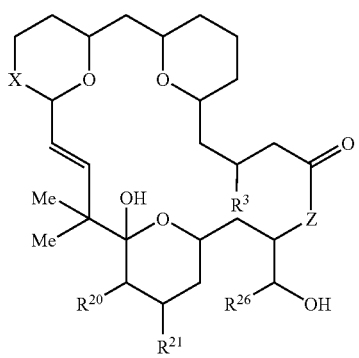

Formula III-A

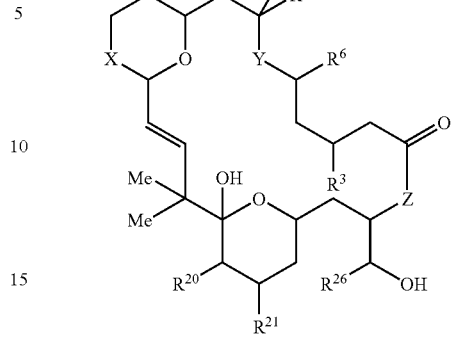

Formula IV-A

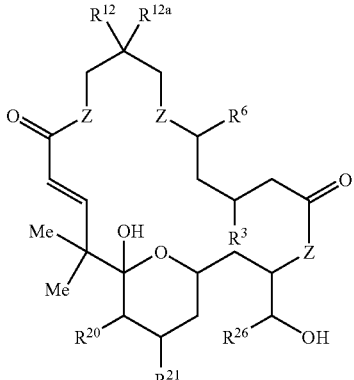

Formula V-A

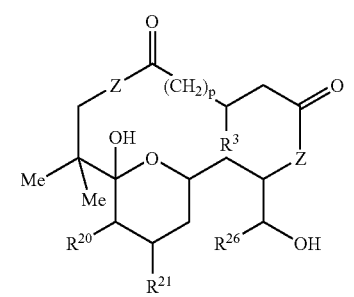

wherein:
- $R^3$, $R^6$, $R^9$, $R^{20}$, $R^{21}$, $R^{26}$, R', X, Z and p are as defined above with respect to Formulae II to V;
- $R^7$ is absent or represents from 1 to 4 substituents on the ring to which it is attached, selected from lower alkyl, hydroxyl, amino, alkoxyl; alkylamino, =O, acylamino, or acyloxy;
- $R^8$ is as defined above including substituted or unsubstituted alkyl, alkenyl, alkynyl, aryl, heteroaryl, aralkyl, or heteroaralkyl, e.g., substituted with an alkoxy, acyloxy, acylamino, or alkylamino substituent, or, in Formula III-A when $R^6$ represents H, H, then $R^8$ and $R^9$ taken together can represent =O;
- $R^{12}$ and $R^{12a}$ are independently for each occurrence, H, OH, lower alkyl, lower alkoxyl, or lower acyloxy, or $R^{12}$ and $R^{12a}$ taken together represent =O; and
- Y is CH$_2$, —O— or —N(H)—, and the pharmaceutically acceptable salts thereof. The compounds of Formulae II-A to V-A preferably have one or more of the stereochemical configurations respectively represented in Formulae II to V.

In a preferred aspect, the invention relates to the C26 des-methyl analogue of Formula IIa

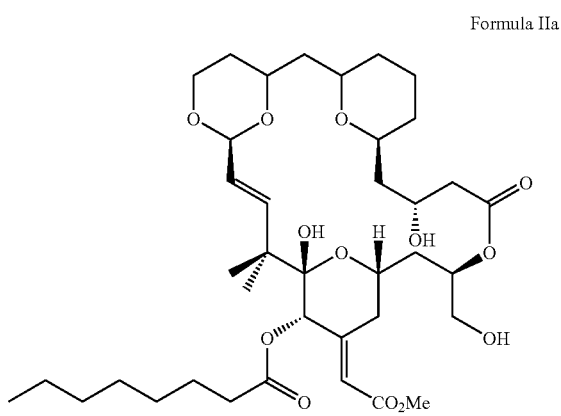

Formula IIa and to pharmaceutical compositions and methods of treatment therewith.

Still another aspect of the invention relates to the C26 des-methyl homologues of the native bryostatins, as illustrated in Formula VI:

Formula VI where $R^A$ and $R^B$ correspond to the naturally occurring bryostatin substituents, such as C26 des-methyl Bryostatin 1, the compound of Formula VIa:

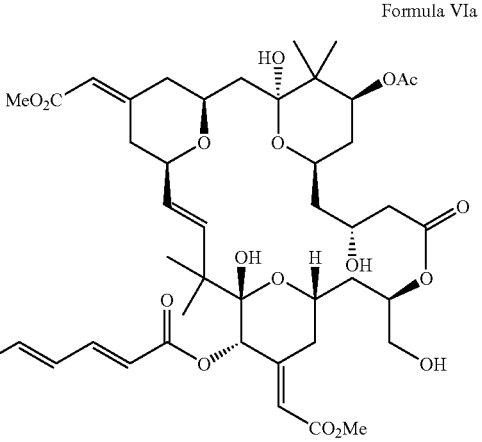

Formula VIa and to pharmaceutical compositions and methods of treatment therewith.

Excluded from the scope of compositions of matter and methods of treatment (as opposed to the novel synthetic processes) in the present invention are the analogues of Formula 1998a where $R^3$ is H or OH and where $R^{20}$ is —O—C(O)—CH$_3$ or —O—C(O)—(CH$_2$)$_6$—CH$_3$, and those of Formula 1998b where $R^8$ is H or t-Bu:

1998a

1998b

Also excluded from the scope of certain embodiments of the present invention is the subject matter disclosed in co-pending U.S. application Ser. No. 09/728,929, filed Nov. 30, 2000 (and companion application PCT/US00/32896 published as WO 01/40214).

In another aspect, the invention relates to a pharmaceutical composition containing a therapeutically effective amount of a compound of Formula I or a pharmaceutically acceptable salt thereof admixed with at least one pharmaceutically acceptable excipient.

In still another aspect, the invention relates to a method of treating hyperproliferative cellular disorders, particularly cancer in a mammal by administering to a mammal in need of such treatment a therapeutically effective amount of a compound of Formula I or a pharmaceutically acceptable salt thereof, either alone or in combination with a second agent, preferably a second anti-cancer agent that acts by a distinct mechanism vis-a-vis the mechanism of the compound of Formula I.

In yet another aspect, the invention relates to methods of treatment for a mammal having an immune-related disease or receiving immunosuppressive therapy, by administering of a therapeutically effective amount of a compound of Formula I or a pharmaceutically acceptable salt thereof.

In another aspect of the invention, there is provided a method for the synthesis of bryostatin analogues, including the steps of esterification and macrotrasacetylization of a protected recognition domain with a protected linker synthon, followed by deprotection. Particularly preferred is reduction of a C26 OBn protected precursor to give the corresponding C26 des-methyl bryostatin analogue. A related aspect of the invention entails the novel products made by the foregoing process. Intermediates and steps for preparing them or converting them to bryostatin analogues are also included in the invention.

The invention also includes pharmaceutical compositions containing one or more compounds in accordance with the invention.

In another aspect, the invention includes a method of inhibiting growth, or proliferation, of a cancer cell. In the method, a cancer cell is contacted with a bryostatin analogue compound in accordance with the invention in an amount effective to inhibit growth or proliferation of the cell. In a broader aspect, the invention includes a method of treating cancer in a mammalian subject, especially humans. In the method, a bryostatin analogue compound in accordance with the present invention is administered to the subject in an amount effective to inhibit growth of the cancer in the patient.

These and other objects and features of the invention will be better understood in light of the following detailed description.

DETAILED DESCRIPTION

Definitions

As used in the present specification, the following words and phrases are generally intended to have the meanings as set forth below, except to the extent that the context in which they are used indicates otherwise.

As used herein, the terms "alkyl", "alkenyl" and "alkynyl," refer to saturated and unsaturated monovalent moieties in accordance with their standard meanings, including straight-chain, branched-chain and cyclic moieties, optionally containing one or more intervening heteroatoms, such as oxygen, sulfur, and nitrogen in the chain or ring, respectively. Exemplary alkyl groups include methyl, ethyl, isopropyl, cyclopropyl, 2-butyl, cyclopentyl, and the like. Exemplary alkenyl groups include 2-pentenyl, 2,4-pentadienyl, 2-octenyl, 2,4,6-octatrienyl, $CH_3$—$CH_2$—$CH_2$—$CH$=$CH$—$CH$=$CH$—, cyclopentadienyl, and the like. Exemplary alkynyl groups include $CH_3C$≡$CCH_2$—, 4-pentyn-1-yl, and the like. Exemplary cyclic moieties include cyclopentyl, cyclohexyl, furanyl, pyranyl, tetrahydrofuranyl, 1,3-dioxanyl, 1,4-dioxanyl, pyrrolidyl, piperidyl, morpholino, and reduced forms of furanyl, imidazyl, pyranyl, pyridyl, and the like.

"Lower alkyl", "lower alkenyl", and "lower alkynyl" refer to alkyl, alkenyl, and alkynyl groups containing 1 to 4 carbon atoms.

The term "aryl" denotes an aromatic ring or fused ring structure of carbon atoms with no heteroatoms in the ring(s). Examples are phenyl, naphthyl, anthracyl, and phenanthryl. Preferred examples are phenyl and naphthyl.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

"Aralkyl" and "heteroaralkyl" refer to aryl and heteroaryl moieties, respectively, that are linked to a main structure by an intervening alkyl group, e.g., containing one or more methylene groups.

"Alkoxy", "alkenoxy", and "alkynoxy" refer to an alkyl, alkenyl, or alkynyl moiety, respectively, that is linked to a main structure by an intervening oxygen atom.

It will be appreciated that the alkyl, alkenyl, alkynyl, aryl, heteroaryl, aralkyl, and heteroaralkyl moieties utilized herein can be unsubstituted or substituted with one or more of the same or different substituents, which are typically selected from —X, —R', =O, —OR', —SR', =S, —NR'R', —NR'R'R'+, =NR', —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R', —C(O)R', —C(O)X, —C(S)R', —C(S)X, —C(O)OR', —C(O)O$^-$, —C(S)OR', —C(O)SR', —C(S)SR', —C(O)NR'R', —C(S)NR'R' and —C(NR)NR'R', where each X is independently a halogen (F, Cl, Br, or I, preferably F or Cl) and each R' is independently hydrogen, alkyl, alkenyl, or alkynyl. In one embodiment, R' is lower alkyl, lower alkenyl, or lower alkynyl. NR'R' also includes moieties wherein the two R' groups form a ring with the nitrogen atom.

While practical size limits for the various substituent groups will be apparent to those skilled in the art, generally preferred are the alkyl, alkenyl, alkynyl, aryl, heteroaryl, aralkyl, and heteroaralkyl moieties containing up to about 40 carbon atoms, more preferably up to about 20 carbon atoms and most preferably up to about 10 carbon atoms (except as otherwise specifically noted, for example, with reference to the embodiment of the invention where a preferred $R^{20}$ substituent has about 7 to 20 carbon atoms).

As to any of the above groups that contain one or more substituents, it is understood, of course, that such groups do not contain any substitution or substitution patterns which are sterically impractical and/or synthetically non-feasible. In addition, the compounds of this invention include all stereochemical isomers and mixtures thereof arising from the substitution of these compounds.

Except as otherwise specifically provided or clear from the context, the term "compounds" of the invention should be construed as including the "pharmaceutically acceptable salts" thereof (which expression has been eliminated in certain instances for the sake of brevity).

The term "pharmaceutically acceptable salt" refers to salts which retain the biological effectiveness and properties of the compounds of this invention and which are not biologically or otherwise undesirable. In some cases, the compounds of this invention are capable of forming acid and/or base salts, derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Relatively lipophilic," as the term is used herein, describes a molecule, moiety, or region which is uncharged at neutral pH, and, taken alone, is only partially soluble in water. Relatively lipophilic moieties preferably have no more than one OH or NH bond for every five carbon atoms, even more preferably for every eight carbon atoms. Relatively lipophilic means that the molecule, moiety or region facilitates therapeutic use, helping to maintain a balance between lipophilicity (e.g., to permit cellular uptake) and hydrophilicity (e.g., to permit aqueous formulation).

"Mammal" is intended to have its conventional meaning. Examples include humans, mice, rats, guinea pigs, horses, dogs, cats, sheep, cows, etc.

The term "treatment" or "treating" means any treatment of a disease in a mammal, including:

preventing the disease, that is, causing the clinical symptoms of the disease not to develop;

inhibiting the disease, that is, arresting the development of clinical symptoms; and/or relieving the disease, that is, causing the regression of clinical symptoms.

The term "effective amount" means a dosage sufficient to provide treatment for the disease state being treated. This will vary depending on the patient, the disease and the treatment being effected.

Compounds

The present invention provides new analogues of bryostatin that can be synthesized conveniently in high yields and which have useful biological activities. The compounds of the invention can be broadly described as having two main regions that are referred to herein as a "recognition domain" (or pharmacophoric region) and a relatively lipophilic "spacer domain" (or linker region). The recognition domain contains structural features that are analogous to those spanning C17 through C26 to C1, including the C ring formed in part by atoms C19 through C23, and the lactone linkage between C1 and C25 of the native bryostatin macrocycle. The spacer domain, on the other hand, joins the atoms corresponding to C1 through C17 of the native bryostatin macrocycle to substantially maintain the relative distance between the C1 and C17 atoms and the directionality of the C1C2 and C16C17 bonds, as illustrated by the arrows and distance "d" in Formula Ia (in which the substituent groups are as defined with reference to Formula I).

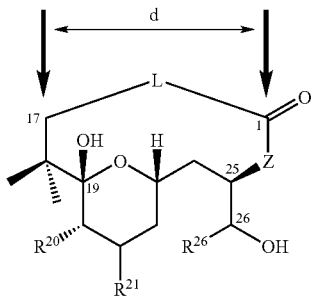

Formula Ia

In addition to its function of maintaining the recognition domain in an active conformation, the spacer domain (shown as "L" in Formula 1a and sometimes also referred to as a linker region) provides a moiety that can be readily derivatized according to known synthetic techniques to generate analogues having improved in vivo stability and pharmacological properties (e.g., by modulating side effect profiles) while retaining biological activity.

It has been found in the present invention that the linker region of the bryostatin family can be varied significantly without eliminating activity. Thus, a wide variety of linkers can be used while retaining significant anticancer and PKC-binding activities. Preferably, the compounds of the present invention include a linker moiety L, which is a linear, cyclic, or polycyclic linker moiety containing a continuous chain of from 6 to 14 chain atoms, one embodiment of which defines the shortest path from C25 via C1 to C17. Distance "d" should be about 2.5 to 5.0 angstroms, preferably about 3.5 to 4.5 angstroms and most preferably about 4.0 angstroms, such as about 3.92 angstroms (as experimentally determined, for example, by NMR spectroscopy). Thus, L may consist solely of a linear chain of atoms that links C17 via C1 to C25, or alternatively, may contain one or more ring structures which help link C17 via C1 to C25. Preferably, the linker region includes a lactone group (—C(=O)O—), or a lactam group (—C(=O)NH—), which is linked to C25 of the recognition region, by analogy to the C1 lactone moiety that is present in the naturally occurring bryostatins. In addition, it is preferred that the linker include a hydroxyl group analogous to the C3 hydroxyl found in naturally occurring bryostatins, to permit formation of an intramolecular hydrogen bond between the C3 hydroxyl of the linker and the C19 hydroxyl group of the recognition region (and optionally with the oxygen of the native B ring). In one preferred embodiment, the linker terminates with —CH(OH)CH$_2$C(=O)O—, for joining to C25 of the recognition region via an ester (or when cyclized a lactone) linkage.

In one embodiment of the invention where $R^{26}$ is H, the compounds of the invention differ from known bryostatins and bryostatin analogues in that the present compounds contain a primary alcohol moiety at C26, i.e., the present analogues lack a methyl group corresponding to the C27 methyl that is ordinarily present in naturally occurring bryostatins. Surprisingly, while the C27 methyl moiety was previously believed to limit rotation of the C26 alcohol and contribute to PKC binding affinity, it has been found that this structural modification can significantly increase PKC binding and also increases efficacy against cancer cells. Other modifications of $R^{26}$ are provided to further modulate these characteristics, as are the C26 des-methyl homologues of the native bryostatins.

In another aspect, the present invention provides bryostatins and bryostatin analogues in which $R^{20}$ is longer (e.g., having 9 to 20 or more carbon atoms) than the corresponding substituents at C20 in the native bryostatins (e.g., Bryostatin 3 having an 8-carbon atom moiety).

Certain preferred spacer domains employed in the compounds of the invention are illustrated in Formulae II throught V:

Formula II

Formula III

Formula IV

Formula V

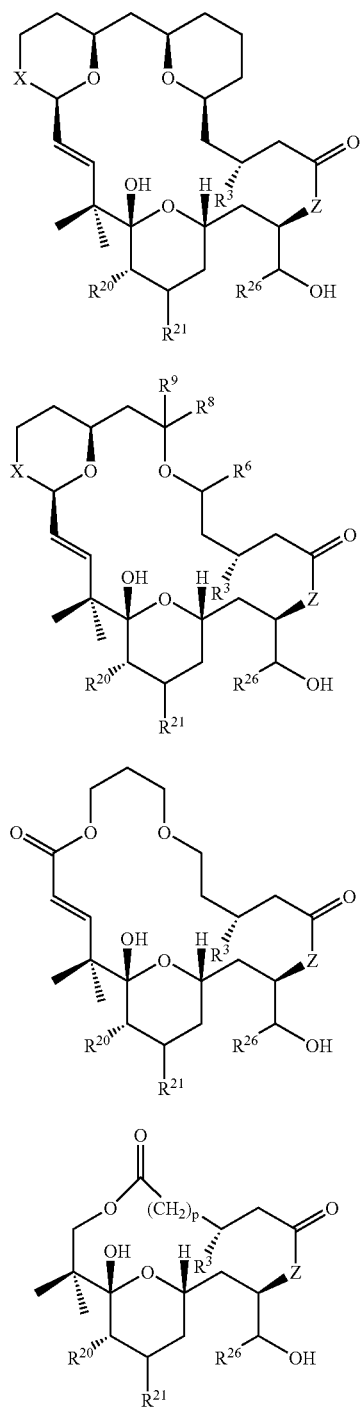

wherein:
- $R^3$ is H, OH or a protecting group;
- $R^6$ is H, H or =O;
- $R^8$ is selected from the group: H, OH, =O, R', —(CH$_2$)$_n$O(O)CR' or (CH$_2$)$_n$CO$_2$-haloalkyl where
  - n is 0, 1, 2, 3, 4 or 5,
  - provided that $R^6$ and $R^8$ are not both =O;
- $R^9$ is H, OH or is absent;
- $R^{20}$, $R^{21}$, $R^{26}$, R' and Z are as defined above with respect to Formula I;
- p is 1, 2 or 3; and
- X is —CH$_2$—, —O—, —S— or —N(R$^e$)— where R$^e$ is COH, CO$_2$R' or SO$_2$R', X preferably being —O—, and the pharmaceutically acceptable salts thereof.

Additional embodiments of the spacer domains employed in the compounds of the invention are illustrated in Formulae II-A to V-A:

Formula II-A

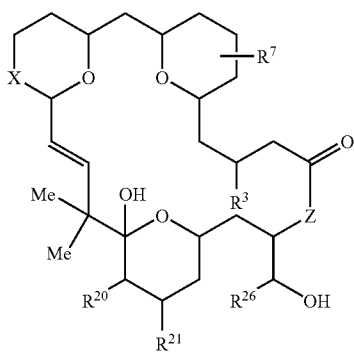

Formula III-A

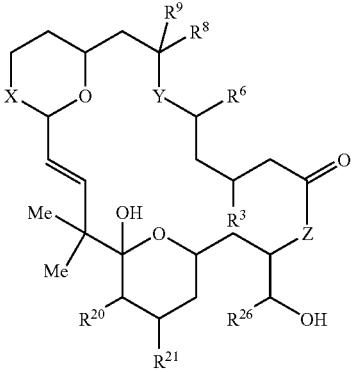

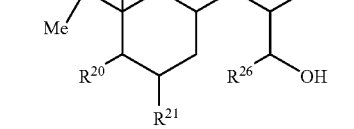

Formula IV-A

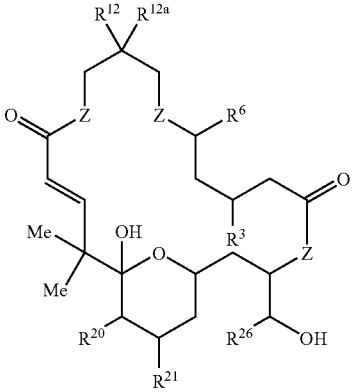

-continued

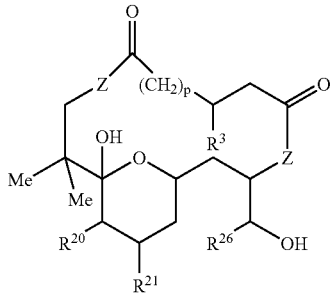
Formula V-A

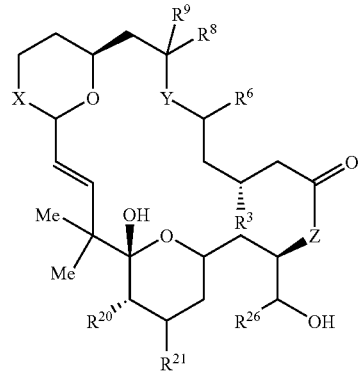
Formula III-B

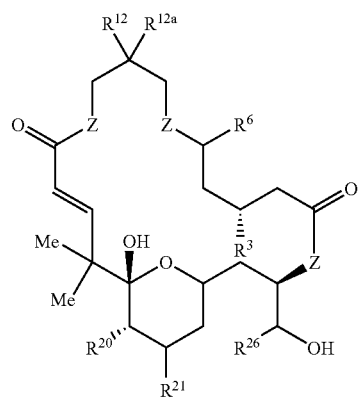
Formula IV-B wherein:

$R^3$, $R^6$, $R^9$, $R^{20}$, $R^{21}$, $R^{26}$, R', X, Z and p are as defined above with respect to Formulae II to V;

$R^7$ is absent or represents from 1 to 4 substituents on the ring to which it is attached, selected from lower alkyl, hydroxyl, amino, alkoxyl, alkylamino, =O, acylamino, or acyloxy;

$R^8$ is as defined above including substituted or unsubstituted alkyl, alkenyl, alkynyl, aryl, heteroaryl, aralkyl, or heteroaralkyl, e.g., substituted with an alkoxy, acyloxy, acylamino, or alkylamino substituent, or, in Formula III-A when $R^6$ represents H, H, then $R^8$ and $R^9$ taken together can represent =O;

$R^{12}$ and $R^{12a}$ are independently for each occurrence, H, OH, lower alkyl, lower alkoxyl, or lower acyloxy, or $R^{12}$ and $R^{12a}$ taken together represent =O; and Y is $CH_2$, —O— or —N(H)—, and the pharmaceutically acceptable salts thereof. The compounds of Formulae II-A to V-A preferably have one or more of the stereochemical configurations respectively represented in Formulae II to V.

In certain preferred embodiments, the analogues illustrated in Formulae 11-A to V-A have one or more, preferably all of the following stereochemical dispositions:

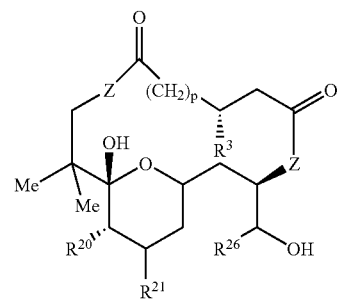
Formula V-B

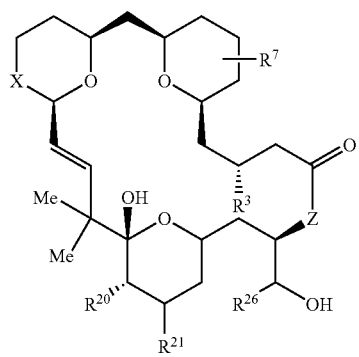
Formula II-B

Other preferred embodiments include the compounds of the above formulae (I through V-B) where $R^{26}$ is H or lower alkyl, preferably H or Me, and most preferably H. Also preferred are those compounds where $R^{21}$ represents =$CHCO_2R'$, where R' is preferably lower alkyl, especially Me or Et. Also preferred are those compounds where $R^{20}$ represents a carbonate, urea, thiourea, thiocarbamate or carbamate substituent. Further preferred are those compounds where $R^3$ is OH. Particularly preferred are those compounds, respectively having one or more of the stereochemical configurations illustrated in Formulae I throught V.

Excluded from the scope of compositions of matter and methods of treatment (as opposed to the novel synthetic processes) in present invention are the analogues of Formula 1998a where $R^3$ is H or OH and where $R^{20}$ is —O—C(O)—$CH_3$ or —O—C(O)—$(CH_2)_6$—$CH_3$, and those of Formula 1998b where $R^8$ is H or t-Bu:

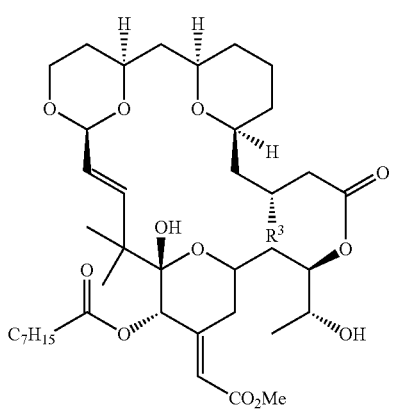

1998a

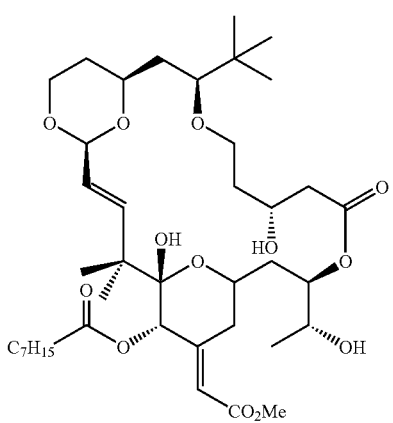

1998b

Also excluded from the scope of certain embodiments of the present invention is the subject matter disclosed in co-pending U.S. application Ser. No. 09/728,929, filed Nov. 30, 2000 (and companion application PCT/US00/32896 published as WO 01/40214).

Nomenclature

For simplicity of reference, the compounds of Formulae I–V are named and numbered herein as corresponding to the naturally occurring bryostatin macrocycle, described above with reference to Formula A. For example, the C26 des-methyl homologue of native bryostatin 1 (a compound of the present invention) has the structure illustrated in Formula VIa:

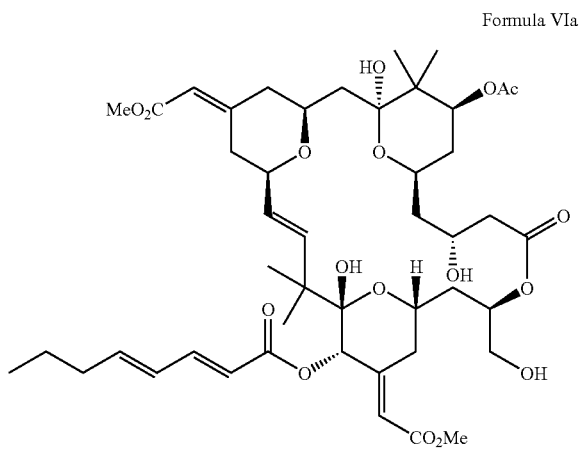

Formula VIa

By way of comparison, the analogues of the invention in which $R^{26}$ is hydrogen, such as those of Formula IIa and Formula IVa:

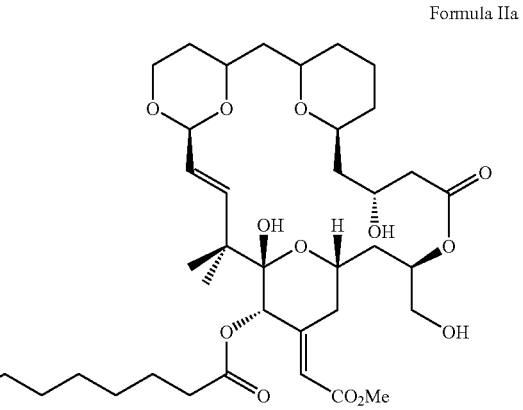

Formula IIa

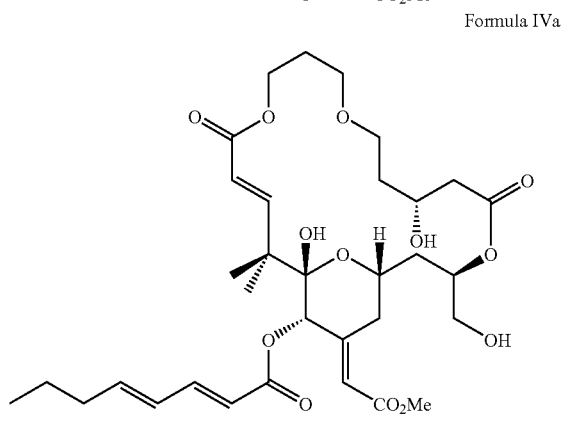

Formula IVa are also referred to as "C26 des-methyl", notwithstanding that the structures corresponding to L (in Formula I) or the corresponding spacer domain (in Formulae II–V), or even the recognition domain, contain fewer carbon atoms than native bryostatin such that the "C26" position would be assigned a lower number were these analogues to be named without reference to the native structure.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The terms "protecting group" or "blocking group" refer to any group which when bound to a functional group such as one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl or like functionality and later selectively removed either by chemical or enzymatic methods in mild conditions compatible with the nature of the product.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from about 5° C. to 100° C. (preferably from 10° C. to 50° C.; most preferably at "room" or "ambient" temperature, e.g., 25° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 25° C.) over a period of about 0.5 to about 10 hours (preferably about 1 hour). Parameters given in the Examples are intended to be specific, not approximate.

Isolation and purification of the compounds and intermediates described herein can be effected, if desired, by any suitable separation or purification procedure such as, for example, distillation, filtration, extraction, crystallization, column chromatography, thin-layer chromatography or thick-layer chromatography, or a combination of these procedures. Specific illustrations of suitable separation and isolation procedures can be had by reference to the general description and examples. However, other equivalent separation or isolation procedures can, of course, also be used.

Synthesis of the Compounds of Formula I

The compounds of the invention may be produced by any methods available in the art, including chemical and biological (e.g., recombinant and in vitro enzyme-catalyzed) methods. In one embodiment, the present invention provides a convergent synthesis in which subunits primarily corresponding to the recognition and spacer domains are separately prepared and then joined by esterification-macrotransacetalization (Wender et al., 1998a, 1998b, 1998c). Additional syntheses of the compounds of Formulae I–VI are described below with reference to the Reaction Schemes. The stereochemical relationships illustrated for the various substituents should be taken to be optional, but individually and collectively preferred; the stereochemical relationships corresponding to the native bryostatins are particularly preferred.

Reaction Scheme 1 illustrates synthesis of precursors for the recognition domain in compounds of the invention.

Reaction Scheme 1

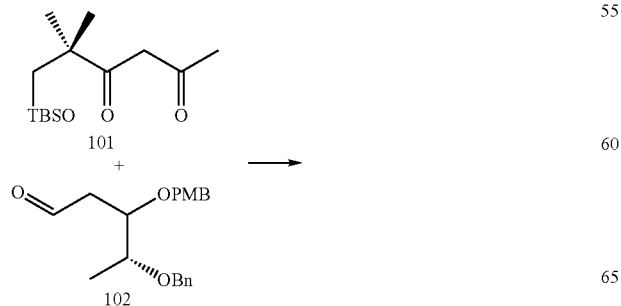

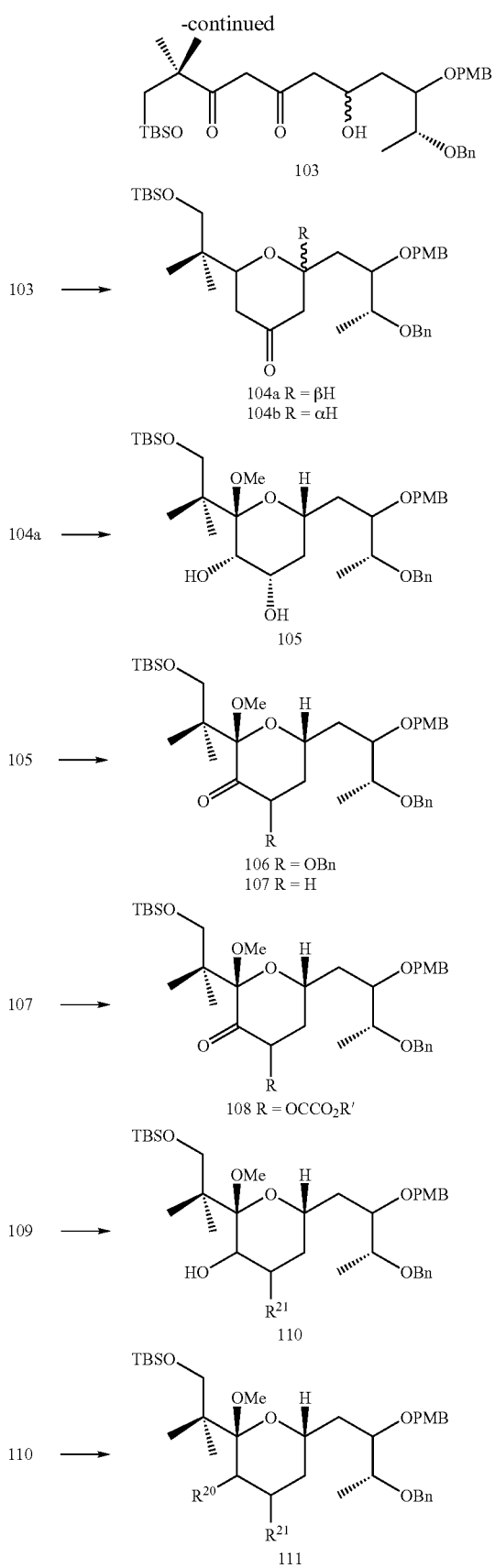

Reaction Scheme 2 illustrates the further synthesis of recognition domains for C26 des-methyl compounds of the invention.
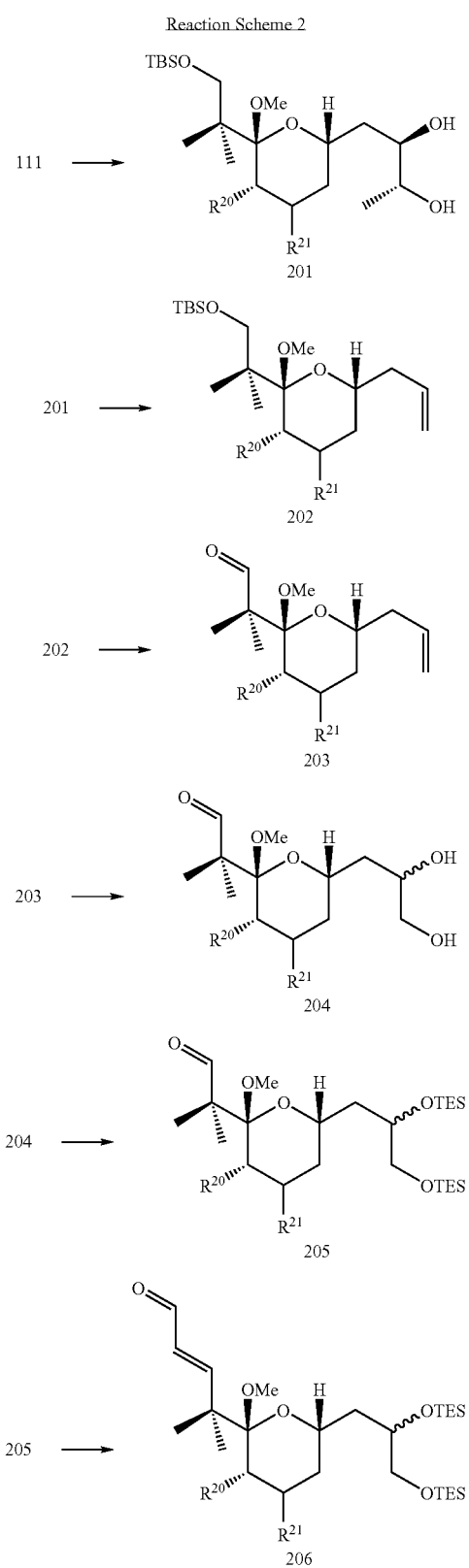
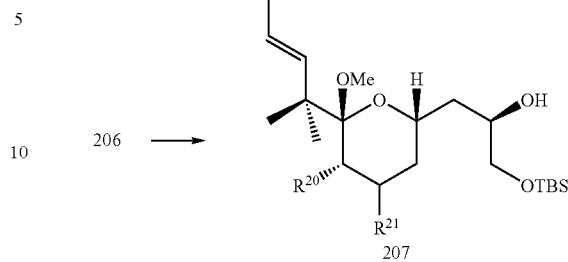
Reaction Scheme 3 illustrates synthesis of the protected alcohol precursor to many of the C26 methyl analogues of the invention.
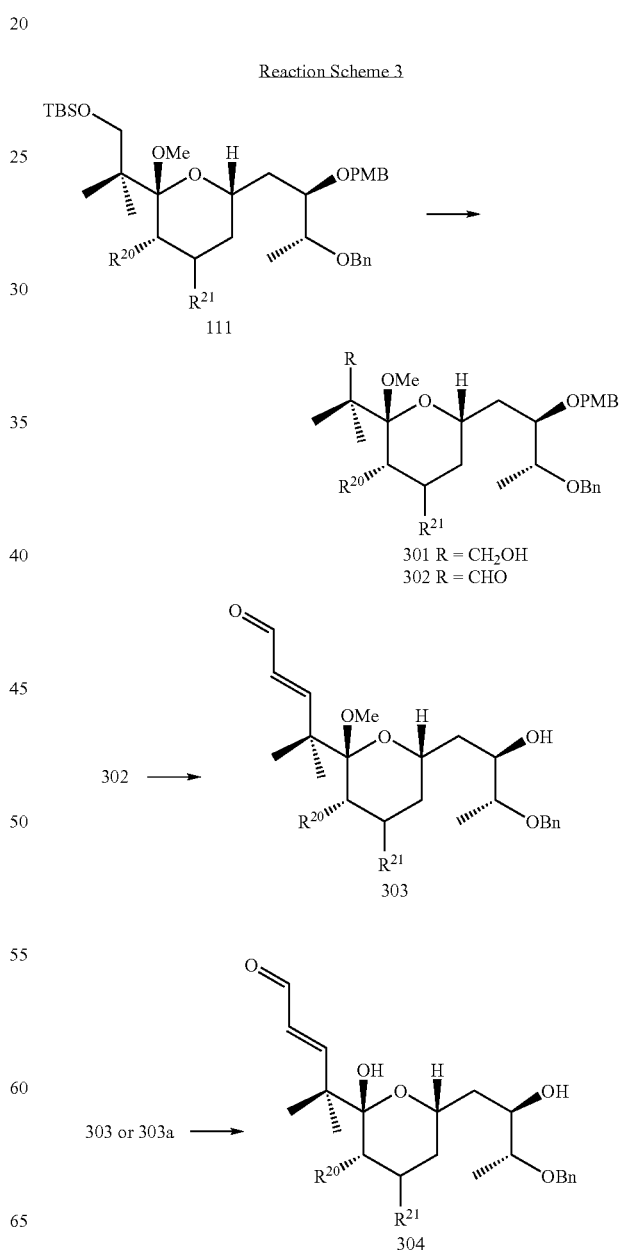

-continued
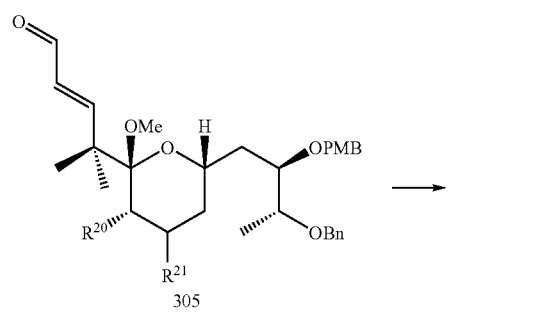
305
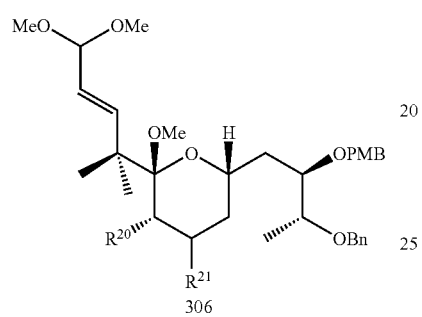
306
306 →
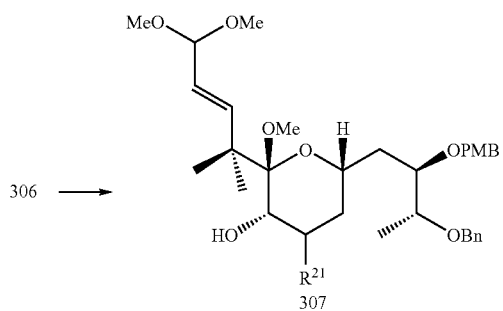
307
307 →
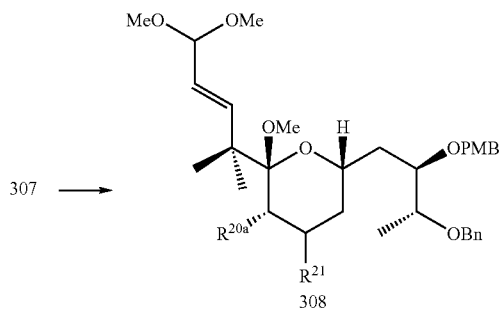
308
308 →
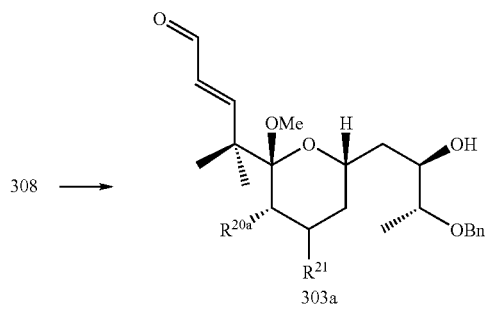
303a
Reaction Scheme 4 illustrates the synthesis of linker synthons for preparing the compounds of Formula II.
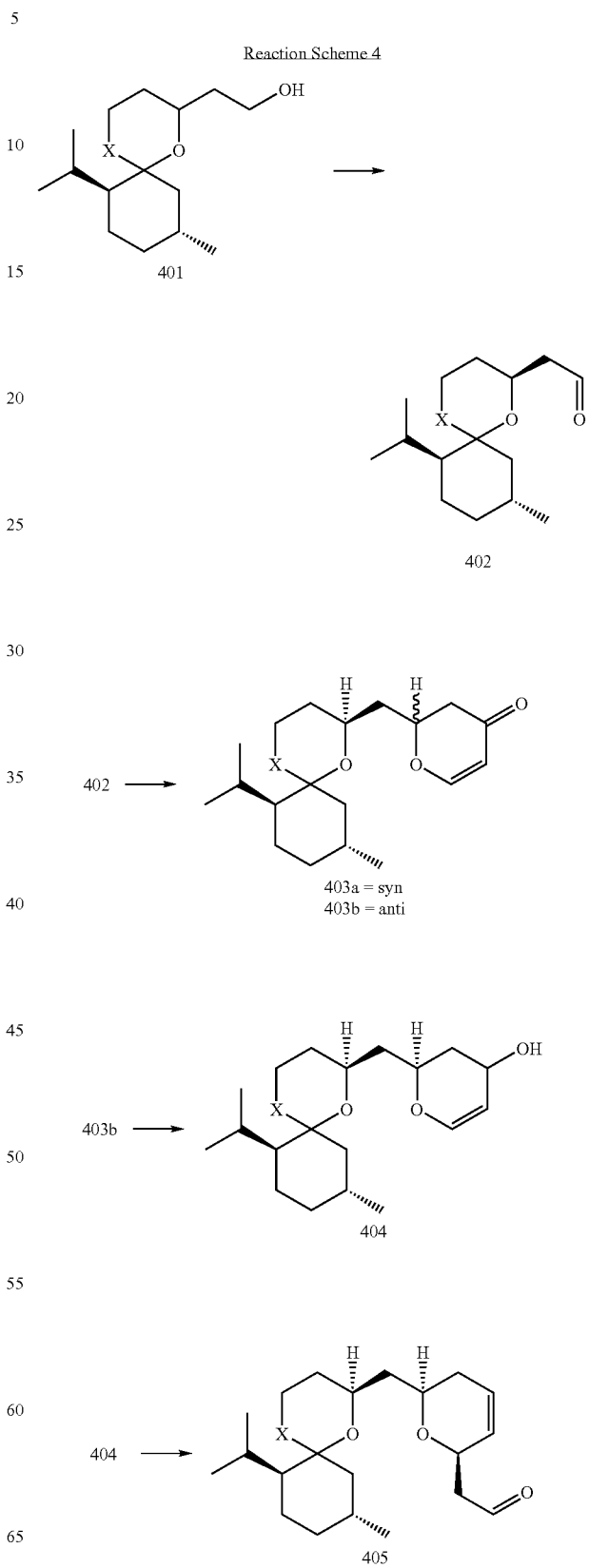
403a = syn
403b = anti

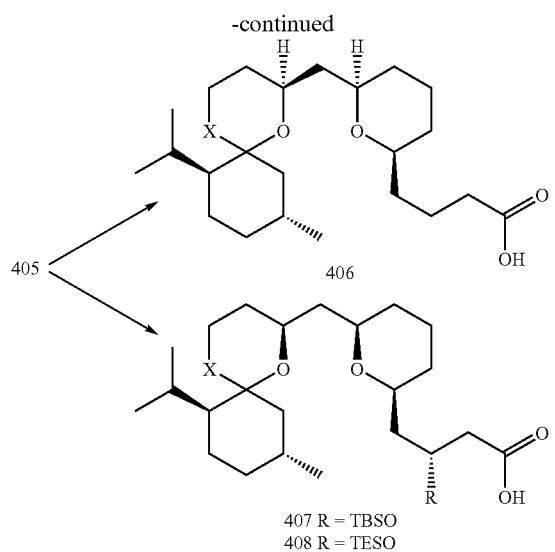

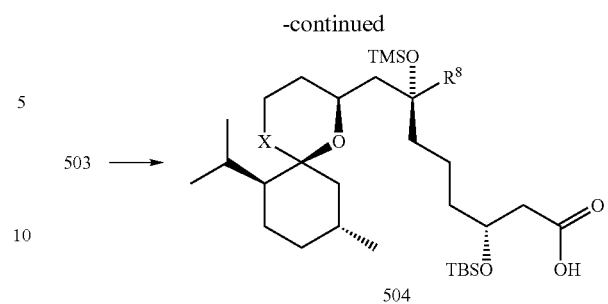

Reaction Scheme 5A illustrates the synthesis of linker synthons for preparing the compounds of Formula III where $R^9$ is OH.

Reaction Scheme 5B illustrates the synthesis of linker synthons for preparing the compounds of Formula III where $R^8$ and/or $R^9$ are H.

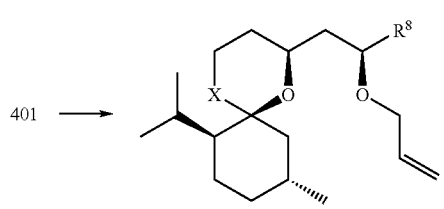

Reaction Scheme 5C illustrates the synthesis of linker synthons for preparing the compounds of Formula III where $R^6$ is =O with a variety of possible substituents at $R^8$.

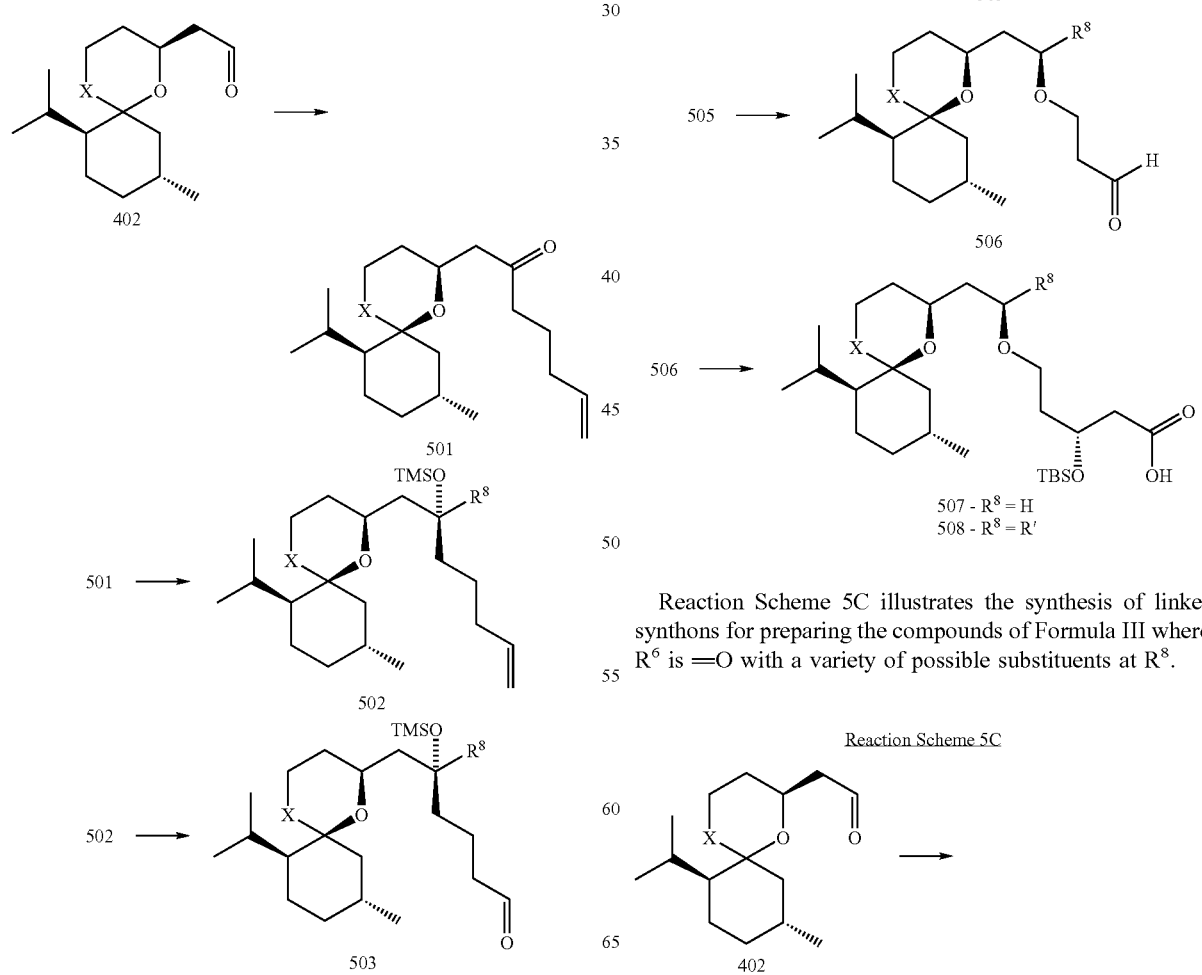

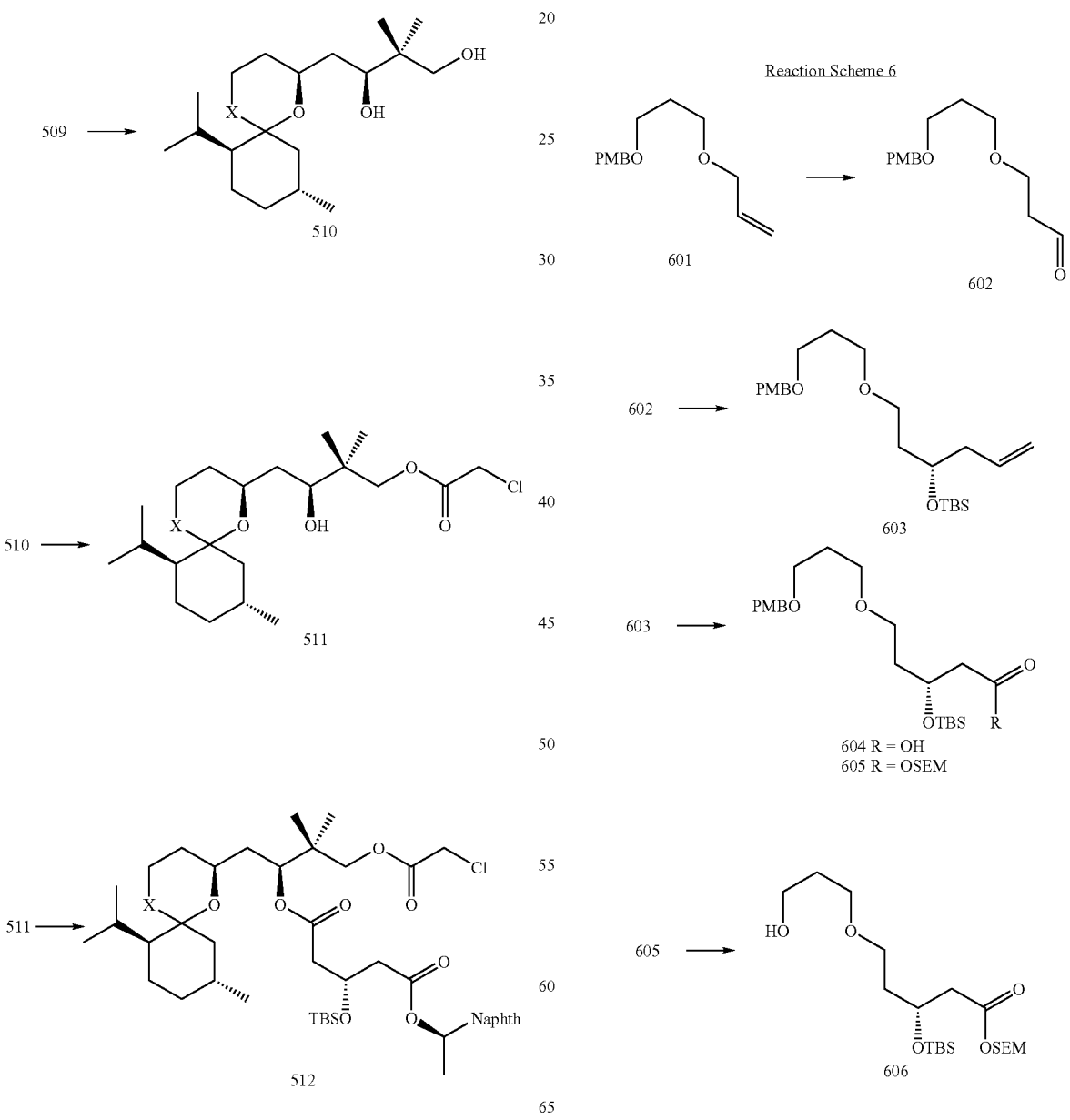
Reaction Scheme 6 illustrates the synthesis of linker synthons for preparing the compounds of Formula IV.
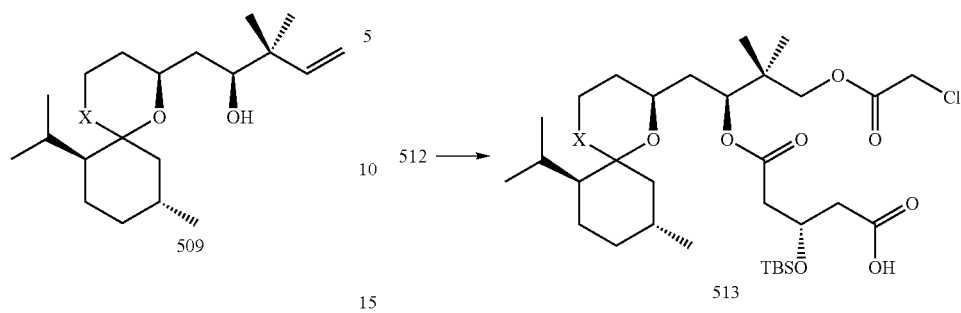

Reaction Scheme 7A illustrates the synthesis of the compounds of Formula II and II-A.
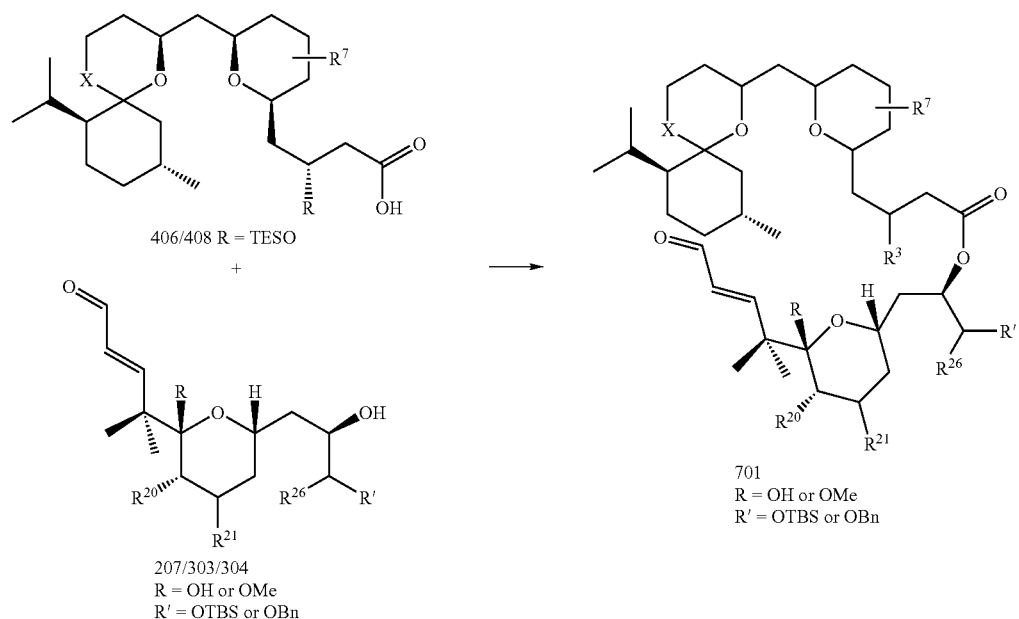
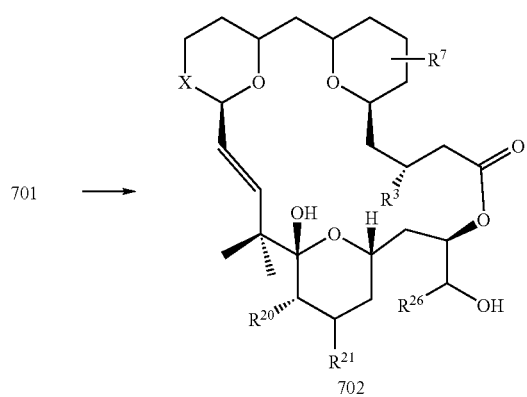

Reaction Scheme 7B illustrates the synthesis of the compounds of Formula III.
Reaction Scheme 8 illustrates synthesis of the Compounds of Formula IV, particularly where $R^{26}$ is methyl, the C26 des-methyl analogues and compounds of Formula IV where $R^{12}$ and $R^{12a}$ are other than H being obtained by like synthesis.
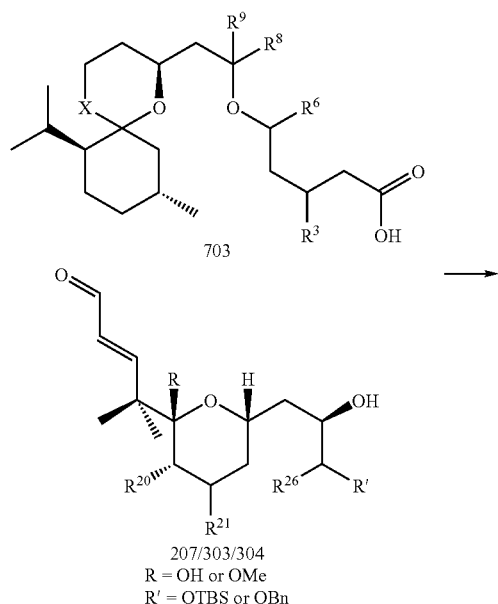
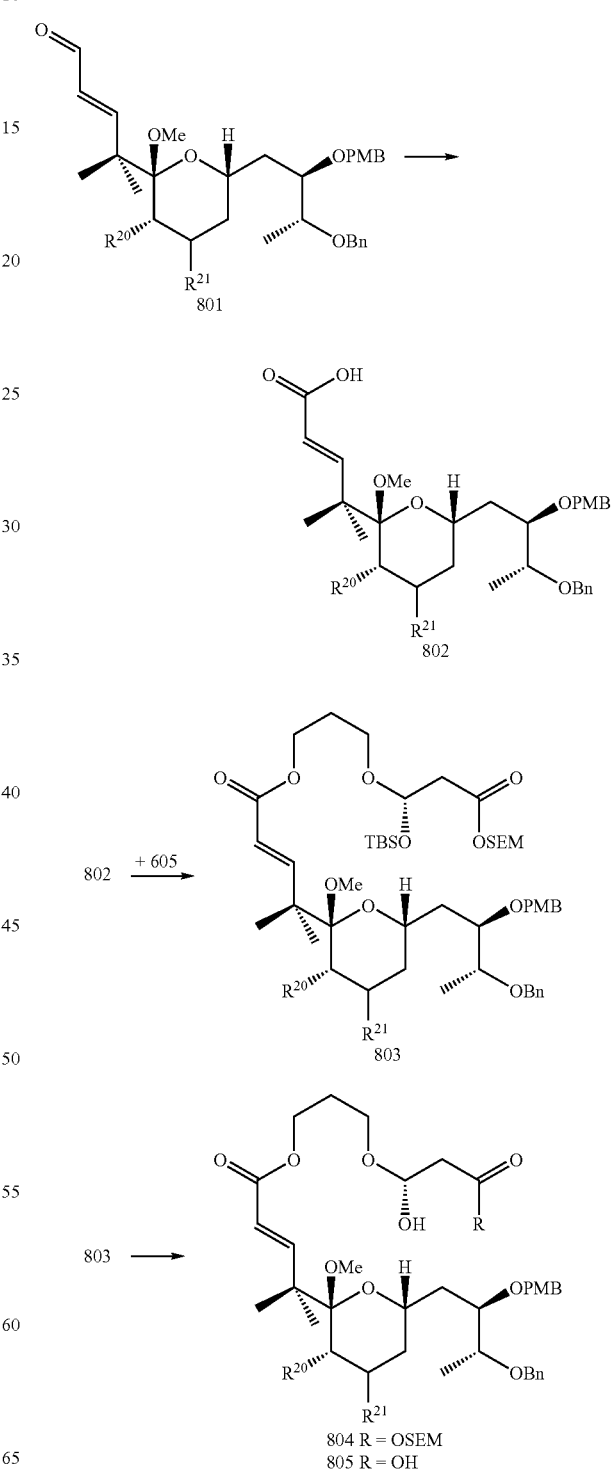

-continued
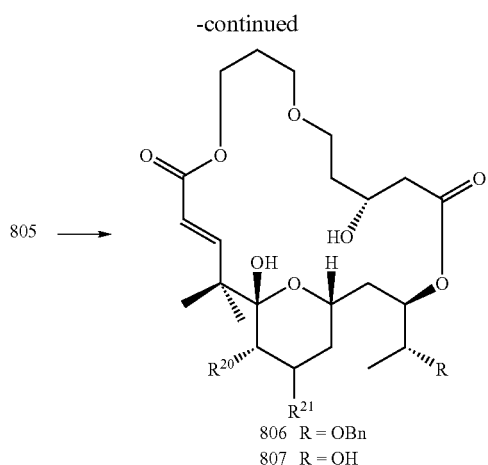
806 R = OBn
807 R = OH
Reaction Scheme 9 illustrates synthesis of the Compounds of Formula V.
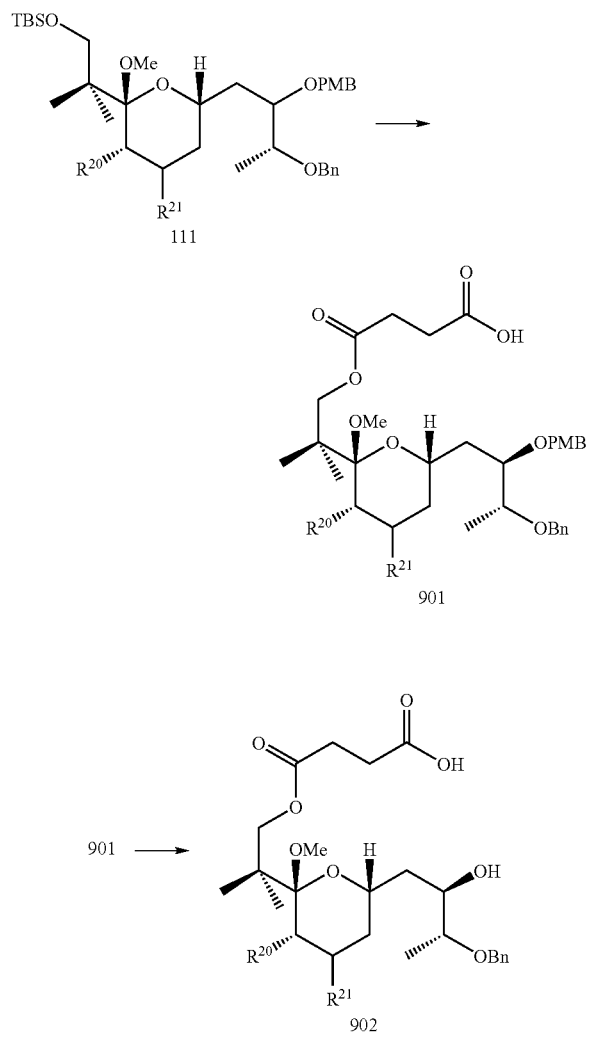
-continued
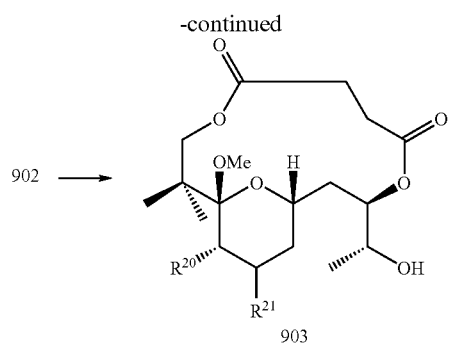
903
Reaction Schemes 10 and 11 illustrate the synthesis of compounds of the invention that are further derivatized at the C20 position, as discussed in Examples 4B, 4C and 4D.
Reaction Scheme 10
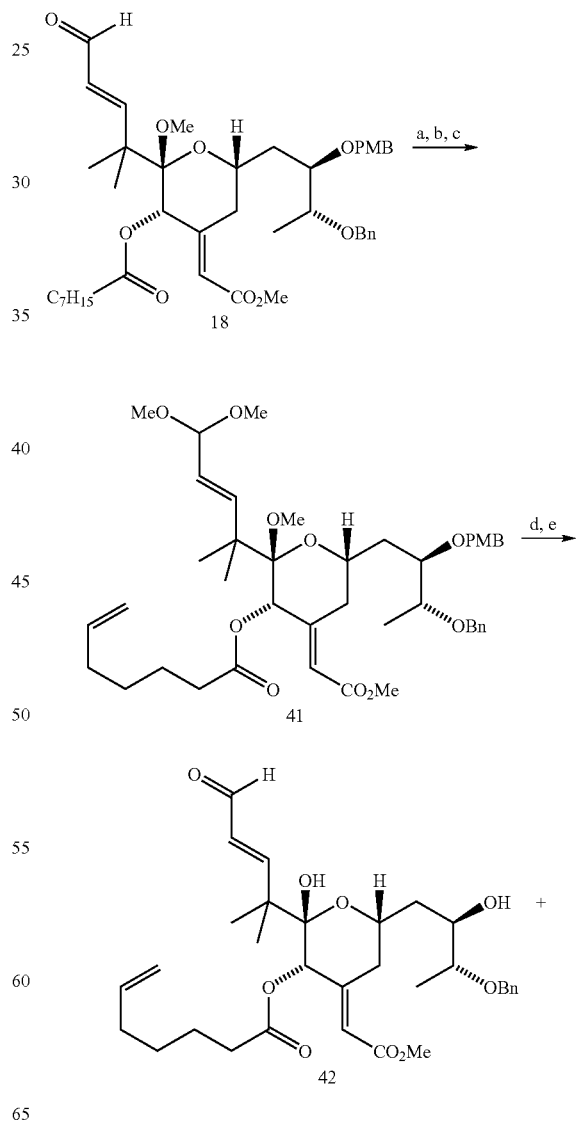

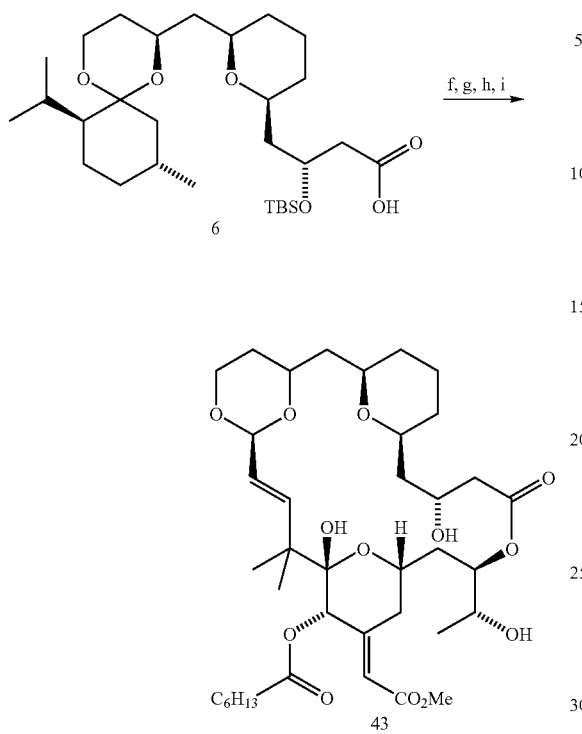

a) CH(OMe)₃, PPTS, MeOH;
b) K₂CO₃, MeOH;
c) heptenoic acid, Et₃N, DMAP, Yamaguchi's reagent, CH₂Cl₂ (84% for three steps);
d) DDQ, CH₂Cl₂/H₂O (85%);
e) 48% HF, CH₃CN/H₂O (80% yield);
f) Yamaguchi's reagent, Et₃N, DMAP (80%);
g) HF-Pyridine, THF (68%);
h) Amberlyst 15, CH₂Cl₂ (70%);
i) Pd(OH)₂, EtOAc, H₂, 1 atm (63% yield)

Reaction Scheme 11

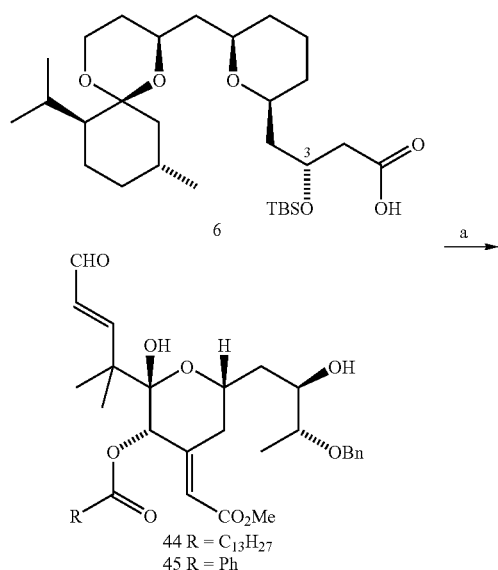

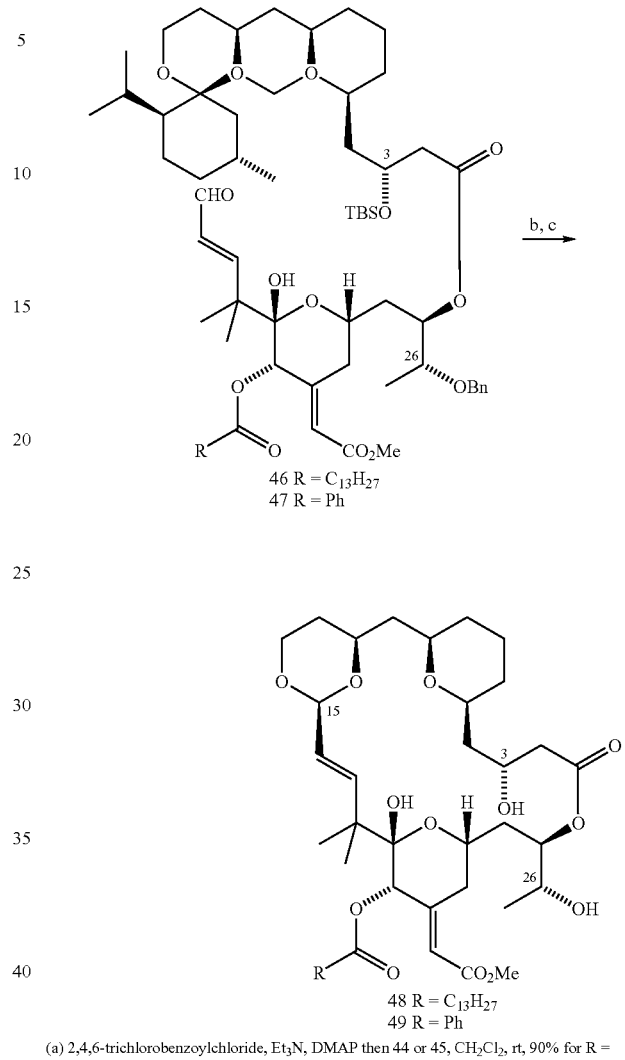

(a) 2,4,6-trichlorobenzoylchloride, Et₃N, DMAP then 44 or 45, CH₂Cl₂, rt, 90% for R = C₁₃H₂₇, 89% for R = Ph.
(b) HF·pyridine, THF, rt, 83% for R = C₁₃H₂₇, 80% for R = Ph.
(c) Pd(OH)₂, H₂, EtOAc, 1 atm, 97% for 48, 63% for 49.

Starting Materials. Conveniently, compounds of the invention can be prepared from starting materials that are commercially available or may be readily prepared by those skilled in the art using commonly employed synthetic methodology.

Reaction Scheme 1 illustrates a method for forming a synthon designated herein as 111 which is useful for providing the recognition domain in compounds of the invention, for example as detailed in Example 1. 6-(Tert-butyldimethylsilylhydroxy)-5-dimethylhexane-2,4-dione (101, Example 1B) is stirred with 2 equivalents of LDA (lithium diisopropylamine) in THF (tetrahydrofuran), followed by addition of 0.9 equivalents of 3R-p-methoxybenzyl-4R-benzylhydroxypentane-1-al (102, Example 1A) to afford diasteriomeric aldol mixture 103 after suitable purification. To 103 is then added a catalytic amount of p-methylphenylsulfonic acid (p-TsOH) with stirring at room temperature followed by base quenching to produce pyranone condensation product 104 as a mixture of α and β-isomers at C23

(104a and 104b). The β-isomer (104a) is separated from the α-isomer and is reacted with NaBH$_4$ in the presence of CeCl$_3$.7H$_2$O, followed by quenching with aqueous brine to form an allylic alcohol (not shown) that can then be epoxidized with m-chloroperbenzoic acid (mCPBA) in 2:1 CH$_2$Cl$_2$:MeOH containing sodium bicarbonate as a buffer to yield a C19-methoxylated C20, C21 syn-diol 105. Selective benzoylation of the C21 equatorial alcohol with benzoyl chloride to afford C21 monobenzoate (not shown), followed by oxidation of the C20 hydroxyl with Dess-Martin periodinane (1,1,1-triacetoxy-1,1-dihydro-1,2-benziodoxol-3 (1H)-one) at room temperature affords the corresponding 20-keto-21-benzoate product 106. Treatment of 106 with SmI$_2$ (2 equiv) yields a ketone 107 selectively deoxygenated at C21. Next, ketone 107 is reacted with LDA and OHCCO$_2$CH$_3$ in THF at −78° C. to afford aldol mixture 108. After purification, 108 is reacted with methanesulfonylchloride in CH$_2$Cl$_2$ containing triethylamine, followed by reaction with DBU (1,8-diazabicyclo[5.4.0]undec-7-ene) in THF to effect an aldol condensation and elimination of water, to yield an α,β-unsaturated methyl ester (enone 109) with an E-stereoconfiguration. Treatment of enone 109 with NaBH$_4$ in the presence of CeCl$_3$.7H$_2$O produces exclusively the C20 axial alcohol 110. This product can then be esterified at C20, with octanoic acid for example, to yield the desired synthon 111.

It will be appreciated how the foregoing procedures can be exploited or modified to produce recognition region synthons having different substituents. For example, compounds where $R^{21}$ contains a C35 ester group having a Z-configuration are produced during formation of intermediate 109 (Example 1C) and can be isolated by chromatography. Similarly, other ester groups can be introduced at C35 by replacing the OHCCO$_2$CH$_3$ reactant used to form 108 above with an appropriately substituted compound of the form OHCCO$_2$R', in which R' is other than methyl.

In addition, as detailed below, other substituents can be introduced in synthon 111 to generate substituent $R^{20}$ at C20 by substituting any of a variety of carboxylic acids for the octanoic acid reacted with axial alcohol 110 (as in the last step of Example 1C), including other saturated, unsaturated, aryl, and carboxylic acids. In synthesizing the compounds of the invention where $R^{20}$ has been varied, the substituent (e.g., a desired C20 ester substituent, carbonate, urea, thiourea, thiocarbamate or carbamate) can be introduced into a recognition region synthon prior to condensing the recognition region synthon with a linker synthon using the procedures described in Example 4 and via other synthetic routes well known to those skilled in the art. In Example 4A, the C20 octanoate substituent in synthon 111 can be replaced with an acetyl group by first protecting the base labile aldehyde group using trimethyl orthoformate to form the dimethyl acetal. The C20 octanoate ester can then be cleaved using a basic solution, such as K$_2$CO$_3$ in methanol, to afford the free C20 alcohol, followed by reaction with an activated form of acetic acid, such as acetic anhydride or acetyl chloride, to obtain the C20 acetate product. The product can then be deprotected at the C15 aldehyde, C19 oxygen, and C25 oxygen using benzoquinone compound DDQ (to remove the p-methoxybenzyl group and cleave the dimethyl acetal) followed by aqueous HF (demethylation at C19) to afford the corresponding C19 alcohol. This product can then be condensed with an appropriately substituted linker synthon to produce a desired bryostatin analogue, such as analogue 702.1, as detailed in Example 4A.

The protected alcohol precursor to many of the C26-desmethyl bryostatin analogues of the invention (the compounds of Formula I where $R^{26}$ is H) can be made as illustrated in Reaction Scheme 2. Di(benzyl ether) 111 can be hydrogenated over Pearlman's catalyst to produce the corresponding C25,C26 diol 201. Treatment of the diol with lead tetraacetate yields the corresponding C25 aldehyde (not shown), with the release of C26 and C27. Reaction of the aldehyde with Cp$_2$Ti(Cl)CH$_2$Al(CH$_3$)$_2$ (Tebbe's reagent) yields C25,C26 olefin 202. Alternatively, sodium periodate can be used in place of lead tetraacetate.

Treatment of olefin 202 with HF/pyridine is effective to remove the silyl protecting group, followed by treatment with Dess-Martin periodinane (supra) to oxidize the C17 alcohol to an aldehyde group, affording aldehyde 203. The C25,C26 olefin of 203 can be converted to C25,C26 diol 204 by reaction with chiral dihydroxylating reagent (DHQD)$_2$ AQN in the presence of K$_3$Fe(CN)$_6$, K$_2$CO$_3$ and K$_2$OsO$_2$ (OH)$_4$ in t-butanol. Product 204 is obtained as a 2:1 (β:α) mixture of 25-hydroxy diastereomers. The α-diastereomer can be removed later in the synthesis. Treatment of 204 with triethylsilyl chloride yields protected diol 205, which can be employed in the synthesis of the compounds of Formula V.

Addition of backbone atoms corresponding to C15 and C16 of the bryostatin backbone to 205 can be accomplished in four steps. First, the C17 aldehyde is allylated with allyl diethylborane. The reaction is quenched with saturated sodium bicarbonate to yield the desired C17 allyl adduct. The C17 hydroxyl group can then be acylated with acetic anhydride in the presence of triethylamine and 4-dimethylaminopyridine (DMAP), to afford a diastereomeric mixture of homoallylic C17 acetates. This product mixture can be oxidized using N-methylmorpholine N-oxide and osmium tetraoxide, followed by neutralization with sodium bicarbonate. After extraction, the residue is reacted with lead tetraacetate, followed by addition of DBU to cause elimination of the acetate group, yielding enal 206.

The C25 hydroxyl group of 206 can be unmasked in preparation for closure of the macrocycle as follows. First, enal 206 is treated with aqueous hydrofluoric acid to provide a crude diol intermediate in which the C19 methoxy group is converted to a free hydroxyl. Next, the diol product is reacted with tert-butyldimethylsilyl chloride (TBSCl) in the presence of imidazole to produce alcohol 207 containing a C25 hydroxyl group and C26 OTBS group as a 2:1 (β:α) mixture of C25 diastereomers. Silica gel chromatography can be used to resolve the diastereomers, affording the β diastereomer in 50–60% yield.

The protected alcohol precursor to many of the C26-methyl bryostatin analogues of the invention (Formula I where $R^{26}$ is methyl) can be made as illustrated in Reaction Scheme 3, via methods analogous to the preparations for 205 and 206. Deprotection and acylation of formula 111 may be accomplished, for example, by following the procedures described in Wender et al., (1998a).

Linker synthons for the compounds of Formula II (where X is a heteroatom) can be prepared, for example, as illustrated with reference to Reaction Scheme 4, and later described in Examples 2A and 2B. These compounds contain two rings that are analogous to the A and B rings of bryostatin, but lack the naturally occurring substituents at C7, C8, C9, and C13. The presence of a heteroatom, such as an oxygen, sulfur or nitrogen atom (the lone electron pair of which is stabilized) in place of C14 does not adversely affect activity of the end product, but is required for transacetylization in the later synthetic steps. The compounds of formulae 406 and 408 differ in that 402 provides a protecting group precursor for a hydroxyl group attached to C3, whereas 406 does not provide for a hydroxyl at C3.

The linker synthons for the compounds of Formula III (in which X is a heteroatom), which contain a B-ring-like structure but lack an A-ring, are prepared, for example, as illustrated with reference to Reaction Schemes 5A through 5C. Examples 2C and 2D describe methods for preparing synthons 504 and 508. In both examples, $R^8$ is a tert butyl group attached to C9. However, with reference to the preparation of 505, the t-BuLi reactant can be replaced by R'Li to generate the corresponding linker synthons of 508 where $R^8$ is R'. 504 additionally contains a TMS protecting group for synthesis of the compounds where $R^9$ is a hydroxyl attached to C9, rather than hydrogen. Also, both synthons contain a TBS protecting group for the compounds where $R^3$ is a hydroxyl group attached to C3. Example 2E describes the corresponding method for making synthon 507, which is unsubstituted at C9. Example 2G describes a method for preparing linker synthons in which C5 is provided as an ester carbonyl. In addition, the synthons in this Example contain an $R^6$ substituent that is preferably a saturated or unsaturated substituent containing 1 to 20 carbon atoms and optionally (1) one or more oxygen atoms and (2) optionally one or more nitrogen atoms. In synthon 514 in Example 2G, $R^8$ is —C(CH$_3$)$_2$CH$_2$OC(=O)C$_{13}$H$_{27}$. However, other $R^6$ substituents can be introduced by suitable modification of the procedure as will be evident to one of ordinary skill in the chemical arts.

Synthesis of a completely acyclic linker synthon 606 (where neither an A- nor a B-ring-like structure is present) is described with reference to Reaction Scheme 6 and in Example 2F.

As illustrated with reference to Reaction Scheme 7A, and further described in Example 3A, an alcohol such as 207, 303 or 304 is reacted with an acid such as 406 or 408 in a two step process to form the desired macrocyclic structure. After in situ conversion of the acid (408) to a mixed anhydride, the alcohol (207) is added to form ester 701. The ketal portion of 408 is then joined (in a process referred to as macrotranacetylization) to C15 of 701 by adding 70% HF/pyridine hydrofluoric acid to catalyze cleavage of the menthone ketal, cleavage of the TBS ethers at C3 and C26, and formation of a new ketal between the C15 aldehyde group and the linker diol moiety generated by release of the menthone (where X is oxygen), to afford desired analogue of Formula II where X is a heteroatom and $R^{26}$ is H (starting with alcohol 207) or methyl (starting with 303 or 304), i.e., compound of formula 702. This last reaction is also effective to set the stereocenter at C15 to a thermodynamically preferred configuration. The analogous synthesis of compounds of Formula III (where X is a heteroatom), first forming the ether bond between C1 and C25, is illustrated with reference to Reaction Scheme 7B (where formula 703 corresponds to any of formulae 504, 507, 508 or 513) and further described in Example 3C.

As illustrated with reference to Reaction Scheme 8, and further described in Example 3B, the compounds of Formula IV (such as formula 807) can be made from pharmacophoric synthon 801 and linker synthon 606 from Example 2F.

Reaction Scheme 9 illustrates synthesis of the compounds of Formula V, e.g., as further described in Example 3D, from synthon 111 and an activated dicarboxylic acid (succinic anhydride) to give formula 903.

Although the bryostatin analogues produced in Examples 3B, 3C and 3D all contain a C27 methyl group, analogous C26 desmethyl analogues can be readily synthesized using an appropriate C26 desmethyl synthon, such as C26 desmethyl synthon 207 described in Example 1C. Compounds of the invention having a naturally occurring bryostatin backbone (e.g., including a naturally occurring linker region), but lacking the C27 methyl group, can also be prepared by adapting synthetic protocols published by Kageyama et al. (1990) and Evans et al. (1998) In brief, the published methods are modified by utilizing synthons in which the C27 methyl group has been omitted, to afford the desired C26-desmethyl analogues.

As illustrated with reference to Reaction Scheme 10, synthesis of a C20 heptanoate ester 43 is described in Example 4B, using a similar reaction scheme to that employed in Example 4A, except that heptenoic acid in the presence of triethylamine, DMAP, and Yamaguchi's agent is used in place of acetic anhydride. Yamaguchi's reagent is again employed in step f to activate the COOH group of formula 6, followed by removal of the TBS group in step g, hydrolysis of the menthone and transacetylization in step h, and saturation of the double bond upon removal of the benzyl group by hydrogenolysis in step i. Synthesis of a C20 myristate ester analogue 48 (14 carbon atom chain) is illustrated with reference to Reaction Scheme 11 and described in Example 4C. Reaction Scheme 11 and Example 4D describes synthesis of a bryostatin analogue containing an aryl ester group (benzoate) at C20, by suitable adaptation of the procedure in Example 1C for making compound 207. It will be appreciated how these procedures can be modified to introduce other C20 esters by substituting the starting materials necessary to produce the desired products. In particular, C26 des-methyl analogues can be made using an appropriate C26 des-methyl synthon, such as 207 noted above.

The lactam analogues of the invention (wherein Z attached to C25 is NH) are obtained by converting the C25 hydroxyl group (e.g., of formula 207) to an amine under Mitsonobu conditions, after first protecting the aldehyde (and the C19 hydroxyl group in the corresponding compounds in Reaction Schemes 10 and 11) followed by formation of the macrocycle and de-protection under conditions analogous to those employed for the lactone analogues, as will be apparent to one skilled in the art. Lactam embodiments, can also be prepared by performing an aminohydroxylation reation, such as has been disclosed by Sharpless et al., instead of dihydroxylation with OsO$_4$.(employing protection/deprotection as described above). Chiral ligands for this reaction are known, and can be used to influence the stereochemical and/or regiochemical outcomes of the aminohydroxylation. This strategy can be employed on substrates in which the terminal alkene of the above scheme is further substituted, thereby providing access to compounds wherein $R^{26}$ is other than hydrogen. Such starting materials can be prepared by cleaving the olefin to the aldehyde (e.g., by OsO$_4$/periodate or ozonolysis) and performing a Wittig or other olefination reaction to obtain a desired secondary alkene.

The C26 des-methyl bryostatin homologues of the invention can be obtained by substituting homologous des-methyl starting materials for the starting materials employed in published bryostatin syntheses (e.g., Masamune 1988a, 1988b, Evans et al. 1998, Kageyama et al. 1990). For example, in the total synthesis of bryostatin 7, Serine is substituted for threonine in a Masamune's C17–C26 southern bryostatin synthesis to yield the corresponding C26 des-methyl sulfone. Other synthetic methodology will be apparent to those skilled in the art given the objective of providing such C26 des-methyl bryostatin homologues.

In certain embodiments, the fragment corresponding to the recognition domain (or C-ring portion) of bryostatin is prepared by a method that includes one or more of the steps illustrated with regard to Reaction Schemes 12 to 15, wherein:

R', $R^{20}$ and $R^{26}$ are as defined above (for example, $R^{20}$ being —$O_2$CR' or —$O_2$CNHR');

R* represents, independently for each occurrence, H or a lower alkyl group such as methyl or ethyl;

q represents 0 or 1;

E represents an aldehyde, hydroxymethyl, carboxyl group, or a protected form thereof, such as CHO, $CH_2OP$, $CH(OP)_2$, or $CO_2P$;

P represents H or a protecting group, including protecting groups wherein two occurrences of P, taken together, form a ring having 5–7 members including the atoms through which they are connected (e.g., $CH(OP)_2$ may represent a cyclic acetal, e.g., with ethylene glycol or pinacol); and G is absent or represents P.

With respect to the reactions illustrated in Reaction Schemes 13 to 15, the group identified as R' is preferably hydrogen or lower alkyl (such as methyl or ethyl).

In certain embodiments wherein P is a protecting group for a hydroxyl, P represents a trialkylsilyl, dialkylarylsilyl, benzyl, substituted benzyl, benzhydryl, substituted benzhydryl, 5-dibenzosuberyl, triphenylmethyl, substituted triarylmethyl, naphthyldiphenylmethyl, 2- or 4-picolyl, 3-methyl-2-picolyl-N-oxide, 4-(4'-bromophenacyloxyphenyl) diphenylmethyl, 4,4',4''-tris(4,5-dichlorophthalamidophenyl)methyl, 4,4',4''-tris (levulinoyloxyphenyl)methyl, 4,4',4''-tris (benzoyloxyphenyl)methyl, 9-(9-phenyl)xanthenyl, pivaloyl, adamantoyl, and 2,2,2-trichloroethylcarbonyl.

In certain embodiments wherein P is a protecting group for an acetal, P represents lower alkyl (such as methyl, ethyl, isopropyl, etc.) or, taken together with a second occurrence of P, represents a lower alkylene group (such as $CH_2CH_2$, $CH_2CMe_2CH_2$, etc.).

In certain embodiments wheren P is a protecting group for a carboxylic acid, P represents dialkylarylsilyl, benzyl, substituted benzyl, trichloroethyl, t-butyl, trimethylsilylethyl, lower alkyl, lower alkenyl (such as allyl), or other suitable protecting group.

In certain embodiments, E represents a carboxylic acid derivative that can be readily converted to an aldehyde, such as a thioester (reduction by triethylsilane in the presence of a transition-metal catalyst), CONMe(OMe) (reduction by a hydride reagent), an ester (reduction by diisobutylaluminum hydride (DIBAL-H)), etc. Other such groups and reaction conditions are well known to those of skill in the art.

The starting materials for Reaction Schemes 13 and 14 can be prepared, for example, as illustrated in Reaction Scheme 12.

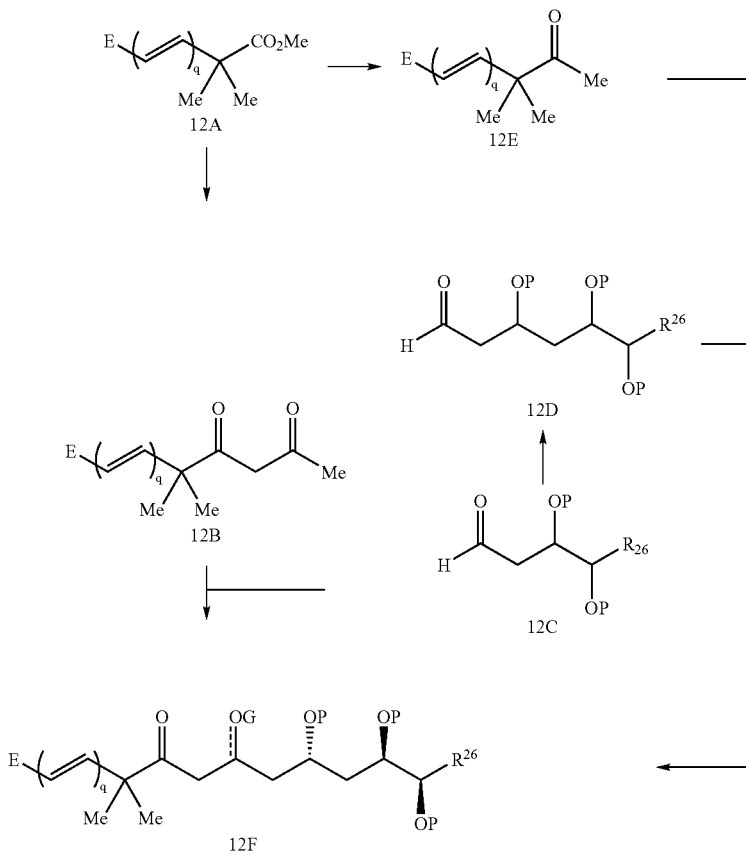

Reaction Scheme 12

In one embodiment, compound 12A can be converted to compound 12B by reaction with an acetone enolate or equivalent thereof, such as a lithium or magnesium anion of the N,N-dimethylhydrazone of acetone. Alternatively, the methyl ester of 12A can be reduced to an aldehyde (e.g., by reduction with DIBAL-H, or reduction by lithium aluminum hydride (LAH) followed by Swern oxidation), followed by aldol addition with an acetone enolate or equivalent and oxidation of the aldol product to the diketone. The dienolate of diketone 12B can then be reacted with aldehyde 12C to give aldol product 12F, which can be subsequently protected and/or reduced at the $C^{21}$ ketone selectively (e.g., with tetramethylammonium triacetoxyborohydride, with an aldehyde in the presence of a Lewis acid via an intramolecular hydride transfer, etc.).

Alternatively, ester 12A can be converted to ketone 12E, e.g., by reduction to the aldehyde, reaction with methyllithium or methyl magnesium halide, and oxidation to the ketone. Aldehyde 12C can be extended to aldehyde 12D by aldol addition of an acetaldehyde equivalent (e.g., reaction with an allylsilane, allylborane, or allyltin reagent followed by ozonolysis or dihydroxylation/periodate cleavage, reaction with a silyl ketene acetal of an acetate ester in the presence of a Lewis acid catalyst such as $TiCl_3(OiPr)$, $TiCl_2(OiPr)_2$, $SnCl_4$, or $Sn(OTf)_2$ followed by reduction to the aldehyde, reaction of an enolate of an acetate ester followed by reduction to the aldehyde, etc. For many of these reactions, chiral reagents or ligands are available that may be used to favor a desired diastereomer of the aldol product, while others may be sufficiently stereoselective without use of a chiral reagent. An enolate of ketone 12E can then be added to aldehyde 12D to arrive at aldol 12F by a different route.

Compounds wherein q is 0 can be readily converted to compounds wherein q is 1 as is described in detail above, e.g., by converting 12E to an aldehyde and performing a Horner-Emmons reaction with a phosphonoacetate reagent, performing a Peterson reaction with a trimethylsilylacetate reagent, or by other techniques known to those of skill in the art or described above.

Compounds useful in executing this strategy also include compounds represented by Formula 12G:

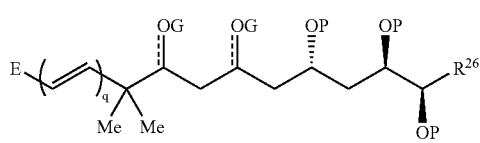

Formula 12G where, as valence and stability permit, q, E, P, G and $R^{26}$ are as defined above (with and without regard to the illustrated stereochemical relationships).

In Reaction Scheme 13 (below) Step a can be performed by treating the diketone compound 12F (produced as described in Reaction Scheme 12, where G at $C_{21}$ is absent) with acid, preferably under conditions that favor the removal of the water generated, such as distillation of the generated water (optionally as an azeotrope), addition of a dehydrating agent (such as molecular sieves, a carboxylic acid anhydride, or sodium or calcium sulfate), or other suitable means. If P on the $C_{23}$ hydroxyl represents a protecting group, the cyclization can be performed under conditions that selectively remove this protecting group, or this protecting group can be removed prior to the cyclization.

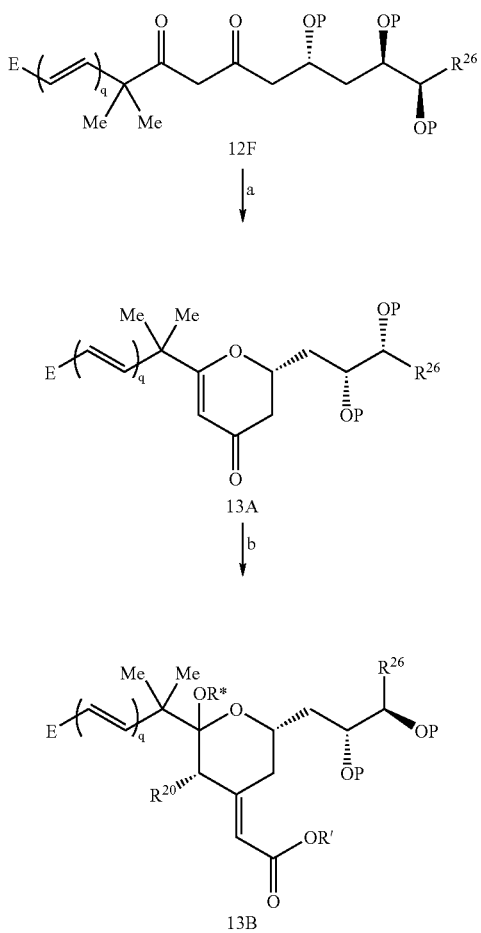

Reaction Scheme 13

Step b can be performed by a series of reactions. For example, step b may begin with reduction of the ketone 13A with a hydride source, such as lithium or sodium borohydride, lithium aluminum hydride, etc. In certain embodiments, a reduction selective for the ketone over the unsaturation is performed, such as a Luche reduction (sodium borohydride in the presence of cerium (III) chloride heptahydrate). Oxidation of the alkene can then be performed with monoperoxyphthalate hexahydrate (MMPP), by epoxidation (e.g., with mCPBA, or dimethyldioxirane), or by dihydroxylation (e.g., with osmium tetroxide, optionally with an asymmetric ligand as is well known in the art). The product of the oxidation, if performed in the presence of water, will be the hemiketal, and if performed in the presence of an alcohol, will be the corresponding mixed ketal. These and other reactions necessary to perform step b can be conducted in analogy with Wender et al., *J. Am. Chem. Soc.* 1998, 120, 4534–4535.

The present invention also encompasses the intermediate compounds useful in executing this strategy, including the compounds of Formulae 13A and 13B (with and without regard to the illustrated stereochemical relationships).

Compounds where $R^{20}$ is H can be prepared by a method including one or more steps of the following sequence:

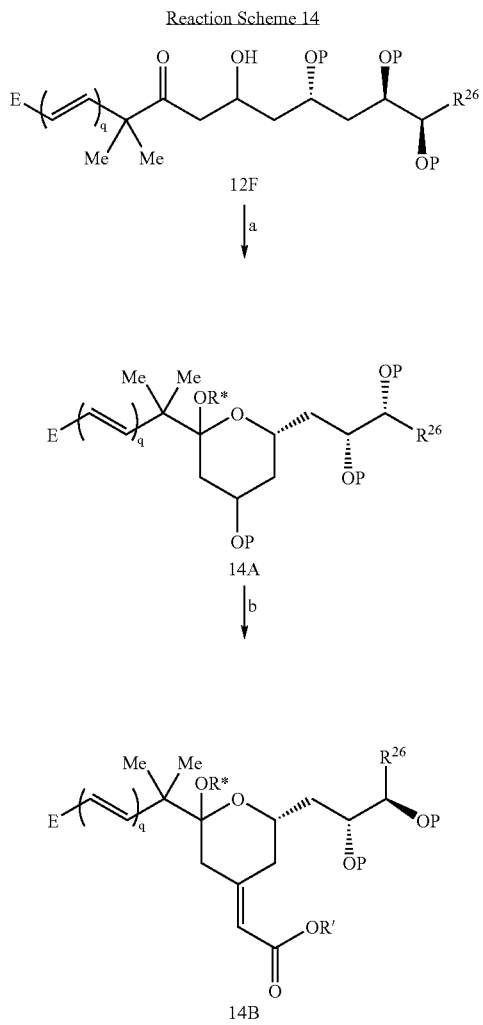

Step a can be performed starting with a compound of Formula 12F (produced as described in Reaction Scheme 12, where G at $C_{21}$ is hydrogen) by an acid-catalyzed cyclization in a reaction mixture including an alcohol HOR*, preferably as a solvent or cosolvent, in order to form the mixed ketal. If P on the C23 hydroxyl represents a protecting group, the cyclization can be performed under conditions that selectively remove this protecting group (and possibly also any protecting group at C21), or one or both of these protecting groups can be removed prior to the cyclization.

Step b can be performed by oxidation of the C21 alcohol (e.g., by Swern oxidation, Dess-Martin periodinane, etc.), after removing any protecting group at this position, followed by reaction with a reagent such as $R'O_2CCH_2SiMe_3$ or $R'O_2CCH_2PO_3Me_2$. Optionally, a chiral phosophonoacetate (e.g., a phosphonate ester of BINOL, or other chiral diols or alcohols) or phosphonamidoacetate (e.g., a phosphonate derivative of ephedrine or another chiral aminoalcohol) may be employed in order to favor the desired stereochemical outcome of the enoate installation. Subsequent steps may be performed in analogy to well known procedures as discussed above.

In embodiments wherein q is 0, extension to embodiments wherein q is 1 can be readily accomplished by reaction of a compound wherein E is an aldehyde and q is 0 with a reagent such as Li—CH=CHOEt, $ECH_2P(O)(OMe)_2$, $ECH_2SiMe_3$, etc., wherein E represents an aldehyde or ester moiety. In certain preferred embodiments, a compound wherein E is aldehyde and q is 0 is converted to a compound wherein E is aldehyde and q is 1 by treatment with a preparation of a 2-alkoxyvinyllithium (such as 2-ethoxyvinyllithium) and a dialkylzinc (such as dimethylzinc), followed by treatment with acid, such as HCl, to convert the beta-hydroxyenol ether adduct to the unsaturated aldehyde, as is described in greater detail below. Other suitable reagents will be well known to those of skill in the art.

The present invention also encompasses the intermediate compounds useful in executing this strategy, including the compounds of Formulae 14A and 14B (with and without regard to the illustrated stereochemical relationships).

Alternatively, the C-ring fragment analog for compounds where $R^{26}$ is H can be prepared as illustrated in Reaction Scheme 15.

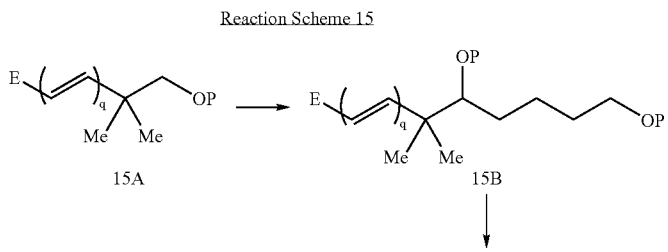

-continued

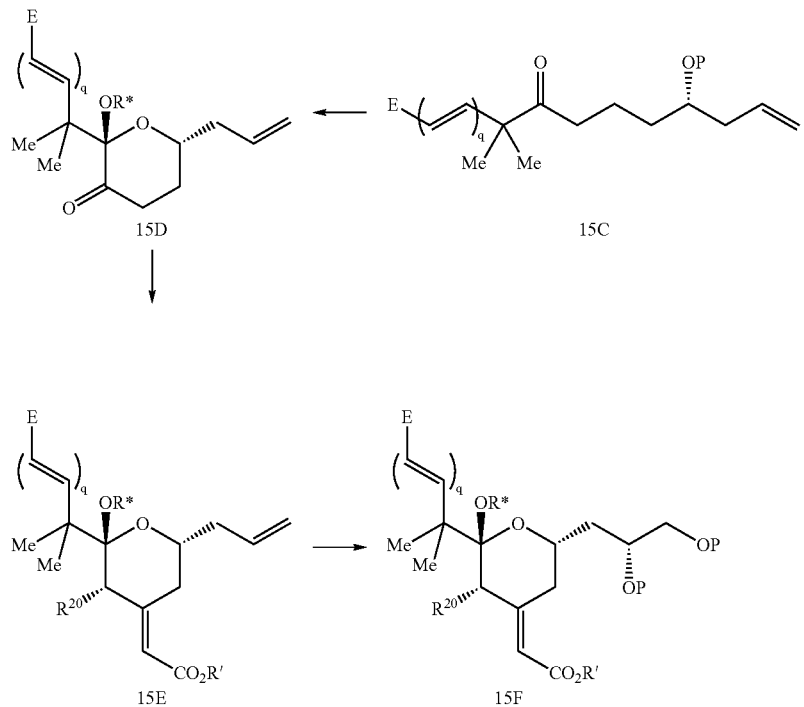

In this scheme, alcohol 15A can be oxidized to an aldehyde (e.g., by Swern or TPAP/NMO oxidation), followed by addition of a Grignard or lithium reagent derived from a 4-halo-1-butanol, such as 4-chloro- or 4-bromo-1-butanol. Both alcohols of 15B can then be oxidized (e.g., by Swern or TPAP/NMO oxidation), followed by selective addition of an allyl group to the aldehyde (e.g., by treatment with an allylstannane or allylsilane in the presence of a Lewis acid catalyst, optionally in the presence of a chiral ligand for the Lewis acid, such as BINOL, Ti(OPr)$_4$, and B(OMe)$_3$ together) to give ketoalcohol 15C. Cyclization and elaboration of this piece can be performed in analogy with the scheme presented above, for example, by cyclizing in the presence of an acid under dehydrating conditions, followed by oxidation of the enol ether with magnesium monoperoxyphthalate hexahydrate (MMPP), and oxidation of the resulting alcohol (e.g., by Swern or TPAP/NMO oxidation) to give ketone 15D. The exocyclic enoate can then be installed by an aldol condensation with methyl glyoxylate, e.g., by forming the lithium anion of ketone 15D with lithium diusopropylamide (LDA) under anhydrous conditions, or in an alcoholic solvent (such as methanol) in the presence of a base (such as sodium, potassium, or cesium carbonate). The terminal alkene can then be oxidized to the diol (e.g., by OSO$_4$ or certain hypervalent iodine reagents), optionally in the presence of a chiral ligand, as is well known in the art. Embodiments wherein q is 0 can be converted to embodiments wherein q is 1 as described in detail above.

The present invention also encompasses the intermediate compounds useful in executing this strategy, including the compounds of Formulae 15C, 15D, 15E and 15F (with and without regard to the illustrated stereochemical relationships).

In certain embodiments, a fragment analogous to the A and B rings of bryostatin can be prepared for incorporation into an analog of the present invention by a method including the steps illustrated in Reaction Scheme 16, where the substituents R*, R$^7$ and P are as defined above:

Reaction Scheme 16

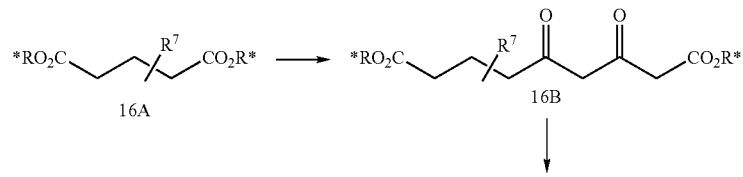

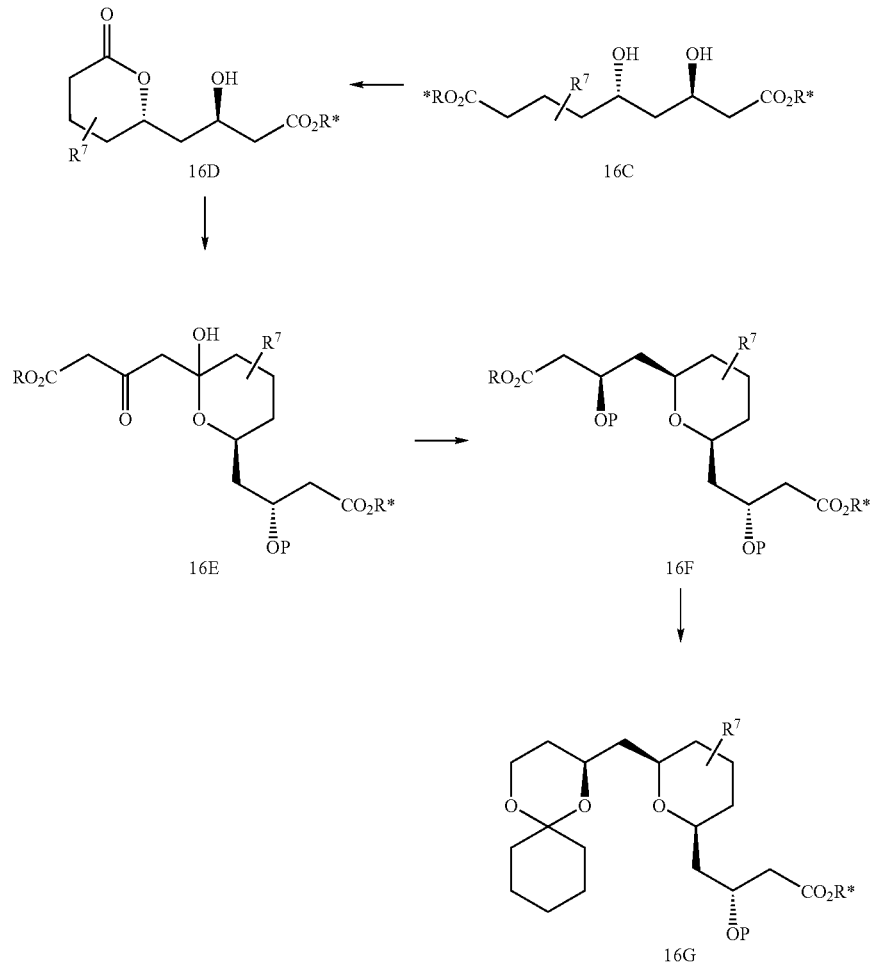

Thus, a glutaric diester 16A can be condensed with a dienolate of an acetoacetate ester to provide diketoester 16B, followed by reduction of the two ketones to give diol 16C. One ketone can be reduced by a Noyori hydrogenation in the presence of a chiral catalyst to impart a first asymmetric center, and the second can be reduced stereoselectively using the newly formed stereocenter (tetramethylammonium triacetoxyborohydride for anti, $Et_2BOMe$ and $NaBH_4$ for syn, for example). Acid-catalyzed lactonization followed by protection of the remaining alcohol to give lactone 16D provides a substrate for a second reaction with a dienolate of an acetoacetate ester to give ketoester 16E. Acid-catalyzed reduction of the hemiketal with triethylsilane, or dehydration of the hemiketal followed by hydrogenation, generates the tetrahydropyran of the A-ring analog. The remaining ketone can be reduced using a Noyori hydrogenation for a second time, or by hydride reduction in the presence of a chelating Lewis acid to take advantage of the tetrahydropyran stereochemistry, thereby producing alcohol 16F. Optionally, the terminal 1,3-diol can be converted to a ketal 16G in the presence of acid and a ketone, ketal, or enol ether.

The present invention also encompasses the intermediate compounds useful in executing this strategy, including the compounds of Formulae 16F, 16F and 16G (with and without regard to the illustrated stereochemical relationships). Compounds useful in executing this strategy also include compounds represented by Formulae 16H, 16I and 16J:

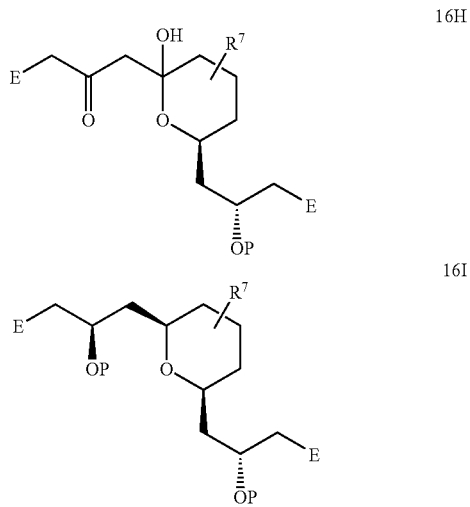

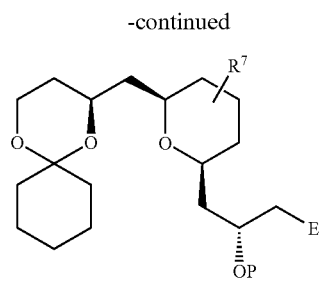

Preferred Processes and Last Steps

A C19,C26 hydroxyl-protected, C26 des-methyl bryostatin recognition domaine precursor and an optionally protected linker synthon are esterified, macrotransacetylated and de-protected to give the corresponding C26 des-methyl bryostatin analogue.

A bryostatin analogue precursor having the C26 hydroxyl substituted by a protecting group (particularly OBn) is reduced to give the corresponding compound of Formula I.

Serine is substituted for threonine in a Masamune's C17–C26 southern bryostatin synthesis to yield the corresponding C26 des-methyl sulfone, which in turn is employed in synthesis of a C26 des-methyl bryostatin homologue.

A pyran-4-ol of Formula 404 is converted to the corresponding pyran-2-yl-acetaldehyde of Formula 405 under reaction conditions including the presence of isobutylvinyl ether and Hg(II) diacetate. The reaction conditions further include carrying the crude vinylated pyran forward without delay, contacting it with anhydrous decane.

A diketone of Formula 12F is converted to the corresponding dihydropyranone of Formula 13A under reaction conditions including the presence of an acid, particularly where $R^{26}$ represents H or $C_1$ to $C_6$ alkyl. The reaction conditions can further include means for removing water.

A ketone of Formula 12F is converted to a tetrahydropyran of Formula 14A under reaction conditions including the presence of an acid and an alcohol (R*OH), particularly where $R^{26}$ represents H or $C_1$ to $C_6$ alkyl. The alcohol can be present as a solvent or cosolvent making up at least 20% of total solvent.

A ketone of Formula 15C is converted to the corresponding dihydropyranone of Formula 15D under reaction conditions including the presence of an acid. The reaction conditions can further include means for removing water.

A ketone of Formula 15D is converted to the corresponding ketoenoate of Formula 15E under reaction conditions including the presence of an alkyl glutarate ester.

An optionally protected lactone of Formula 16E is contacted with a dienolate of an ester of acetoacetate under conditions that provide the corresponding tetrahydropyran of Formula 16F.

A compound of Formula I–VI is contacted with a pharmaceutically acceptable acid to form the corresponding acid addition salt.

A pharmaceutically acceptable acid addition salt of Formula I–VI is contacted with a base to form the corresponding compound of Formula I–VI.

Also preferred is a stereospecific synthesis for preparing a bryostatin analog, having a step selected from the group:

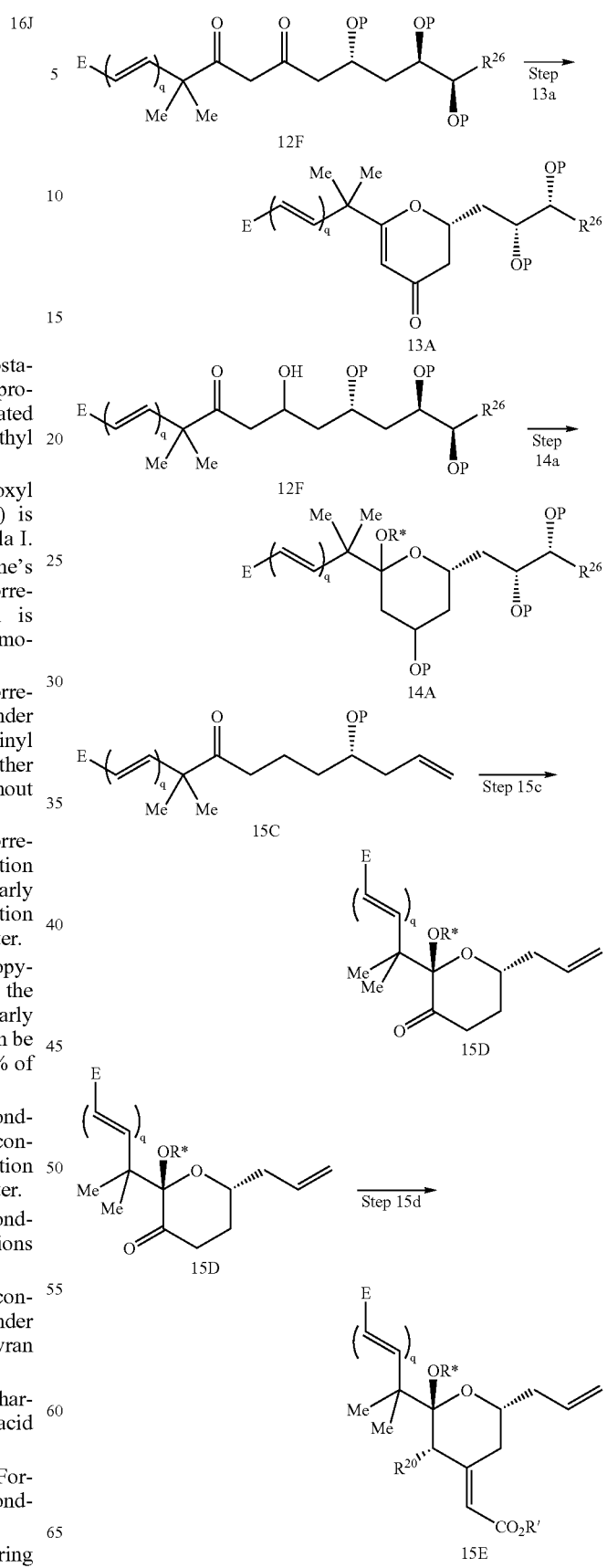

-continued

16D

16E particularly where the starting material for Step 13a, 14a, 15c, 15d or 16d has one or more of the stereochemical configurations represented by formulae 12F, 12F, 15C, 15D or 16D, respectively, and especially where:

$R^7$ is absent;
$R^{20}$ is $R^{20}$ is H, OH, —$O_2$C-lower alkyl or —$O_2$C-alkenyl;
$R^{26}$ is H or OH;
R' is independently selected from: H and methyl;
R* is independently selected from: H and methyl;
q is 1;
E is OPMB, TBSO—$CH_2$— or —C(O)H; and/or
P is H, benzyl, OPMB or TBSO.

Further preferred are those processes where:
Step 13a takes place under reaction conditions including the presence of an acid;
Step 14a takes place under reaction conditions including the presence of an acid and an alcohol of the formula R*—OH, where R* is lower alkyl;
Step 15c takes place under reaction conditions including the presence of an acid;
Step 15d takes place under reaction conditions including the presence of an alkyl glutarate ester; and/or
Step 16d takes place under reaction conditions including the presence of a dienolate of an ester of acetoacetate.

Preferred Compounds

The following substituents, compounds and groups of compounds are presently preferred.

In the compounds of Formulae I–V, especially those of Formulae II–V, it is preferred that $R^{26}$ is H. Most preferred are the compounds of Formula II where $R^{26}$ is H, and of those where X is oxygen. Of the compounds where $R^{26}$ is H, additionally preferred are those compounds where $R^{20}$ is $O_2CR'$, especially where R' is alkyl (preferably about $C_7$–$C_{20}$ alkyl), alkenyl (preferably about $C_7$–$C_{20}$ alkenyl such as $CH_3$—$CH_2$—$CH_2$—CH=CH—CH=CH—) or aryl (preferably phenyl or naphthyl). Another group of preferred compounds where $R^{26}$ is H are those where $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl). Further preferred are those compounds where $R^3$ is OH.

The compounds of Formulae I–V, especially II–V, are preferred where $R^{20}$ is $O_2CR'$ and R' is alkyl (preferably about $C_7$–$C_{20}$ alkyl), alkenyl (preferably about $C_7$–$C_{20}$ alkenyl such as $CH_3$—$CH_2$—$CH_2$—CH=CH—CH=CH—) or aryl (preferably phenyl or naphthyl). Particularly preferred are those compounds where $R^{20}$ is $O_2CR'$ and $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl). Further preferred are the compounds where $R^3$ is OH, $R^{26}$ is H and/or Z is —O—.

The compounds of Formulae I–V, especially II–V, are preferred where $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl). Further preferred are the compounds where $R^3$ is OH, $R^{26}$ is H and/or Z is —O—.

Of the compounds according to Formula I, it is preferred that L be a group having from about 6 to about 14 carbon atoms. Also preferred are those compounds where distance "d" (in Formula Ia) is about 2.5 to 5.0 angstroms, preferably about 3.5 to 4.5 angstroms and most preferably about 4.0 angstroms, such as about 3.92 angstroms. Further preferred are those compounds where L contains a hydroxyl on the carbon atom corresponding to C3 in the native bryostatin structure.

Of the compounds according to Formulae II or III, it is preferred that X is oxygen. Further preferred are the compounds where $R^3$ is OH, $R^{26}$ is H and/or Z is —O—.

Of the compounds according to Formulae II–IV, it is preferred that $R^3$ is OH, and especially preferred that X is oxygen in the case of Formulae II and III. Further preferred are the compounds where $R^{26}$ is H and/or Z is —O—.

Of the compounds according to Formula II, it is preferred that $R^{20}$ is $O_2CR'$ where R' is alkyl (preferably about $C_7$–$C_{20}$ alkyl), alkenyl (preferably about $C_7$–$C_{20}$ alkenyl such as $CH_3$—$CH_2$—$CH_2$—CH=CH—CH=CH—) or aryl (preferably phenyl or naphthyl). Of these, further preferred are the compounds where $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl). Also preferred are those compounds where $R^3$ is OH, $R^{26}$ is H and/or Z is —O—.

Of the compounds according to Formula III, it is preferred that $R^9$ is H. It is further preferred that $R^8$ is H, alkyl (especially t-butyl), aralkyl, —$CH_2(CH_3)_2$—$CH_2$—O—R [particularly where R is $COCH_2Cl$, COt-Bu, 2,4,6-trichlorobenzoate, or myristate] or —$(CH_2)_nO(O)CR'$ [particularly where R' is alkyl], $R^6$ optionally being =O. Further preferred are those compounds where $R^3$ is OH, $R^{26}$ is H and/or Z is —O—.

The compounds according to Formula 12G, particularly where $R^{26}$ is H or $C_1$–$C_6$ alkyl.

The compounds according to Formula 13A, particularly where $R^{26}$ is H or $C_1$–$C_6$ alkyl.

The compounds according to Formula 13B, particularly where $R^{26}$ is H or $C_1$–$C_6$ alkyl.

The compounds according to Formulae 15C, 15D and/or 15E.

The compounds according to Formula 15F where q is zero.

The compounds according to Formulae 16H, 16I and/or 16J, particularly where $R^7$ is absent.

The compounds acording to Formulae 204, 207, 304 (and the C26-desmethyl homologue of 304), and 502.

The compounds according to Formula 705, particularly where $R^{26}$ is H and/or where $R^8$ and $R^9$ are H.

Further preferred are those compounds that combine various of the above-mentioned features. The single isomers highlighted in the reaction schemes and examples are also preferred.

Also preferred (individually, collectively and in any combination) are the compounds having the structures represented by the following formulae:

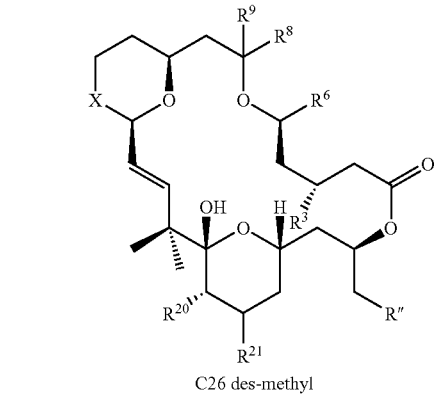
705
C26 des-methyl

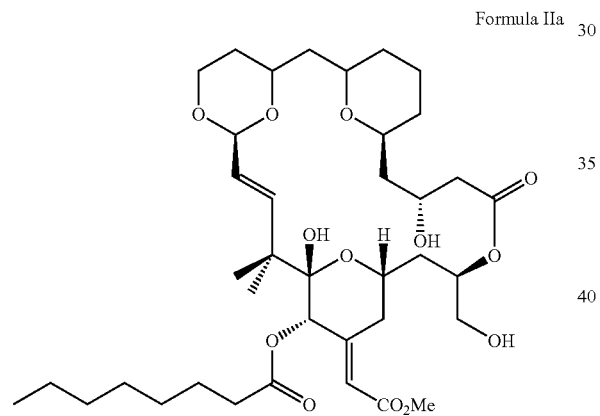
Formula IIa
1998a

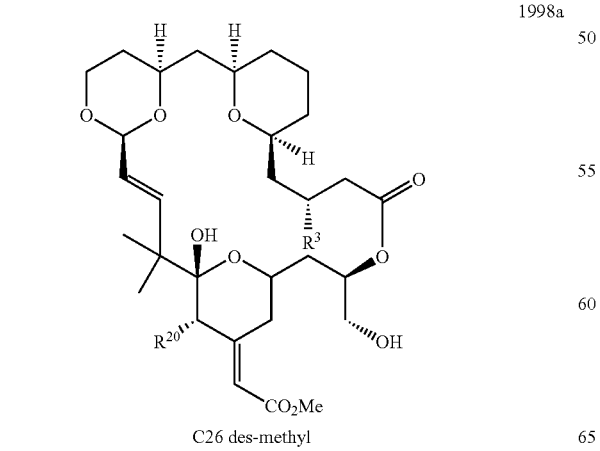
C26 des-methyl

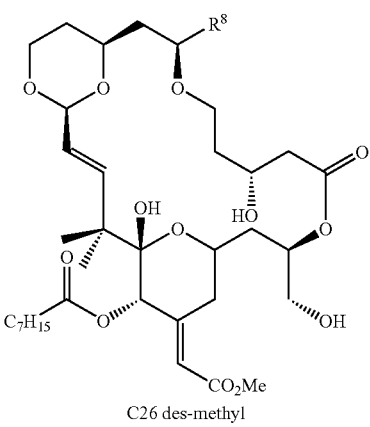
1998b
C26 des-methyl

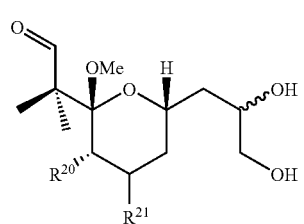
Formula 204

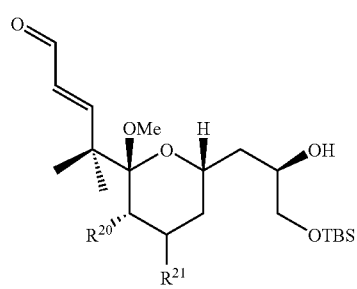
Formula 207

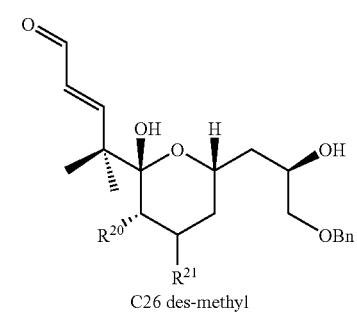
304
C26 des-methyl

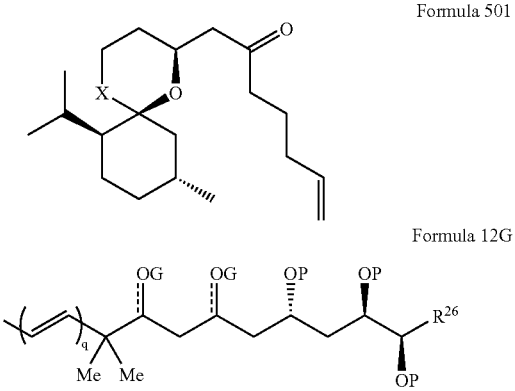
Formula 501
Formula 12G

-continued

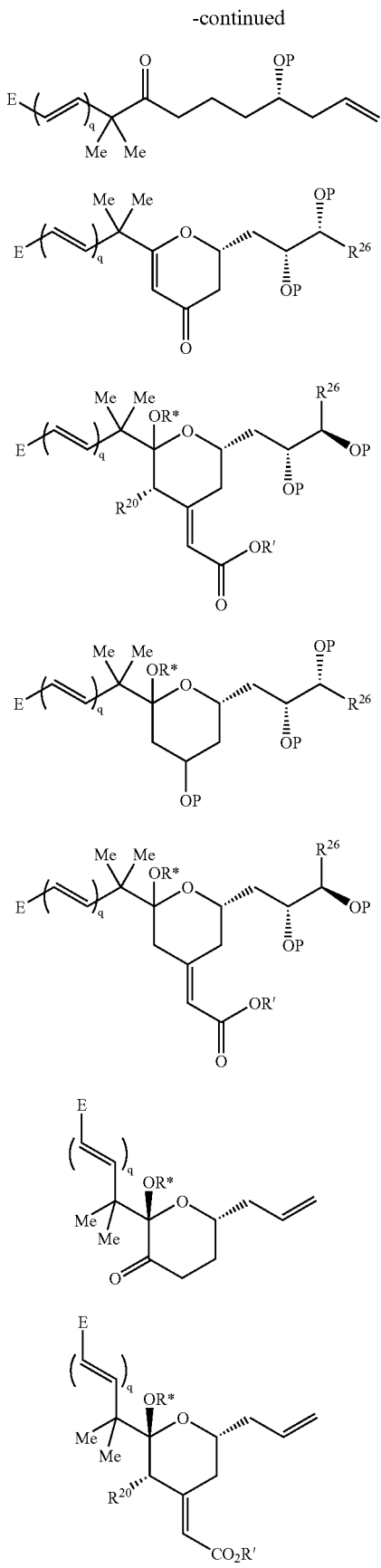

Formula 15C

Formula 13A

Formula 13B

Formula 14A

Formula 14B

Formula 15D

Formula 15E

-continued

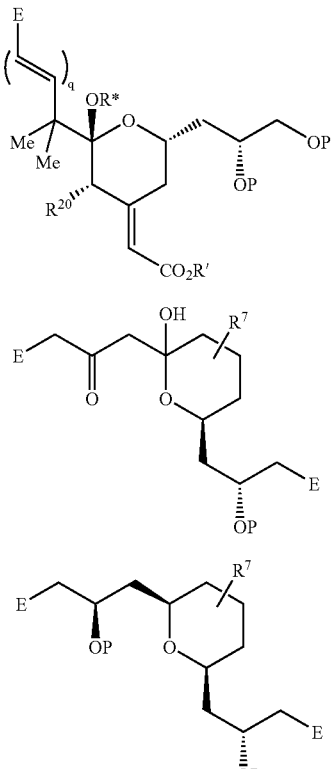

Formula 15F

Formula 16H

Formula 16I

Formula 16J

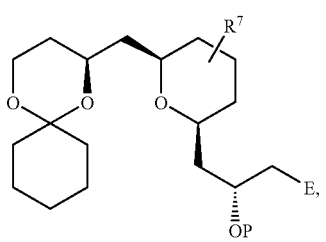

particularly those compounds having one or more of the illustrated stereochemical configurations. Similarly preferred are the synthetic processes leading to the above compounds and carrying those that are intermediates forward.

Presently, most preferred is the compound of Formula II where X is oxygen, $R^3$ is OH, $R^{20}$ is —O—CO—$C_7H_{15}$, $R^{21}$ is =CH—$CO_2$Me and $R^{26}$ is H.

Utility, Testing and Administration

General Utility

The compounds of the present invention are useful as bryostatin-like therapeutic agents, and in pharmaceutical formulations and methods of treatment employing the same. Other compounds of the invention are useful a precursors in the synthesis of such agents. Importantly, in many cases, the compounds of the present invention can be readily synthesized on a large scale, and thus can be made readily available for commercial purposes as compared to the low yields and environmental problems inherent in the isolation of bryostatins from natural sources.

In one aspect, the compounds of the invention find use as anticancer agents in mammalian subjects. For example, representative cancer conditions and cell types against which the compounds of the invention may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer. The compounds appear to operate by a mechanism distinct from the mechanisms of other anticancer compounds, and thus can be used synergistically in combination with other anticancer drugs and therapies to treat cancers via a multimechanistic approach. The compounds of the invention exhibit potencies comparable to or better than previous bryostatins against many human cancer types.

In another aspect, the compounds of the invention can be used to strengthen the immune system of a mammalian subject, wherein a compound of the invention is administered to the subject in an amount effective to increase one or more components of the immune system. For example, strengthening of the immune system can be evidenced by increased levels of T cells, antibody-producing cells, tumor necrosis factors, interleukins, interferons, and the like. Effective dosages may be comparable to those for anticancer uses, and can be optimized with the aid of various immune response assay protocols such as are known in the art (e.g., see Kraft, 1996; Lind, 1993; and U.S. Pat. No. 5,358,711, which is incorporated herein by reference). The compound can be administered prophylactically, e.g., for subjects who are about to undergo anticancer therapies, as well as therapeutically, e.g., for subjects suffering from microbial infection, burn victims, subjects with diabetes, anemia, radiation treatment, or anticancer chemotherapy. The immunostimulatory activity of the compounds of the present invention is unusual among anticancer compounds and provides a dual benefit for anticancer applications. First, the immunostimulatory activity allows the compounds of the invention to be used in greater doses and for longer periods of time than would be possible for compounds of similar anticancer activity but lacking immunostimulatory activity. Second, the compounds of the present invention can offset the immunosuppressive effects of other drugs or treatment regimens when used in combination therapies. Additional features of the invention can be further understood from the following illustrative examples which are not intended to limit the scope of the invention in any way.

Testing

In practicing various aspects of the present invention, compounds in accordance with the invention can be tested for a biological activity of interest using any assay protocol that is predictive of activity in vivo. For example, a variety of convenient assay protocols are available that are generally predictive of anticancer activity in vivo.

In one approach, anticancer activity of compounds of the invention can be assessed using the protein kinase C assay detailed in Example 5. In this assay, $K_i$ values are determined for analogues based on competition with radiolabeled phorbol 12,13-dibutyrate for binding to a mixture of PKC isoenzymes. PKC enzymes are implicated in a variety of cellular responses which may be involved in the activity of the bryostatins.

Example 6 describes another protein kinase C assay which can be used to assess the binding affinities of compounds of the invention for binding to the C1B domain of PKCδ. Although all PKC isozymes are upregulated immediately after administration of bryostatin or tumor promoting phorbol esters followed by an extended down-regulation period, PKCδ appears to be protected against down regulation by bryostatin 1. Overexpression of PKCδ inhibits tumor cell growth and induces cellular apoptosis, whereas depleting cells of PKCδ can cause tumor promotion. Accordingly, this assay provides useful binding data for assessing potential anticancer activity.

Another useful method for assessing anticancer activities of compounds of the invention involves the multiple-human cancer cell line screening assays run by the National Cancer Institute (e.g., Boyd, 1989). This screening panel, which involves approximately 60 different human cancer cell lines, is a useful indicator of in vivo antitumor activity for a broad variety of tumor types (Grever et al., 1992, Monks et al., 1991), such as leukemia, non-small cell lung, colon, central nervous system (CNS), melanoma, ovarian, renal, prostate, and breast cancers. Antitumor activities can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values. Example 7 describes a P388 murine lymphocytic leukemia cell assay which measures the ability of compounds of the invention to inhibit cellular growth.

Upon the confirmation of a compounds potential activity in the above in vitro assays, further evaluation is typically conducted in vivo in laboratory animals, for example, measuring reduction of lung nodule metastases in mice with B16 melanoma (e.g., Schuchter et al, 1991). The efficacy of drug combination chemotherapy can be evaluated, for example, using the human B-CLL xenograft model in mice (e.g., Mohammad et al, 1996). Ultimately, the safety and efficacy of compounds of the invention are evaluated in human clinical trials.

Experiments conducted in support of the present invention demonstrate that compounds of the present invention exhibit high potencies in several anticancer assays, as summarized in the Examples.

Administration

The invention includes a method of inhibiting growth, or proliferation, of a cancer cell, or enhancing the effectiveness of other drugs. In the method, a cancer cell is contacted with a bryostatin analogue compound in accordance with the invention in an amount effective to inhibit growth or proliferation of the cell. In a broader aspect, the invention includes a method of treating cancer in a mammalian subject, especially humans. In the method, a bryostatin analogue compound in accordance with the invention is administered to the subject in an amount effective to inhibit growth of the cancer in the patient. Similarly, in the immune modulation methods of the invention, a compound of the invention is administered to a subject in need thereof, in an amount herapeutically effective for bolstering of the immune system predisposed toward apoptosis Compositions and methods of the present invention have particular utility in the area of human and veterinary therapeutics. Generally, administered dosages will be effective to deliver picomolar to micromolar concentrations of the therapeutic composition to the target site. Typically, nanomolar to micromolar concentration at the target site should be adequate for many applications. Appropriate dosages and concentrations will depend on factors such as the particular compound or compounds being administered, the site of intended delivery, and the route of administration, all of which can be derived empirically according to methods well known in the art.

Administration of compounds of the invention in an appropriate pharmaceutical form can be carried out by any appropriate mode of administration. Thus, administration can be, for example, intravenous, topical, subcutaneous, transocular transcutaneous, intramuscular, oral, intra-joint, parenteral, peritoneal, intranasal, or by inhalation. The formulations may take the form of solid, semi-solid, lyophilized powder, or liquid dosage forms, such as, for example, tablets, pills, capsules, powders, sustained-release formulations, solutions, suspensions, emulsions, suppositories, retention enemas, creams, ointments, lotions, aerosols, and the like. In one embodiment, the formulation has a unit dosage form suitable for administration of a precise dose.

Pharmaceutical compositions of the invention typically include a conventional pharmaceutical carrier or excipient and may additionally include other medicinal agents, carriers, adjuvants, antioxidants, and the like. In one embodiment, the composition may comprise from about 1% to about 75% by weight of one or more compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, for example. Appropriate excipients can be tailored to the particular composition and route of administration by methods well known in the art, e.g., (Gennaro, 1990). Additional guidance for formulations and methods of administration can be found in patent references concerning previously known bryostatins, such as U.S. Pat. Nos. 4,560,774 and 4,611,066 to Pettit et al., which are incorporated herein by reference.

Usually, for oral administration, the compositions will take the form of a pill, tablet or capsule. Thus the composition will contain, along with active drug, a diluent such as lactose, sucrose, dicalcium phosphate, and/or other material, a disintegrant such as starch or derivatives thereof; a lubricant such as magnesium stearate and the like; and a binder such a starch, gum acacia, polyvinylpyrrolidone, gelatin, cellulose and/or derivatives thereof.

The compounds of the invention may also be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (e.g., from about 0.5% to about 20% of final volume), and optional pharmaceutical adjuvants in a carrier, such as, for example, aqueous saline, aqueous dextrose, glycerol, ethanol and the like, to form a solution or suspension. Useful vehicles also include polyoxyethylene sorbitan fatty acid monoesters, such as TWEEN™ 80, and polyethoxylated castor oils, such as Cremophor EL™ available from BASF (Wyandotte, Md.), as discussed in PCT Publ. No. WO 97/23208, which can be diluted into conventional saline solutions for intravenous administration. Such liquid compositions are useful for intravenous administration. One such formulation is PET diluent which is a 60/30/10 v/v/v mixture of PEG 400, dehydrated ethanol, and TWEEN™-80. Liquid compositions may also be formulated as retention enemas.

The compounds of the invention may also be formulated as liposomes using liposome preparation methods known in the art. Preferably, the liposomes are formulated either as small unilamellar vesicles or as larger vesicles.

If desired, the composition to be administered may also contain minor amounts of non-toxic auxiliary substances such as wetting or emulsifying agents, pH buffering agents, such as, for example, sodium acetate, sorbitan monolaurate, triethanolamine oleate, and antioxidants.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Gennaro (1990). The composition to be administered will, in any event, contain a quantity of one or more compounds of the invention in a pharmaceutically effective amount for relief of the condition being treated.

The compounds of the invention may also be introduced in a controlled-release form, for long-term delivery of drug to a selected site over a period of several days or weeks. In this case, the compound of the invention is incorporated into an implantation device or matrix for delayed or controlled release from the device.

The compounds can be incorporated in a biodegradable material, such as a biodegradable molded article or sponge. Exemplary biodegradable materials include matrices of collagen, polylactic acid-polyglycolic acid, and the like. In preparing bryostatin compounds in matrix form, the compounds may be mixed with matrix precursor, which is then crosslinked by covalent or non-covalent means to form the desired matrix. Alternatively, the compound can be diffused into a preformed matrix. Examples of suitable materials for use as polymeric delivery systems have been described e.g., Aprahamian, 1986; Emmanuel, 1987; Friendenstein, 1982; and Uchida, 1987.

Generally, compounds of the invention are administered in a therapeutically effective amount, i.e., a dosage sufficient to effect treatment, which may vary depending on the individual and condition being treated. Typically, a therapeutically effective daily dose is from 0.1 µg/kg to 100 mg/kg of body weight per day of drug. Given the high therapeutic activities of the compounds of the invention, daily dosages of from about 1 µg/kg and about 1 mg/kg of body weight may be adequate, although dosages greater than or less than this range can also be used.

It will be appreciated that the compounds of the invention may be administered in combination (i.e., together in the same formulation or in separate formulations administered by the same or different routes) with any other anti-cancer regimen deemed appropriate for the patient. For example, the compounds of the invention may be used in combination with other anticancer drugs such as vincristine, cisplatin, ara-C, taxanes, edatrexate, L-buthionine sulfoxide, tiazofurin, gallium nitrate, doxorubicin, etoposide, podophyllotoxins, cyclophosphamide, camptothecins, dolastatin, and auristatin-PE, for example, and may also be used in combination with radiation therapy. In a preferred embodiment, the combination therapy entails co-administration of an agent selected from: ara-C, taxol, cisplatin and vincristine.

EXAMPLES

General Techniques. Unless noted otherwise, materials were obtained from commercially available sources and used without further purification. Tetrahydrofuran (THF) and diethyl ether ($Et_2O$) were distilled from sodium benzophenone ketyl under a nitrogen atmosphere. Benzene, dichloromethane (CH$_2$Cl$_2$), acetonitrile (CH$_3$CN), triethylamine (Et$_3$N) and pyridine were distilled from calcium hydride under a nitrogen atmosphere. Chloroform (CHCl$_3$), carbon tetrachloride (CCl$_4$) and deuterated NMR solvents were dried over 1/16" bead 4 Å molecular sieves.

All operations involving moisture-sensitive materials were conducted in oven- and/or flame-dried glassware under an atmosphere of anhydrous nitrogen. Hygroscopic solvents and liquid reagents were transferred using dry Gastight™ syringes or cannulating needles. In cases where rigorous exclusion of dissolved oxygen was required, solvents were degassed via consecutive freeze, pump, thaw cycles or inert gas purge.

Nuclear magnetic resonance (NMR) spectra were recorded on either a Varian UNITY INOVA-500, XL-400 or Gemini-300 magnetic resonance spectrometer. $^1$H chemical shifts are given in parts per million (δ) downfield from tetramethylsilane (TMS) using the residual solvent signal (CHCl$_3$=δ 7.27, benzene=δ 7.15, acetone=δ 2.04) as internal standard. Proton ($^1$H) NMR information is tabulated in the following format: number of protons, multiplicity (s, singlet; d, doublet; t, triplet; q, quartet; sept, septet, m, multiplet), coupling constant(s) (J) in hertz and, in cases where mixtures are present, assignment as the major or minor isomer, if possible. The prefix app is occasionally applied in cases where the true signal multiplicity was unresolved and br indicates the signal in question was broadened. Proton decoupled $^{13}$C NMR spectra are reported in ppm (δ) relative to residual CHCl$_3$ (δ 77.25) unless noted otherwise.

Infrared spectra were recorded on a Perkin-Elmer 1600 series FTIR using samples prepared as thin films between salt plates. High-resolution mass spectra (HRMS) were recorded at the NIH regional mass spectrometry facility at the University of California, San Francisco. Fast Atom Bombardment (FAB) high-resolution mass spectra were recorded at the University of California, Riverside. Combustion analyses were performed by Desert Analytics, Tucson, Ariz., 85719 and optical rotations were measured on a Jasco DIP-1000 digital polarimeter.

Flash chromatography was performed using E. Merck silica gel 60 (240–400 mesh) according to the protocol of Still et al. (1978). Thin layer chromatography was performed using precoated plates purchased from E. Merck (silica gel 60 PF254, 0.25 mm) that were visualized using either a p-anisaldehyde or Ce(IV) stain.

For binding and cell-inhibition studies, dilutions of bryostatin and bryostatin analogues were performed in glass rather than plastic, to avoid problems associated with adsorption to plastic.

Example 1

Exemplary Precursors

1A. Protected Diol Aldehyde 102

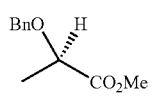

Benzyl bromide (7.0 mL, 57.7 mmol) and freshly prepared Ag$_2$O (11.0 g, 48.1 mmol) were added successively to an Et$_2$O (150 mL) solution of R-(+)-methyl lactate (5.0 g, 48.1 mmol) at rt (room temperature). The resulting suspension was brought to reflux and stirred for 2 h. The reaction was cooled to rt, filtered through a pad of Celite™ and concentrated in vacuo. Chromatography on silica gel (10% EtOAc/hexanes) afforded 7.5 g (80%) of benzyl ether A1 as a colorless oil:

A1: R$_f$ (15% EtOAc/hexanes)=0.66; IR 2988, 2952, 2874, 1750, 1497, 1454, 1372, 1275, 1207, 1143, 1066, 1025, 739, 698 cm$^{-1}$; $^1$H NMR (300 MHz, CDCl$_3$) δ 1.44 (3H, d, J=6.8 Hz, C27), 3.75 (3H, S, CH$_3$O), 4.07 (1H, q, J=6.8 Hz, C26), 4.45 (1H, d, J=11.7 Hz, CH$_2$Ph), 4.69 (1H, d, J=11.7 Hz, CH$_2$Ph), 7.28–7.37 (5H, m, Ph); $^{13}$C NMR (75 MHz, CDCl$_3$) δ 18.6, 51.8, 71.9, 73.9, 127.7, 127.8, 128.3, 137.4, 173.6; HRMS Calcd for C$_{11}$H$_{14}$O$_3$ (M$^+$): 194.0943. Found: 194.0942.

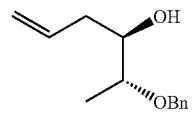

To a solution of methyl ester A1 (6.3 g, 32.3 mmol) in Et$_2$O (150 mL) was added DIBAL-H (1.0M in hexanes, 38.75 mL) dropwise at −78° C. via cannulating needle. After 5 min at −78° C., the reaction was quenched with H$_2$O and gradually warmed to rt. The resultant thick emulsion was filtered through a pad of Celite™ and sand, rinsing thoroughly with Et$_2$O and EtOAc. The organic phase was washed with NaHCO$_3$ (2×), dried over MgSO$_4$ and concentrated in vacuo to afford crude aldehyde A2 (not shown) as a light yellow liquid.

To a solution of SnCl$_4$ (1.0M in CH$_2$Cl$_2$, 32.3 mmol) in CH$_2$Cl$_2$ (120 mL) was slowly added a CH$_2$Cl$_2$ solution of aldehyde A2 at −78° C. The mixture was stirred for an additional 10 min before allyltrimethylsilane (5.65 mL, 35.53 mmol) was added via syringe. The ensuing white suspension was kept at −78° C. for 10 min, quenched by addition of H$_2$O and allowed to warm to rt. The aqueous layer was extracted with Et$_2$O and the combined organics were dried over MgSO$_4$ and concentrated in vacuo. Chromatography on silica gel (10% EtOAc/hexanes) afforded 4.87 g (76%) of desired diastereomer A3 plus 300 mg (5%) of a putative mixture.

A3: R$_f$ (15% EtOAc/hexanes)=0.44; IR (film) 3454, 3066, 3030, 2976, 2871, 1641, 1497, 1554, 1375, 1071, 1028, 992, 914, 737, 698 cm$^{-1}$; $^1$H NMR (300 MHz, CDCl$_3$) δ 1.20 (3H, d, J=6.2 Hz, C27), 2.22 (1H, m, C24), 2.35 (1H, m, C24), 2.56 (1H, br s, OH), 3.45 (1H, m, C25), 4.25 (1H, m, C26), 4.44 (1H, d, J=11.5 Hz, CH$_2$Ph), 4.66 (1H, d, J=11.5 Hz, CH$_2$Ph), 5.10 (2H, m, CH$_2$=CH), 5.87 (1H, m, CH$_2$=CH), 7.28–7.35 (5H, m, Ph); $^{13}$C-NMR (75 MHz, CDCl$_3$) δ 15.3, 37.4, 70.9, 74.1, 77.3, 117.03, 127.6, 127.7, 128.3, 134.7, 138.2; HRMS Calcd for C$_{13}$H$_{18}$O$_2$ (M$^+$): 206.1307. Found: 206.1313.

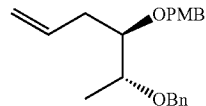

To a suspension of potassium tert-butoxide (4.0 g, 35.7 mmol) in 120 mL anhydrous THF was added a solution of alcohol A3 (in 30 mL of THF) slowly over 15 min at 0° C. When complete, the mixture was stirred at rt for 45 min and then warmed to 60° C. for an additional 30 min. p-Methoxybenzylchloride (3.56 mL, 26 mmol) was added and the mixture was stirred at 60° C. for 4 h. The reaction was cooled to rt and quenched with sat. NH$_4$Cl. The aqueous layer was extracted with Et$_2$O (3×) and the combined organics were dried over MgSO$_4$ and concentrated in vacuo. The crude product was purified by flash chromatography (5% EtOAc/hexanes) to provide 6.80 g (88%) of differentially protected diol A4 as a colorless oil.

A4: R$_f$(15% EtOAc/hexanes)=0.59; IR (film) 3065, 2935, 2868, 1641, 1613, 1586, 1514, 1464, 1380, 1302, 1248, 1094, 1037, 913, 821, 737 cm$^{-1}$; $^1$H NMR (300 MHz, CDCl$_3$) δ 1.17 (3H, d, J=6.3 Hz, C27), 2.27 (1H, m, C24), 2.40 (1H, m, C24), 3.44 (1H, ddd, J=7.7, 4.7, 4.6 Hz, C25), 3.62 (1H, dq, J=7.7, 6.3 Hz, C26), 3.78 (3H, s, CH$_3$O), 4.51 (1H, d, J=11.9 Hz, CH$_2$Ph), 4.52 (2H, s, CH$_2$Ph), 4.60 (1H, d, J=11.9 Hz, CH$_2$Ph), 5.04 (2H, m, CH$_2$=CH), 5.84 (1H, m, CH=CH$_2$), 6.83 (2H, d, J=8.7 Hz, Ar), 7.23–7.33 (7H, m, Ar); $^{13}$C-NMR (75 MHz, CDCl$_3$) δ 15.0, 34.4, 55.1, 71.2, 72.1, 75.7, 80.9, 113.6, 116.6, 127.4, 127.6, 127.6, 128.3, 129.4, 130.9, 135.6, 138.9, 159.2; HRMS Calcd for C$_{21}$H$_{26}$O$_3$ (M$^+$): 326.1882. Found: 326.1876; Anal. Calcd for C$_{21}$H$_{26}$O$_3$: C, 77.27; H, 8.03. Found: C, 77.22; H, 8.16; [α]$_D^{20}$=-8.9° (c 1.43, CH$_2$Cl$_2$).

Formula 102

A4 (3.0 g, 9.2 mmol) was dissolved in 90 mL CH$_2$Cl$_2$/22.5 mL MeOH and cooled to -78° C. Ozone was bubbled through the solution which was carefully monitored for the disappearance of starting material by TLC (thin layer chromatography). When the consumption of A4 was judged complete, the system was immediately purged with N$_2$ for 20 min and treated with solid thiourea (840 mg, 11.04 mmol). The reaction was warmed to rt slowly over 5 hours and stirred at rt for 6 hours. The solvents were removed in vacuo, and the crude mixture was purified by flash chromatography (20% EtOAc/hexanes) to afford 2.40 g (80%) of aldehyde 102 as a colorless oil.

102: R$_f$ (15% EtOAc/hexanes)=0.31; IR (film) 2868, 2729, 1723, 1612, 1513, 1458, 1384, 1303, 1249, 1174, 1094, 822, 742 cm$^{-1}$; $^1$H NMR (300 MHz, CDCl$_3$) δ 1.17 (3H, d, J=6.4 Hz, C27), 2.57 (1H, ddd, J=16.6, 7.8, 2.4 Hz, C24), 2.67 (1H, ddd, J=16.6, 4.4, 1.6 Hz, C24), 3.71 (1H, dq, J=6.4, 4.5 Hz, C26), 3.78 (3H, s, CH$_3$O), 4.05 (1H, ddd, J=7.8, 4.5, 4.4 Hz, C25), 4.45 (1H, d, J=11.8 Hz, CH$_2$Ph), 4.50 (2H, s, CH$_2$Ph), 4.58 (1H, d, J=11.8 Hz, CH$_2$Ph), 6.84 (2H, d, J=8.7 Hz, Ar), 7.20–7.35 (7H, m, Ar), 9.70 (1H, dd, J=2.4, 1.6 Hz, CHO); $^{13}$C NMR (75 MHz, CDCl$_3$) δ 14.2, 44.1, 55.1, 70.9, 72.0, 74.5, 75.1, 113.8, 127.7, 127.7, 128.4, 129.5, 130.2, 138.4, 159.4, 201.4; HRMS Calcd for C$_{20}$H$_{24}$O$_4$ (M$^+$): 328.1675. Found: 328.1664; Anal. Calcd for C$_{20}$H$_{24}$O$_4$: C, 73.13; H, 7.37. Found: C, 72.81; H, 7.40; [α]$_D^{20}$=9.1° (c 1.06, CH$_2$Cl$_2$).

1B. Diketone 101

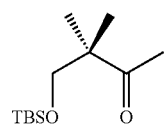

A6

A mixture of methylisopropyl ketone (53.4 mL, 0.5 mol) and paraformaldehyde (19.5 g, 0.65 mol) in 200 mL CF$_3$CO$_2$H was stirred at 60° C. for 18 h. The reaction mixture was concentrated on a rotary evaporator (warm water bath) with a KOH trap and poured into a cold (5° C.) mixture of EtOAc and sat. aqueous NaHCO$_3$. The layers were separated and the organic layer was washed with brine, dried over MgSO$_4$, and concentrated in vacuo. Short path distillation gave the trifluoroacetate ester of 3,3-dimethyl-4-hydroxy butanone (bp=53–55° C. at 2 mm Hg, 72.4 g) in 68% yield. This material was dissolved in 400 mL MeOH and treated with 190 mL of 2N NaOH at 0° C. After 1 h at 0° C., the reaction mixture was concentrated in vacuo and the residue was partitioned between EtOAc and sat. aqueous NH$_4$Cl. The organic layer was washed with brine, dried over MgSO$_4$, and concentrated to afford 40.1 g (~100%) of 3,3-dimethyl-4-hydroxy butanone (A5) as a colorless liquid. Crude A5 was taken up in 200 mL anhydrous DMF and treated with t-butyldimethylsilylchloride (57.3 g, 0.38 mol) and imidazole (25.9 g, 0.38 mol) at 0° C. After stirring at rt for 2 h, the solution was diluted with EtOAc, washed with sat. aqueous NaHCO$_3$ solution and brine, dried over MgSO$_4$ and concentrated in vacuo. The residue was distilled under reduced pressure to afford silyl ether ketone A6 (bp=65° C. at 1.5 mm Hg, 55.76 g, 81%) as a colorless oil.

A6: R$_f$(25% EtOAc/hexanes)=0.90; IR (film) 2957, 2931, 2858, 1713, 1473, 1362, 1257, 1136, 1097, 838, 777 cm$^{-1}$; $^1$H NMR (300 MHZ, CDCl$_3$) δ 0.03 (6H, s), 0.87 (9H, s), 1.09 (6H, s), 2.17 (3H, s), 3.57 (2H, s); $^{13}$C NMR (75 MHz, CDCl$_3$) δ 5.7, 18.1, 21.4, 25.7, 26.1, 49.6, 70.2, 213.4; HRMS Calcd for C$_{12}$H$_{26}$O$_2$Si (M$^+$-CH$_3$): 215.1467. Found: 215.1469.

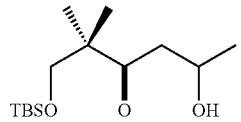

A7

To a stirred solution of diisopropylamine (12.6 mL, 96 mmol) in THF (200 mL) was added n-butyllithium (38.4 mL, 2.5M in hexane, 96 mmol) dropwise at 0° C. The mixture was stirred at 0° C. for 30 min, cooled to -78° C., and treated with a solution of ketone A6 (20.0 g, 87 mmol) in THF (50 mL) slowly over 10 min. After stirring at -78° C. for 40 min, acetaldehyde (5.34 mL, 96 mmol) was added and the mixture was kept at -78° C. for 2 h and at -40° C. for 1.5 h. The reaction was quenched with saturated NH$_4$Cl solution (20 mL) and allowed to warm gradually to rt. The mixture was extracted with ether and the combined organics were washed with brine, dried over MgSO$_4$ and concentrated in vacuo to afford nearly pure aldol A7 (19 g, 80%) as a pale yellow oil. An analytical sample was obtained following chromatography on silica gel.

A7: R$_f$(15% EtOAc/hexanes)=0.33; IR (film) 2958, 2930, 2858, 1699, 1472, 1392, 1363, 1258, 1101, 838, 777 cm$^{-1}$; $^1$H NMR (300 MHz, CDCl$_3$) δ 4.16 (1H, m), 3.55 (2H, s), 3.36 (1H, s), 2.74 (1H, dd, J=18.0, 2.4 Hz), 2.68 (1H, dd, J=18.0, 9.0 Hz), 1.16 (3H, d, J=6.3 Hz), 1.08 (3H, s), 1.07 (3H, s), 0.85 (9H, s), 0.01 (6H, s); $^{13}$C NMR (75 MHz, CDCl$_3$) δ -5.7, 18.1, 21.3, 22.3, 25.8, 46.2, 49.7, 63.9, 70.2, 216.8; Anal. Calcd for C$_{14}$H$_{30}$O$_3$Si: C, 61.26; H, 11.02. Found: C, 61.01; H. 11.28.

Formula 101

To a solution of oxalyl chloride (5.3 mL, 60.4 mmol) in $CH_2Cl_2$ (150 mL) was added dimethyl sulfoxide (8.56 mL, 120.8 mmol) dropwise at −78° C. After 20 min, a solution of crude alcohol A7 (15.0 g, 54.9 mmol) in $CH_2Cl_2$ (150 mL) was added over 10 min and the mixture was stirred at −78° C. for 1 h. $Et_3N$ (38 mL, 275 mmol) was added and the mixture was stirred for 20 min, brought to 0° C., quenched with sat. aqueous $NH_4Cl$ and diluted with EtOAc. The layers were separated and the aqueous layer was extracted with EtOAc (2×). The combined organics were washed with brine, dried over $MgSO_4$, and concentrated in vacuo. Flash chromatography on silica gel (5→10% EtOAc/hexanes) provided enolic β-diketone 101 (12.0 g, 81%) as a yellow oil.

101: $R_f$ (15% EtOAc/hexanes)=0.68; IR (film) 2957, 2930, 1606, 1472, 1362, 1257, 1102, 838, 777 $cm^{-1}$; $^1H$ NMR (300 MHZ, $CDCl_3$) δ 0.01 (6H, s), 0.85 (9H, s), 1.10 (6H, s), 2.05 (3H, s), 3.53 (2H, s), 5.62 (1H, s); $^{13}C$ NMR (75 MHz, $CDCl_3$) δ −5.5, 18.3, 22.1, 25.5, 25.9, 44.9, 70.0, 98.0, 192.6, 198.5; Anal. Calcd for $C_{14}H_{28}O_3Si$: C, 61.72; H, 10.36. Found: C, 61.08; H, 10.43.

1C. Dibenzyl Ether Octanoate 111

Formulae 104a and 104b

To a solution of diisopropylamine (3.21 mL, 23 mmol) in 25 mL THF at −60° C. was added n-butyllithium (1.6 M in hexanes, 13.83 mL, 22.13 mmol) dropwise. The colorless solution was warmed to 0° C. and stirred for 30 min. A THF solution (35 mL) of diketone 101 (Example 1B) (2.98 g, 10.9 mmol) was subsequently added via cannula and the mixture was stirred for 1 h at 0° C. The reaction was re-cooled to −78° C. and treated with a solution of aldehyde 102 (Example 1A) (3.0 g, 9.15 mmol) in 35 mL THF. After 30 min at −78° C., the mixture was quenched with sat. $NH_4Cl$ and brought to rt. The aqueous layer was extracted with $Et_2O$, the combined organics were dried over $MgSO_4$ and the solvent was removed in vacuo. The crude residue was quickly passed through a column of silica gel (20% EtOAc/hexanes) to provide 5.40 g (98%) of aldol diastereomer mixture 103 as an approximately 1:1 mixture of diastereomers.

A portion of isolated 103 (2.50 g, 4.2 mmol) was dissolved in 60 mL anhydrous toluene and treated with 4 Å molecular sieves (1.55 g) and p-toluenesulfonic acid (60 mg). The reaction was stirred at room temperature for 4.5 h, quenched with 2 mL pyridine and concentrated. The residue was taken up in $Et_2O$, washed with sat. $NaHCO_3$, dried over $MgSO_4$ and the solvent was removed in vacuo. Flash chromatography (20→25% EtOAc/hexanes) afforded pyrone compounds 104a (1.0 g) and 104b (1.2 g) in 90% overall yield as colorless oils.

104b: $R_f$ (30% EtOAc/hexanes)=0.59; $^1H$ NMR (300 MHz, $CDCl_3$) δ 0.05 (6H, s, TBS), 0.85 (9H, s, TBS), 1.05 (3H, s, C18 Me), 1.06 (3H, s, C18 Me), 1.20 (3H, d, J=5.8 Hz, C27), 1.98 (2H, m, C24), 2.12 (1H, dd, J=16.7, 3.6 Hz, C24), 2.28 (1H, dd, J=16.7, 13.7 Hz, C22), 3.44 (2H, s, C17), 3.54 (1H, m, C25), 3.72 (1H, m, C26), 3.81 (3H, s, $CH_3O$), 4.23 (1H, m, C23), 4.40 (1H, d, J=11.2 Hz, $CH_2Ph$), 4.47 (1H, d, J=11.8 Hz, $CH_2Ph$), 4.52 (1H, d, J=11.2 Hz, $CH_2Ph$), 4.63 (1H, d, J=11.8 Hz, $CH_2Ph$), 5.39 (1H, s, C20), 6.85 (2H, d, J=8.7 Hz, Ar), 7.17–7.35 (7H, m, Ar); $^{13}C$ NMR (75 MHz, $CDCl_3$) δ −5.5, 14.7, 18.2, 22.4, 25.9, 34.5, 40.9, 42.4, 55.4, 69.6, 71.2, 72.0, 74.3, 76.2, 103.5, 114.1, 127.9, 128.0, 128.7, 128.8, 129.9, 130.4, 138.8, 159.7, 182.2, 193.7; HRMS Calcd for $C_{34}H_{50}O_6Si$ ($M^+$): 582.3377. Found: 582.3370

104a: $R_f$ (30% EtOAc/hexanes)=0.52; IR 2955, 2857, 1667, 1599, 1514, 1397, 1336, 1301, 1249, 1174, 1102, 838 $cm^{-1}$; $^1H$ NMR (300 MHz, $CDCl_3$) δ 0.05 (6H, s, TBS), 0.87 (9H, s, TBS), 1.10 (3H, s, C18 Me), 1.14 (3H, s, C18 Me), 1.21 (3H, d, J=6.3 Hz, C27), 1.71 (1H, m, C24), 2.10 (1H, m, C24), 2.42 (2H, m, C22), 3.48 (1H, d, J=9.3 Hz, C17), 3.58 (1H, d, J=9.3 Hz, C17), 3.76 (1H, m, C26), 3.82 (3H, s, $CH_3O$), 3.83 (1H, m, C25), 4.43 (1H, d, J=10.7 Hz, $CH_2Ph$), 4.56 (1H, br m, C23), 4.57 (1H, d, J=11.8 Hz, $CH_2Ph$), 4.63 (1H, d, J=10.7 Hz, $CH_2Ph$), 4.65 (1H, d, J=11.8 Hz, $CH_2Ph$), 5.47 (1H, s, C20), 6.87 (2H, d, J=8.6 Hz, Ar), 7.20 (2H, d, J=8.6 Hz, Ar), 7.32–7.38 (5H, m, Ar); $^{13}C$-NMR (75 MHz, $CDCl_3$) δ −5.6, 14.4, 18.1, 22.3, 22.5, 25.7, 35.2, 41.5, 42.3, 55.2, 69.4, 71.1, 72.8, 74.8, 75.9, 76.4, 103.2, 113.8, 127.5, 128.3, 129.3, 130.3, 138.5, 159.2, 181.1, 193.4; HRMS Calcd for $C_{34}H_{50}O_6Si$ ($M^+$): 582.3377. Found: 582.3369; Anal. Calcd for $C_{34}H_{50}O_6Si$: C, 70.06; H, 8.65. Found: C, 69.95; H, 8.77; $[α]_D^{20}$=+43.9° (c 0.70, $CH_2Cl_2$).

Formula 105

To a solution of pyrone 104a (680 mg, 2.4 mmol) and $CeCl_3·7H_2O$ (218 mg, 0.59 mmol) in 40 mL methanol was added solid $NaBH_4$ (89 mg, 2.3 mmol) in a single portion at −20° C. The reaction mixture was stirred for 1 h at −20° C. and then quenched with 50 mL brine. The mixture was brought to rt, filtered through a pad of Celite™ and extracted with EtOAc (4×). The combined organics were dried over $Na_2SO_4$ and concentrated in vacuo to afford a crude allylic alcohol. This moderately stable oil was carried forward without purification.

Crude allylic alcohol was dissolved in 45 mL $CH_2Cl_2$/MeOH (2:1) and treated with solid $NaHCO_3$ (243 mg, 2.9 mmol). Purified m-CPBA (377 mg, 2.20 mmol) was added in a single portion and the reaction mixture was stirred at rt for 1 h. The mixture was quenched with $Et_3N$ (15 mL), stirred for 20 min, diluted with 200 mL $Et_2O$, and filtered through a pad of Celite™. The filtrate was concentrated in vacuo and the residue was purified by flash chromatography (40% EtOAc/hexanes) to give 650 mg (71% from 104a) of syn diol 105 as a colorless oil.

105: $R_f$ (30% EtOAc/hexanes)=0.29; IR (film) 3372, 1613, 1514, 1465, 1390, 1302, 1249, 1180, 1150, 1072, 935, 837, 779, 736, 698, 673 $cm^{-1}$; $^1H$ NMR (300 MHz, $CDCl_3$) δ 0.09 (6H, s, TBS), 0.91 (9H, s, TBS), 1.03 (3H, s, C18 Me), 1.07 (3H, s, C18 Me), 1.18 (3H, d, J=6.3 Hz, C27), 1.50–1.68 (2H, m, C24/C22), 1.80 (1H, m, C22), 2.57 (1H, app d, J=11.2 Hz, C24), 3.28 (3H, s, $CH_3O$), 3.39 (1H, d, J=10.1 Hz, C17), 3.62 (1H, d, J=11.2 Hz, C17), 3.79 (3H, s, $CH_3O$), 3.71–3.94 (5H, m, $CH_2Ph$, C23/C25/C26), 4.40 (1H, d, J=10.7 Hz, $CH_2Ph$), 4.56 (1H, d, J=11.8 Hz, $CH_2Ph$), 4.62 (1H, d, J=11.5 Hz, $CH_2Ph$), 5.40 (1H, d, J=2.5 Hz, OH), 6.84 (2H, d, J=8.7 Hz, PMB), 7.18 (2H, d, J=8.7 Hz, PMB), 7.37–7.26 (5H, m, Bn).

Formula 106

A solution of diol 105 (0.81 g, 1.28 mmol) and 4-dimethylaminopyridine (DMAP, 0.55 g, 4.48 mmol) in 22 mL $CH_2Cl_2$ was cooled to −10° C. and treated with benzoyl chloride (193 μL, 1.66 mmol) dropwise via syringe. The resulting mixture was stirred at −10° C. for 30 min, quenched with sat $NaHCO_3$ and diluted with EtOAc (150 mL). The organic layer was washed with H₂O and brine, dried over Na₂SO₄ and concentrated in vacuo to afford a crude mixture of C21 monobenzoate and 4-dimethylaminopyridine as a colorless paste.

The crude C21 monobenzoate was taken up in 45 mL CH₂Cl₂ and treated with solid 1,1,1-triacetoxy-1,1-dihydro-1,2-benziodoxol-3(1H)-one (Dess-Martin periodinane or DMP, 1.78 g, 4.20 mmol) at rt. The solution was stirred for 10 h at rt after which a second portion (0.50 g, 1.18 mmol) of DMP was added. The opaque white mixture was stirred for another 1.5 h and quenched with 30 mL sat. NaHCO₃/Na₂S₂O₃. The two phase system was vigorously stirred until the organic layer cleared (~25 min). The layers were separated and the aqueous phase was extracted with CH₂Cl₂ (2×). The combined organics were dried over Na₂SO₄ and concentrated in vacuo to provide a colorless semi-solid. Flash chromatography on silica gel (25% EtOAc/hexanes) gave 106 (0.85 g-90% from 105) as a colorless oil.

106: $R_f$ (15% EtOAc/hexanes)=0.43; IR (film) 2954, 2933, 1754, 1723, 1610, 1513, 1451, 1267, 1251 cm⁻¹; ¹H NMR (300 MHz, CDCl₃) δ 0.01 (6H, s, TBS), 0.88 (9H, s, TBS), 1.12 (3H, s, C18 Me), 1.14 (3H, s, C18 Me), 1.19 (3H, d, J=6.3 Hz, C27), 1.64–1.73 (1H, m, C24), 1.82–1.90 (1H, m, C24), 2.13 (1H, app q, J=12.4 Hz, C22), 2.40 (1H, ddd, J=12.4, 6.5, 1.6 Hz, C22), 3.54 (3H, s, C19 OCH₃), 3.65 (1H, d, J=9.2 Hz, C17), 3.69 (1H, d, J=9.2 Hz, C17), 3.72–3.81 (2H, m), 3.81 (3H, s, ArOCH₃), 3.89 (1H, m), 4.49 (1H, d, J=10.7 Hz, CH₂Ar), 4.57 (1H, d, J=13.0 Hz, CH₂Ar), 4.61 (1H, d, J=13.0 Hz, CH₂Ar), 4.62 (1H, d, J=10.7 Hz, CH₂Ar), 5.80 (1H, dd, J=12.9, 6.3 Hz, C21), 6.87 (2H, d, J=8.3 Hz, Ar), 7.26–7.36 (7H, m, Ar), 7.45 (2H, m, Ar), 7.58 (1H, app t, J=7.2 Hz, Ar), 8.09 (2H, d, J=7.2 Hz, Ar); ¹³C-NMR (75 MHz, CDCl₃) δ −5.3, 14.7, 18.5, 20.4, 20.6, 26.1, 35.5, 40.4, 45.1, 53.8, 55.5, 65.4, 67.2, 71.4, 73.0, 73.3, 75.1, 103.8, 114.1, 127.9, 128.6, 128.7, 129.7, 129.9, 130.2, 131.0, 133.6, 138.9, 159.6, 165.9, 198.6; HRMS Calcd for C₄₂H₅₈O₉Si (M⁺-MeOH): 702.3588. Found: 702.3563; Anal. Calcd for C₄₂H₅₈O₉Si: C, 68.63; H, 7.96. Found: C, 68.28; H, 8.11; $[\alpha]_D^{20}$=+22.4° (c 1.53, CH₂Cl₂).

Formula 107

A solution of benzoate 106 (0.85 g, 1.16 mmol) in 20 mL THF/MeOH (3:1) was titrated with SmI₂ (0.1 M in THF, 25.5 mL, 2.55 mmol) at −78° C. until an olive green color persisted. The reaction mixture was quenched with 4 mL sat. NaHCO₃, warmed to rt and diluted with EtOAc (150 mL). The organic layer was washed with NaHCO₃, H₂O and brine, dried over Na₂SO₄ and concentrated in vacuo. Flash chromatography on silica gel (20% EtOAc/hexanes) afforded ketone 107 (675 mg, 95%) as a light yellow oil.

107: $R_f$ (15% EtOAc/hexanes)=0.39; IR (film) 2954, 2930, 1723, 1612, 1514, 1464, 1250, 1088 cm⁻¹; ¹H NMR (300 MHz, CDCl₃) δ 0.01 (6H, s, TBS), 0.87 (9H, s, TBS), 0.95 (3H, s, C18 Me), 1.05 (3H, s, C18 Me), 1.19 (3H, d, J=6.3 Hz, C27), 1.64 (1H, m, C24), 1.85–1.96 (3H, m, C21+C24), 2.29 (1H, 5 line m, C22), 2.65 (1H, m, C22), 3.23 (3H, s, C19 OCH₃), 3.31 (1H, d, J=9.9 Hz, C17), 3.71 (1H, d, J=9.9 Hz, C17), 3.78 (3H, s, ArOCH₃), 3.79 (1H, m), 3.98 (1H, m), 4.17 (1H, m), 4.43 (1H, d, J=11.0 Hz, CH₂Ar), 4.58 (2H, s, CH₂Ar), 4.60 (1H, d, J=11.0 Hz, CH₂Ar), 6.84 (2H, d, J=8.7 Hz, PMB), 7.19 (2H, d, J=8.7 Hz, PMB), 7.28–7.35 (5H, m, Bn); ¹³C NMR (75 MHz, CDCl₃) δ −5.5, −5.4, 14.5, 18.6, 19.8, 20.2, 26.0, 29.7, 36.5, 38.2, 46.2, 52.4, 55.4, 68.6, 70.6, 71.3, 72.3, 74.7, 103.6, 114.1, 127.9, 128.7, 129.6, 131.0, 138.9, 159.5, 207.5; HRMS Calcd for C₃₅H₅₄O₇Si (M⁺-MeOH): 582.3377. Found: 582.3372; Anal. Calcd for C₃₅H₅₄O₇Si: C, 68.37; H, 8.85. Found: C, 68.04; H, 8.84; $[\alpha]_D^{20}$=+21.9° (c 0.72, CH₂Cl₂).

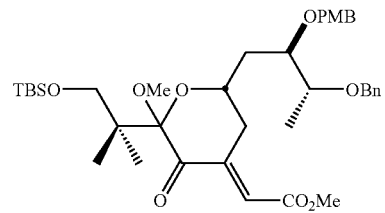

109.1 (Formula 109 where R²¹ is =CH—CO₂Me)

To a solution of diisopropylamine (150 μL, 1.15 mmol) in THF (1.61 mL) was added n-BuLi (2.5 M in hexanes, 440 μL, 1.10 mmol) dropwise at 0° C. After 5 min at 0° C., a 1.81 mL aliquot (0.5 M LDA, 0.90 mmol) was removed via syringe and slowly added to a solution of ketone 107 (483 mg, 0.79 mmol) in THF (20 mL) at −78° C. The solution was stirred for 10 min, treated with a stock solution of OHCCO₂Me (0.5 M in Et₂O, 4.0 mL, 2.0 mmol), kept at −78° C. for 20 min and quenched with 3 mL sat. NH₄Cl. The reaction mixture was brought to rt and diluted with 200 mL EtOAc. The organic layer was washed with H₂O (2×) and brine, dried over Na₂SO₄ and concentrated in vacuo. The crude residue was chromatographed on silica gel (35% EtOAc/hexanes) to afford residual 107 (142 mg) and aldols 108 as a mixture of diastereomers (352 mg, 90% based on recovered 107).

The isolated 108 mixture and Et₃N (418 μL, 3.0 mmol) were dissolved in anhydrous CH₂Cl₂ (15 mL) and cooled to −10° C. Methanesulfonylchloride (116 μL, 1.5 mmol) was added via syringe and the solution was stirred at −10° C. for 30 min. 5 mL sat. NaHCO₃ was added, the reaction mixture was warmed to rt and diluted with 100 mL EtOAc. The organic layer was washed with H₂O and brine, dried over Na₂SO₄ and concentrated in vacuo. The residue was immediately dissolved in THF (30 mL) and treated with 1,8-diazabicyclo[5.4.0]undec-7-ene (DBU, 75 μL, 0.50 mmol) dropwise at rt. The resulting bright yellow solution was stirred at rt for 20 min, treated with sat. NH₄Cl and diluted with 150 mL EtOAc. The organic layer was washed with H₂O and brine, dried over Na₂SO₄ and concentrated in vacuo to afford an orange residue which was chromatographed on silica gel (20% EtOAc/hexanes) to afford exocyclic methacrylate (enone) 109.1 (267 mg, 78% from 108) as a yellow oil.

109.1: $R_f$ (30% EtOAc/hexanes)=0.63; IR (film) 2954, 2930, 1724, 1707, 1612, 1514, 1464, 1250, 1088 cm⁻¹; ¹H NMR (300 MHz, CDCl₃) δ 0.05 (6H, s, TBS), 0.81 (9H, s, TBS), 0.91 (3H, s, C18 Me), 1.00 (3H, s, C18 Me), 1.19 (3H, d, J=6.4 Hz, C27), 1.74 (1H, m, C24), 1.94 (1H, m, C24), 2.71 (1H, ddd, J=17.6, 12.4, 3.1 Hz, C22), 3.19 (3H, s, C19 OCH₃), 3.26 (1H, d, J=10.0 Hz, C17), 3.49 (1H, d, J=17.6 Hz, C22), 3.68 (1H, d, J=10.0 Hz, C17), 3.74 (3H, s), 3.77 (3H, s), 3.80 (1H, m), 3.97 (1H, m), 4.19 (1H, m), 4.40 (1H, d, J=10.9 Hz, CH₂Ar), 4.53–4.63 (3H, m, CH₂Ar), 6.64 (1H, d, J=1.9 Hz, C34), 6.82 (2H, d, J=8.7 Hz, PMB), 7.14 (2H, d, J=8.7 Hz, PMB), 7.27–7.36 (5H, m, Bn); ¹³C-NMR (75 MHz, CDCl₃) δ −5.9, −5.8, 14.1, 18.3, 19.3, 19.8, 25.7, 35.2, 36.0, 46.6, 51.6, 52.1, 55.1, 68.2, 69.5, 71.0, 71.7, 74.2, 76.0, 104.0, 113.8, 122.4, 127.6, 128.4, 129.1, 130.6, 138.6, 147.3, 159.2, 166.4, 196.2; HRMS Calcd for C₃₈H₅₆O₉Si (M+-MeOH): 652.3433. Found: 652.3435; Anal. Calcd for C$_{38}$H$_{56}$O$_9$Si: C, 66.64; H, 8.24. Found: C, 66.87; H, 8.13; $[\alpha]_D^{20}$=−55.8° (c 0.78, CH$_2$Cl$_2$).

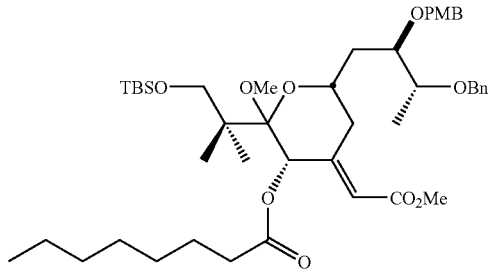

111.1 (Formula 111 where R$^{20}$ is
—O—CO—C$_7$H$_{15}$ and R$^{21}$ is =CH—CO$_2$Me)

To a solution of enone 109.1 (502 mg, 0.734 mmol) and CeCl$_3$·7H$_2$O (137 mg, 0.367 mmol) in methanol (23 mL) was added solid NaBH$_4$ (56 mg, 1.47 mmol) in a single portion at −30° C. Rapid gas evolution subsided after 3 min. After an additional 30 min at −30° C., the reaction mixture was poured directly onto a silica gel column and the product quickly eluted with 25% EtOAc/hexanes to afford the corresponding axial alcohol 110.1 (478 mg) as a colorless oil.

Octanoic acid (232 mg, 1.61 mmol) and Et$_3$N (292 μL, 2.20 mmol) were dissolved in 20 mL toluene and treated with 2,4,6-trichlorobenzoylchloride (230 μL, 1.47 mmol) dropwise at rt. After 1 h at rt, a toluene solution (7 mL) of freshly prepared 110.1 was added gradually via syringe and stirring was continued for 40 min. The reaction mixture was quenched with 10 mL sat. NaHCO$_3$, diluted with EtOAc and washed successively with sat. NH$_4$Cl and brine. The organics were dried over Na$_2$SO$_4$, the solvent was removed in vacuo, and the residue was chromatographed on silica gel (25% EtOAc/hexanes) to provide octanoate 111.1 as a colorless oil (551 mg, 93% from 109.1).

111.1: R$_f$ (25% Et$_2$O/hexanes)=0.33; IR (film) 2928, 2857, 1747, 1722, 1667, 1614, 1514, 1463, 1250, 1155, 1081, 836.2 cm$^{-1}$; $^1$H NMR (300 MHz, CDCl$_3$) δ −0.01 (6H, s, TBS), 0.88 (12H, br s, TBS+octanoate Me), 0.99 (3H, s, C18 Me), 1.03 (3H, s, C18 Me), 1.19 (3H, d, J=6.3 Hz, C27), 1.20–1.35 (8H, m), 1.60–1.80 (3H, m), 1.89 (1H, m, C24), 2.31–2.40 (3H, m), 3.26 (3H, s, C19 OCH$_3$), 3.44 (1H, dd, J=15.6, 1.8 Hz, C22), 3.56 (1H, d, J=9.3 Hz, C17), 3.60 (1H, d, J=9.3 Hz, C17), 3.68 (3H, s), 3.78 (1H, m), 3.79 (3H, s), 3.93 (1H, dd, J=8.4, 4.8 Hz), 4.13 (1H, m), 4.38 (1H, d, J=10.8 Hz, CH$_2$Ar), 4.57 (1H, d, J=10.8 Hz, CH$_2$Ar), 4.60 (2H, s, CH$_2$Ar), 5.57 (1H, s, C20), 5.89 (1H, s, C34), 6.83 (2H, d, J=8.4 Hz, PMB), 7.16 (2H, d, J=8.4 Hz, PMB), 7.28–7.38 (5H, m, Bn); $^{13}$C NMR (75 MHz, CDCl$_3$) δ −5.4, 14.1, 14.2, 14.4, 18.4, 20.7, 22.7, 24.8, 26.0, 28.9, 26.0, 28.9, 31.7, 33.2, 34.6, 36.4, 47.1, 51.2, 55.3, 67.6, 68.1, 71.2, 72.2, 74.7, 76.5, 103.1, 114.0, 117.0, 127.8, 128.6, 129.5, 129.9, 130.9, 139.0, 153.1, 159.5, 166.7, 172.2; HRMS Calcd for C$_{46}$H$_{72}$O$_{10}$Si (M+-MeOH): 780.4632. Found: 780.4610; $[\alpha]_D^{20}$=−5.1° (c 1.80, CH$_2$Cl$_2$).

Example 2

Exemplary Linkers

2A. Ketal Acid 406

Formula 402

To a stirred solution of the 1,3 menthone acetal of 1,3,5-pentanetriol 401 (3.33 g, 13 mmol) prepared by the method of Harada et al. (1993) in 23 mL of anhydrous CH$_2$Cl$_2$ was added 1,1,1-triacetoxy-1,1-dihydro-1,2-benziodoxol-3(1H)-one (Dess-Martin periodinane, 6.60 g, 15.6 mmol) in a single portion. The mixture was stirred at rt for 30 min, poured onto a column of silica gel and the product eluted with 15% EtOAc/hexanes to afford 3.013 g (90%) of pure aldehyde 402 as a colorless oil.

402: R$_f$ (20% EtOAc/hexanes)=0.50; IR (film) 2952, 2869, 1728, 1456, 1383, 1308, 1265 cm$^{-1}$; $^1$H NMR (300 MHz, CDCl$_3$) δ 9.80 (1H, dd, J=1.8, 2.5 Hz), 4.36 (1H, dddd, J=2.9, 4.3, 7.4, 8.2 Hz), 4.13 (1H, ddd, J=2.7, 11.7, 11.9 Hz), 3.83 (1H, ddd, J=1.3, 5.2, 11.7 Hz), 2.72 (1H, ddd, J=1.9, 3.1, 13.5 Hz), 2.56 (1H, ddd, J=2.5, 8.2, 16.1 Hz), 2.44 (1H, ddd, J=1.8, 4.3, 16.1 Hz), 2.39 (1H, dsept, J=1.6, 7.1 Hz), 1.54–1.76 (3H, m), 1.29–1.53 (4H, m), 1.17 (1H, ddd, J=1.9, 4.1, 12.4 Hz), 0.90 (3H, d, J=6.3 Hz), 0.87 (3H, d, J=7.0 Hz), 0.85 (3H, d, J=7.0 Hz), 0.72 (1H, t, J=13.2 Hz); $^{13}$C NMR (75 MHz, CDCl$_3$) δ 201.4, 100.9, 63.8, 58.7, 51.1, 49.9, 37.2, 34.8, 31.1, 28.9, 24.2, 23.7, 22.2, 21.7, 18.8; HRMS Calc'd for C$_{15}$H$_{26}$O$_3$: 254.1882. Found: 254.1877; $[\alpha]_D^{20}$−11.2° (c 1.28, CHCl$_3$).

Formulae 403a and 403b

To a stirred solution of aldehyde 402 (3.013 g, 11.86 mmol) in 40 mL of anhydrous CH$_2$Cl$_2$ was added a solution of (+)-Eu(hfc)$_3$ (1.42 g, 1.19 mmol) in CH$_2$Cl$_2$ (16 mL) at rt. The resultant clear yellow solution was stirred for 5 min before 1-methoxy-3-(trimethylsilyloxy)-1,3-butadiene (3.47 mL, 3.07 g, 17.8 mmol) was introduced via syringe. The yellow solution was stirred at rt for 20 h, treated with 0.5 mL CF$_3$CO$_2$H and stirred for an additional 15 min. The solution was quenched with sat. NaHCO$_3$, diluted with EtOAc (200 mL), washed with H$_2$O and brine, dried over MgSO$_4$ and concentrated in vacuo. Purification by flash chromatography (20→25% EtOAc/hexanes) provided anti pyrone 403b (2.53 g, 66%) and syn pyrone 403a (1.30 g, 34%) as colorless solids.

403b: mp=113–114° C. (hexanes); R$_f$ (15% EtOAc/hexanes)=0.25; $^1$H NMR (300 MHz, CDCl$_3$) δ 7.31 (1H, d, J=6.0 Hz), 5.40 (1H, d, J=6.0 Hz), 4.67 (1H, dddd, J=3.0, 5.8, 9.6, 11.8 Hz), 4.03–4.15 (2H, m), 3.81 (1H, ddd, J=1.2, 5.2, 11.6 Hz), 2.70 (1H, ddd, J=1.9, 2.8, 13.5 Hz), 2.42–2.56 (2H, m), 2.38 (1H, dsept, J=1.6, 6.9 Hz), 1.91 (1H, ddd, J=2.3, 9.6, 14.3 Hz), 1.28–1.75 (8H, m), 1.18 (1H, ddd, J=1.9, 3.9, 12.5 Hz), 0.88 (3H, d, J=6.6 Hz), 0.87 (3H, d, J=7.1 Hz), 0.83 (3H, d, J=6.9 Hz), 0.70 (1H, t, J=12.6 Hz); $^{13}$C NMR (75 MHz, CDCl$_3$) δ 192.7, 162.9, 107.3, 100.7, 75.7, 63.3, 58.9, 51.1, 42.5, 41.7, 37.3, 34.8, 31.7, 29.0, 24.2, 23.6, 22.2, 21.9, 18.9; LRMS (EI): 322 (68), 307 (22), 265 (33), 237 (67), 153 (24), 191 (94), 139 (52), 112 (20), 97 (100), 83 (31), 81 (47), 71 (24), 69 (35); HRMS Calcd for C$_{19}$H$_{30}$O$_4$: 322.2144. Found: 322.2142; Anal. Calcd for C$_{19}$H$_{30}$O$_4$: C, 70.77; H, 9.38. Found: C, 70.91; H, 9.58; $[\alpha]_D^{20}$+42.5° (c 1.59, CH$_2$Cl$_2$).

403a: R$_f$ (15% EtOAc/hexanes)=0.15; IR 2952, 2869, 1682, 1597, 1456, 1405, 1269 cm$^{-1}$; $^1$H NMR (300 MHz, CDCl$_3$) δ 7.33 (1H, d, J=6.0 Hz), 5.40 (1H, dd, J=0.9, 6.0 Hz), 4.61 (1H, dddd, J=2.8, 11.6, 12.0 Hz), 4.09 (1H, ddd, J=2.8, 11.6, 12.0 Hz), 4.00 (1H, dddd, J=1.0, 4.2, 8.3, 15.5 Hz), 3.81 (1H, ddd, J=1.4, 5.4, 11.6 Hz), 2.67 (1H, ddd, J=1.9, 3.2, 13.5 Hz), 2.63 (1H, dd, J=13.3, 16.8 Hz), 2.47 (1H, ddd, J=0.9, 4.0, 16.8 Hz), 2.39 (1H, dsept, J=1.6, 6.9 Hz), 2.02 (1H, ddd, J=5.6, 8.3, 14.0 Hz), 1.79 (1H, ddd, J=4.2, 6.9, 14.0 Hz), 1.20–1.75 (7H, m), 1.17 (1H, ddd, J=1.9, 3.8, 12.6 Hz), 0.89 (3H, d, J=6.7 Hz), 0.87 (3H, d, J=6.9 Hz), 0.86 (3H, d, J=6.9 Hz), 0.70 (1H, t, J=13.5 Hz); $^{13}$C NMR (75 MHz, CDCl$_3$) δ 192.6, 163.3, 107.1, 100.7, 76.4, 63.9, 58.8, 51.1, 41.6, 40.9, 37.3, 34.7, 31.4, 29.3, 24.2, 23.7, 22.2, 21.8, 18.8; LRMS (EI): 322 (61), 307 (18), 265 (27), 237 (56), 151 (21), 139 (33), 112 (17), 97 (100), 83 (26), 81 (34), 71 (17), 69 (60); HRMS Calcd for C$_{19}$H$_{30}$O$_4$: 322.2144. Found: 322.2146; [α]$_D^{20}$ −57.8° (c 1.5, CH$_2$Cl$_2$).

Formula 404

To a stirred solution of pyrone 403a (1.30 g, 4.04 mmol) in 40 mL of anhydrous MeOH was added CeCl$_3$.7H$_2$O (904 mg, 2.43 mmol) at rt. After stirring for 10 min, the mixture was cooled to −40° C. and NaBH$_4$ (306 mg, 8.09 mmol) was added in one portion. The mixture was stirred for an additional 15 min before quenching with a 1:1 mixture of brine and H$_2$O. The aqueous layer was extracted with EtOAc (4×). The combined organics were washed with sat. NaHCO$_3$ and brine, dried over Na$_2$SO$_4$ and concentrated to afford a clear oil. Purification by flash chromatography (30% EtOAc/hexanes containing 1% Et$_3$N) afforded unstable allylic alcohol 404 (1.08 g, 82%) as a single diastereomer.

404: IR (film) 3386, 2951, 2869, 1643, 1456, 1380, 1307, 1268, 1231 cm$^{-1}$; $^1$H NMR (300 MHz, CDCl$_3$) δ 6.35 (1H, br d, J=5.4 Hz), 4.75 (1H, ddd, J=1.9, 1.9, 6.1 Hz), 4.36–4.46 (1H, m), 4.08–4.17 (1H, m), 4.08 (1H, ddd, J=2.7, 12.4, 12.4 Hz), 3.98 (1H, dddd, J=2.7, 5.2, 7.9, 10.9 Hz), 3.81 (1H, ddd, J=1.5, 5.2, 11.5 Hz), 2.69 (1H, br d, J=13.5 Hz), 2.39 (1H, dsept, J=1.7, 6.9 Hz), 2.18 (1H, dddd, J=1.7, 1.9, 6.4, 13.0 Hz), 1.90 (1H, ddd, J=6.6, 7.7, 14.0 Hz), 1.33–1.74 (9H, m), 1.17 (1H, ddd, J=1.9, 4.4, 12.3 Hz), 0.90 (3H, d, J=6.2 Hz), 0.88 (6H, d, J=6.9 Hz), 0.69 (1H, t, J=12.7 Hz); $^{13}$C NMR (75 MHz, CDCl$_3$) δ 145.3, 105.5, 100.6, 71.4, 64.3, 63.0, 58.9, 51.2, 41.5, 37.7, 37.4, 34.9, 31.3, 29.2, 24.2, 23.7, 22.2, 21.8, 18.8; [α]$_D^{20}$ +2.0° (c 0.59, CHCl$_3$).

Formula 405

To a solution of 1.08 g (3.32 mmol) of allylic alcohol 404 in 66 mL of ethylvinylether was added mercury(II)trifluoroacetate (142 mg, 0.33 mmol) in a single portion at −10° C. The resulting colorless solution was stirred for 20 h at 5° C., diluted with Et$_2$O, washed with sat. NaHCO$_3$ and brine, dried over Na$_2$SO$_4$, and concentrated in vacuo to give a clear, colorless oil. Rapid flash chromatography (10% EtOAc/hexanes containing 1% Et$_3$N) afforded 865 mg (74%) of the corresponding allyl vinyl ether along with 208 mg (19%) of recovered 404. The vinyl ether was immediately dissolved in 100 mL n-nonane and heated at 145° C. for 3.5 h. The solution was cooled to 70–80° C. and the solvent was removed by short path distillation at reduced pressure. The remaining residue was purified by flash chromatography (10% EtOAc/hexanes) to provide Claisen product 405 (612 mg, 71%) as a colorless oil.

405: R$_f$ (30% EtOAc/hexanes)=0.75; IR (film) 2950, 2869, 1728, 1646, 1456, 1373, 1307, 1267 cm$^{-1}$; $^1$H NMR (300 MHz, CDCl$_3$) δ 9.78 (1H, t, J=2.4 Hz), 5.89 (1H, dddd, J=2.0, 2.0, 4.7, 10.0 Hz), 5.64 (1H, dddd, J=1.3, 1.3, 2.5, 10.0 Hz), 4.57–4.66 (1H, m), 4.08 (1H, ddd, J=2.7, 12.1, 12.1 Hz), 3.90–4.01 (1H, m), 3.66–3.82 (2H, m), 2.69 (1H, ddd, J=1.9, 3.0, 13.4 Hz), 2.55 (2H, dd, J=2.4, 6.2 Hz), 2.40 (1H, dsept, J=1.6, 6.9 Hz), 1.12–2.14 (12H, m), 0.89 (3H, d, J=6.6 Hz), 0.88 (6H, d, J=7.1 Hz), 0.68 (1H, t, J=12.9 Hz); $^{13}$C NMR (75 MHz, CDCl$_3$) δ 201.7, 128.5, 126.3, 100.5, 70.6, 70.5, 64.4, 59.1, 51.2, 48.5, 42.5, 37.4, 34.9, 31.5, 30.7, 29.1, 24.3, 23.7, 22.2, 21.9, 18.9; MS (EI) 350 (51), 335 (45), 322 (14), 293 (65), 279 (15), 265 (52), 255 (15), 139 (17), 135 (29), 97 (28), 83 (43), 81 (100), 79 (17), 69 (27), 67 (24); HRMS Calcd for C$_{21}$H$_{34}$O$_4$: 350.2457. Found: 350.2466; [α]$_D^{27}$ 0° (CH$_2$Cl$_2$).

Formula 406

To a stirred mixture of trimethylsilyl diethylphosphonoacetate (72 μl, 76.7 mg, 0.286 mmol) in anhydrous THF (1 mL) was added of n-butyllithium (2.5 M in hexanes, 109 μL, 0.272 mmol) dropwise at −78° C. After stirring for 20 min at −78° C. and 15 min at rt, the mixture was cooled to −78° C. and treated with a THF solution (1 mL) of aldehyde 405 (45 mg, 0.129 mmol). The mixture was allowed to warm to rt over 2 h and stirring was continued for 1 h. The mixture was diluted with 50 mL EtOAc and acidified with 10 mL of a 0.1 N aqueous NaHSO$_4$ solution. The phases were separated and the aqueous phase was extracted with EtOAc (3×). The combined organic extracts were washed with brine, dried over MgSO$_4$, and concentrated to give a colorless oil. Rapid filtration through a short pad of silica gel (20% acetoneibenzene) gave a crude product which was dissolved in 2 mL methanol. Palladium on activated charcoal (10%, ~5 mg) was added and the mixture was stirred at room temperature for 18 h under balloon pressure of hydrogen gas. Filtration through Celite™ and flash chromatography on silica gel (40% EtOAc/hexanes containing 1% acetic acid) gave 21.8 mg (0.055 mmol, 43%) of ketal carboxylic acid 406 as a clear, colorless oil. R$_f$ (40% EtOAc/hexanes+1% AcOH)=0.44; IR (film) 3500–2500, 2938, 2868, 1711, 1456, 1377, 1307, 1268, 1158, 1113 cm$^{-1}$; $^1$H NMR (300 MHz, CDCl$_3$) δ 4.08 (ddd, 1H, J=2.6, 12.4, 12.4 Hz), 3.98 (dddd, 1H, J=2.4, 6.6, 6.6, 10.7 Hz), 3.81 (ddd, 1H, J=1.2, 5.2, 11.5 Hz), 3.38–3.47 (m, 1H), 3.21–3.31 (m, 1H), 2.70 (br d, 1H, J=12.5 Hz), 2.29–2.47 (m, 3H), 1.62–1.86 (m, 5H), 1.34–1.62 (m, 11H), 1.07–1.30 (m, 3H), 0.78–0.98 (m, 1H), 0.88 (d, 6H, J=7.2 Hz), 0.88 (d, 3H, J=7.0 Hz), 0.67 (t, 1H, J=12.9 Hz); $^{13}$C NMR (75 MHz, CDCl$_3$) δ 179.1, 100.5, 74.2, 64.6, 59.2, 51.2, 42.9, 37.3, 35.4, 34.9, 33.7, 31.50, 31.46, 31.3, 29.0, 24.2, 23.7, 23.6, 22.2, 21.8, 20.9, 18.8; HRMS Calcd for C$_{23}$H$_{40}$O$_5$: 396.2876. Found: 396.2870; [α]$^{28}$$_D$ −10.5° (c 1.66, CHCl$_3$).

2B. Ketal Acid 408

Formula 407

To a solution of the aldehyde 405 (Example 2A, 274 mg, 0.778 mmol) in ethyl acetate (5 mL) was added Pd/C (10 mg) and the atmosphere was exchanged to hydrogen, which was applied for 30 min. The mixture was filtered and concentrated to give the corresponding crude saturated aldehyde, which was directly used in the next step.

A stock solution of Ipc$_2$B(allyl) was prepared by first dissolving (−)-Ipc$_2$BOMe (700 mg, 2.22 mmol) in ether (4.15 mL) at 0° C. and adding 1M allyl magnesium bromide (1.78 mL, 1.78 mmol). The mixture was warmed to rt and stirred for 30 min. In a separate flask, the aldehyde was dissolved in ether (4 mL) and treated with the stock solution of Ipc$_2$B(allyl) (0.3 M, 3.9 mL, 1.17 mmol) at −78° C. After stirring for 2 h at −78° C., the mixture was treated with hydrogen peroxide (30%, 2 mL) and sodium hydroxide (15%, 2 mL) and warmed to rt. After another 2 h, the mixture was partitioned between ethyl acetate and brine. The aqueous layer was extracted with ethyl acetate. The combined organic layers were dried over sodium sulfate, and concentrated to give the corresponding crude homoallylic alcohol, which was directly used in the next step.

To a solution of the crude homoallylic alcohol in methylene chloride (5 mL) at 0° C. was added TBSOTf (534 mL, 2.33 mmol) and diisopropyl ethyl amine (676 µL, 3.89 mmol) and stirred for 30 min. The mixture was directly loaded onto silica gel and purified to give the corresponding alkene (237 mg, 60% in 3 steps).

To a solution of the alkene (10 mg, 0.0197 mmol) in tert-butanol (1 mL) at rt was added a solution of KMnO$_4$ (0.6 mg, 0.0039 mmol) and NaIO$_4$ (17 mg, 0.0788 mmol) in water (buffered pH 7, 1 mL). After 30 min, the reaction mixture was quenched with sodium thiosulfate. The mixture was partitioned between ethyl acetate and brine. The aqueous layer was extracted with ethyl acetate. The combined organic layers were dried over sodium sulfate, and concentrated. Column chromatography afforded TBS ether 407 (6.3 mg, 71%).

407: Rf=0.20 (25% ethyl acetate/hexane); $[\alpha]^{25}_D$=22.6° (c 0.58, CH$_2$Cl$_2$); IR (neat)=2933, 1712, 1457, 1255, 1114 cm$^{-1}$; $^1$H NMR (400 MHz, CDCl$_3$) δ 4.32 (m, 1H), 4.08 (m, 1H), 3.93 (m, 1H), 3.81 (m, 1H), 3.44 (m, 2H), 2.69 (d, J=13.2 Hz, 1H), 2.62 (dd, J=15.2, 5.2 Hz, 1H), 2.48 (dd, J=15.2, 5.2 Hz, 1H), 2.40 (quint, J=6.8 Hz, 1H), 1.85–1.15 (m, 20H), 0.88 (br s, 18H), 0.12 (s, 3H), 0.11 (s, 3H); $^{13}$C NMR (100 MHz, CDCl$_3$) δ 173.48, 100.44, 73.88, 73.52, 66.15, 64.26, 59.14, 51.24, 43.89, 43.25, 42.48, 37.43, 43.97, 32.13, 31.89, 30.93, 29.23, 25.74, 24.31, 23.77, 23.52, 22.25, 21.89, 19.15, 17.92, −4.77; HRMS: calcd for (C$_{29}$H$_{54}$O$_6$Si)=526.3689; found (M)=526.3687

Formula 408

To a solution of TBS ether 407 (9.3 mg, 0.0177 mmol) in THF (0.5 mL) at rt was added pyridine (127 µL) and HF.pyridine (51 µL, 1.77 mmol) and stirred for 18 h. The mixture was partitioned between ethyl acetate and water (pH 4). The aqueous layer was extracted with ethyl acetate. The combined organic extracts were dried over sodium sulfate, concentrated in vacuo and the resulting crude hydroxy acid was used in the next step without further purification.

To a solution of crude hydroxy acid in methylene chloride (1.5 mL) at rt was added TESCl (26 µL, 0.0708 mmol) and TEA (19 µL, 0.142 mmol) and the mixture was stirred for 4 h. The mixture was treated with water (pH 4, 1 mL) and stirred for another 10 min. The aqueous layer was extracted with ethyl acetate. The combined organic extracts were dried over sodium sulfate and then concentrated. The crude product was purified by silica gel chromatography to give the TES acid 408 (7 mg, 75%—2 steps).

408: R$_f$=0.30 (33% ethyl acetate in hexane); $[\alpha]^{25}_D$=34.0° (c 0.42, CH$_2$Cl$_2$); IR (film)=2951, 1711, 1457, 1378, 1114, 1005, 976 cm$^{-1}$; $^1$H NMR (400 MHz, CDCl$_3$) δ 4.33 (m, 1H), 4.09 (m, 1H), 3.95 (m, 1H), 3.81 (m, 1H), 3.45 (m, 1H), 2.70 (d, J=14 Hz, 1H), 2.64 (dd, J=15.6, 5.2 Hz, 1H), 2.51 (dd, J=15.6, 5.2 Hz, 1H), 2.40 (m, 1H), 1.86–1.15 (m, 21H), 0.98 (t, J=8.0 Hz, 9H), 0.89 (m, 9H), 0.66 (q, J=8.0 Hz, 6H); $^{13}$C NMR (100 MHz, CDCl$_3$) δ 173.06, 100.45, 73.94, 73.70, 66.33, 64.28, 59.12, 51.21, 43.90, 43.23, 42.48, 37.40, 34.96, 32.12, 31.86, 31.00, 29.20, 24.33, 23.77, 23.52, 22.23, 21.89, 19.00, 6.79, 4.73; HRMS: calcd for (C$_{29}$H$_{54}$O$_6$Si)=526.3689; found (M)=526.3717.

2C. 9-Hydroxy-9-t-Butyl L3 Linker Synthon 504

Formula 501

To a solution of aldehyde 402 (Example 2A supra, 803 mg, 3.16 mmol) in ether (10 mL) was added a solution of 4-pentenyl magnesium bromide (0.8M in ether, 4.74 mL, 3.79 mmol) at −78° C. and the mixture was stirred for 30 min. The reaction was quenched with aq. sat. NH$_4$Cl (10 mL) and allowed to warm to rt. The mixture was then extracted with EtOAc (3×10 mL) and the combined organics were dried over MgSO$_4$, and concentrated in vacuo. The resulting residue was dissolved in CH$_2$Cl$_2$ (15 mL) and Dess-Martin Periodinane (2.02 g, 4.74 mmol) was added at rt. After 3 hours, sat. aq. Na$_2$SO$_3$ (10 mL) and sat. aq. NaHCO$_3$ (10 mL) was added. The mixture was extracted with CHCl$_3$ (3×10 mL), washed with sat. aq. NaHCO$_3$ (10 mL), dried over MgSO$_4$, and concentrated in vacuo. The residue was purified by column chromatography (90% EtOAc/hexane) to obtain ketone 501 (730 mg, 71.6%) as a colorless oil. 501: IR (film) 2957, 2362, 1716, 1637 cm$^{-1}$; $^1$H NMR (300 MHz, CDCl$_3$) δ, 0.62–0.92 (11H, m), 1.12–1.70 (9H, m), 2.03 (2H, dd,J=14.77, 7.63 Hz), 2.24–2.71 (6H, m), 3.79 (1H, ddd,J=11.53, 5.22, 1.37 Hz), 4.10 (1H, td, J=11.88, 2.81 Hz), 4.22–4.31 (1H, m), 4.94–5.03 (2H, m), 5.68 (1H, m); $^{13}$C NMR (75 MHz, CDCl$_3$) δ, 18.82, 21.70, 22.13, 22.37, 23.62, 24.18, 28.59, 31.34, 32.95, 34.76, 37.32, 43.73, 49.33, 51.09, 58.81, 65.39, 100.73, 115.21, 138.04, 209.56; HRMS (EI) Calc'd. for C$_{20}$H$_{34}$O$_3$: 322.2508. Found: 322.2497. $[\alpha]_D^{25}$=5.52° (c 4.79, CH$_2$Cl$_2$).

502.1 (Formula 502 where R$^8$ is t-butyl)

To a solution of ketone 501 (35 mg, 0.109 mmol) in ether (0.6 mL) was added t-BuLi (1.6 M in pentane, 75 µL, 0.12 mmol) dropwise at −78° C. The mixture was stirred at rt for 30 min. and then quenched with sat. aq. NH$_4$Cl (2 mL). The mixture was allowed to warm to rt and was then extracted with EtOAc (3×5 mL). The combined organics were washed with brine, dried over Na$_2$SO$_4$, and concentrated in vacuo. Chromatography (10% EtOAc/hexane) afforded a major diastereomer A31a (17.5 mg, 42%) along with a minor diastereomer A31b. (7.4 mg, 18%) as colorless oils (structures not shown). A31a: IR (film): 2956, 1639, 1456 cm$^{-1}$; $^1$H NMR (400 MHz, CDCl$_3$) δ, 0.73 (1H, t, J=12.88 Hz), 0.89–0.94 (18H, m), 1,17–1.76 (14H, m), 2.00–2.09 (2H, m), 2.38–2.42 (1H, m), 2.73 (1H, d, J=13.73 Hz), 3.47 (1H, s), 3.79 (1H, dd, J=11.60, 5.06 Hz), 4.12 (1H, td, J=11.97, 2.44 Hz), 4.25–4.29 (1H, m), 4.91 (1H, d, J=10.17 Hz), 4.98 (1H, d, J=17.63 Hz), 5.77–5.84 (1H, m); $^{13}$C NMR (75 MHz, CDCl$_3$) δ 19.07, 22.20, 22.25, 23.15, 23.45, 24.66, 25.43, 25.52, 28.98, 31.80, 34.36, 34.51, 34.60, 36.84, 37.54, 39.29, 39.63, 51.30, 58.92, 67.73, 79.0, 101.26, 114.31, 139.03; HRMS (EI) Calc'd. for C$_{24}$H$_{44}$O$_3$: 380.3290. Found: 380.3281. $[\alpha]_D^{25}$=5.89° (c 0.85, CDCl$_3$).

To a solution of major diastereomer A31a (332 mg, 0.872 mmol) in THF (5 mL) Was added KHMDS (0.5M in toluene, 5.24 mL, 2.62 mmol) in an ice bath. TMSCl (284 mg, 2.62 mmol) was added and the mixture was stirred for 30 minutes. The mixture was quenched with sat. aq. NH$_4$Cl (5 mL) and extracted with EtOAc (3×5 mL). The combined organics were washed with brine (5 mL), dried over MgSO$_4$, and then concentrated in vacuo. Chromatography (5%

EtOAc/hexane) providing 502.1 (395 mg, 100%) as a white solid. 502.1: m.p.=60.0° C.; IR (film) 2953, 1642, 1455 cm$^{-1}$; $^1$H NMR (300 MHz, CDCl$_3$) δ, 0.132 (6H, s), 0.134 (3H, s), 0.67–1.71 (33H, m), 1.95–1.99 (2H, m), 2.36–2.46 (1H, m), 2.71 (1H, app d, J=14.3 Hz), 3.74–3.79 (1H, m), 3.88–3.94 (1H, m), 4.07 (1H, td, J=11.75, 2.96 Hz), 4.95 (1H, d, J=10.41 Hz), 5.00 (1H, d, J=17.33 Hz), 5.74–5.85 (1H, m); $^{13}$C NMR (75 MHz, CDCl$_3$) δ 2.9, 5.3, 18.9, 21.7, 22.2, 23.8, 24.3, 25.3, 26.2, 29.1, 34.2, 34.8, 35.0, 37.6, 39.2, 40.0, 51.3, 59.3, 65.6, 82.9, 100.7, 114.6, 138.7; HRMS (EI) Calc'd. for C$_{27}$H$_{52}$O$_3$Si: 452.3686. Found: 452.3670; [α]$_D^{26}$=−11.33° (c 1.56, CDCl$_3$).

503.1 (Formula 503 where R$^8$ is t-butyl)

To a solution of 502.1 (98 mg, 0.216 mmol) in CH$_2$Cl$_2$ (8 mL) and MeOH (0.5 mL) was bubbled O$_3$ at −78° C. until a blue color persists. Nitrogen gas was then used to purge the system and (EtO)$_3$P (54 mg, 0.324 mmol) was subsequently added. The mixture was stirred for 3 h and then slowly warmed to rt. Sat. aq. Na$_2$SO$_3$ (10 mL) was added and the mixture was extracted with CHCl$_3$ (3×10 mL). The combined organics were then washed with brine (10 mL), dried over MgSO$_4$ and concentrated in vacuo. Chromatography (0.5% EtOAc/hexane) afforded 503.1 (63 mg, 64.1%) as a colorless oil. 503.1: IR (film) 2941, 1715, 1454 cm$^{-1}$; $^1$H NMR (400 MHz, CDCl$_3$) δ 0.134 (9H, s), 0.73 (1H, t, J=13.13 Hz), 0.9–1.81 (32H, m), 2.34–2.42 (3H, m), 2.72 (1H, d, J=12.29 Hz), 3.77 (1H, dd, J=11.59, 4.58 Hz), 3.92–3.96 (1H, m), 4.08 (1H, td, J=12.28, 2.01 Hz), 9.77 (1H, s); $^{13}$C NMR (100 MHz, CDCl$_3$) δ, 3.39, 18.98, 19.29, 22.60, 24.23, 24.71, 26.75, 29.76, 34.41, 35.15, 37.77, 38.01, 39.66, 42.95, 45.26, 51.67, 59.64, 65.90, 83.08, 100.99, 202.26; HRMS (EI) Calc'd. for C$_{26}$H$_{50}$O$_4$Si: 454.3478. Found: 452.3475; [α]$_D^{27}$=−6.33° (c 2.9, CH$_2$Cl$_2$).

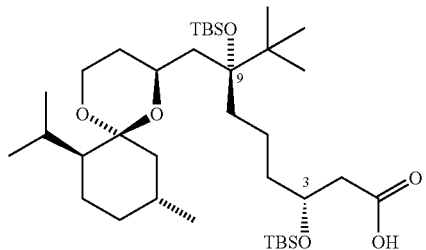

504.1 (Formula 504 where R$^8$ is t-butyl)

To (−)-Ipc$_2$BOMe (108.8 mg, 0.34 mmol) (weighed in an inert atmosphere) was added diethyl ether (340 μL). The flask was cooled to −78° C. and allylmagnesium bromide (1.0 M, 310 μL, 0.31 mmol) was added. The precipitous mixture was stirred for 15 min. at −78° C. and then slowly warmed to rt and stirred for 1 hour. Diethyl ether (340 mL) was added and then a pre-cooled solution of aldehyde 503.1 (40.1 mg, 0.109 mmol) in diethyl ether (160 μL) was added dropwise. The suspension was stirred for 1 h, then the temperature was slowly raised to rt and 3N NaOH (240 μL), 30% hydrogen peroxide (100 μL) and diethyl ether (400 μL) was added. The biphasic mixture was refluxed for 1 h and then quenched with water (9 mL) and extracted with ethyl acetate (4×10 mL). The combined organics were washed with brine (10 mL), dried over sodium sulfate and the solvent was removed in vacuo. Chromatography on silica gel (12.5% EtOAc/hexane) afforded the crude homoallylic alcohol as a yellow oil. To this oil in methylene chloride (500 μL) was added imidazole (19 mg, 0.276 mmol) and TBSCl (21 mg, 0.138 mmol). The reaction was sealed and stirred for 14 h. The reaction was then quenched with a saturated solution of sodium bicarbonate (2 mL) and extracted with ethyl acetate (3×5 mL). The combined organics were washed with brine (5 mL), dried over sodium sulfate, filtered and the solvent was removed in vacuo. Filtration over silica gel (5% EtOAc/hexane) afforded a crude silyl ether A34 as a yellow oil (structure not shown). A34: IR (film) 2956, 1644, 1462 cm$^{-1}$; $^1$H NMR (400 MHz, CDCl$_3$) δ 0.05 (6H, s), 0.05 (9H, s), 0.7–1.70 (42H, m), 2.21 (2H, d, J=6.48 Hz), 2.38–2.44 (2H, m), 2.72 (2H, d, J=13.36 Hz), 3.71 (1H, t, J=5.43 Hz), 3.77 (1H, dd, J=11.53, 3.59 Hz), 3.88–3.93 (1H, m), 4.07 (1H, td, J=11.91, 3.06 Hz), 5.02 (1H, s), 5.06 (1H, d, J=3.66 Hz), 5.77–5.88 (1H, m); $^{13}$C NMR (100 MHz, CDCl$_3$) δ −4.06, 3.39, 19.38, 21.48, 22.23, 22.72, 24.25, 24.78, 26.27, 26.69, 29.52, 34.58, 35.25, 38.06, 38.38, 38.50, 39.68, 42.02, 43.11, 59.68, 51.72, 65.98, 72.08, 83.20, 100.98, 117.06, 135.66; [α]$_D$=−4.18° (c 1.0, CDCl$_3$).

To crude silyl ether A34 in t-butanol (2.3 mL), water (1.4 mL) and pH 7 phosphate buffer (465 μL) was added NaIO$_4$ (79 mg, 0.368 mmol) followed by KMnO$_4$ (2.9 mg, 0.0184 mmol). The purple solution was stirred for 3 h and then water (3 mL) was added. This mixture was then extracted with ethyl acetate (4×5 mL) and the combined organics were washed with brine (5 mL), dried over sodium sulfate and filtered. The solvent was removed in vacuo and chromatography on silica gel (12.5% EtOAc, 0.1% acetic acid/hexanes) afforded acid 504.1 as well as the β-C3 diastereomeric alcohol. 504.1: IR (film): 3433, 2956, 1712, 1461 cm$^{-1}$; $^1$H NMR (400 MHz, CDCl$_3$) δ 0.08 (3H, s), 0.09 (3H, s), 0.13 (6H, s), 0.70–1.70 (48H, m), 2.35–2.55 (3H, m), 2.72 (1H, d, J=12.74 Hz), 3.78 (1H, dd, J=11.34, 3.97 Hz,), 3.90–3.92 (1H, m), 4.75 (1H, dd, J=12.45, 11.97 Hz), 4.15 (1H, t, J=4.89 Hz); $^{13}$C NMR (100 MHz, CDCl$_3$) δ −4.53, −4.10, 3.39, 18.32, 19.39, 21.29, 22.29, 22.66, 24.23, 24.75, 26.12, 26,72, 29.64, 34.49, 35.19, 38.04, 38.38, 38.81, 39.71, 42.11, 43.08, 51.67, 59,65, 65.93, 69.51, 83.10, 101.01, 176.69; [α]$_D^{28}$=−8.19° (c 2.70, CDCl$_3$).

2D. 9-t-Butyl L4 Linker Synthon 508

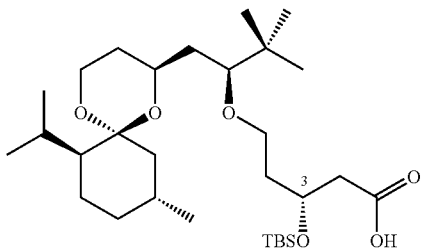

508.1 (Formula 508 where R$^8$ is t-butyl)

To (−)-Ipc$_2$BOMe (108.8 mg, 0.34 mmol) (weighed in an inert atmosphere) was added diethyl ether (340 μL). The flask was cooled to −78° C. and allylmagnesium bromide (1.0 M, 310 μL, 0.31 mmol) was added. The precipitous mixture was stirred for 15 min. at −78° C. and then slowly warmed to rt and stirred for 1 hour. Diethyl ether (340 mL) was added and then a pre-cooled solution of an aldehyde 506(0.109 mmol) (structure not shown) prepared as described for compound 10 in Wender et al. (1998c) in diethyl ether (160 μL) was added dropwise. The suspension was stirred for 1 h, then the temperature was slowly raised to rt and 3N NaOH (240 μL), 30% hydrogen peroxide (100 μL) and diethyl ether (400 μL) was added. The biphasic mixture was refluxed for 1 h and then quenched with water (9 mL) and extracted with ethyl acetate (4×10 mL). The combined organics were washed with brine (10 mL), dried over sodium sulfate and the solvent was removed in vacuo. Chromatography on silica gel (12.5% EtOAc/hexane) afforded the crude homoallylic alcohol as a yellow oil. To this oil in methylene chloride (500 μL) was added imidazole (19 mg, 0.276 mmol) and TBSCl (21 mg, 0.138 mmol). The reaction was sealed and stirred for 14 h. The reaction was then quenched with a saturated solution of sodium bicarbonate (2 mL) and extracted with ethyl acetate (3×5 mL). The combined organics were washed with brine (5 mL), dried over sodium sulfate, filtered and the solvent was removed in vacuo. Filtration over silica gel (5% EtOAc/hexane) afforded a crude silyl ether as a yellow oil. To this oil in t-butanol (2.3 mL), water (1.4 mL) and pH 7 phosphate buffer (465 μL) was added NaIO$_4$ (79 mg, 0.368 mmol) followed by KMnO$_4$ (2.9 mg, 0.0184 mmol). The purple solution was stirred for 3 h and then water (3 mL) was added. This mixture was then extracted with ethyl acetate (4×5 mL) and the combined organics were washed with brine (5 mL), dried over sodium sulfate and filtered. The solvent was removed in vacuo and chromatography on silica gel (12.5% EtOAc, 0.1% acetic acid/hexanes) afforded acid 508.1 (34 mg, 56%) as a colorless oil. 508.1: Rf (15% ethyl acetate/hexanes)=0.17; IR (film) 2700–3300, 2954, 2869, 1713, 1107, 837, 776 cm$^{-1}$; $^1$H NMR (300 MHz, CDCl$_3$) δ 0.08 (6H, s), 0.69 (1H, t, J=13.1 Hz), 0.76–0.90 (27H, m), 1.17–1.25 (3H, m), 1.39–1.61 (6H, m), 1.70–1.82 (3H, m), 2.40 (1H, dsept, J=7.2, 0.9 Hz), 2.58 (1H, dd, J=13.1, 5.6 Hz), 2.68 (1H, br d, J=12.6 Hz), 2.91 (1H, t, J=4.8 Hz), 3.41 (1H, dd, J=5.9, 2.3 Hz), 3.63–3.77 (2H, m), 3.82 (1H, dd, J=11.7, 4.2 Hz), 4.066 (1H, td, J=12.0, 2.7 Hz), 4.23–4.29 (1H, m), 9.20–9.40 (1H, br s); $^{13}$C NMR (100 MHz, C$_6$D$_6$) δ −5.1, −4.8, 17.8, 18.9, 21.9, 22.1, 23.7, 24.3, 25.6, 26.0, 29.1, 31.8, 34.9, 35.7, 37.3, 38.7, 41.8, 51.3, 59.2, 66.6, 66.9, 67.2, 84.5, 174.7; HRMS (FAB) Calc'd. for C$_{30}$H$_{58}$O$_6$Si: 542.4002, Found: 542.4005; [α]$_D^{22}$=−5.88° (c 1.67, CH$_2$Cl$_2$).

2E. Linker Synthon 507

To (−)-Ipc$_2$BOMe (108.8 mg, 0.34 mmol) (weighed in an inert atmosphere) was added diethyl ether (340 μL). The flask was cooled to −78° C. and allylmagnesium bromide (1.0 M, 310 μL, 0.31 mmol) was added. The precipitous mixture was stirred for 15 min. at −78° C. and then slowly warmed to rt and stirred for 1 hour. Diethyl ether (340 mL) was added and then a pre-cooled solution of an aldehyde 506 (0.109 mmol) (structure not shown) prepared as described for compound 9 in Wender et al. (1998c) in diethyl ether (160 μL) was added dropwise. The suspension was stirred for 1 h, then the temperature was slowly raised to rt and 3N NaOH (240 μL), 30% hydrogen peroxide (100 μL) and diethyl ether (400 μL) was added. The biphasic mixture was refluxed for 1 h and then quenched with water (9 mL) and extracted with ethyl acetate (4×10 mL). The combined organics were washed with brine (10 mL), dried over sodium sulfate and the solvent was removed in vacuo. Chromatography on silica gel (12.5% EtOAc/hexane) afforded the crude homoallylic alcohol A40 (structure not shown) as a yellow oil. Rf (35% ethyl acetate/hexanes)=0.65; IR (film) 3455, 2950, 2868, 1456, 1373, 1308, 1265, 1110, 997 cm$^{-1}$; $^1$H NMR (300 MHz, CDCl$_3$) δ 0.68 (1H, t, J=13.5 Hz), 0.83–0.92 (10H, m), 1.39–1.52 (5H, m), 1.57–1.72 (3H, m), 1.71 (1H, d, J=4.9 Hz), 2.24 (1H, t, J=4.9 Hz), 2.35–2.42 (2H, m), 2.70 (3H, br d, J=12.4 Hz), 3.46–3.60 (3H, m), 3.62–3.70 (1H, m), 3.77–3.95 (3H, m), 4.11 (1H, dd, J=11.9, 2.7 Hz), 5.07 (2H, dd, J=9.5, 1.9 Hz), 5.70–5.91 (1H, m); $^{13}$C NMR (100 MHz, CDCl$_3$) δ 13.9, 16.4, 17.5, 21.1, 22.0, 23.1, 29.1, 30.7, 31.1, 31.8, 33.7, 37.3, 46.1, 51.1, 56.9, 64.7, 65.0, 66.8, 113.3, 129.3; [α]$_D^{20}$=2.5° (c 0.8, CDCl$_3$).

To A40 in methylene chloride (500 μL) was added imidazole (19 mg, 0.276 mmol) and TBSCl (21 mg, 0.138 mmol). The reaction was sealed and stirred for 14 h. The reaction was then quenched with a saturated solution of sodium bicarbonate (2 mL) and extracted with ethyl acetate (3×5 mL). The combined organics were washed with brine (5 mL), dried over sodium sulfate, filtered and the solvent was removed in vacuo. Filtration over silica gel (5% EtOAc/hexane) afforded a crude silyl ether A41 (structure not shown) as a yellow oil. Rf (35% ethyl acetate/hexanes)=0.65; IR (film): 2953, 2864, 1641, 1472, 1372, 1255, 1108, 830 cm$^{-1}$; $^1$H NMR (300 MHz, CDCl$_3$) δ 0.05 (3H, s), 0.05 (3H, s), 0.67 (1H, t, J=13.5 Hz), 0.81–0.96 (18H, m), 1.11–1.20 (1H, m), 1.35–1.47 (4H, m), 1.52–1.71 (5H, m), 2.22 (1H, br s), 2.35–2.42 (2H, m), 2.70 (3H, br d, J=12.2 Hz), 3.38–3.54 (4H, m), 3.78–3.97 (3H, m), 4.10 (1H, dd, J=11.9, 2.8 Hz), 5.05 (2H, dd, J=9.4, 1.8 Hz), 5.69–5.91 (1H, m); $^{13}$C NMR (100 MHz, CDCl$_3$) δ −9.5, −9.1, 13.3, 14.1, 17.1, 17.5, 18.9, 19.5, 21.1, 24.1, 27.0, 30.2, 31.8, 32.0, 32.6, 37.5, 46.4, 54.4, 59.5, 61.9, 62.8, 64.1, 95.6, 112.0, 130.0; [α]$_D^{20}$=16.2° (c 1.0, CH$_2$Cl$_2$).

To A41 in t-butanol (2.3 mL), water (1.4 mL) and pH 7 phosphate buffer (465 μL) was added NaIO$_4$ (79 mg, 0.368 mmol) followed by KMnO$_4$ (2.9 mg, 0.0184 mmol). The purple solution was stirred for 3 h and then water (3 mL) was added. This mixture was then extracted with ethyl acetate (4×5 mL) and the combined organics were washed with brine (5 mL), dried over sodium sulfate and filtered. The solvent was removed in vacuo and chromatography on silica gel (12.5% EtOAc, 0.1% acetic acid/hexanes) afforded acid 507. IR (film): 2700–3300, 2952, 2866, 1738, 1471, 1373, 1307, 1146, 1103, 837, cm$^{-1}$; $^1$H NMR (300 MHz, CDCl$_3$) δ 0.06 (3H, s), 0.07 (3H, s), 0.67 (1H, app t, J=13.1 Hz), 0.81–0.89 (19H, m), 1.14–1.20 (1H, m), 1.35–1.47 (5H, m), 1.50–1.82 (4H, m), 2.34–2.41 (1H, m), 2.45–2.53 (2H, m), 2.69 (3H, br d, J=13.7 Hz), 3.44–3.51 (4H, m), 3.80 (1H, dd, J=11.5, 3.9 Hz), 3.87–3.95 (1H, m), 4.02–4.09 (1H, m), 4.22–4.29 (1H, m); $^{13}$C NMR (100 MHz, CDCl$_3$) δ −9.6, 13.1, 14.1, 17.1, 17.5, 18.9, 19.5, 20.9, 24.2, 26.9, 30.1, 32.0, 32.3, 32.6, 37.7, 46.4, 54.3, 59.6, 61.9, 62.1, 95.7, 171.5; HRMS (FAB) Calc'd. for C$_{26}$H$_{50}$O$_6$Si: 486.3379, Found: 486.3377; [α]$_D^{20}$=9.4° (c 1.3, CH$_2$Cl$_2$).

2F. Ether Diester Linker Synthon 606

The following procedure, referred to as the "general isolation procedure", was used to purify various reaction products below. The reaction mixture is quenched by dropwise addition of saturated aqueous ammonium chloride, and the resultant mixture is allowed to partition between solvent and brine or water. The aqueous layer is extracted with 1 to 3 portions of ethyl acetate. The combined organic extracts are dried over sodium sulfate and concentrated in vacuo.

Formula 602

To a solution of 3-p-methoxybenzyloxy)propyl allyl ether 601 (1.0 g, 4.3 mmol) in THF (10 mL) was added 9-BBN (20.6 mL of 0.5 M solution in THF, 10.3 mmol), and the mixture was stirred for 2 h at rt. Hydrogen peroxide (30%, 10 mL) and sodium hydroxide (15%, 10 mL) were added and the mixture was stirred for 3 h. The general isolation procedure afforded crude product which was purified further by silica gel chromatography to give the expected purified alcohol A51 (870 mg, 75%) (structure not shown). $R_f$=0.25 (50% ethyl acetate in hexane); IR (neat)=3423, 2934, 2864, 1612, 1513, 1248, 1098 cm$^{-1}$; $^1$H NMR (300 MHz, CDCl$_3$) δ 7.25 (d, J=8.7 Hz, 2H), 6.87 (d, J=8.7 Hz, 2H), 4.43 (s, 2H), 3.80 (s, 3H), 3.75 (q, J=5.7 Hz, 2H), 3.60 (t, J=5.7 Hz, 2H), 3.52 (m, 4H), 2.46 (br t, 1H), 1.84 (m, 4H); $^{13}$C NMR (75 MHz, CDCl$_3$) δ 129.36, 113.83, 72.63, 70.34, 68.33, 66.89, 62.20, 55.23, 31.88, 29.96.

To a solution of DMSO (1.38 mL, 19.5 mmol) in methylene chloride (5 mL) at −78° C. was added oxalyl chloride (850:L, 9.74 mmol) dropwise. After 5 min, alcohol A51 from the preceding step (870 mg, 6.49 mmol) in methylene chloride (2 mL) was added and the mixture was stirred for another 20 min. TEA (triethylamine, 4.31 mL, 32.5 mmol) was added. After 10 min, the mixture was warmed to rt. The standard isolation procedure afforded the expected aldehyde 602 (760 mg, 89%). $R_f$=0.40 (33% ethyl acetate in hexane); IR (neat)=2863, 1724, 1612, 1513, 1248, 1098 cm$^{-1}$; $^1$H NMR (300 MHz, CDCl$_3$) δ 9.75 (s, 1H), 7.25 (d, J=9.0 Hz, 2H), 6.87 (d, J=9.0 Hz, 2H), 4.42 (s, 2H), 3.80 (s, 3H), 3.74 (t, J=6.0 Hz, 2H), 3.51 (m, 4H), 2.62 (m, 2H), 1.84 (quint, J=6.3 Hz, 2H); $^{13}$C NMR (75 MHz, CDCl$_3$) δ 201.49, 159.26, 130.65, 129.31, 113.78, 72.57, 68.08, 66.69, 64.40, 55.19, 43.75, 29.86.

Formula 603

(−)-Ipc$_2$BOMe (1.91 g, 6.04 mmol) in ether (4 mL) was treated with allylmagnesium bromide (4.83 mL, 4.83 mmol) at rt. After 30 min, the mixture was cooled to −78° C. The aldehyde 602 (370 mg, 2.76 mmol) in ether (1.5 mL) was added and stirred for 2 h at −78° C. 15% NaOH (1.5 mL) and 30% hydrogen peroxide (1.5 mL) were added and the mixture was warmed to rt. After 2 h, the mixture was diluted with ethyl acetate and washed with brine. Column chromatography yielded the expected alcohol A53 (383 mg, 80%) (structure not shown). Alcohol A53 (150 mg, 0.852 mmol) in methylene chloride (4 mL) was treated with TBSCl (168 mg, 1.11 mmol) and imidazole (116 mg, 1.7 mmol) at rt. After overnight, the reaction was worked up by the standard procedure. Column chromatography afforded expected TBS alkene ether 603 (195 mg, 79%). 603: $R_f$=0.50 (10% ethyl acetate in hexane); [α]$^{25}_D$=13.6° (c 1.08, CH$_2$Cl$_2$); IR (neat)=2952, 2856, 1717, 1613, 1513, 1471, 1362, 1248, 1110 cm$^{-1}$; $^1$H NMR (400 MHz, CDCl$_3$) δ 7.26 (d, J=8.4 Hz, 2H), 6.88 (d, J=8.4 Hz, 2H), 5.81 (m, 1H), 5.04 (m, 2H), 4.43 (s, 2H), 3.86 (s, 3H), 3.49 (m, 7H), 2.23 (m, 2H), 1.87 (m, 2H), 1.69 (m, 2H), 0.89 (s, 9H), 0.06 (s, 3H), 0.05 (s, 3H); $^{13}$C NMR (100 MHz, CDCl$_3$) δ 159.09, 134.96, 130.60, 116.93, 113.71, 72.59, 68.91, 67.80, 67.48, 67.18, 55.23, 42.28, 36.62, 30.16, 25.85, 18.08, −4.39, −4.76

Formula 605

Alkene ether 603 (195 mg, 0.672 mmol) in tert-butanol-water (pH 7) (1:1, 4 mL) was treated with KMnO$_4$ (11 mg, 0.0672 mmol) and sodium periodate (548 mg, 2.56 mmol) in water (0.5 mL). After 30 min, the reaction was quenched with sodium thiosulfate. The mixture was diluted with ethyl acetate. The organic layer was washed with brine, dried over sodium sulfate, and concentrated to give a crude acid 604.

The crude acid in. methylene chloride (3 mL) was treated with SEMCl (2-(trimethylsilyl)ethoxymethyl chloride, 301:L, 1.7 mmol) and TEA (452:L, 3.4 mmol) at rt and stirred for 2 h. The reaction was worked up by the standard procedure to afford the expected SEM ester 605.

SEM ester 605 in wet methylene chloride (3 mL) was treated with DDQ (291 mg, 1.28 mmol). After 1 h, the mixture was directly purified by silica gel chromatography to give the alcohol product 606 (86 mg, 29% for 3 steps). 606: $R_f$=0.25 (25% ethyl acetate in hexane); [α]$^{25}_D$=0.4° (c 0.82, CH$_2$Cl$_2$); IR (neat)=3458, 2955, 1741, 1472, 1378, 1250, 1116 cm$^{-1}$; $^1$H NMR (400 MHz, CDCl$_3$) δ 5.25 (q, J=2.8 Hz, 2H), 4.25 (quint, J=6.4 Hz, 2H), 3.71 (m, 4H), 3.52 (m, 4H), 2.50 (d, J=6.0 Hz, 2H), 2.44 (br, 1H), 1.79 (m, 4H), 0.94 (t, J=8.4 Hz, 2H), 0.85 (s, 9H), 0.05 (s, 3H), 0.03 (s, 3H), 0.00 (s, 9H); $^{13}$C NMR (100 MHz, CDCl$_3$) δ 171.04, 88.97, 69.88, 67.88, 67.25, 66.45, 61.81, 42.84, 37.12, 32.02, 25.71, 17.97, 17.91, −1.48, −4.81, −4.86

2G. C5 Ester-Open C7 Linker Synthon 513

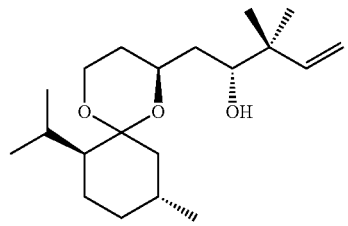

509a

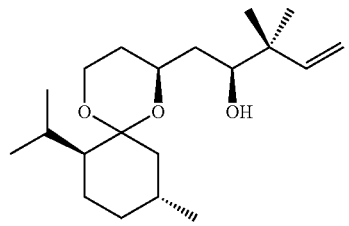

509b

To menthone aldehyde 402 (400 mg, 1.56 mmol) from Example 2A in DMF (12 mL) was added prenyl bromide (396 mg, 1.56 mmol) followed by indium powder (359 mg, 3.13 mmol) at rt. After 30 min., the reaction was diluted with EtOAc (20 mL) and saturated aqueous ammonium chloride (15 mL). The layers were separated and the aqueous layer was re-extracted with EtOAc (3×10 mL). The combined organics were washed with brine (15 mL) and dried over sodium sulfate. The solvent was removed in vacuo and chromatography (7.5% EtOAc/pentane) to afford 509a (105 mg, 21%) and 509b (321 mg, 63%).

Undesired isomer 509a can be recycled by the following procedure: To 509a (320.8 mg, 0.98 mmol) in methylene chloride (3 mL) was added Dess-Martin Periodinane (707 mg, 1.67 mmol) and stirred for 1 h at room temperature. The reaction was diluted with methylene chloride (3 mL), saturated sodium bicarbonate (3 mL) and sodium thiosulfate (3 mL) and stirred for 1 h. The layers were separated and the aqueous layer was re-extracted with EtOAc (4×5 mL). The combined organics were dried over sodium sulfate and the solvent was removed in vacuo. The crude ketone was dissolved in MeOH (17.3 mL) and CeCl$_3$.7H$_2$O (1.83 g, 4.9 mmol) was added and stirred for 5 min. The solution was cooled to −50° C. and NaBH$_4$ (74.5 mg, 19.6 mmol) was added. The reaction was stirred for 30 min. and then poured into a separatory funnel containing EtOAc (30 mL), water (18 mL) and brine (30 mL). The layers were separated and the aqueous layer was extracted with EtOAc (3×10 mL). The combined organics were dried over sodium sulfate and the solvent was removed in vacuo. Chromatography (7.5%–20% EtOAc/pentane) provided 509b (177 mg, 53%) and 509a (56 mg, 18%). 509a: $R_f$ (7.5% EtOAc/pentane)= 0.186; IR (film): 3496.8, 2953.9, 2869.6, 1458.0, 1374.4, 1308.3, 1266.5, 1157.8, 1130.7, 1102.0, 977.6, 912.2 cm$^{-1}$; $^1$H-NMR (300 MHz, CDCl$_3$) δ 0.68 (1H, t, J=12.9 Hz), 0.85–0.89 (9H, m), 0.98 (3H, s), 0.99 (3H, s), 1.14–1.76 (10H, m), 2.38 (1H, sept, J=6.9 Hz), 2.73 (1H, br. d, J=13.5 Hz), 3.59 (1H, br. d, J=9.9 Hz), 3.78 (1H, dd, J=11.7, 5.4 Hz), 4.02 (1H, d, J=11.4), 4.11 (1H, d, J=13.2), 5.00–5.09 (2H, m), 5.81 (1H, dd, J=17.6, 11.0 Hz); $^{13}$C-NMR (75 MHz, CDCl$_3$) δ 18.8, 21.7, 22.0, 22.4, 23.1, 23.8, 24.3, 29.1, 31.9, 34.9, 37.4, 38.5, 41.2, 51.2, 59.1, 64.5, 73.5, 100.4, 113.2, 145.4; HRMS calc'd for $C_{20}H_{36}O_3$: 324.2664; found: 324.2664; $[\alpha]^{24.0}_d$:+19.36° (c 8.16, CH$_2$Cl$_2$). 509b: $R_f$(7.5% EtOAc/pentane)=0.37; IR (film): 3520.4, 2953.6, 2870.2, 1455.8, 1375.6, 1309.4, 1266.0, 1130.3, 1090.0, 973.3, 914.4 cm$^{-1}$; $^1$H-NMR (300 MHz, CDCl$_3$) δ 0.73 (1H, t, J=13 Hz), 0.83–0.92 (9H, m), 1.00 (3H, s), 1.01 (3H, s), 1.18–1.77 (10H, m), 2.39 (1H, sept, J=7 Hz), 2.73 (1H, br. d, J=13.5 Hz), 3.53 (1H, d, J=9.9 Hz), 3.57 (1H, s), 3.79 (1H, dd, J=11.7, 4.8 Hz), 4.00–4.15 (2H, m), 4.96–5.02 (2H, m), 5.87 (1H, dd, J=17.1, 1.1 Hz); $^{13}$C-NMR (75 MHz, CDCl$_3$) δ 18.9, 21.9, 22.2, 22.3, 23.3, 23.8, 24.2, 28.9, 31.8, 34.6, 37.3, 38.0, 41.1, 50.9, 58.8, 70.3, 78.9, 101.0, 111.9, 145.7; HRMS calc'd for $C_{20}H_{36}O_3$: 324.2664; found: 324.2665; $[\alpha]^{25.1}_d$: −1.94° (c 9.75, CH$_2$Cl$_2$).

Formula 510

To a solution of 509b (282 mg, 0.87 mmol) in MeOH (3.3 mL) and methylene chloride (13 mL) at −78° C. was bubbled ozone for 5 min. or until a blue color persisted. The solution was then purged with nitrogen for 5 min. NaBH$_4$ (138 mg, 3.65 mmol) was then added and stirred for 1 h at −78° C., and 2 h at 0° C. Saturated ammonium chloride (15 mL) and water (5 mL) were then poured into the reaction and the layers were separated. The aqueous layer was extracted with methylene chloride (4×5 mL). The combined organics were dried over sodium sulfate and the solvent was removed in vacuo, yielding crude diol 510: $R_f$ (20% EtOAc/pentane)=0.195; IR (film): 3452.3, 2954.1, 2871.3, 1455.5, 1383.4, 1308.9, 1266.9, 1131.4, 1047.2, 972.6 cm$^{-1}$; $^1$H-NMR (300 MHz, CDCl$_3$) δ 0.74 (1H, t, J=13 Hz), 0.85–0.89 (12H, m), 0.92 (3H, d, J=6.6 Hz), 1.12–1.25 (2H, m), 1.39–1.78 (7H, m), 2.39 (1H, sept, J=6.9 Hz), 2.73 (1H, br. d, J=13.5 Hz), 3.48 (3H, m), 3.70–3.73 (1H, m), 3.80 (1H, dd, J=11.4, 5.1 Hz), 4.08–4.15 (3H, m); $^{13}$C-NMR (75 MHz, CDCl$_3$) δ 18.8, 19.0, 22.2, 22.3, 22.5, 23.7, 24.2, 29.0, 31.8, 34.5, 37.3, 37.6, 38.0, 50.9, 58.8, 70.6, 72.0, 80.5, 101.0; HRMS calc'd for $C_{19}H_{36}O_4$: 328.2614; found: 328.2619; $[\alpha]^{26.0}_d$: −0.78° (c 5.48, CH$_2$Cl$_2$).

Formula 511

To crude diol 510 was added pyridine (316 µL, 3.91 mmol) and chloroacetic anhydride (229 mg, 1.3 mmol) at −78° C. and stirred for 2 hr. Saturated aqueous sodium bicarbonate (10 mL) was added and the layers were separated. The aqueous layer was extracted with methylene chloride (3×5 mL). The combined organics were dried over sodium sulfate and the solvent was removed in vacuo. Chromatography (10%–20%–30% EtOAc/pentane) provided residual starting material A61 (89.8 mg, 31%) and chloroacetate ester 511 (152.5 mg, 44%). 511: $R_f$ (20% EtOAc/pentane)=0.56; IR (film): 3515.2, 2954.4, 2871.9, 1738.5, 1455.8, 1371.6, 1308.7, 1132.8, 972.7 cm$^{-1}$; $^1$H-NMR (300 MHz, CDCl$_3$) δ 0.75 (1H, t, J=13.2 Hz), 0.87 (3H, d, J=2.7 Hz), 0.89 (3H, d, J=3 Hz), 0.92–0.93 (10H, m), 1.19–1.26 (2H, m), 1.39–1.79 (7H, m), 2.40 (1H, quin, J=6.9 Hz), 2.74 (1H, br. d, J=13.2 Hz), 3.65–3.66 (2H, m), 3.81 (1H, dd, J=11.6, 4.7 Hz), 4.00–4.17 (4H, m), 4.07 (2H, s); $^{13}$C-NMR (75 MHz, CDCl$_3$) δ 18.9, 19.3, 21.4, 22.2, 22.3, 23.8, 24.2, 29.0, 31.8, 34.5, 37.3, 37.4, 38.2, 40.9, 50.9, 58.8, 70.5, 71.6, 76.1, 101.0, 167.3; HRMS calc'd for $C_{21}H_{37}ClO_5$: 404.2330; found: 404.2329; $[\alpha]^{24.3}_d$: +4.95° (c 3.43, CH$_2$Cl$_2$)

Formula 512

To acid 28 (structure not shown) prepared as described in Theisen et al. (1998) (hydrogen (3R,1'R)-1-(1'-naphthyl) ethyl 3-[(tert-butyldimethylsilyl)oxy] pentanedioate, 309 mg, 0.744 mmol) in toluene (6 mL) was added triethylamine (263 µL, 1.98 mmol) followed by the Yamaguchi reagent (124 µL, 0.79 mmol) and stirred for 2 hr at room temperature. DMAP (303 mg, 2.50 mmol) was then added followed by 511 (190 mg, 0.469 mmol) and the mixture was stirred for 45 min. The reaction was then diluted with EtOAc (5 mL) and saturated aqueous sodium bicarbonate (10 mL) was added. The layers were separated and the aqueous layer was extracted with EtOAc (3×5 mL). The combined organics were washed with saturated aqueous ammonium chloride (10 mL), the layers were separated and the aqueous layer was extracted with EtOAc (2×5 mL). The combined organics were dried over sodium sulfate and the solvent was removed in vacuo. Chromatography (5%–10% EtOAc/pentane) provided 512 (311.9 mg, 83%): $R_f$ (10% EtOAc/pentane)=0.46; IR (film): 2953.8, 2868.2, 1738.1, 1471.9, 1373.6, 1307.9, 1258.5, 1160.3, 1108.7, 1069.3, 977.5, 837.0, 777.9 cm$^{-1}$; $^1$H-NMR (500 MHz, CDCl$_3$) δ 0.04 (3H, s), 0.12 (3H, s), 0.61 (1H, t, J=13.2 Hz), 0.79 (9H, s), 0.82–0.92 (9H, m), 0.94 (3H, s), 0.95 (3H, s), 1.12–1.15 (1H, m), 1.35–1.47 (1H, m), 1.56–1.65 (4H, m), 1.69 (3H, d, J=6.5 Hz), 1.72–1.79 (1H, m), 2.37 (1H, quin, J=6.9 Hz), 2.56–2.63 (4H, m), 2.68 (1H, dd, J=15.3, 5.3 Hz), 3.64–3.68 (1H, m), 3.76 (1H, dd, J=11.8, 4.8 Hz), 3.86 (1H, d, J=11 Hz), 3.97 (1H, td, J=12.6, 1.8 Hz), 4.01 (1H, d, J=11 Hz), 4.05 (2H, s), 4.51 (1H, quin, J=6 Hz), 4.98 (1H, dd, J=9.5, 1.0 Hz), 6.64 (1H, q, J=6.5 Hz), 7.42–7.53 (3H, m), 7.57 (1H, d, J=7.0 Hz), 7.78 (1H, d, J=8.0 Hz), 7.85 (1H, d, J=8.5 Hz), 8.06 (1H, d, J=8.5 Hz)); $^{13}$C-NMR (125 MHz, CDCl$_3$) δ −5.1, −4.8, 14.2, 17.8, 19.0, 20.3, 21.4, 21.7, 21.8, 22.3, 23.7, 24.3, 25.6, 28.8, 31.0, 34.9, 37.2, 37.3, 38.1, 40.7, 41.8, 42.1, 51.1, 58.9, 65.6, 65.7, 69.7, 70.9, 73.0, 100.5, 123.1, 123.2, 125.3, 125.6, 126.2, 128.4, 128.8, 130.1, 133.8, 137.3, 167.1, 170.1, 170.4; HRMS calc'd for $C_{44}H_{67}ClO_9Si$ (+1Na): 825.4149; found: 825.4141; $[\alpha]^{25.5}_d$: −2.17° (c 8.42, CH$_2$Cl$_2$).

Formula 513

To 512 (156 mg, 0.194 mmol) in EtOAc (4.4 mL) at room temperature was added Pd(OH)$_2$/C (75 mg). The black slurry was stirred and the flask was evacuated and refilled with hydrogen (5 times). After 5.5 h under 1 atm. of hydrogen, the reaction was poured directly onto a silica column pre-packed with pentane and eluted (20% EtOAc+ 1% AcOH/pentane) to provide 119 mg of linker synthon 513 in 95% yield. 513: $R_f$ (20% EtOAc+1% AcOH/pentane)

=0.27; IR (film): 2800.0–3422.4, 2954.1, 2866.6, 1738.3, 1714.1, 1473.1, 1375.8, 1308.0, 1258.4, 1159.6, 1107.3, 977.0, 837.3, 778.8 cm$^{-1}$; $^1$H-NMR (300 MHz, CDCl$_3$) δ 0.08 (3H, s), 0.09 (3H, s), 0.66 (1H, t, J=13.0 Hz), 0.85–0.92 (19H, m), 0.95 (3H, s), 0.97 (3H, s), 1.06–1.25 (1H, m), 1.33–1.50 (4H, m), 1.58–1.81 (4H, m), 2.37 (1H, dsept, J=6.6, 1.2 Hz), 2.53 (1H, dd, J=15.3, 6.9 Hz), 2.58–2.60 (3H, m), 2.66 (1H, dd, J=15.0, 4.8 Hz), 3.64–3.68 (1H, m), 3.79 (1H, dd, J=11.7, 4.2 Hz), 3.86 (1H, d, J=11.1 Hz), 3.98–4.03 (1H, m), 4.00 (1H, d, J=11.1 Hz), 4.06 (2H, s), 4.49 (1H, quin, J=5.9 Hz), 4.98 (1H, dd, J=9.6, 1.8 Hz)); $^{13}$C-NMR (75 MHz, CDCl$_3$) δ −5.1, −4.8, 17.9, 19.0, 20.3, 21.4, 21.7, 22.3, 23.7, 24.3, 25.7, 28.8, 31.1, 34.9, 37.3, 37.4, 38.2, 40.7, 41.9, 42.0, 51.1, 58.9, 65.7, 65.7, 70.9, 73.3, 100.6, 167.2, 170.2, 176.4; HRMS calc'd for C$_{32}$H$_{57}$ClO$_9$Si (+1Na): 671.3348; found: 671.3358; [α]$^{27.4}_d$: −20.46° (c 7.46, CH$_2$Cl$_2$).

Example 3

Exemplary Bryostatin Analogues

3A. Formula II-C26 Des-Methyl Bryostatin Analogue (702)

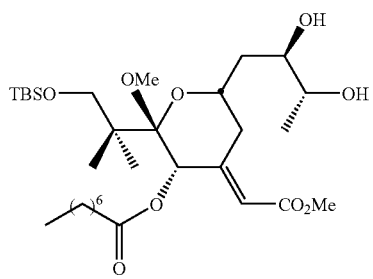

201.1 (Formula 201 where R$^{20}$ is
—O—CO—C$_7$H$_{15}$ and R$^{21}$ is =CH—CO$_2$Me)

To di-benzyl ether 111.1 (Example 1C, 503 mg, 0.169 mmol) in EtOAc (12.3 mL) at room temperature is added Pd(OH)$_2$/C (82 mg). The black slurry was stirred vigorously and the flask was evacuated and refilled 4 times with hydrogen (1 atm). After 1 h, the reaction was poured directly onto a silica column and eluted (50% EtOAc/pentane to 100% EtOAc) to provide 201.1 (240.2 mg, 65%) as a colorless oil.

201.1: R$_f$ (50% EtOAc/pentane)=0.36; IR (film)=3424, 2955, 2930, 2857, 1748, 1722, 1156, 1081, 837, 776 cm$^{-1}$; $^1$H NMR (300 MHz, CDCl$_3$) δ 0.00 (6H, s), 0.84–0.93 (12H, m), 0.96 (3H, s), 0.98 (3H, s), 1.20 (3H, d, J=6.0 Hz), 1.15–1.38 (10H, m), 1.62 (1H, t, J=7.1 Hz), 1.71 (1H, t, J=5.7 Hz), 2.25–2.45 (2H, m), 2.54 (1H, s), 2.89 (1H, d, J=4.2 Hz), 3.34–3.48 (1H, m), 3.36 (3H, s), 3.52 (2H, dd, J=15.9, 9.6 Hz), 3.58–3.76 (3H, m), 3.67 (3H, s), 4.14–4.26 (1H, m), 5.55 (1H, s), 5.89 (1H, s); $^{13}$C NMR (75 MHz, CDCl$_3$) δ −5.5, 14.0, 18.4, 19.4, 20.7, 22.5, 24.6, 25.9, 28.8, 29.0, 31.6, 32.4, 34.4, 39.0, 46.6, 51.1, 51.3, 67.5, 68.4, 70.9, 71.9, 72.3, 103.1, 116.9, 152.4, 166.5, 171.8; [α]$^{23.9}_D$=−2.240 (c=6.53, CH$_2$Cl$_2$).

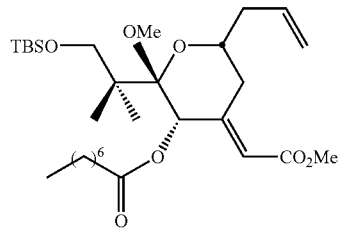

202.1 (Formula 202 where R$^{20}$ is
—O—CO—C$_7$H$_{15}$ and R$^{21}$ is =CH—CO$_2$Me)

To diol 201.1 (26.8 mg, 0.045 mmol) in benzene (1.2 mL) under nitrogen at 0° C. was added triethylamine (30 μL, 0.227 mmol) followed by lead tetraacetate (50 mg, 0.113 mmol). The resulting suspension was stirred at 0° C. for 20 min. and was then quenched with an aqueous solution of saturated ammonium chloride (5 mL) and extracted with ethyl acetate (3×5 mL). The combined organic layers were dried over sodium sulfate, the solution was decanted and then the solvent was removed in vacuo to provide the crude aldehyde (structure not shown) which was taken immediately to the next step.

To the crude aldehyde (34 mg, 0.061 mmol) in THF (1.4 mL) under nitrogen at 0° C. was added a 0.5M solution of the Tebbe reagent in toluene (122 μL, 0.061 mmol) dropwise. The reddish-black slurry was stirred at 0° C. for 15 min. and was then quenched with a saturated aqueous solution of sodium bicarbonate (5 mL). The biphasic mixture was extracted with ethyl acetate (3×5 mL). The combined organic layers were dried over sodium sulfate, the solution was decanted and then the solvent was removed in vacuo. Chromatography (5% EtOAc/pentane) provides olefin 202.1 (19 mg, 56%—2 steps) as a colorless oil.

202.1: R$_f$ (10% EtOAc/pentane)=0.62; IR (film)=2955, 2930, 2857, 1747, 1722, 1667, 1155, 1082, 837, 775 cm$^{-1}$; $^1$H NMR (300 MHz, CDCl$_3$) δ 0.01 (6H, s), 0.80–0.90 (12H, m), 0.96 (3H, s), 1.00 (3H, s), 1.20–1.38 (10H, m), 1.56–1.72 (1H, m), 2.24–2.46 (4H, m), 3.43 (1H, d, J=15.9 Hz), 3.30 (3H, s), 3.54 (2H, dd, J=18.9, 9.3 Hz), 3.68 (3H, s), 3.87–3.91 (1H, m), 5.09–5.16 (2H, m), 5.53 (1H, s), 5.80–5.98 (1H, m), 5.88 (1H, s); $^{13}$C NMR (75 MHz, CDCl$_3$) δ −5.4, 14.0, 18.4, 20.5, 20.6, 22.6, 24.7, 25.9, 28.9, 29.0, 31.6, 32.1, 34.5, 40.0, 47.0, 51.1, 67.3, 71.0, 72.1, 103.0, 116.6, 117.7, 133.8, 153.1, 166.6, 171.9; [α]$^{22.0}_D$=−7.91° (c=1.91, CH$_2$Cl$_2$).

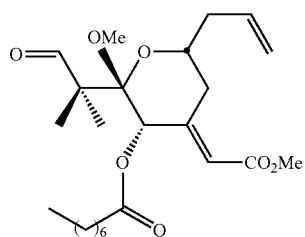

203.1 (Formula 203 where R$^{20}$ is
—O—CO—C$_7$H$_{15}$ and R$^{21}$ is =CH—CO$_2$Me)

To a solution of silyl ether 202.1 (101.7 mg, 0.1833 mmol) and pyridine (267 μL, 3.30 mmol) in THF (1.53 mL)

in a polypropylene vial was added 70% HF/pyridine complex (104.8 μL, 3.67 mmol) at room temperature. The solution was stirred for 18 hours and was then quenched with a saturated aqueous solution of sodium bicarbonate (5 mL). The biphasic mixture was extracted with ethyl acetate (4×5 mL). The combined organic layers were dried over sodium sulfate, the solution was decanted, and the solvent was removed in vacuo to afford the corresponding desilylated alcohol (structure not shown) as a pale yellow oil which was used immediately in the next step.

The crude alcohol was dissolved in $CH_2Cl_2$ (2 mL) and treated with a single portion of 1,1,1-triacetoxy-1,1-dihydro-1,2-benziodoxol-3(1H)-one (Dess-Martin periodinane, 117 mg, 0.275 mmol) at room temperature. The mixture was stirred for 45 min and quenched with saturated aqueous $NaHCO_3/Na_2S_2O_3$ (2 mL). The two phase system was vigorously stirred until the organic layer has cleared (90 min). The layers were then separated and the aqueous phase was extracted with $CH_2Cl_2$ (4×5 mL). The combined organic layers were dried over sodium sulfate, the solution was decanted and then the solvent was removed in vacuo. Chromatography on silica gel (7.5% EtOAc/hexanes) provides aldehyde 203.1 (43.7 mg, 54%—2 steps) as a colorless oil.

203.1: $R_f$ (15% EtOAc/pentane)=0.58; IR (film)=2930, 2857, 1750, 1723, 1668, 1160, 1048 $cm^{-1}$; $^1$H NMR (300 MHz, $CDCl_3$) δ 0.86 (3H, t, J=6.3 Hz, octanoate Me), 1.00 (3H, s, C18 Me), 1.16 (3H, s, C18 Me), 1.18–1.31 (10H, m), 1.46–1.60 (2H, m), 2.18 (2H, t, J=7.4 Hz), 2.43 (2H, t, J=6.6 Hz), 3.39 (3H, s), 3.66 (1H, d, J=18.9 Hz), 3.69 (3H, s), 3.74–3.84 (1H, m), 5.13–5.20 (2H, m), 5.85–6.00 (1H, m), 5.96 (1H, s), 9.71 (1H, s); $^{13}$C NMR (75 MHz, $CDCl_3$) δ 14.1, 16.3, 19.1, 22.6, 24.3, 28.9, 30.4, 31.6, 38.9, 40.0, 51.2, 51.4, 54.0, 71.5, 71.9, 102.2, 118.2, 119.8, 133.4, 150.3, 166.4, 171.7, 202.4; $[α]^{23.6}_D$=−6.07° (c=2.23, $CH_2Cl_2$).

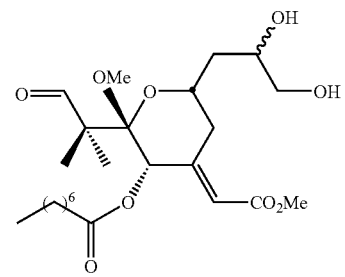

204.1 (Formula 204 where $R^{20}$ is
—O—CO—$C_7H_{15}$ and $R^{21}$ is =CH—$CO_2$Me)

A dihydroxylating stock solution was generated by dissolving $(DHQD)_2AQN$ (3.6 mg, 0.00425 mmol), $K_3Fe(CN)_6$ (425 mg, 1.275 mmol), $K_2CO_3$ (175 mg, 1.275 mmol) and $K_2OsO_2(OH)_4$ (0.65 mg, 0.00175 mmol) in t-BuOH (2.1 mL) and water (2.1 mL). The resulting solution was stirred at room temperature for 3 h. 504 μL of this stock solution was added to olefin 203.1 (7.4 mg, 0.017 mmol) predissolved in t-BuOH (200 μL) and water (200 μL) under nitrogen at 0° C. The resulting solution was stirred at 0–5° C. for 2 days. Water (2 mL) was then added and the biphasic mixture was then extracted with EtOAc (4×5 mL). The combined organic layers were dried over sodium sulfate, the solution was decanted and then the solvent was removed in vacuo. Chromatography (90% EtOAc/pentane to 100% EtOAc) provides diol 204.1 (5.6 mg, 70%) as an approximately 2.2:1 (β:α) mixture of diastereomers as a colorless oil.

204.1: $R_f$ (90% EtOAc/pentane)=0.36; IR (film)=3418, 2932, 2860, 1750, 1722, 1668, 1159, 1081, 1052 $cm^{-1}$; $^1$H NMR (400 MHz, $CDCl_3$) δ 0.86 (3H, t, J=6.8 Hz), 1.01 (3H, s, major), 1.02 (3H, s, minor), 1.15 (3H, s, minor), 1.17 (3H, s, major), 1.20–1.36 (10H, m), 1.47–1.61 (1H, m), 1.70–1.85 (1H, m), 2.10–2.32 (3H, m), 2.55 (1H, br. s, major), 3.09 (1H, br. s, minor), 3.42–3.80 (4H, m), 3.45 (3H, s, minor), 3.46 (3H, s, major), 3.69 (3H, s), 3.98–4.20 (2H, m), 5.20 (1H, s, major), 5.25 (1H, s, minor), 5.96 (1H, s), 9.68 (1H, s, minor), 9.68 (1H, s, major); $^{13}$C NMR (100 MHz, $CDCl_3$) δ 14.0, 16.5, 16.7, 19.0, 19.1, 22.5, 24.3, 28.9, 31.3, 31.3, 31.6, 33.9, 38.8, 38.9, 51.3, 51.3, 51.5, 51.6, 53.9, 66.7, 67.2, 68.2, 68.7, 70.3, 71.0, 71.4, 71.7, 102.2, 102.6, 119.6, 119.7, 150.0, 166.3, 171.7, 183.9, 201.8, 202.2.

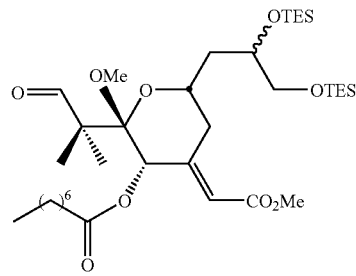

205.1 (Formula 205 where $R^{20}$ is
—O—CO—$C_7H_{15}$ and $R^{21}$ is =CH—$CO_2$Me)

To diol 204.1 (28.5 mg, 0.0603 mmol) in methylene chloride (2.45 mL) was added pyridine (141.3 μL, 1.75 mmol) followed by TESCl (176 mL, 1.05 mmol) at room temperature. The resulting clear solution was stirred at room temperature for 15 h. Triethylamine (250 μL) was then added and the solution was directly loaded onto a silica column and eluted (5% EtOAc+5% triethylamine/pentane) to afford bis silyl ether 205.1 (42.2 mg, 100%) as an approximately 2.2:1 (β:α) mixture of diastereomers as a colorless oil.

205.1: $R_f$ (5% EtOAc+5% triethylamine/pentane)=0.58; IR (film)=2955, 2877, 1754, 1724, 1668, 1462, 1231, 1159, 1107, 1007, 743 $cm^{-1}$; $^1$H NMR (400 MHz, $CDCl_3$) δ 0.44–0.65 (12H, m), 0.86 (3H, t, J=6.8 Hz), 0.88–0.98 (18H, m), 0.98 (3H, s, major), 1.00 (3H, s, minor), 1.14 (3H, s, major), 1.15 (3H, s, minor), 1.18–1.32 (10H, m), 1.58–1.71 (1H, m), 1.82–2.00 (1H, m), 2.09–2.21 (3H, m), 3.30–3.71 (3H, m), 3.41 (3H, s, minor), 3.43 (3H, s, major), 3.68 (3H, s, minor), 3.69 (3H, s, major), 3.90–4.10 (2H, m), 5.19 (1H, s, minor), 5.22 (1H, s, major), 5.94 (1H, s, minor), 6.00 (1H, s, major), 9.69 (1H, s, major) 9.70 (1H, s, minor); $^{13}$C NMR (100 MHz, $CDCl_3$) δ 4.3, 4.3, 4.9, 5.2, 6.2, 6.7, 6.8, 6.9, 14.0, 16.4, 16.5, 18.9, 19.0, 22.5, 24.3, 28.9, 29.7, 31.4, 31.6, 31.8, 33.9, 41.2, 41.5, 51.1, 51.2, 51.4, 51.7, 53.9, 67.3, 67.5, 68.0, 69.3, 69.8, 70.3, 71.1, 71.3, 102.1, 102.3, 119.4, 119.5, 150.2, 150.3, 151.0, 166.2, 166.2, 171.7, 202.5, 202.6.

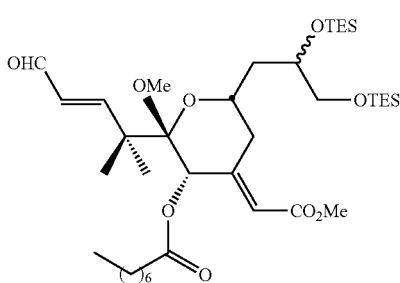

206.1 (Formula 206 where $R^{20}$ is —O—CO—$C_7H_5$ and $R^{21}$ is =CH—$CO_2Me$)

To a solution of diethylmethoxyborane (361 µL, 2.75 mmol) in Et₂O (2.14 mL) was added allylmagnesium bromide (1.0M in Et₂O, 2.50 mmol, 2.50 mL) dropwise at 0° C. The white precipitous mixture was stirred at 0° C. for 60 min. and then allowed to stand for 5 min. A 41.6 µL aliquot (0.5 M allyldiethylborane, 0.021 mmol) of this solution was added dropwise to aldehyde 205.1 (7.3 mg, 0.01 mmol) in 0.5 mL Et₂O at −10° C. After stirring for 30 min., the reaction was quenched with aqueous saturated NH₄Cl (5 mL). The biphasic mixture was then extracted with EtOAc (3×5 mL). The combined organic layers were dried over sodium sulfate, the solution was decanted and then the solvent was removed in vacuo to provide a colorless oil which was taken directly onto the next step.

The crude residue was dissolved in CH₂Cl₂ (1 mL) and treated successively with triethylamine (17.4 µL, 0.125 mmol), 4-dimethylaminopyridine (15.3 mg, 0.125 mmol) and Ac₂O (6 µL, 0.06 mmol) at room temperature. The solution was stirred for 17 h and then pipetted directly onto a short column of silica gel and the products eluted with 7.5% EtOAc/hexanes to afford a diastereomeric mixture of homoallylic acetates (7.9 mg, 97%—2 steps) as a colorless oil.

A portion of the isolated homoallylic acetate (5 mg, 0.0064 mmol) was dissolved in THF (253 µL) and H₂O (25.3 µL) and treated with N-methylmorpholine N-oxide (1.6 mg, 0.014 mmol) followed by OsO₄ (4 wt % in H₂O—16 µL, 0.0025 mmol) at room temperature. The homogeneous solution was stirred for 3 h, and then aqueous saturated sodium bicarbonate (4 mL) and water (1 mL) was added. The biphasic mixture was extracted with EtOAc (5×5 mL). The combined organic layers were dried over sodium sulfate, the solution was decanted and then the solvent was removed in vacuo to provide a colorless oil which was taken directly to the next step.

The resulting residue was immediately dissolved in benzene (0.4 mL) and treated with Et₃N (2.6 µL, 0.025 mmol) at room temperature. Solid Pb(OAc)₄ (4.2 mg, 0.0096 mmol) was quickly added in one portion and the resulting yellow precipitous mixture was stirred vigorously for 30 min. 1,8-Diazabicyclo[5.4.0]undec-7-ene (DBU, 12 µL, 0.08 mmol) was introduced and the reaction mixture was stirred for another 30 min. The mixture was added directly to a silica column and eluted (10% EtOAc/Pet. ether) to provide unsaturated aldehyde 206.1 (3.4 mg, 73%—2 steps) as an approximately 2.2:1 (β:α) mixture of diastereomers as a colorless oil.

206.1: $R_f$ (10% EtOAc/Pet. ether)=0.42; IR (film)=2955, 2877, 1748, 1723, 1692, 1461, 1229, 1154, 1105, 1008, 743 cm⁻¹; ¹H NMR (400 MHz, CDCl₃) δ 0.55–0.68 (12H, m), 0.87 (3H, t, J=6.8 Hz), 0.92–1.02 (18H, m), 1.15 (3H, s), 1.18 (3H, s), 1.20–1.34 (10H, m), 1.48–1.60 (2H, m), 1.85–2.03 (1H, m), 2.04–2.23 (2H, m), 2.27–2.39 (1H, m), 3.45–3.68 (2H, m), 3.38 (3H, s, minor), 3.40 (3H, s, major), 3.69 (3H, s, minor), 3.70 (3H, s, major), 3.95–4.05 (1H, m), 4.06–4.17 (1H, m), 5.45 (1H, s, minor), 5.47 (1H, s, major), 5.89 (1H, s), 5.93 (1H, dd, J=16.1/7.8 Hz, major), 5.93 (1H, dd, J=16.1/7.8 Hz, minor), 7.33 (1H, d, J=16.1 Hz, major), 7.36 (1H, d, J=16.1 Hz, minor), 9.53 (1H, d, J=7.8 Hz, major), 9.54 (1H, d, J=7.8 Hz, minor); ¹³C NMR (100 MHz, CDCl₃) δ 4.3, 4.4, 4.9, 5.4, 6.7, 6.8, 6.9, 7.0, 14.0, 21.7, 21.8, 22.5, 23.6, 23.8, 24.5, 28.9, 28.9, 31.6, 32.5, 32.8, 34.4, 41.2, 41.6, 47.3, 51.2, 51.4, 51.5, 67.3, 67.6, 68.9, 69.2, 69.8, 70.3, 71.0, 71.1, 102.4, 102.6, 117.6, 117.7, 126.7, 151.6, 166.2, 167.2, 171.7, 194.6.

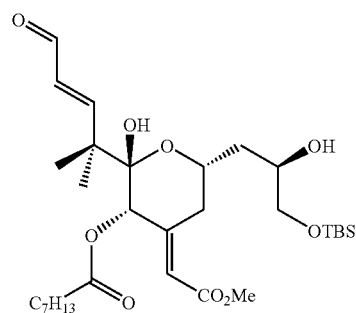

207.1b (Formula 207 where $R^{20}$ is —O—CO—$C_7H_{15}$ and $R^{21}$ is =CH—$CO_2Me$)

Enal 206.1 (22 mg, 0.03 mmol) was dissolved in acetonitrile (2 mL) and water (205 µL) at room temperature. 48% aqueous HF (388 µL, 12.1 mmol) was added dropwise and the resulting clear solution was stirred at room temperature for 75 min. and was then quenched with a saturated aqueous solution of sodium bicarbonate (15 mL) and water (3 mL). The mixture was extracted with ethyl acetate (5×10 mL). The combined organic layers were dried over sodium sulfate, the solution was decanted and then the solvent was removed in vacuo to provide a crude diol which was taken immediately to the next step.

A 0.75 mM silylating solution was generated by the addition of imidazole (62 mg, 0.91 mmol) and TBSCI (45.6 mg, 0.3 mmol) to methylene chloride (3.9 mL) at room temperature under nitrogen. To the crude diol dissolved in methylene chloride (3.9 mL) and DMF (0.4 mL) was added the above stock solution (1 mL) and stirred at room temperature for 2 h. The solution was then quenched with an aqueous solution of saturated ammonium chloride (10 mL) and extracted with methylene chloride (4×10 mL). The combined organic layers were further washed with brine (10 mL) and then dried over sodium sulfate. The solution was decanted and then the solvent was removed in vacuo. Chromatography (40% EtOAc/pentane) provides the silylated C25 β isomer 207.1b (10.4 mg, 57.4%) along with the silylated C25 α isomer 207.1a (4.6 mg, 25.4%) as colorless oils.

207.1b: $R_f$ (40% EtOAc/pentane)=0.38; IR (film)=3421, 2930, 2857, 1723, 1691, 1257, 1156, 1110, 837, 779 cm$^{-1}$; $^1$H NMR (400 MHz, CDCl$_3$) δ 0.10 (6H, s), 0.87 (3H, t, J=6.8 Hz), 0.92 (9H, s), 1.14 (3H, s), 1.15 (3H, s), 1.18–1.32 (10H, m), 1.49 (1H, t, J=7.2 Hz), 1.66–1.74 (1H, m), 1.84–2.00 (1H, m), 1.98–2.15 (3H, m), 3.49 (1H, dd, J=10.0, 6.0 Hz), 3.66–3.76 (1H, m), 3.70 (3H, s), 3.82–4.00 (2H, m), 4.07 (1H, t, J=6.6 Hz), 4.20 (1H, t, J=10.8 Hz), 5.13 (1H, s), 5.96 (1H, dd, J=16.0/7.7 Hz), 6.03 (1H, s), 7.35 (1H, d, J=16.0 Hz), 9.57 (1H, d, J=7.7 Hz); $^{13}$C NMR (100 MHz, CDCl$_3$) δ −5.3, 14.0, 18.4, 20.0, 22.5, 23.1, 24.4, 25.9, 28.9, 28.9, 31.1, 31.6, 34.5, 39.0, 45.7, 51.3, 67.1, 67.2, 67.9, 72.6, 99.7, 120.7, 127.6, 150.1, 166.1, 171.7, 194.5; $[\alpha]^{26.6}_D$=−27.24° (c=1.04, CH$_2$Cl$_2$).

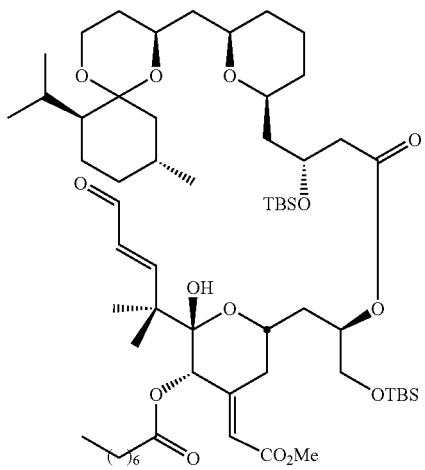

701.1 (Formula 701 where $R^{20}$ is —O—CO—C$_7$H$_{15}$, $R^{21}$ is =CH—CO$_2$Me and $R^{26}$ is H)

To a solution of acid 408 (Example 2B, 11.2 mg, 0.02 mmol) in toluene (0.9 mL) was added 2,4,6-trichlorobenzoyl chloride (3.2 μl, 0.02 mmol) at room temperature and the mixture was stirred for 45 min. Alcohol 207.1b (10.2 mg, 0.017 mmol) and DMAP (10.4 mg, 0.085 mmol) in toluene (1.4 mL) were added and stirred for 30 min. The mixture was directly loaded onto a silica gel column and eluted (7.5% EtOAc/pentane) to afford the ester 701.1 (15.2 mg, 79%).

701.1: $R_f$ (15% ethyl acetate/pentane)=0.29; IR (film) =3492, 2930, 2859, 1725, 1691, 1155, 1112, 837, 777 cm$^{-1}$; $^1$H NMR (400 MHz, CDCl$_3$) δ 0.04 (3H, s), 0.05 (3H, s), 0.07 (6H, s), 0.68 (1H, t, J=13.2 Hz), 0.60–0.92 (30H, m), 1.10–1.30 (18H, m), 1.34–1.84 (18H, m), 1.85–2.14 (3H, m), 2.34–2.52 (3H, m), 2.68 (1H, d, J=12.3 Hz), 3.13 (1H, s), 3.34–3.46 (2H, m), 3.60–3.70 (3H, m), 3.68 (3H, s), 3.76–3.86 (2H, m), 3.86–3.96 (1H, m), 4.06 (1H, dt, J=11.9, 2.1 Hz), 4.24–4.34 (1H, m), 5.11 (1H, s), 5.20–5.32 (1H, m), 5.96 (1H, dd, J=16.1, 7.8 Hz), 6.00 (1H, s), 7.42 (1H, d, J=16.1 Hz), 9.58 (1H, d, J=7.8 Hz); $^{13}$C NMR (100 MHz, CDCl$_3$) δ −5.3, −5.3, −4.7, −4.6, 14.0, 18.0, 18.3, 19.2, 20.1, 21.9, 22.3, 22.5, 22.9, 23.6, 23.7, 23.8, 24.3, 24.5, 25.8, 28.9, 28.9, 29.2, 30.9, 31.0, 31.6, 31.8, 31.9, 32.0, 34.5, 35.0, 37.4, 37.4, 43.5, 43.8, 44.7, 45.6, 51.2, 51.3, 59.2, 64.4, 64.9, 65.7, 66.3, 71.1, 72.7, 73.4, 73.8, 99.5, 100.4, 120.5, 127.5, 150.5, 166.4, 166.5, 171.7, 172.1, 194.6; $[\alpha]^{24.4}_D$=−27.42° (c=0.87, CH$_2$Cl$_2$).

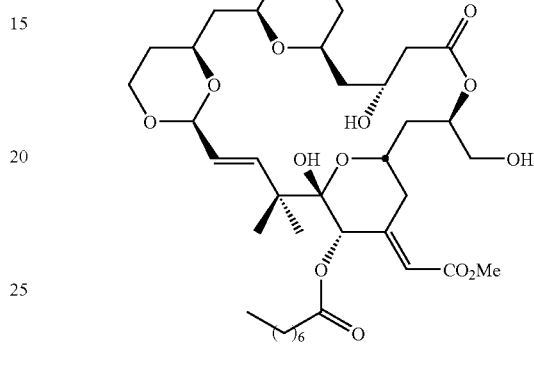

702.1 (Formula 702 where $R^3$ is OH, $R^{20}$ is —O—CO—C$_7$H$_{15}$, $R^{21}$ is =CH—CO$_2$Me and $R^{26}$ is H)

To seco aldehyde 701.1 (15 mg, 0.013 mmol) in THF (3.7 mL) at room temperature in a plastic flask was added 70% HF/pyridine dropwise. The resulting yellow solution was stirred for 2 hr and was then quenched with a saturated aqueous solution of sodium bicarbonate (12.5 mL) and water (7.5 mL). The biphasic mixture was extracted with ethyl acetate (5×15 mL). The combined organic layers were dried over sodium sulfate, the solution was decanted and then the solvent was removed in vacuo. Chromatography (70% EtOAc/pentane) provides 702.1 (7 mg, 73%) (the corresponding compound of Formula II where X is oxygen) as an amorphous solid.

702.1: $R_f$ (80% EtOAc/pentane)=0.29; IR (film)=3454, 3332, 2932, 2858, 1723, 1663, 1138, 976 cm$^{-1}$; $^1$H NMR (400 MHz, CDCl$_3$) δ 0.86 (3H, t, J=6.7 Hz), 1.01 (3H, s), 1.17 (3H, s), 1.18–1.38 (12H, m), 1.40–1.66 (7H, m), 1.72–1.88 (3H, m), 1.94–2.14 (3H, m), 2.29 (1H, dt, J=7.5/1.7 Hz), 2.52 (1H, d, J=7.2 Hz), 3.45 (1H, t, J=11.2 Hz), 3.53 (1H, t, J=10.6 Hz), 3.61–3.72 (4H, m), 3.68 (3H, s), 3.88 (3H, t, J=12.4 Hz), 4.02–4.09 (2H, m), 4.10–4.19 (1H, m), 4.48 (1H, d, J=11.6 Hz), 5.02 (1H, d, J=7.6 Hz), 5.10 (1H, s), 5.13 (1H, s), 5.34–5.39 (1H, m), 5.40 (1H, dd, J=15.0/7.6 Hz), 5.97 (1H, d, J=15 Hz), 5.99 (1H, s); $^{13}$C NMR (100 MHz, CDCl$_3$) δ 14.1, 19.3, 22.5, 23.0, 24.4, 24.7, 28.9, 29.0, 31.0, 31.3, 31.4, 31.6, 32.4, 34.6, 35.9, 39.9, 42.5, 42.9, 45.1, 51.1, 64.5, 65.8, 66.3, 68.6, 71.6, 74.1, 75.8, 76.0, 78.7, 98.9, 102.4, 119.9, 125.7, 142.6, 151.7, 167.0, 172.1, 172.6; $[\alpha]^{24.0}_D$=−20.02° (c=0.70, CH$_2$Cl$_2$).

3B. Formula IV—Bryostatin Analogue Containing Ether Diester Linker (807)

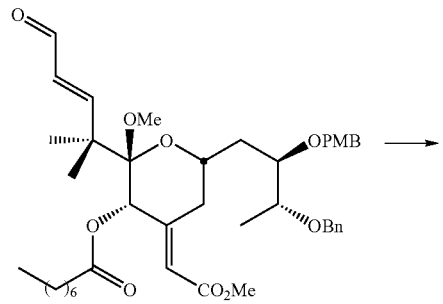

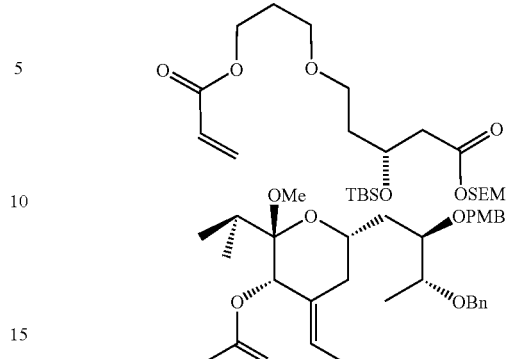

803.1 (Formula 803 where $R^{20}$ is —O—CO—$C_7H_{15}$ and $R^{21}$ is =CH—$CO_2$Me)

Acid 802.1 (22 mg, 0.030 mmol) in toluene (3 mL) was treated with Yamaguchi's reagent (6:L, 0.0395 mmol) and TEA (16:L, 0.122 mmol). After 30 min, alcohol 606 from Example 2F (17 mg, 0.0395 mmol) and DMAP (11 mg, 0.0912 mmol) in toluene (1 mL) was added and stirred for 1 h. The mixture was directly purified by silica gel column to give ester 803.1 (27 mg, 77% yield): $R_f$=(25% ethyl acetate in hexane); $[\alpha]^{25}_D$=−21.4° (c 0.82, $CH_2Cl_2$); IR (neat)=2930, 2858, 1720, 1652, 1612, 1514, 1464, 1383, 1250, 1110 cm$^{-1}$; $^1$H NMR (500 MHz, CDCl$_3$) δ 7.46 (d, J=16.0 Hz, 1H), 7.36 (m, 5H), 7.18 (d, J=8.5 Hz, 2H), 6.85 (d, J=8.5 Hz, 2H), 5.87 (s, 1H), 5.67 (d, J=16.0 Hz, 1H), 5.50 (s, 1H), 5.29 (q, J=6.0 Hz, 2H), 4.63 (m, 3H), 4.39 (d, J=11.0 Hz, 1H), 4.29 (t, J=11.0 Hz, 1H), 4.20 (m, 2H), 4.12 (t, J=11.0 Hz, 1H), 3.96 (m, 1H), 3.86~3.66 (m, 7H), 3.47 (m, 5H), 3.25 (s, 3H), 2.53 (d, J=6.5 Hz, 2H), 2.39 (br, 1H), 2.24 (m, 2H), 1.99~0.85 (m, 26H), 0.09 (s, 3H), 0.07 (s, 3H), 0.04 (s, 9H); $^{13}$C NMR (125 MHz, CDCl$_3$) δ 172.04, 171.07, 167.24, 166.30, 159.10, 157.02, 152.11, 138.68, 130.56, 129.18, 128.35, 128.17, 127.61, 117.04, 115.34, 113.74, 102.42, 88.96, 76.35, 74.48, 71.74, 71.13, 70.90, 68.59, 67.86, 67.34, 67.02, 66.59, 66.61, 61.52, 55.22, 51.12, 46.70, 42.93, 37.24, 36.17, 34.12, 31.64, 29.18, 28.99, 28.88, 25.75, 24.53, 23.45, 22.54, 22.38, 18.00, 17.95, 14.36, 14.06, −1.46, −4.80.

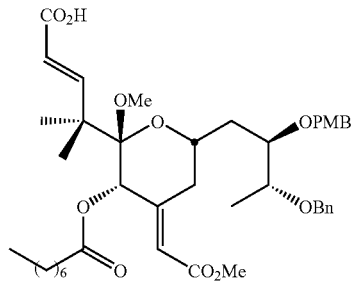

801.1 and 802.1(Formulae 801 and 802 where $R^{20}$ is —O—CO—$C_7H_{15}$ and $R^{21}$ is =CH—$CO_2$Me)

Enal 801.1, prepared as described for compound 13 in Wender et al. (1998a) (22 mg, 0.030 mmol) in a tert-butanol-THF solution of 2-methyl 2-butene (1:1, 3 mL) was treated with sodium chlorite (14 mg, 0.152 mmol) and monobasic sodium phosphate (21 mg, 0.152 mmol) in water (0.5 mL). After 1 h, the mixture was diluted with ethyl acetate. The organic layer was dried over sodium sulfate. Column chromatography afforded acid 802.1: $R_f$=(25% ethyl acetate in hexane); $[\alpha]^{25}_D$=−5.97° (c 0.40, $CH_2Cl_2$); IR (neat)=2932, 1716, 1644, 1514, 1456, 1374 cm$^{-1}$; $^1$H NMR (500 MHz, CDCl$_3$) δ 7.59 (d, J=16.0 Hz, 1H), 7.38 (m, 5H), 7.18 (d, J=8.5 Hz, 2H), 6.85 (d, J=8.5 Hz, 2H), 5.88 (s, 1H), 5.24 (d, J=16.0 Hz, 1H), 5.51 (s, 1H), 5.66 (d, J=11.0 Hz, 1H), 5.60 (d, J=11.0 Hz, 2H), 5.39 (d, J=11.0 Hz, 1H), 4.13 (br, 1H), 3.97 (m, 1H), 3.85 (m, 1H), 3.81 (s, 3H), 3.70 (s, 3H), 3.49 (d, J=14.5 Hz, 1H), 3.26 (s, 3H), 2.41 (t, J=14.5 Hz, 1H), 2.26 (m, 2H), 2.00 (m, 1H), 1.76 (m, 1H), 1.29~1.16 (m, 21H), 0.88 (t, J=7.0 Hz, 3H); $^{13}$C NMR (125 MHz, CDCl$_3$) δ 172.28, 172.05, 166.29, 159.69, 159.10, 152.00, 138.62, 130.51, 129.17, 128.35, 127.61, 127.52, 117.07, 114.72, 113.75, 102.40, 76.19, 74.30, 71.68, 71.11, 70.80, 68.65, 55.23, 51.16, 48.83, 46.87, 36.08, 35.35, 34.13, 32.97, 31.62, 28.89, 24.53, 23.32, 22.50, 22.25, 14.25, 14.07,

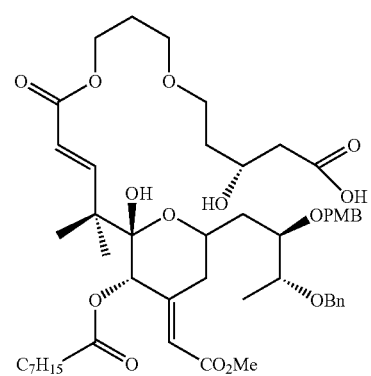

805.1 (Formula 805 where $R^{20}$ is
—O—CO—$C_7H_{15}$ and $R^{21}$ is =CH—$CO_2Me$)

Ester 803.1 (27 mg, 0.0233 mmol) in wet methylene chloride (2 mL) was treated with DDQ (11 mg, 0.0466 mmol) and stirred for 1 h. The mixture was directly purified by silica gel to give the expected alcohol silyl ether product of Formula 804. This silyl ether in acetonitrile-water (10:1, 1.5 mL) was treated with aqueous HF (100:L, 48%). After 4 h, the mixture was neutralized with aqueous sodium bicarbonate. The aqueous layer was extracted with ethyl acetate. The combined organic layer was dried over sodium sulfate. The crude hydroxy acid product 805.1 was used for the next step.

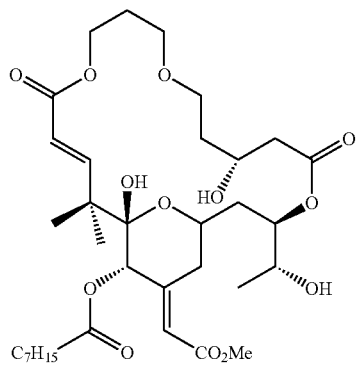

807.1 (Formula 807 where $R^{20}$ is
—O—CO—$C_7H_{15}$ and $R^{21}$ is =CH—$CO_2Me$)

To a solution of DCC (13 mg, 0.0623 mmol), DMAP.HCl (10 mg, 0.0623 mmol) and DMAP (11 mg, 0.089 mmol) was added hydroxy acid 805.1 (7 mg, 0.0089 mmol) in methylene chloride (3 mL) by syringe pump over 10 h. The resultant mixture was loaded directly onto a silica gel column and purified to give C26-O-benzyl ether lactone of Formula 806 where $R^{20}$ is —O—CO—$C_7H_{15}$ and $R^{21}$ is =CH—$CO_2Me$ (806.1) (3.5 mg, 50%). 806.1: $R_f$=(25% ethyl acetate in hexane); $[\alpha]^{25}{}_D$=4.74° (c 0.47, $CH_2Cl_2$); IR (neat)=3746, 3323, 2926, 2851, 1739, 1718, 1624, 1436, 1159 cm$^{-1}$; $^1$H NMR (500 MHz, $CDCl_3$) δ 7.39 (br s, 5H), 6.84 (d, J=16.0 Hz, 1H), 6.03 (s, 1H), 5.80 (d, J=16.0 Hz, 1H), 5.41 (br d, J=12.5 Hz, 1H), 5.20 (s, 1H), 5.15 (s, 1H), 4.64 (q, J=12.0 Hz, 2H), 4.47 (q, J=5.5, 11.5 Hz, 1H), 4.31 (m, 3H), 3.99 (t, J=11.0 Hz, 1H), 3.80~3.43 (m, 8H), 2.52 (m, 2H), 2.37~1.07 (m, 22H), 0.89 (t, J=6.5 Hz, 3H).

To a solution of benzyl ether 806.1 (1 mg) in methylene dichloride (0.5 mL) was added boron trichloride (excess) at −78° C., and the mixture was warmed to −20° C. over 1 h. The reaction mixture was quenched with aqueous sodium bicarbonate. The standard isolation procedure afforded bryostatin analogue 807.1. $R_f$=(25% ethyl acetate in hexane); $[\alpha]^{25}{}_D$=4.17° (c=0.30, $CH_2Cl_2$); IR (neat)=3480, 2927, 2856, 2361, 1718, 1281, 1161, 1105 cm$^{-1}$; $^1$H NMR (500 MHz, PhH) δ 6.82 (d, J=16.5 Hz, 1H), 6.03 (s, 1H), 5.80 (d, J=16.5 Hz, 1H), 5.24 (s, 1H), 5.17 (br s, 2H), 4.36 (m, 3H), 4.01 (t, J=2.5 Hz, 1H), 3.84 (q, J=6.5 Hz, 1H), 3.68 (m, 7H), 3.46 (t, J=9.0 Hz, 1H), 2.57 (m, 2H), 2.33 (m, 2H), 2.18 (m, 1H), 2.11~1.23 (m, 23H), 0.90 (t, J=10.0 Hz, 3H); $^{13}$C NMR (125 MHz, PhH) δ 174.37, 172.11, 171.38, 152.76, 151.21, 121.46, 120.31, 119.94, 99.21, 86.71, 73.84, 73.67, 71.96, 70.03, 68.76, 68.38, 65.14, 51.13, 45.48, 41.06, 35.99, 34.58, 32.91, 31.63, 31.14, 29.00, 28.86, 28.65, 24.68, 23.18, 22.55, 21.13, 19.64, 14.05.

3C. Formula III—Bryostatin Analogue Containing Selected C7 Substituent (705)

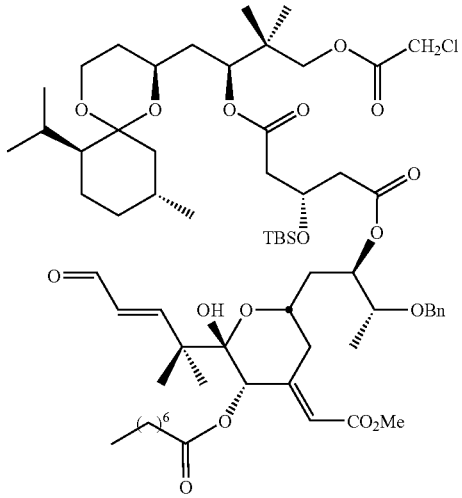

704.1 (Formula 704 where R is OH, R' is OBn, $R^3$ is TBSO, $R^5$ is =O, $R^7$ is t-Bu-$O_2$CMeCl, $R^8$ is H, $R^{20}$ is —O—CO—$C_7H_{15}$, $R^{21}$ is =CH—$CO_2Me$ and $R^{26}$ is Me)

To a methyl hemiacetal prepared as described for compound 14 in Wender et al. (1998a) (30 mg, 0.05 mmol) in acetonitrile (2.8 mL) and water (0.3 mL) was added 48% aq. HF (480 µL) and stirred at room temp. for 2 hrs. The reaction was then quenched with a saturated solution of sodium bicarbonate (5 mL) and extracted with EtOAc (5 mL×4). The combined organics were dried over sodium sulfate and the solvent was removed in vacuo to give expected hemiacetal (a compound according to Formula 303 where $R^{20}$ is —O—CO—$C_7H_{15}$ and $R^{21}$ is =CH—$CO_2Me$).

To crude acid 513 from Example 2G (47 mg, 0.075 mmol) in toluene (2.6 mL) was added triethylamine (27 µL, 0.2 mmol) and trichlorobenzoyl chloride (12.5 µL, 0.08 mmol), and the mixture was stirred for 90 min. To the resulting solution is added a solution containing the crude hemiacetal and DMAP (30.4 mg, 0.25 mmol) in toluene (4 mL). The resulting precipitous mixture was stirred for 2 h and then added directly to a silica column and eluted (15% EtOAc/pentane to 25% EtOAc/pentane) to afford seco aldehyde 704.1 (41.7 mg, 70%): $R_f$ (15% EtOAc/pentane)=0.14; IR (film): 3497.9, 2953.6, 2867.5, 1738.2, 1688.9, 1469.9, 1378.0, 1258.1, 1158.4, 1109.2, 982.5, 835.5, 779.2, 734.9 cm$^{-1}$; $^1$H-NMR (500 MHz, $CDCl_3$) δ 0.05 (3H, s), 0.08 (3H, s), 0.66 (1H, t, J=13.0 Hz), 0.79–0.88 (21H, m), 0.91–0.96 (1H, m), 0.95 (3H, s), 0.97 (3H, s), 1.15 (3H, s), 1.17–1.29 (15H, m), 1.36–1.50 (6H, m), 1.59–1.78 (5H, m), 1.87–2.13 (5H, m), 2.38 (1H, dquin, J=6.8, 1.3 Hz), 2.51–2.64 (5H, m), 3.31 (1H, s), 3.60–3.68 (2H, m), 3.68 (3H, s), 3.76–3.80 (1H, m), 3.78 (1H, d, J=11.0 Hz), 3.83–3.93 (1H, m), 3.99–4.07 (1H, m), 4.00 (1H, d, J=11.0 Hz), 4.07 (2H, d, J=3.0 Hz), 4.43–4.48 (1H, m), 4.56 (1H, d, J=12.0 Hz), 4.63 (1H, d, J=12.0 Hz), 4.96 (1H, dd, J=9.5, 2.0 Hz), 5.12 (1H, s), 5.41–5.44 (1H, m), 5.95 (1H, dd, J=16.0, 8.0 Hz), 6.00 (1H, d, J=2.0 Hz), 7.27–7.35 (5H, m), 7.38 (1H, d, J=16.0

Hz), 9.49 (1H, d, J=8.0 Hz); $^{13}$C-NMR (125 MHz, CDCl$_3$) δ −5.1, −4.8, 14.0, 15.0, 17.9, 19.0, 19.8, 20.2, 21.6, 21.7, 22.4, 22.5, 22.8, 23.7, 24.3, 24.4, 25.7, 28.8, 28.8, 28.9, 30.9, 31.1, 31.6, 34.5, 34.9, 35.4, 37.2, 37.5, 38.1, 40.7, 41.6, 42.0, 45.7, 51.1, 51.2, 58.9, 65.6, 65.7, 66.1, 70.8, 71.1, 71.4, 72.5, 73.1, 74.8, 99.5, 100.5, 120.7, 127.5, 127.6, 127.8, 128.4, 138.2, 150.3, 166.2, 166.3, 167.3, 170.5, 171.7, 171.8, 194.6; HRMS calc'd for $C_{65}H_{103}ClO_{17}Si$ (+1Na): 1241.6532; found: 1241.6551; $[α]^{27.0}_d$: −31.67° (c 4.17, CH$_2$Cl$_2$).

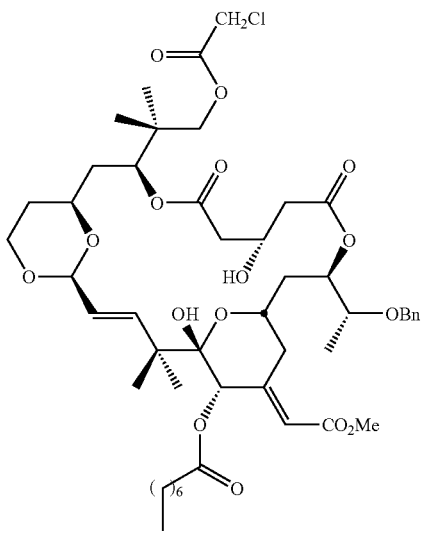

705.1 (Formula 705 where R is OH, R' is OBn, R$^3$ is OH, R$^5$ is =O, R$^8$ is t-Bu-OMeCl, R$^9$ is H, R$^{20}$ is —O—CO—C$_7$H$_{15}$, R$^{21}$ is =CH—CO$_2$Me and R$^{26}$ is Me)

To 704.1 (38 mg, 0.031 mmol) in THF (9.5 mL) was added freshly dried 4 Angstrom molecular sieve beads (57 beads) and 70% HF/pyridine (2.3 mL), and the resulting solution was stirred for 45 min. in a plastic flask. The reaction was then poured into a saturated solution of sodium bicarbonate (95 mL) and diluted with EtOAc (30 mL). The layers were separated and the aqueous layer was extracted with EtOAc (40 mL×3). The combined organic layers were dried over sodium sulfate and the solvent was removed in vacuo. Silica chromatography (40% to 100% EtOAc/pentane) afforded 705.1 (13.4 mg, 45%) and a putative diol 705.1a without the 3-hydroxy TBS protecting group (9.0 mg, 30%).

To putative diol 705.1a (4.8 mg, 4.95 μmol) in THF (0.5 mL) was added freshly dried 4A molecular sieve beads (3 beads) and 70% HF/pyridine (0.1 mL) and the resulting solution was stirred for 40 min. in a plastic flask. The reaction was then poured into a saturated solution of sodium bicarbonate (5 mL) and diluted with EtOAc (30 mL). The layers were separated and the aqueous layer was extracted with EtOAc (4 mL×4). The combined organics were dried over sodium sulfate and the solvent was removed in vacuo. Chromatography (30% to 100% EtOAc/pentane) afforded 705.1 (a compound of Formula III where R$^3$ is OH, R$^5$ is =O, R$^8$ is t-Bu-chloroacetate, R$^9$ is H, R$^{20}$ is —O—CO—C$_7$H$_{15}$, R$^{21}$ is =CH—CO$_2$Me and R$^{26}$ is Me). (1.1 mg, effectively adding 7% to above yield=52%). 705.1: R$_f$ (30% EtOAc/pentane)=0.23; IR (film): 3391.9, 2929.4, 2856.8, 1731.9, 1664.5, 1434.2, 1375.1, 1249.6, 1160.5, 1133.2, 1098.3, 982.1, 735.8 cm$^{-1}$; $^1$H-NMR (500 MHz, CDCl$_3$) δ 0.87 (3H, t, J=7.0 Hz), 0.93 (3H, s), 0.96 (3H, s), 1.03 (3H, s), 1.18 (3H, d, J=6.0 Hz), 1.20 (3H, s), 1.22–1.30 (10H, m), 1.51 (1H, br. d, J=12.5 Hz), 1.69–1.81 (3H, m), 2.00–2.08 (4H, m), 2.29–2.34 (3H, m), 2.41 (1H, dd, J=12.5, 4.0 Hz), 2.63 (1H, dd, J=14.3, 2.5 Hz), 2.82 (1H, dd, J=12.5, 4.5 Hz), 3.58 (1H, d, J=11.0 Hz), 3.61–3.64 (1H, m), 3.67–3.74 (2H, m), 3.68 (3H, s), 3.80 (1H, d, J=11.0 Hz), 3.82 (1H, t, J=12.0 Hz), 3.95–3.99 (1H, m), 3.97 (1H, d, J=11.0 Hz), 4.05–4.10 (1H, m), 4.08 (2H, s), 4.34 (1H, s), 4.39–4.44 (1H, m), 4.53 (1H, d, J=12.0 Hz), 4.65 (1H, d, J=12.0 Hz), 5.12 (1H, s), 5.19 (1H, dd, J=12.0, 3.0 Hz), 5.41 (1H, dd, J=16.0, 7.3 Hz), 5.50 (1H, ddd, J=12.3, 4.0, 3.0 Hz), 5.98 (1H, d, J=2.0 Hz), 6.08 (1H, d, J=16.0 Hz), 7.29–7.38 (5H, m); $^3$C-NMR (125 MHz, CDCl$_3$) δ 14.0, 15.3, 19.4, 20.0, 21.4, 22.5, 23.9, 24.7, 28.8, 29.0, 31.2, 31.6, 32.6, 34.5, 34.6, 37.1, 38.5, 40.8, 42.2, 43.2, 45.0, 51.1, 65.0, 65.8, 66.5, 71.0, 71.1, 71.1, 73.2, 74.0, 75.0, 75.5, 98.7, 101.2, 119.7, 126.9, 127.7, 127.8, 128.4, 138.2, 142.7, 151.4, 166.8, 167.2, 170.1, 170.1, 172.1; HRMS calc'd for $C_{49}H_{71}ClO_{16}$ (+1Na): 973.4350; found: 973.4328; $[α]^{25.0}_d$: −3.04° (c 1.34, CH$_2$Cl$_2$)

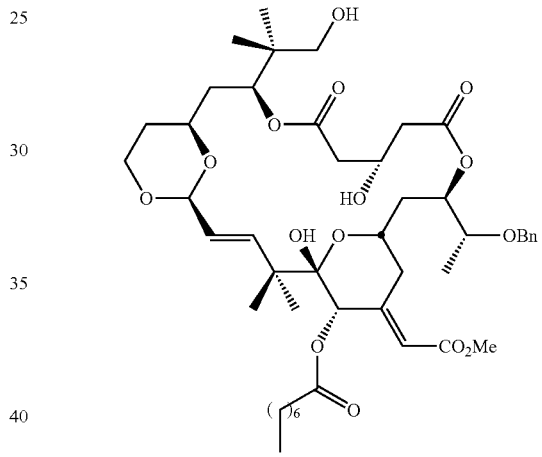

705.2 (Formula 705 where R is OH, R' is OBn, R$^3$ is OH, R$^5$ is =O, R$^8$ is t-Bu-OH, R$^9$ is H, R$^{20}$ is —O—CO—C$_7$H$_{15}$, R$^{21}$ is =CH—CO$_2$Me and R$^{26}$ is Me)

To 705.1 (7.4 mg, 7.785 μmol) in THF (0.66 mL) was added thiourea (66 mg, 0.84 mmol) and the resulting slurry was stirred at room temperature for 3 days. The reaction was then added directly to a silica column and eluted (50% to 58% to 70% EtOAc/pentane) to afford 705.2 (a compound of Formula III where R$^3$ is OH, R$^5$ is =O, R$^8$ is t-Bu-OH, R$^9$ is H, R$^{20}$ is —O—CO—C$_7$H$_{15}$, R$^{21}$ is =CH—CO$_2$Me and R$^{26}$ is Me). (6.3 mg, 92%). 705.2: R$_f$ (50% EtOAc/pentane)=0.18; IR (film): 3423.1, 2926.7, 2856.8, 1726.4, 1659.2, 1376.1, 1253.2, 1159.3, 1098.3, 980.8, 799.1, 729.7 cm$^{-1}$; $^1$H-NMR (300 MHz, CDCl$_3$) δ 0.77 (3H, s), 0.86 (3H, t, J=10.8 Hz), 0.96 (3H, s), 1.03 (3H, s), 1.18 (3H, d, J=8.1 Hz), 1.20 (3H, s), 1.22–1.34 (10H, m), 1.68–1.82 (3H, m), 2.01–2.12 (3H, m), 2.18–2.33 (3H, m), 2.45 (1H, dd, J=12.6, 4.5 Hz), 2.62–2.67 (2H, m), 2.85 (1H, dd, J=12.6, 3.6 Hz), 3.09–3.21 (2H, m), 3.60–3.88 (5H, m), 3.68 (3H, s), 3.93–4.00 (1H, m), 4.09 (1H, dd, J=11.1, 4.5 Hz), 4.35 (1H, s), 4.35–4.60 (1H, m), 4.52 (1H, d, J=12.0 Hz), 4.65 (1H, d, J=12.0 Hz), 5.06 (1H, d, J=9.6 Hz), 5.12 (1H, s), 5.18 (1H, d, J=7.2 Hz), 5.42 (1H, dd, J=15.9, 7.2 Hz), 5.44–5.51 (1H, m), 5.98 (1H, s), 6.08 (1H, d, J=15.9 Hz), 7.35–7.39 (5H, m); $^{13}$C-NMR (125 MHz, CDCl$_3$) δ 14.1, 15.3, 18.4, 19.4, 22.4, 22.5, 23.9, 24.7, 28.9, 29.0, 29.7, 31.2, 31.6, 32.7, 34.5, 34.7, 36.8, 39.7, 42.3, 43.2, 45.0, 51.1, 65.0, 65.9, 66.5, 69.0, 71.1, 71.2, 74.0, 75.0, 77.2, 98.7, 101.3, 119.7, 126.9, 127.7, 127.9, 128.4, 138.2, 142.8, 151.5, 166.9, 170.1, 171.8, 172.1; HRMS calc'd for C$_{47}$H$_{69}$O$_{15}$ (+1Na): 897.4595; found: 897.4612; [α]$^{25.0}_d$: −9.50° (c 0.47, CH$_2$Cl$_2$).

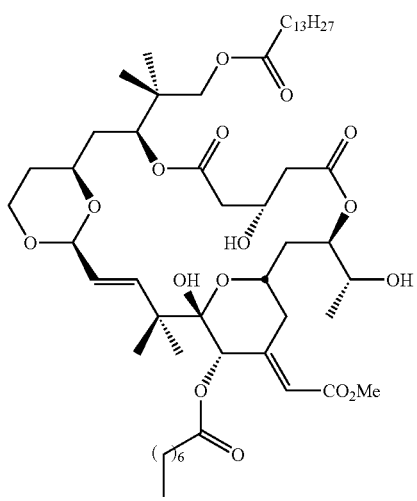

Formula 705.3

To myristic acid (10 mg, 0.044 mmol) in toluene (2.14 mL) at rt under nitrogen is added triethylamine (23.3 µL, 0.175 mmol) followed by 2,4,6-trichlorobenzoylchlonide (6.8 µL, 0.044 mmol). The resulting solution was stirred for 45 min. An aliquot of this solution (63 µL, 0.0013 mmol) was added to a solution of 705.2 (1 mg, 0.00114 mmol) and DMAP (0.7 mg, 0.0059 mmol) in toluene (500 µL). The slightly yellow, cloudy solution is stirred at rt for 30 min. and then added directly to a silica column and eluted (30% EtOAC/pentane). The eluted material is then re-chromatographed (30% EtOAC/pentane). The resulting material was then dissolved in EtOAc (500 µL) and Pearlman's catalyst (2 mg) was added. The resulting suspension was evacuated and re-filled with hydrogen (5 times) while the reaction was stirred vigorously. After 30 min., the reaction is added directly to a silica column and eluted (EtOAc). This provided C7 myristate analogue 705.3 (360 µg, 32%—2 steps) (a compound of Formula III where R$^3$ is OH, R$^5$ is =O, R$^8$ is t-Bu-myristate, R$^9$ is H, R$^{20}$ is —O—CO—C$_7$H$_{15}$, R$^{21}$ is =CH—CO$_2$Me and R$^{26}$ is Me). R$_f$ (40% EtOAc/pentane)= 0.19. IR (film) 3256.8, 2915.8, 2845.2, 1746.4, 1722.9, 1158.4, 1029.0, 864.4, 793.8 cm$^{-1}$. $^1$H-NMR (500 MHz, CDCl$_3$) δ 0.86–0.94 (12H, m), 1.05 (3H, s), 1.14–1.38 (38H, m), 1.59–1.63 (2H, m), 1.63–1.88 (3H, m), 2.03–2.07 (3H, m), 2.31–2.42 (4H, m), 2.47 (1H, dd, J=12.8, 3.8 Hz), 2.72–2.74 (2H, m), 2.86 (1H, dd, J=12.5, 5.0 Hz), 3.70 (3H, s), 3.62–3.75 (3H, m), 3.78–3.87 (3H, m), 3.99–4.04 (1H, m), 4.09–4.14 (1H, m), 4.37–4.50 (2H, m), 5.15 (1H, s), 5.16 (1H, d, J=7.4 Hz), 5.21 (1H, d, J=12.0 Hz), 5.33–5.34 (1H, m), 5.43 (1H, dd, J=15.6, 7.4 Hz), 6.01 (1H, s), 6.07 (1H, d, J=15.6 Hz). $^{13}$C-NMR (500 MHz, CDCl$_3$) δ 14.1, 19.9, 20.5, 21.1, 22.7, 23.2, 23.9, 24.7, 24.7, 24.9, 26.7, 29.1, 29.3, 29.4, 29.4, 29.7, 30.2, 31.1, 31.6, 31.9, 33.5, 33.7, 34.3, 34.5, 35.8, 37.2, 38.4, 42.3, 43.3, 45.0, 51.1, 65.0, 65.9, 66.6, 69.4, 70.0, 73.3, 73.5, 74.0, 75.9, 77.2, 98.7, 101.2, 119.8, 126.9, 128.8, 142.7, 151.3, 166.8, 170.4, 170.9, 172.4. HRMS (FAB) calc'd for C$_{54}$H$_{90}$O$_{16}$Na: 1017.6133, found: 1017.6127. [α]$^{21.1}_D$=−7.14° (c 0.035, CH$_2$Cl$_2$).

3D. Formula V—Bryostatin Analogue Containing Diester Linker (903.1)

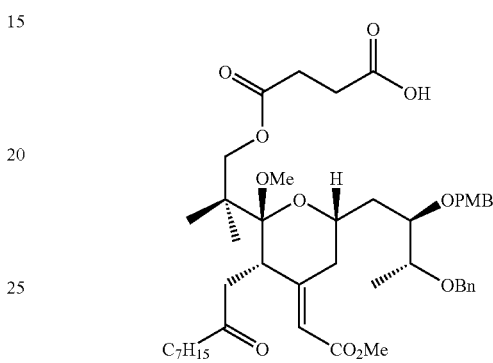

901.1 (Formula 901 where R$^{20}$ is —O—CO—C$_7$H$_{15}$, R$^{21}$ is =CH—CO$_2$Me To a solution of silyl ether 111 from Example 1C (1.17 g, 1.44 mmol) and pyridine (2.07 mL, 25.65 mmol) in 12 mL THF in a polypropylene vial was added HF/pyridine complex (0.83 mL, 28.83 mmol) at rt. The solution was stirred for 24 hours and diluted with EtOAc. The organic layer was washed with sat. CuSO$_4$ and brine, dried over Na$_2$SO$_4$ and concentrated in vacuo to afford the corresponding alcohol (not shown) as a pale yellow oil. To the alcohol (24.6 mg, 0.036 mmol) in methylene chloride (0.7 mL) was added DMAP (24.5 mg, 0.201 mmol) followed by succinic anhydride (8.6 mg, 0.086 mmol) at rt. The solution was heated to 42° C. for 3 hours and then slowly cooled to rt. Col. chromatography (40% EtOAc+1% AcOH/hexane) provided crude 901.1 (28.6 mg, 0.0353 mmol).

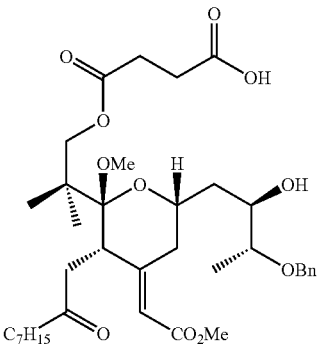

902.1 (Formula 902 where $R^{20}$ is —O—CO—$C_7H_{15}$, $R^{21}$ is —CH—$CO_2Me$ To crude 901.1 (28.6 mg) in methylene chloride (0.8 mL) and water (9.5 µL) was added DDQ (10.4 mg, 0.046 mmol) at rt. After stirring for 2 hours, the reaction was quenched with a saturated aqueous solution of ammonium chloride and extracted with EtOAc (3×5 mL). The combined organics were then dried over sodium sulfate and the solvent was removed in vacuo. Chromatography (40% EtOAc+1% AcOH/hexane) provided seco acid 902.1 (21.9 mg, 0.032 mmol, 91% in 2 steps).

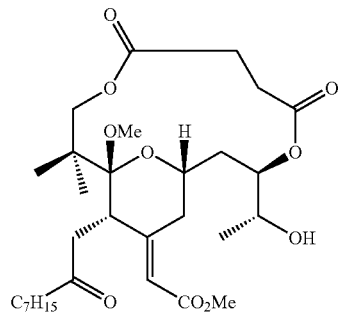

903.1

To 902.1 (5 mg, 7.38 µmol) in acetonitrile (0.4 mL) and water (42 µL) at rt was added 48% aqueous HF dropwise (24 µL, 0.738 mmol). The reaction was stirred for 40 min. and then quenched with a saturated aqueous solution of sodium bicarbonate (5 mL). The layers were separated and then the aqueous layer was extracted with EtOAc (6×5 mL). The combined organics were dried over sodium sulfate and then the solvent was removed in vacuo. The resulting clear oil (not shown) was then used immediately in the next step.

To DMAP (9 mg, 0.074 mmol) and DMAP.HCl (8.2 mg, 0.052 mmol) in methylene chloride (1.4 mL) was added DCC (10.6 mg, 0.052 mmol) at rt. The clear oil from the preceding step in methylene chloride (2.2 mL) was then added over 3 h. The resulting mixture was stirred at rt for 4 h and then quenched with a saturated aqueous solution of sodium bicarbonate (5 mL). The layers were separated and then the aqueous layer was extracted with EtOAc (3×5 mL). The combined organics were then dried over sodium sulfate and the solvent was removed in vacuo. Silica gel chromatography (30% EtOAc/hexane) provided corresponding crude macrocycle (not shown) as a colorless oil.

The crude macrocycle from the preceding step was dissolved in ethyl acetate (2.6 mL) and Pd(OH)$_2$/C (2.4 mg, 20% wt. on carbon) was added. The resulting suspension was evacuated and refilled with 1 Atm. hydrogen gas (×5) and was vigorously stirred under a hydrogen atmosphere for 3 hours. The crude mixture was pipetted directly onto a silica gel column and the product was eluted (50% EtOAc/hexane) to afford bryostatin analogue 903.1 (0.3 mg, 7%—3 steps) (a compound of Formula V where p is 2, $R^{20}$ is —O—CO—$C_7H_{15}$, $R^{21}$ is =CH—$CO_2Me$ and $R^{26}$ is Me) as a white solid.

Example 4

Bryostatin Analogues Containing Selected C20 Ester Substituent

This example illustrates methods for preparing bryostatin compounds and analogues that contain selected ester substituents at C20.

4A. Acetyl C20 Ester (702.2)

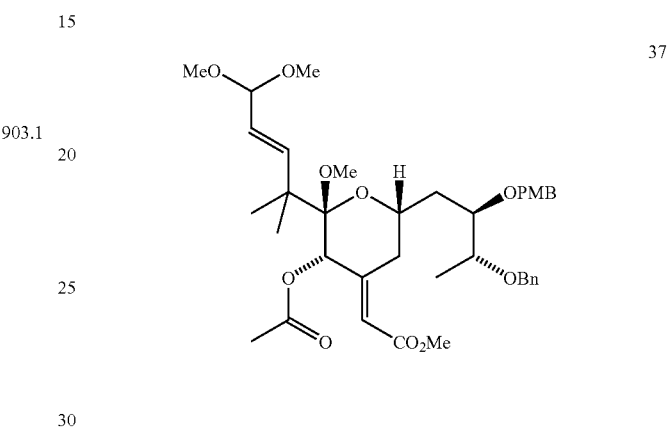

37

To a solution of enal 13, prepared as described for compound 13 in Wender et al. (1998a) (180 mg, 0.03 mmol) in 0.5 mL of MeOH at rt was added pyridinium p-toluenesulfonate (PPTS, 2 mg, catalytic) and trimethylorthoformate (5 drops). The progress of the reaction was monitored by thin layer chromatography (TLC). After 30 min the reaction was quenched with 1.0 mL Et$_3$N. The solvent was removed under reduced pressure to afford the expected crude dimethylacetal product (not shown). This product was immediately dissolved in MeOH (0.5 mL) and K$_2$CO$_3$ (3 mg, catalytic). The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure to afford the crude C20 free hydroxyl product (not shown). The crude product was immediately dissolved in methylene chloride (0.5 mL) and acetic anhydride (0.3 mL, excess) and DMAP (5 mg, catalytic) was added at rt. The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure. The crude product was purified by column chromatography on silica gel with 20% EtOAc-hexanes as eluant affording 14 mg (82% for four steps) of dimethylacetal 37. Rf (20% ethyl acetate/hexanes)=0.17; R$_f$ (25% EtOAc/hexanes)=0.44; IR 2927, 2859, 1744, 1719, 1687, 1514, 1249, 1156, 1103, 1079, 1037 cm$^{-1}$; $^1$H NMR (300 MHz, CDCl$_3$) δ 0.85 (6H, m) 1.16–1.30 (10H, m), 1.14 (3H, s), 1.18 (3H, s), 1.75 (1H, m), 1.98–2.17 (3H, m), 2.32 (1H, m), 3.27 (3H, s), 3.52 (1H, d, J=16.5 Hz), 3.68 (3H, s), 3.79 (3H, s), 3.87 (1H, m), 3.95 (1H, m), 4.09 (1H, m), 4.47 (2H, ABq, J=11.4 Hz), 5.41 (1H, s), 5.88 (1H, s), 5.91 (1H, dd, J=16.2, 7.7 Hz), 6.83 (2H, d, J=8.7 Hz), 7.16 (2H, d, J=8.7 Hz), 7.27–7.35 (6H, m), 9.44 (1H, d, J=7.7 Hz, C15); $^{13}$C NMR (75 MHz, CDCl$_3$) δ 14.1, 21.7, 22.6, 24.0, 24.6, 28.9, 29.0, 31.7, 32.6, 34.5, 36.2, 47.5, 51.3, 51.5, 55.4, 69.2, 71.3, 71.8, 74.4, 76.3, 102.7, 114.1, 118.2, 127.1, 127.7, 127.9, 128.7, 129.5, 130.7, 138.9, 151.6, 159.6, 166.6, 167.3, 172.1, 195.0; $[\alpha]_D^{20}$=−0.7° (c 1.7, $CH_2Cl_2$).

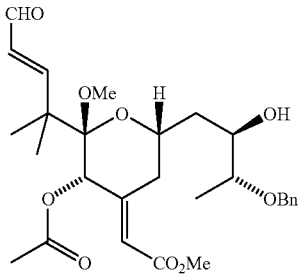

303.1 (Formula 303 where $R^{20}$ is —O—CO-Me, $R^{21}$ is =CH—$CO_2Me$)

To a solution of dimethylacetal 37 (14 mg, 0.02 mmol) in 0.6 mL 1% aqueous $CH_2Cl_2$ was added solid 2,3-dichloro-5,6-dicyano-1,4-benzoquinone (DDQ, 10 mg, 0.03 mmol) at rt. The mixture was stirred for 2 h, pipetted directly onto a column of silica gel, and the product eluted with 35% EtOAc/hexanes to provide intermediate alcohol 303.1 (10 mg, 91%) as a colorless oil: $R_f$ (35% EtOAc/hexanes)=0.22; IR 3528, 2930, 2858, 1745, 1720, 1686, 1458, 1437, 1380 cm$^{-1}$; $^1$H NMR (300 MHz, $CDCl_3$) δ 0.86 (3H, t, J=6.9 Hz), 1.13 (3H, s), 1.17 (3H, s), 1.25 (10H, m), 1.52 (2H, m), 1.71 (2H, m), 2.12 (2H, m), 2.35 (1H, t, J=14.1 Hz), 2.60 (1H, d, J=3.6 Hz), 3.41 (3H, s, C19 $OCH_3$), 3.45 (1H, m), 3.68 (3H, s), 3.82 (1H, s), 4.24 (1H, m), 4.55 (2H, ABq, J=11.4 Hz), 5.47 (1H, s), 5.86 (1H, s), 5.91 (1H, dd, J=15.9, 7.5 Hz), 7.29 (1H, d, J=15.9 Hz), 7.34 (5H, s), 9.52 (1H, d, J=7.5 Hz); $^{13}$C-NMR (75 MHz, $CDCl_3$) δ 13.6, 15.3, 21.6, 22.4, 23.5, 24.7, 28.6, 28.8, 31.5, 32.8, 34.1, 39.5, 47.4, 51.1, 51.2, 68.3, 70.9, 71.0, 71.1, 78.8, 102.4, 117.4, 126.8, 127.9, 128.0, 128.5, 138.1, 151.8, 166.4, 167.3, 171.4, 194.5; $[\alpha]_D^{20}$=−21.0° (c 1.0, $CH_2Cl_2$).

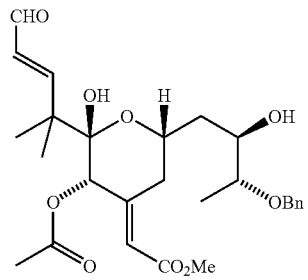

304.1 (Formula 304 where $R^{20}$ is —O—CO-Me, $R^{21}$ is =CH—$CO_2Me$)

Alcohol 303.1 (10 mg, 0.02 mmol) was dissolved in 1.1 mL $CH_3CN/H_2O$ (9:1) and treated with 48% aqueous HF (200 μL, 300 mol % excess) at rt. The resulting mixture was stirred for 1 h, quenched with sat. $NaHCO_3$ and diluted with 10 mL EtOAc. The aqueous layer was separated and extracted with EtOAc (2×). The combined organics were dried over $Na_2SO_4$ and concentrated in vacuo to afford crude hemiketal enal 304.1 as a colorless oil. The crude product was purified by column chromatography on silica gel with 35% EtOAc-hexanes as eluant affording 8 mg (89%) of hemiketal enal 304.1. $R_f$ (35% EtOAc/hexanes)=0.15; IR 3528, 2930, 2858, 1745, 1720, 1686, 1458, 1437, 1380 cm$^{-1}$; $^1$H NMR (300 MHz, $CDCl_3$) δ 0.86 (3H, t, J=6.9 Hz, octanoate Me), 1.13 (3H, s, C18 Me), 1.17 (3H, s, C18 Me), 1.25 (10H, m), 1.52 (2H, m), 1.71 (2H, m), 2.12 (2H, m), 2.35 (1H, t, J=14.1 Hz), 2.60 (1H, d, J=3.6 Hz), 3.41 (3H, s, C19 $OCH_3$), 3.45 (1H, m), 3.68 (3H, s, methyl ester), 3.82 (1H, s), 4.24 (1H, m), 4.44 (1H, d, J=11.1 Hz, $CH_2Ph$), 4.69 (1H, d, J=11.4 Hz, $CH_2Ph$), 5.47 (1H, s, C20), 5.86 (1H, s, C34), 5.91 (1H, dd, J=15.9, 7.5 Hz, C16), 7.29 (1H, d, J=15.9 Hz, C17), 7.34 (5H, s, Ph), 9.52 (1H, d, J=7.5 Hz, C15); $^{13}$C-NMR (75 MHz, $CDCl_3$) δ 13.8, 15.4, 21.7, 22.3, 23.6, 24.3, 28.7, 28.8, 31.4, 32.7, 34.2, 39.5, 47.3, 51.1, 51.2, 68.3, 70.8, 71.0, 71.1, 78.1, 102.3, 117.4, 126.8, 128.0, 128.1, 128.6, 138.1, 151.8, 166.4, 167.1, 171.7, 194.7; $[\alpha]_D^{20}$=−19.0° (c 1.4, $CH_2Cl_2$).

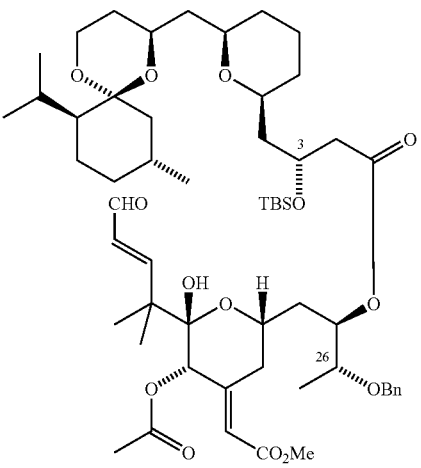

701.1 (Formula 701 where R is OH, R' is OBn, $R^3$ is TBSO, $R^{20}$ is —O—CO-Me, $R^{21}$ is =CH—$CO_2Me$, $R^{26}$ is Me and X is oxygen)

Carboxylic acid 407 (Example 2B, 15 mg, 0.03 mmol) and $Et_3N$ (16.5 μL, 0.12 mmol) were dissolved in 300 μL toluene and treated with 2,4,6-trichlorobenzoylchloride (4.8 μL, 0.03 mmol) dropwise at rt. After 1 h at rt, a toluene solution of freshly prepared 304.1 and 4-dimethylaminopyridine (14 mg, 0.12 mmol) was added gradually and stirring was continued for 40 min. The crude mixture was pipetted directly onto a column of silica gel and the product eluted with 20% EtOAc/hexanes to provide ester 701.1 as a colorless oil (15 mg, 63%). $R_f$ (35% EtOAc/hexanes)=0.71; IR 3487, 2927, 2856, 1723, 1689, 1455, 1379, 1228, 1156, 1113, 1084, 1032, 981 cm$^{-1}$; $^1$H NMR (300 MHz, $C_6D_6$) δ 0.80 (1H, t, J=12.7 Hz), 0.93 (3H, t, J=7.0 Hz), 0.97 (3H, d, J=6.6 Hz), 1.10–1.36 (24H, m), 1.36–1.85 (21H, m), 1.91–2.13 (6H, m), 2.39 (1H, t, J=12.8 Hz), 2.79 (1H, d, J=13.2 Hz), 2.93 (1H, m), 3.05 (1H, m), 3.29 (3H, s), 3.33 (1H, s), 3.37–3.48 (2H, m), 3.80 (1H, dd, J=11.4, 5.1 Hz), 3.95–4.05 (2H, m), 4.15 (1H, td, J=10.8, 0.9 Hz), 4.23 (1H, d, J=13.5 Hz), 4.40 (1H, d, J=12.0 Hz), 4.47 (1H, d, J=12.0 Hz), 5.57 (1H, s), 5.64 (1H, dd, J=10.6, 4.6 Hz), 6.05 (1H, dd, J=16.1, 7.6 Hz), 6.39 (1H, s), 7.10–7.35 (5H, m), 7.45 (1H, d, J=16.1 Hz), 9.60 (1H, d, J=7.6 Hz); $^{13}$C-NMR (75 MHz, $C_6D_6$) δ 14.1, 15.1, 19.3, 20.1, 21.3, 22.3, 22.4, 22.7, 23.8, 24.0, 24.6, 24.6, 29.0, 29.0, 29.3, 31.3, 31.6, 31.8, 34.2, 34.5, 35.2, 35.7, 36.2, 37.6, 43.5, 45.7, 51.6, 59.1, 64.9, 66.7, 71.1, 72.0, 72.9, 74.1, 75.3, 77.1, 100.2, 100.6, 121.2, 127.2, 127.3, 127.9, 128.6, 138.9, 151.2, 164.5, 166.3, 171.5, 175.1, 193.4; $[\alpha]^{20}_D$ −19° (c 1.5, $CH_2Cl_2$).

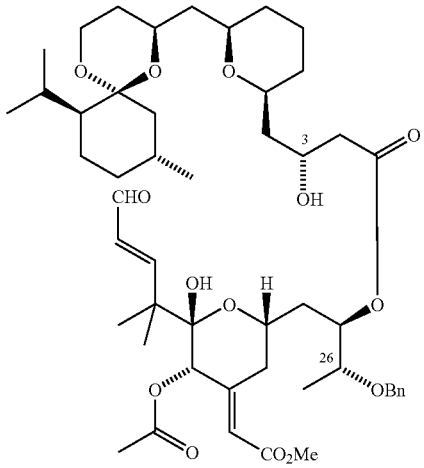

701.2 (Formula 701 where R is OH, R' is OBn, $R^3$ is OH, $R^{20}$ is —O—CO-Me $R^{21}$ is =CH—$CO_2$Me, $R^{26}$ is Me and X is oxygen)

To ester 701.1 (13 mg, 0.02 mmol) in THF (0.5 mL) was added pyridine (360 μL, 0.45 mmol) followed by 70% HF/pyridine (144 μL, 500 mol % excess) and stirred for 20 hours. The reaction was then quenched with a saturated solution of sodium bicarbonate. The biphasic mixture was extracted with ethyl acetate (×4) and the combined organics were dried over sodium sulfate. The solvent was removed in vacuo to provide crude C3 hydroxyester 701.2. The crude mixture was pipetted directly onto a column of silica gel and the product eluted with 35% EtOAc/hexanes to provide ester 701.2 as a colorless oil (9 mg, 82%). $R_f$ (40% EtOAc/hexanes)=0.19; IR 3522, 2927, 2857, 1724, 1664, 1230, 1158, 1136, 1107, 979 cm$^{-1}$; $^1$H NMR (400 MHz, $C_6D_6$) δ 0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, $C_6D_6$) δ 14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2 $[\alpha]^{20}_D$ −13.5° (c 0.9, $CDCl_3$).

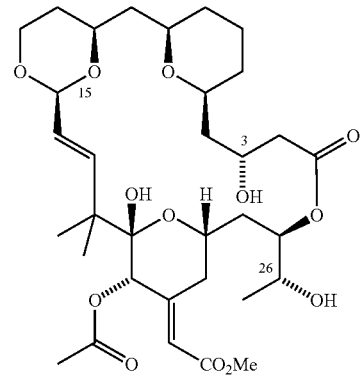

702.2 (Formula 702 where $R^3$ is OH, $R^{20}$ is —O—CO-Me $R^{21}$ is =CH—$CO_2$Me, $R^{26}$ is Me and X is oxygen)

To a solution of C3 hydroxyester 701.2 (8 mg, 0.01 mmol) in 2.0 mL $CH_2Cl_2$ was added 4 Å molecular sieves and the mixture was aged for 20 min. 45–50 beads of Amberlyst-15 sulfonic acid resin were added and the mixture was stirred at rt for 2 h. The crude mixture was pipetted directly onto a column of silica gel and the product eluted with 35% EtOAc/hexanes to provide the expected macrocyclic product (not shown) as a colorless oil (5 mg, 83%). $R_f$ (35% EtOAc/hexanes)=0.21; IR 3522, 2927, 2857, 1724, 1664, 1230, 1158, 1136, 1107, 979 cm$^{-1}$; $^1$H NMR (400 MHz, $C_6D_6$) δ 0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, $C_6D_6$) δ 14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2.

The macrocyclic product from the preceding step was dissolved in 0.5 mL EtOAc and 2.2 mg Pd(OH)$_2$ (20% wt. on carbon) was added. The resulting suspension was vigorously stirred under balloon pressure of hydrogen gas for 35 min. The crude mixture was pipetted directly onto a column of silica gel and the product was eluted with 60% EtOAc/hexanes to afford acetate analogue 702.2 (4 mg, 93%) (a compound of Formula II where $R^3$ is OH, $R^{20}$ is —O—CO-Me, $R^{21}$ is =CH—$CO_2$Me, $R^{26}$ is Me and X is oxygen) as a white semi-solid. $R_f$ (50% EtOAc/hexanes)=0.16; IR 3522, 2927, 2857, 1724, 1664, 1230 IR (neat)=3455, 3319, 2929, 2856, 1735, 1380, 1230, 1138, 976 cm$^{-1}$; $^1$H NMR (500 MHz, $CDCl_3$) δ 0.37 (3H, br, s), 0.77–0.92 (14H, m), 1.06 (3H, d, J=6.4 Hz), 1.07 (1H, t, J=11.0 Hz), 1.10–1.28 (5H, m), 1.27 (3H, s), 1.50 (3H, s), 1.57–1.78 (4H, m), 2.03 (2H, t, J=7.4 Hz), 2.17 (1H, dd, J=9.9, 0.5 Hz), 2.37 (1H, m), 2.40 (1H, m), 2.85 (1H, t, J=11.2 Hz), 2.96 (1H, t, J=10.8 Hz), 3.15 (3H, s), 3.68–3.75 (3H, m), 3.91 (1H, dd, J=11.2, 4.0 Hz), 4.12 (1H, t, J=9.7 Hz), 4.35 (1H, dd, J=13.9, 2.3 Hz), 4.48 (1H, td, J=11.0, 2.8 Hz), 4.70 (1H, d, J=12.1 Hz), 5.44 (1H, quint., J=4.8 Hz), 5.54 (1H, d, J=7.3 Hz), 5.69 (1H, s), 5.76 (1H, s), 5.85 (1H, dd, J=16.1, 7.5 Hz), 6.40 (1H, d, J=1.8 Hz), 6.50 (1H, d, J=15.9 Hz); $^{13}$C NMR (125 MHz, CDCl$_3$) δ 14.3, 19.6, 12.0, 22.9, 23.2, 24.9, 25.0, 29.2, 29.2, 31.4, 31.5, 31.9, 32.9, 34.7, 36.3, 39.9, 42.6, 43.2, 45.4, 50.5, 65.2, 66.2, 67.0, 70.4, 74.2, 74.7, 75.3, 75.9, 78.5, 99.7, 103.1, 120.5, 142.5, 152.5, 171.6, 172.5; $[\alpha]^{25}_D$=−9.0° (c=0.36, CDCl$_3$).

4B. Heptanoate C20 Ester (702.3)

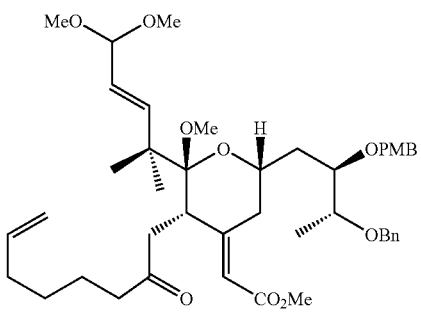

308.1 (Formula 308 where R$^{20a}$ is Heptenoate, and R$^{21}$ is =CH—CO$_2$Me)

To solution of the enal of Formula 305 (in which R$^{20}$ is C$_7$H$_{15}$), prepared as described for compound 13 in Wender et al. (1998a), (224 mg, 0.04 mmol) in 0.5 mL of MeOH at rt was added PPTS (2 mg, catalytic) and trimethylorthoformate (1 drop). The progress of the reaction was monitored by TLC. After 30 min the reaction was quenched with 1.0 mL Et$_3$N. The solvent was removed under reduced pressure to afford the corresponding crude dimethylacetal product of Formula 306. This product was immediately dissolved in MeOH (2.0 mL) and K$_2$CO$_3$ (3 mg, catalytic). The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure to afford the corresponding crude C20 free hydroxyl product of Formula 307.

Heptenoic acid (6 mg, 0.05 mmol) and Et$_3$N (21 μL, 0.16 mmol) were dissolved in 600 μL toluene and treated with 2,4,6-trichlorobenzoylchloride (7.0 μL, 0.05 mmol) dropwise at rt. After 1 h at rt, a toluene solution of the freshly prepared C20 free hydroxyl product of Formula 307 and 4-dimethylaminopyridine (DMAP, 20 mg, 0.17 mmol) was added gradually and stirring was continued for 40 min. After 30 min the reaction was quenched. The solution was quenched with sat. NaHCO$_3$, diluted with EtOAc (10 mL), washed with H$_2$O, dried over MgSO$_4$ and concentrated under reduced pressure. The crude product was purified by column chromatography on silica gel with 20% EtOAc-hexanes as eluant affording 21 mg (84%) of the corresponding dimethylacetal, C20 heptenoate product of Formula 308.1. Rf (20% ethyl acetate/hexanes)=0.22; IR 2927, 2859, 1744, 1719, 1687, 1514, 1249, cm$^{-1}$; $^1$H NMR (300 MHz, CDCl$_3$) δ 0.85 (6H, m) 1.16–1.30 (10H, m), 1.14 (3H, s), 1.18 (3H, s), 1.75 (1H, m), 1.98–2.17 (3H, m), 2.32 (1H, m), 3.27 (3H, s), 3.52 (1H, d, J=16.5 Hz), 3.68 (3H, s), 3.79 (3H, s), 3.87 (1H, m), 3.95 (1H, m), 4.09 (1H, m), 4.42 (2H, ABq, J=11.0 Hz), 4.59 (1H, d, J=11.0 Hz), 4.65 (1H, d, J=11.8 Hz), 4.98 (1H, s), 5.02 (1H, d, J=15.2 Hz), 5.41 (1H, s), 5.88 (1H, s), 5.91 (1H, dd, J=16.2, 7.7 Hz), 6.83 (2H, d, J=8.7 Hz), 7.16 (2H, d, J=8.7 Hz), 7.27–7.35 (6H, m), 9.44 (1H, d, J=7.7 Hz); $^{13}$C NMR (75 MHz, CDCl$_3$) δ 14.1, 21.7, 22.6, 24.0, 24.6, 28.9, 29.0, 31.7, 32.6, 34.5, 36.2, 47.5, 51.3, 51.5, 55.4, 69.2, 71.3, 71.8, 74.4, 76.3, 102.7, 114.1, 118.2, 127.1, 127.7, 127.9, 128.7, 129.5, 130.7, 138.9, 151.6, 159.6, 166.6, 167.3, 172.1, 195.0.

To a solution of 308.1 (17 mg, 0.02 mmol) in 0.5 mL 1% aqueous CH$_2$Cl$_2$ was added solid 2,3-dichloro-5,6-dicyano-1,4-benzoquinone (DDQ, 8 mg, 0.03 mmol) at rt. The mixture was stirred for 2 h, pipetted directly onto a column of silica gel, and the product eluted with 35% EtOAc/hexanes to provide the corresponding intermediate alcohol (11 mg, 85%) as a colorless oil. R$_f$ (50% EtOAc/hexanes)= 0.55; IR 3528, 2930, 2858, 1745, 1720, 1686 cm$^{-1}$; $^1$H NMR (300 MHz, CDCl$_3$) δ 0.86 (3H, t, J=6.9 Hz), 1.13 (3H, s), 1.17 (3H, s), 1.25 (10H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.54 (2H, ABq, J=11.2 Hz), 5.47 (1H, s), 4.98 (1H, s), 5.02 (1H, d, J=15.2 Hz), 5.86 (1H, s), 5.91 (1H, dd, J=15.9, 7.5 Hz), 7.29 (1H, d, J=15.9 Hz), 7.34 (5H, s), 9.52 (1H, d, J=7.5 Hz); $^{13}$C-NMR (75 MHz, CDCl$_3$) δ 13.8, 15.4, 21.7, 22.4, 23.6, 24.4, 28.8, 28.8, 31.5, 32.8, 34.4, 39.5, 47.4, 51.1, 51.2, 68.3, 70.8, 71.1, 71.2, 78.3, 102.5, 117.3, 127.0, 127.9, 128.0, 128.5, 138.1, 151.7, 166.5, 167.4, 171.8, 194.6.

The intermediate alcohol (11 mg, 0.02 mmol) was dissolved in 1.0 mL CH$_3$CN/H$_2$O (9:1) and treated with 48% aqueous HF (200 μL, 300 mol % excess) at rt. The resulting mixture was stirred for 1 h, quenched with sat. NaHCO$_3$ and diluted with 10 mL EtOAc. The aqueous layer was separated and extracted with EtOAc (2×). The combined organics were dried over Na$_2$SO$_4$ and concentrated in vacuo to afford the corresponding crude hemiketal enal of Formula 303a as a colorless oil. The crude product was purified by column chromatography on silica gel with 50% EtOAc-hexanes as eluant affording 8 mg (80%) of the C20 heptenoate hemiketal enal. R$_f$ (35% EtOAc/hexanes)=0.05; IR 3528, 2930, 2858, 1745, 1720, 1686, 1458, 1437, 1380 cm$^{-1}$; $^1$H NMR (300 MHz, CDCl$_3$) δ 0.86 (3H, t, J=6.9 Hz), 1.13 (3H, s), 1.17 (3H, s), 1.25 (10H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.52 (2H, ABq, J=11.4 Hz), 4.98 (1H, s), 5.02 (1H, d, J=15.2 Hz), 5.47 (1H, s), 5.86 (1H, s), 5.91 (1H, dd, J=15.9, 7.5 Hz), 7.29 (1H, d, J=15.9 Hz), 7.34 (5H, s), 9.52 (1H, d, J=7.5 Hz); $^{13}$C-NMR (75 MHz, CDCl$_3$) δ 13.9, 15.4, 21.7, 22.4, 23.6, 24.4, 28.8, 28.8, 31.4, 32.7, 34.2, 39.5, 47.4, 51.1, 51.2, 68.3, 70.9, 71.1, 71.1, 78.5, 102.4, 117.4, 126.8, 128.0, 128.0, 128.6, 138.1, 151.8, 166.4, 167.1, 171.8, 194.7.

Carboxylic acid 407 (21 mg, 0.04 mmol) and Et$_3$N (19 μL, 0.12 mmol) were dissolved in 400 μL toluene and treated with 2,4,6-trichlorobenzoylchloride (6.0 μL, 0.04 mmol) dropwise at rt. After 1 h at rt, a toluene solution of freshly prepared C20 heptenoate hemiketal enal (16 mg, 0.03 mmol) and 4-dimethylaminopyridine (17 mg, 0.13 mmol) was added gradually and stirring was continued for 40 min. The crude mixture was pipetted directly onto a column of silica gel and the product eluted with 20% EtOAc/hexanes to provide the expected ester (Formula 701 where R is OH, R' is OBn, R$^3$ is TBSO, R$^{20}$ is heptenoate, R$^{21}$ is =CH—CO$_2$Me and R$^{26}$ is methyl) as a colorless oil (24 mg, 80%).

IR 3487, 2927, 2856, 1723, 1689, 1455, 1379 cm$^{-1}$; $^1$H NMR (300 MHz, CDCl$_3$) δ 0.80 (1H, t, J=12.7 Hz), 0.93 (3H, t, J=7.0 Hz), 0.97 (3H, d, J=6.6 Hz), 1.10–1.36 (24H, m), 1.36–1.85 (21H, m), 1.91–2.13 (6H, m), 2.39 (1H, t, J=12.8 Hz), 2.79 (1H, d, J=13.2 Hz), 2.93 (1H, m), 3.05 (1H, m), 3.29 (3H, s), 3.33 (1H, s), 3.37–3.48 (2H, m), 3.80 (1H, dd, J=11.4, 5.1 Hz), 3.95–4.05 (2H, m), 4.15 (1H, td, J=10.8, 0.9 Hz), 4.23 (1H, d, J=13.5 Hz), 4.50 (2H, ABq, J=12.0 Hz), 4.98 (1H, s), 5.00 (1H, d, J=15.2 Hz), 5.57 (1H, s), 5.64 (1H, dd, J=10.6, 4.6 Hz), 6.05 (1H, dd, J=16.1, 7.6 Hz), 6.39 (1H, s), 7.10–7.35 (5H, m), 7.45 (1H, d, J=16.1 Hz), 9.60 (1H, d, J=7.6 Hz); $^{13}$C-NMR (75 MHz, CDCl$_3$) δ 14.1, 15.1, 19.3, 20.1, 21.3, 22.3, 22.4, 22.7, 23.8, 24.0, 24.6, 24.6, 29.0, 29.0, 29.3, 31.3, 31.6, 31.8, 34.2, 34.5, 35.2, 35.7, 36.2, 37.6, 43.5, 45.7, 51.6, 59.1, 64.9, 66.7, 71.1, 72.0, 72.9, 74.1, 75.3, 77.1, 100.2, 100.6, 121.2, 127.2, 127.3, 127.9, 128.6, 138.9, 151.2, 164.5, 166.3, 171.5, 175.1, 193.4; $[α]^{20}_D$ –19° (c 1.5, CH$_2$Cl$_2$).

To the ester prepared in the preceding step (21 mg, 0.03 mmol) in THF (0.5 mL) was added pyridine (360 μL, 0.45 mmol) followed by 70% HF/pyridine (144 μL, 500 mol % excess) and stirred for 20 hours. The reaction was then quenched with a saturated solution of sodium bicarbonate. The biphasic mixture was extracted with ethyl acetate (×4) and the combined organics were dried over sodium sulfate. The solvent was removed in vacuo to provide the corresponding crude C3 hydroxyester. The crude mixture was pipetted directly onto a column of silica gel and the product eluted with 30% EtOAc/hexanes to provide this corresponding ester (where R$^3$ is OH) as a colorless oil (13 mg, 68%). R$_f$ (30% EtOAc/hexanes)=0.23; IR 3522, 2927, 2857, 1724, 1664, 1230, 1158, 1136, 1107, 979 cm$^{-1}$; $^1$H NMR (400 MHz, CDCl$_3$) δ 0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 4.97 (1H, s), 5.02 (1H, d, J=15.2 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, CDCl$_3$) δ 14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5,- 98.7, 102.6, 120.5, 140.1, 151.2, 151.5, 166.5, 171.5, 174.2; $[α]^{20}_D$ –13.5° (c 0.9, CDCl$_3$).

To a solution of the C3 hydroxy ester of the preceding step (12 mg, 0.01 mmol) in 1.0 mL CH$_2$Cl$_2$ was added 4 Å molecular sieves and the mixture was allowed to stand for 20 min. 45–50 beads of Amberlyst-15 sulfonic acid resin were added and the mixture was stirred at rt for 2 h. The crude mixture was pipetted directly onto a column of silica gel and the product eluted with 35% EtOAc/hexanes to provide the corresponding heptenoate macrocycle as a colorless oil (7 mg, 70%). R$_f$ (35% EtOAc/hexanes)=0.21; IR 3522, 2927, 2857, 1724, 1664, 1230, 1158, 1136, 1107, 979 cm$^{-1}$; $^1$H NMR (400 MHz, CDCl$_3$) δ 0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 4.99 (1H, s), 5.03 (1H, d, J=15.2 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, CDCl$_3$) δ 14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2.

The crude macrocycle of the preceding step (2 mg, 0.01 mmol) was dissolved in 0.5 mL EtOAc and 2.2 mg Pd(OH)$_2$ (20% wt. on carbon) was added. The resulting suspension was vigorously stirred under balloon pressure of hydrogen gas for 35 min. The crude mixture was pipetted directly onto a column of silica gel and the product was eluted with 60% EtOAc/hexanes to afford heptanoate analogue (702.3) (Formula II where R$^3$ is OH, R$^{20}$ is —O—CO—C$_6$H$_{13}$, R$^{21}$ is =CH—CO$_2$Me, R$^{26}$ is methyl and X is oxygen) (1 mg, 63%) as a white semi-solid. R$_f$(50% EtOAc/hexanes)=0.21; $^1$H NMR (300 MHz, CDCl$_3$) δ 0.37 (3H, br. s), 0.79–0.92 (14H, m), 1.06 (3H, d, J=6.4 Hz), 1.07 (1H, t, J=11.0 Hz), 1.10–1.25 (5H, m), 1.27 (3H, s), 1.50 (3H, s), 1.57–1.78 (4H, m), 2.03 (2H, t, J=7.4 Hz), 2.17 (1H, dd, J=9.9/0.5 Hz), 2.37 (1H, m), 2.40 (1H, m), 2.85 (1H, t, J=11.2 Hz), 2.96 (1H, t, J=10.8 Hz), 3.15 (3H, s), 3.68–3.72 (3H, m), 3.91 (1H, dd, J=11.2, 4.0 Hz), 4.13 (1H, t, J=9.7 Hz), 4.35 (1H, dd, J=13.9, 2.2 Hz), 4.48 (1H, td, J=11.0/2.8 Hz), 4.70 (1H, d, J=12.1 Hz), 5.44 (1H, quint., J=4.8 Hz), 5.54 (1H, d, J=7.3 Hz), 5.69 (1H, s), 5.76 (1H, s), 5.85 (1H, dd, J=16.1, 7.5 Hz), 6.40 (1H, d, J=1.8 Hz), 6.50 (1H, d, J=15.9 Hz); $^{13}$C NMR (125 MHz, CDCl$_3$) δ 14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2.

4C. Myristate C20 Ester (702.4)

To solution of the enal of Formula 305 (in which R$^{20}$ is C$_7$H$_{15}$) (180 mg, 0.03 mmol), prepared as described for compound 13 in Wender et al. (1998a), in 0.5 mL of MeOH at rt was added PPTS (2 mg, catalytic) and trimethylorthoformate (5 drops). The progress of the reaction was monitored by TLC. After 30 min the reaction was quenched with 1.0 mL Et$_3$N. The solvent was removed under reduced pressure to afford the corresponding crude dimethylacetal according to Formula 306. The dimethylacetyl was immediately dissolved in MeOH (0.5 mL) and K$_2$CO$_3$ (3 mg, catalytic). The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure to afford crude C20 free hydroxyl product of Formula 307, which was reacted with myristic acid in the same manner as the reaction of heptenoic acid in Example 4B. After 30 min the reaction was quenched. The solution was quenched with sat. NaHCO$_3$, diluted with EtOAc (10 mL), washed with H$_2$O, dried over MgSO$_4$ and concentrated under reduced pressure. The crude product was purified by column chromatography on silica gel with 35% EtOAc-hexanes as eluant affording 14 mg (70% for three steps) of the desired dimethylacetal myristate of Formula 308. Rf (20% ethyl acetate/hexanes)=0.5; R$_f$ (35% EtOAc/hexanes)=0.50; IR 2927, 2859, 1744, 1719, 1687, 1514, 1249, 1156, 1103, 1079, 1037 cm$^{-1}$; $^1$H NMR (300 MHz, CDCl$_3$) δ 0.85 (6H, m), 1.16–1.30 (10H, m), 1.14 (3H, s), 1.18 (3H, s), 1.75 (1H, m), 1.95–2.17 (3H, m), 2.32 (1H, m), 3.37 (3H, s), 3.52 (1H, d, J=16.5 Hz), 3.68 (3H, s), 3.79 (3H, s), 3.87 (1H, m), 3.95 (1H, m), 4.09 (1H, m), 4.55 (2H, ABq, J=11.0 Hz), 5.41 (1H, s), 5.86 (1H, s), 5.91 (1H, dd, J=16.2, 7.6 Hz), 6.83 (2H, d, J=8.7 Hz), 7.16 (2H, d, J=8.7 Hz), 7.30–7.35 (6H, m), 9.43 (1H, d, J=7.6 Hz); $^{13}$C NMR (75

MHz, CDCl$_3$) δ 14.1, 21.7, 22.6, 24.0, 24.6, 28.9, 29.0, 31.7, 32.6, 34.5, 36.2, 47.5, 51.3, 51.5, 55.4, 69.2, 71.3, 71.8, 74.4, 76.3, 102.7, 114.1, 118.2, 127.1, 127.7, 127.9, 128.7, 129.5, 130.7, 138.9, 151.6, 159.6, 166.6, 167.3, 172.1, 195.0.

To a solution of the dimethylacetal myristate (11 mg, 0.01 mmol) in 0.6 mL 1% aqueous CH$_2$Cl$_2$ was added solid 2,3-dichloro-5,6-dicyano-1,4-benzoquinone (DDQ, 4 mg, 0.02 mmol) at rt. The mixture was stirred for 2 h, pipetted directly onto a column of silica gel, and the product eluted with 35% EtOAc/hexanes to provide the corresponding intermediate alcohol (8 mg, 89%) as a colorless oil: R$_f$ (35% EtOAc/hexanes)=0.22; IR 3528, 2930, 2858, 1745, 1720, 1686, 1458, 1437, 1380 cm$^{-1}$; $^1$H NMR (300 MHz, CDCl$_3$) δ 0.86 (3H, t, J=6.9 Hz), 1.13 (3H, s), 1.17 (3H), 1.25 (10H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.59 (2H, ABq, J=11.4 Hz), 5.47 (1H, s, C20), 5.86 (1H, s), 5.91 (1H, dd, J=15.9, 7.5 Hz), 7.29 (1H, d, J=15.9 Hz), 7.34 (5H, m), 9.52 (1H, d, J=7.5 Hz); $^{13}$C-NMR (75 MHz, CDCl$_3$) δ 13.86, 15.44, 21.70, 22.38, 23.61, 24.39, 28.75, 28.81, 31.45, 32.75, 34.22, 39.50, 47.35, 51.13, 51.23, 68.32, 70.89, 71.06, 71.12, 78.51, 102.36, 117.43, 126.83, 127.97, 127.98, 128.57, 138.11, 151.80, 166.42, 167.11, 171.76, 194.73; $[\alpha]_D^{20}$=−21.0° (c 1.0, CH$_2$Cl$_2$).

The intermediate alcohol (7 mg, 0.02 mmol) was dissolved in 1.1 mL CH$_3$CN/H$_2$O (9:1) and treated with 48% aqueous HF (200 μl, 300 mol % excess) at rt. The resulting mixture was stirred for 1 h, quenched with sat. NaHCO$_3$ and diluted with 10 mL EtOAc. The aqueous layer was separated and extracted with EtOAc (2×). The combined organics were dried over Na$_2$SO$_4$ and concentrated in vacuo to afford the crude hemi-ketal enal (44 in Reaction Scheme 11, which provides the compound number references for the remainder of the present example) as a colorless oil. The crude product was purified by column chromatography on silica gel with 35% EtOAc-hexanes as eluant affording 6 mg (86%) of enal 44. R$_f$(35% EtOAc/hexanes)=0.15; IR 3528, 2930, 2858, 1745, 1720, 1686, 1458, 1437, 1380 cm$^{-1}$; $^1$H NMR (300 MHz, CDCl$_3$) δ 0.87 (3H, t, J=6.9 Hz), 1.13 (3H, s), 1.15 (3H, s), 1.28 (10H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.56 (2H, ABq, J=11.0 Hz), 5.47 (1H, s), 5.86 (1H, s), 5.91 (1H, dd, J=15.9, 7.4 Hz), 7.28 (1H, d, J=15.9 Hz), 7.35 (5H, s), 9.52 (1H, d, J=7.4 Hz); $^{13}$C-NMR (75 MHz, CDCl$_3$) δ 13.9, 14.1, 19.4, 20.0, 22.7, 23.0, 24.4, 24.6, 29.1, 29.1, 29.4, 29.4, 29.6, 29.7, 31.2, 31.4, 31.9, 32.4, 34.6, 36.0, 40.0, 42.6, 42.9, 45.0, 51.1, 64.5, 66.3, 68.7, 70.4, 73.7, 74.1, 75.8, 76.1, 77.2, 78.7, 94.0, 98.9, 102.4, 119.7, 125.7, 142.8, 151.8, 167.0, 172.1, 172.5, 194.7.

Carboxylic acid 6 (6 mg, 0.01 mmol) and Et$_3$N (6 μL, 0.04 mmol) were dissolved in 300 μL toluene and treated with 2,4,6-trichlorobenzoylchloride (2.0 μL, 0.01 mmol) dropwise at rt. After 1 h at rt, a toluene solution of freshly prepared enal 44 and 4-dimethylaminopyridine (5 mg, 0.04 mmol) was added gradually and stirring was continued for 40 min. The crude mixture was pipetted directly onto a column of silica gel and the product eluted with 20% EtOAc/hexanes to provide ester-enal 46 as a colorless oil (9 mg, 90%). R$_f$(35% EtOAc/hexanes)=0.71; IR 3487, 2927, 2856, 1723, 1689, 1455, 1379, 1228, 1156, 1113, 1084, 1032,981 cm$^{-1}$; $^1$H NMR (300 MHz, CDCl$_3$) δ 0.80 (1H, t, J=12.7 Hz), 0.93 (3H, t, J=7.0 Hz), 0.98 (3H, d, J=6.6 Hz), 1.10–1.41 (24H, m), 1.42–1.85 (21H, m), 1.92–2.13 (6H, m), 2.39 (1H, t, J=12.7 Hz), 2.81 (1H, d, J=13.2 Hz), 2.93 (1H, m), 3.05 (1H, m), 3.29 (3H, s), 3.33 (1H, s), 3.37–3.48 (2H, m), 3.80 (1H, dd, J=11.4, 5.1 Hz), 3.95–4.05 (2H, m), 4.15 (1H, td, J=10.8, 0.9 Hz), 4.23 (1H, d, J=13.5 Hz), 4.46 (2H, ABq, J=11.0 Hz), 5.57 (1H, s), 5.64 (1H, dd, J=10.6, 4.6 Hz), 6.05 (1H, dd, J=15.9, 7.5 Hz), 6.39 (1H, s), 7.10–7.35 (5H, m), 7.45 (1H, d, J=15.9 Hz), 9.60 (1H, d, J=7.5 Hz); $^{13}$C-NMR (75 MHz, CDCl$_3$) δ −9.6, −9.4, 9.2, 10.3, 13.2, 14.1, 15.1, 19.3, 20.1, 21.3, 22.3, 22.4, 22.7, 23.8, 24.0, 24.6, 24.6, 29.0, 29.0, 29.3, 31.3, 31.6, 31.8, 34.2, 34.5, 35.2, 35.7, 36.2, 37.6, 43.5, 45.7, 51.6, 59.1, 64.9, 66.7, 71.1, 72.0, 72.9, 74.1, 75.3, 77.1, 100.2, 100.6, 121.2, 127.2, 127.3, 127.9, 128.6, 138.9, 151.2, 164.5, 166.3, 171.5, 175.1, 193.2; $[\alpha]_D^{20}$−19° (c 1.5, CH$_2$Cl$_2$).

To ester-enal 46 (8.0 mg, 0.001 mmol) in THF (0.5 mL) was added 70% HF/pyridine (0.3 mL, 0.3 mmol) and stirred for 2 hours. The reaction was then quenched with a saturated solution of sodium bicarbonate. The biphasic mixture was extracted with ethyl acetate (×4) and the combined organics were dried over sodium sulfate. The solvent was removed in vacuo to provide crude macrocycle. The crude mixture was chromatographed on silica gel and the product was eluted with 50% EtOAc/hexanes to afford 5.0 mg (83%) of the corresponding macrocycle as an clear oil.: R$_f$(40% EtOAc/hexanes)=0.19; IR 3522, 2927, 2857, 1724, 1664, 1230, 1158, 1136, 1107, 979 cm$^{-1}$; $^1$H NMR (300 MHz, CDCl$_3$) δ 0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 4.56 (2H, ABq, J=11.0 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, CDCl$_3$) δ δ 14.1, 19.4, 20.0, 22.7, 23.0, 24.4, 24.6, 29.1, 29.1, 29.4, 29.4, 29.6, 29.7, 31.2, 31.4, 31.9, 32.4, 34.6, 36.0, 40.0, 42.6, 42.9, 45.0, 51.1, 64.5, 66.3, 68.7, 70.4, 73.7, 74.1, 75.8, 76.1, 77.2, 78.7, 94.0, 98.9, 102.4, 119.7, 125.7, 142.8, 151.8, 167.0, 172.1, 172.5.

To 5.0 mg (0.0005 mmol) of crude macrocycle of the preceding step in ethyl acetate (1.0 ml) was added a catalytic amount of Pearlman's catalyst. The flask was evacuated and refilled with a 1 atm. hydrogen atmosphere (×4), stirred under hydrogen for 30 min, and then pipetted directly onto a silica gel column and eluted with 60% ethyl acetate/hexanes. This process afforded 4.8 mg (99%) of analogue 48 (702.4) (Formula II where R$^3$ is OH, R$^{20}$ is —O—CO—C$_{13}$H$_{27}$, R$^{21}$ is =CH—CO$_2$Me, R$^{26}$ is methyl and X is oxygen) as an amorphous solid. R$_f$(50% EtOAc/hexanes)= 0.16; IR 3522, 2927, 2857, 1724, 1664, 1230 IR (neat)= 3455, 3319, 2929, 2856, 1735, 1380, 1230, 1138, 976 cm$^{-1}$; $^1$H NMR (300 MHz, CDCl$_3$) δ 0.37 (3H, bs), 0.79–0.92 (14H, m), 1.06 (3H, d, J=6.4 Hz), 1.07 (1H, t, J=11.0 Hz), 1.10–1.25 (5H, m), 1.27 (3H, s), 1.50 (3H, s), 1.57–1.78 (4H, m), 2.03 (2H, t, J=7.4 Hz), 2.17 (1H, dd, J=9.9/0.5 Hz), 2.37 (1H, m), 2.40 (1H, m), 2.85 (1H, t, J=11.2 Hz), 2.96 (1H, t, J=10.8 Hz), 3.15 (3H, s), 3.68–3.72 (3H, m), 3.91 (1H, dd, J=11.2, 4.0 Hz), 4.13 (1H, t, J=9.7 Hz), 4.35 (1H, dd, J=13.9/2.2 Hz), 4.48 (1H, td, J=11.0, 2.8 Hz), 4.70 (1H, d, J=12.1 Hz), 5.44 (1H, quint., J=4.8 Hz), 5.54 (1H, d, J=7.3 Hz), 5.69 (1H, s), 5.76 (1H, s), 5.85 (1H, dd, J=16.1, 7.5 Hz), 6.40 (1H, d, J=1.8 Hz), 6.50 (1H, d, J=15.9 Hz); $^{13}$C NMR (125 MHz, CDCl$_3$) δ 14.1, 19.4, 20.0, 22.7, 23.0, 24.4, 24.6, 29.1, 29.1, 29.4, 29.4, 29.6, 29.7, 31.2, 31.4, 31.9, 32.4, 34.6, 36.0, 40.0, 42.6, 42.9, 45.0, 51.1, 64.5, 66.3, 68.7, 70.4, 73.7, 74.1, 75.8, 76.1, 77.2, 78.7, 94.0, 98.9, 102.4, 119.7, 125.7, 142.8, 151.8, 167.0, 172.1, 172.5.

4D. Benzoate C20 Ester (702.5)

Enal 45 was prepared following the procedure for compound 111 in Example 1C except that benzoic acid was substituted for octanoic acid, to form the corresponding protected benzoate product.

Carboxylic acid 6 (6 mg, 0.01 mmol) and $Et_3N$ (6 μL, 0.04 mmol) were dissolved in 300 μL toluene and treated with 2,4,6-trichlorobenzoylchloride (2 μL, 0.01 mmol) dropwise at rt. After 1 h at rt, a toluene solution of freshly prepared 45 and 4-dimethylaminopyridine (5 mg, 0.01 mmol) was added gradually and stirring was continued for 40 min. The crude mixture was pipetted directly onto a column of silica gel and the product eluted with 20% EtOAc/hexanes to provide the expected ester product as a colorless oil (8 mg, 89%). $R_f$ (35% EtOAc/hexanes)=0.71; IR 3460, 2927, 2856, 1723 $cm^{-1}$; $^1H$ NMR (300 MHz, $CDCl_3$) δ 0.08 3H, s), 0.08 (3H, s), 0.81 (12H, m), 0.82–0.96 (3H, m), 1.06–1.32 (15H, m), 1.59–1.81 (4H, m), 2.20 (1H, t, J=9.3 Hz), 3.33–3.44 (2H, m), 3.67–3.84 (1H, m), 4.00–4.15 (4H, m), 4.31–4.39 (1H, m), 4.55 (2H, ABq, J=8.5 Hz), 5.41 (1H, s), 5.75 (1H, dd, J=15.5, 3.4 Hz), 6.01 (1H, s), 6.39 (1H, s), 7.28–7.47 (9H, m), 7.84 (1H, d, J=6.9 Hz), 9.17 (1H, d, J=7.3 Hz); $^{13}C$-NMR (75 MHz, $CDCl_3$) δ –9.6, –9.4, 9.2, 10.3, 13.2, 14.2, 18.5, 22.0, 23.5, 28.4, 28.7, 30.7, 31.5, 33.5, 39.1, 41.5, 41.9, 44.0, 50.1, 63.7, 65.3, 67.8, 69.6, 70.3, 73.8, 74.8, 75.1, 76.2, 77.7, 98.1, 101.3, 118.8, 124.7, 126.7, 127.4, 127.5, 128.9, 132.2, 137.3, 141.8, 150.8, 163.6, 165.9, 170.2.

To the ester of the preceding step (13 mg, 0.02 mmol) in THF (0.5 mL) was added pyridine (360 μL, 0.45 mmol) followed by 70% HF/pyridine (144 μL, 500 mol % excess) with stirring for 20 hours. The reaction was then quenched with a saturated solution of sodium bicarbonate. The biphasic mixture was extracted with ethyl acetate (×4) and the combined organics were dried over sodium sulfate. The solvent was removed in vacuo to provide the corresponding crude C3 hydroxyester. The crude mixture was pipetted directly onto a column of silica gel and the product eluted with 35% EtOAc/hexanes to provide the purified C3 hydroxyester as a colorless oil (9 mg, 82%). $R_f$ (40% EtOAc/hexanes)=0.19; IR 3522, 2927, 2857, 1724 $cm^{-1}$; $^1H$ NMR (300 MHz, $CDCl_3$) 0.81–0.91 (3H, m), 1.08 (3H, s), 1.20–1.59 (9H, m), 1.31 (6H, s), 1.92–2.18 (4H, m), 2.45 (2H, bs), 3.40–3.58 (2H, m), 3.67 (3H, s), 3.69–3.78 (2H, m), 3.88–3.98 (2H, m) 4.03–4.24 (3H, m), 4.45 (1H, d, J=9.2 Hz), 4.65 (2H, ABq, J=8.5 Hz), 5.17 (1H, d, J=9.7 Hz), 5.22 (1H, s), 5.40 (1H, s), 5.44 (1H, dd, J=15.5, 7.3 Hz), 6.06 (1H, s), 6.08 (1H, d, J=15.5 Hz), 7.27–7.59 (9H, m), 8.05 (1H, d, J=6.9 Hz); $^{13}C$ NMR (100 MHz, $CDCl_3$) δ 14.2, 18.5, 22.0, 23.5, 28.4, 28.7, 30.7, 31.5, 33.5, 39.1, 41.5, 41.9, 44.0, 50.1, 63.7, 65.3, 67.8, 69.6, 70.3, 73.8, 74.8, 75.1, 76.2, 77.7, 98.1, 101.3, 118.8, 124.7, 126.7, 127.4, 127.5, 128.9, 132.2, 137.3, 141.8, 150.8, 163.6, 165.9, 170.2; $[\alpha]^{20}_D$–11.5 (c 0.9, $CDCl_3$).

To 4.0 mg (0.0011 mmol) of the crude C3 hydroxyester of the preceding step in ethyl acetate (1.0 ml) was added a catalytic amount of Pearlman's catalyst. The flask was evacuated and refilled with a 1 atm. hydrogen atmosphere (×4). Stirred under hydrogen for 30 min. and then pipetted directly onto a silica gel column and eluted with 60% ethyl acetate/hexanes. HPLC (hexane: methylene chloride: i-propanol, 16:3:1) Isolated 2.2 mg (63%) of analogue 49 (702.5) (Formula II where $R^3$ is OH, $R^{20}$ is —O—CO-Ph, $R^{21}$ is =CH—$CO_2$Me, $R^{26}$ is methyl and X is oxygen)as an amorphous solid. $R_f$ (50% EtOAc/hexanes)=0.16; IR 3522, 2927, 2857, 1724, 1664, 1230 IR (neat)=3455, 3319, 2929, 2856, 1735, 1380, 1230, 1138, 976 $cm^{-1}$; $^1H$ NMR (300 MHz, $CDCl_3$) δ 0.81–0.92 (3H, m), 1.08 (3H, s), 1.20–1.59 (9H, m), 1.32 (6H, s), 1.90–2.18 (4H, m), 2.52–2.56 (2H, m), 3.40–3.55 (2H, m), 3.67 (3H, s), 3.73–3.79 (2H, m), 3.82–3.95 (2H, m), 4.02–4.22 (2H, m), 4.51 (1H, d, J=9.1 Hz), 5.11 (1H, d, J=8.9 Hz), 5.26 (1H, s), 5.40 (1H, s), 5.42 (1H, dd, J=15.5, 3.4 Hz), 6.04 (1H, d, J=15.5 Hz), 6.07 (1H, s), 7.34–7.57 (4H, m), 8.04 (1H, d, J=7.3 Hz); $^{13}C$ NMR (125 MHz, $CDCl_3$) δ 13.1, 18.4, 18.9, 21.7, 23.5, 28.7, 30.6, 31.4, 35.0, 39.1, 41.6, 50.1, 63.6, 67.7, 69.2, 72.6, 76.1, 77.7, 93.0, 99.2, 113.0, 124.7, 127.2, 127.5, 128.9, 132.2, 146.3, 148.1, 149.9, 150.6, 171.4, 173.2; $[\alpha]^{25}_D$=–7.0° (c=0.36, $CDCl_3$).

Example 5

Protein Kinase C (Isozyme Mix) Assay Protocol

The following procedure was used, based on a modification of a previous procedure described by Tanaka et al. (1986). Filters (Whatman GF-B, 21 mm diam.) are soaked for 1 h in a solution containing deionized water (97 mL), and 10% polyethyleneamine (3 mL). A filtering buffer solution containing TRIS (1M, pH 7.4, 10 mL) and water (490 mL) is prepared and cooled on ice. An assay buffer solution is prepared by the addition of TRIS (1M, pH 7.4, 1 mL), KCl (1M, 2 mL), $CaCl_2$ (0.1M, 30 μL), bovine serum albumin (40 mg), diluted to 20 mL with deionized water and stored on ice. Phosphatidyl serine vesicles are prepared by the addition of phosphatidyl serine (10 mg/mL in chloroform, 0.4 mL) to a glass test tube followed by removal of the chloroform under a stream of nitrogen (5 min). To this viscous liquid is added a portion of the prepared assay buffer (4 mL) and the resulting mixture is then transferred to a plastic tube with washing. This tube is then sonicated (Branson Sonifier 250, power=6, 40% duty cycle) four times for 30 sec. with a 30 sec. rest period between sonications. The resulting solution is stored over ice. PKC is prepared by addition of cooled assay buffer (10 mL) to PKC (25 μL) purified from rat brain by the method of Mochly-Rosen and Koshland (1986) and then stored on ice. Stock solutions of compounds are diluted with absolute ethanol in glass in serial fashion. Each plastic assay incubation tube is made to contain prepared phosphatidyl serine vesicles (60 μL), prepared PKC solution (200 μL) and analogue (0–20 μL) plus EtOH (20–0 μL) for a total volume of 20 μL). Lastly, tritiated phorbol 12,13-dibutyrate (PDBU) (30 nM, 20 μL) is added to each tube. The assay is carried out using 7–10 analogue concentrations, each in triplicate. Non-specific binding is measured in 1–3 tubes by the substitution of phorbol myristate acetate (PMA) (1 mM, 5 μL) and EtOH (15 μL) for the analogue/EtOH combination. The tubes are incubated at 37° C. for 90 min. and then put on ice for 5 min. Each tube is then filtered separately through a pre-soaked filter disc. Each tube is rinsed with cold 20 mM TRIS buffer (500 μL) and the rinseate is added to the filter. The filter is subsequently rinsed with cold 20 mM TRIS buffer (5 mL) dropwise. The filters are then put in separate scintillation vials and Universol© scintillation fluid is added (3 mL). The filters are immediately counted in a scintillation counter (Beckman LS 6000SC). Counts per minute are averaged among three trials at each concentration. The data is then plotted using a least squares fit algorithm with the Macintosh version of Kaleidagraph© (Abelbeck Software) and an $IC_{50}$ (defined as the concentration of analogue required to displace half of the specific PDBU binding to PKC is calculated. The $IC_{50}$ then allows determination of the $K_i$ for the analogue from the equation: $K_i=IC_{50}/(1+[PDBu]/K_d$ of PDBu). The $K_d$ of [H$^3$]-PDBu was determined under identical conditions to be 1.55 nM.

Example 6

PKCδ-C1B Assay Protocol

All aspects of the PKCδ-C1B assay are identical to the PKC isozyme mix assay from Example 5 except the following features: In the PKCδ-C1B assay system, assay buffer is made without CaCl$_2$. PKCδ-C1B (200 μg, 34.14 nmol), prepared by the method of Wender et al. (1995) and Irie et al. (1998) is dissolved in deionized water (160 μL) and ZnCl$_2$ (5 mM, 40 μL) is added. The resulting solution is allowed to stand at 4° C. for 10 min. An aliquot (10 μL) of this solution is diluted to 2 mL with deionized water. An aliquot (290 μL) is further diluted to 20 mL with assay buffer and is ready for use. The incubation time is shortened from 90 min. to 30 min. Lastly, during the filtering portion of the assay, the tube is not washed with filtering buffer (0.5 mL).

When tested as described above, the C26 desmethyl analogue 702.1 (Example 3A), had significantly higher activity than the corresponding C26 methyl-containing analogue (Formula 1998a where R$^3$ is OH). Similarly, among several analogues having different C20 ester groups, the presence of longer R20 substituents (48) or an aryl substituent (49) also afforded higher activity. The results are shown below in Table 1 (in all compounds tested, R$^3$ was OH and R$^{21}$ was =CH—CO$_2$Me).

TABLE 1

| Compound | R$^{20}$ | R$^{26}$ | PKCδ-C1B Assay Ki (nM) |
|---|---|---|---|
| Phorbol dibutyrate | | | 1.7 (K$_d$ value) |
| Formula 1998a | —OC(O)C$_7$H$_{15}$ | CH$_3$ | 5.1 |
| Formula IIa (702.1) | —OC(O)C$_7$H$_{15}$ | H | 0.30 ± 0.07 |
| Formula 702.2 | —OC(O)CH$_3$ | CH$_3$ | 232 ± 11 |
| Formula 702.3 | —OC(O)C$_6$H$_{13}$ | CH$_3$ | 35 |
| Formula 702.4 | —OC(O)C$_{13}$H$_{27}$ | CH$_3$ | 1.3 |
| Formula 702.5 | —OC(O)Phenyl | CH$_3$ | 1.7 |

Example 7

P388 Murine Lymphocytic Leukemia Cell Assay

Cells from a P388 cell line (CellGate, Inc., Sunnyvale, Calif.) are grown in RPMI 1640 cell medium containing fetal calf serum (10%), L-glutamine, penicillin, streptomycin and are split twice weekly. All compounds are first diluted with DMSO. Later serial dilutions are done with a phosphate buffer solution (HYQ DPBS modified phosphate buffered saline). All dilutions are done in glass vials and the final DMSO concentration is always below 0.5% by volume. Final two-fold dilutions are done in a 96 well plate using cell media so that each well contains 50 μL. All compounds are assayed in quadruplicate over 12 concentrations. Cell concentration is measured using a hemacytometer and the final cell concentration is adjusted to 1×10$^4$ cells/mL with cell medium. The resulting solution of cells (50 μL) is then added to each well and the plates are incubated for 5 days in a 37° C., 5% CO$_2$ humidified incubator (Sanyo CO$_2$ incubator). MTT solution (3-[4,5-dimethylthiazol-2-yl]-2,5-diphenyltetrazolium bromide, 10 μL) is then added to each well and the plates are re-incubated under identical conditions for 2 h. To each well is then added acidified isopropanol (150 μL of i-PrOH solution containing 0.05 N HCl) and mixed thoroughly. The plates are then scanned at 595 nm and the absorbances are read (Wallac Victor 1420 Multilabel Counter). The resulting data is then analyzed to determine an ED$_{50}$ value using the Prism software package (GraphPad).

When tested as described above, the C26 desmethyl analogue 702.1 (Example 3A), had significantly higher activity than the corresponding C26 methyl-containing analogue. Similarly, among several analogues having different C20 ester groups, the presence of longer R20 substituents (48) or an aryl substituent (49) also afforded higher activity. The results are shown below in Table 2 (in all compounds tested, R$^3$ was OH and R$^{21}$ was =CH—CO$_2$Me).

TABLE 2

| Compound | R$^{20}$ | R$^{26}$ | P388 Assay ED$_{50}$ (nM) |
|---|---|---|---|
| Formula 1998a | —OC(O)C$_7$H$_{15}$ | CH$_3$ | 76 |
| Formula IIa (702.1) | —OC(O)C$_7$H$_{15}$ | H | 17 |
| Formula 702.2 | —OC(O)CH$_3$ | CH$_3$ | 181 |
| Formula 702.3 | —OC(O)C$_6$H$_{13}$ | CH$_3$ | 38 |
| Formula 702.4 | —OC(O)C$_{13}$H$_{27}$ | CH$_3$ | 3.6 |
| Formula 702.5 | —OC(O)Phenyl | CH$_3$ | 42 |

Example 8

In Vitro Inhibition of Growth in Human Cancer Cell Lines

Anticancer data were obtained in vitro for C26 desmethyl bryostatin analogue 702.1 (Example 3A) tested against a spectrum of different NCI human cancer cell-lines associated with various cancer conditions. The results are shown in Table 3. Data obtained with Bryostatin-1 are included for comparison. Growth inhibition (GI50) values are expressed as the log of molar concentration at half-maximum inhibition. As can be seen, the C26 desmethyl compound was at least as potent, on average, as bryostatin-1 for all cell groups tested. Moreover, the C26 desmethyl compound was more active than bryostatin-1 by more than 2 orders of magnitude for several cell lines: K-562 and MOLT-4 (leukemia), NCI-H460 (NSC lung), HCC-2998 (colon), TK-10 (renal), and MDA-MB435 (breast). These results are significant and surprising since the C27 methyl group attached to C26 was previously believed to be necessary for activity.

TABLE 3

| Cell Line: | desmethyl | Bryo-1 | Difference |
|---|---|---|---|
| Leukemia | | | |
| CCRF-CEM | −5.81 | −5.30 | −0.51 |
| HL-60(TB) | −5.84 | −5.70 | −0.14 |
| K-562 | −7.5 | −5.40 | −2.10 |
| MOLT-4 | <−8.0 | −5.50 | −2.50 |
| RPMI-8226 | −5.82 | >−5 | −0.82 |
| SR | −5.1 | >−5 | −0.10 |
| NSC Lung | | | |
| A549/ATCC | −6.62 | −5.20 | −1.42 |
| EKVX | −5.58 | −5.30 | −0.28 |
| HOP-62 | −4.79 | >−5 | |
| HOP-92 | −4.67 | −5.30 | 0.63 |
| NCI-H226 | | >−5 | |
| NCI-H23 | | >−5 | |
| NCI-H322M | −4.38 | −6.00 | 1.62 |
| NCI-H460 | <−8 | −5.60 | −2.40 |
| NCI-H522 | | >−5 | |

TABLE 3-continued

| Cell Line: | desmethyl | Bryo-1 | Difference |
|---|---|---|---|
| Colon | | | |
| COLO 205 | −7.08 | −5.40 | −1.68 |
| HCC-2998 | −7.54 | −5.30 | −2.24 |
| HCT-116 | −5.32 | −5.30 | −0.02 |
| HCT-15 | −4.76 | >−5 | |
| HT29 | −5.55 | −5.30 | −0.25 |
| KM12 | −5.34 | −5.20 | −0.14 |
| SW-620 | −5.12 | −5.50 | 0.38 |
| CNS | | | |
| SF-268 | −4.97 | −5.10 | 0.13 |
| SF-295 | −6.05 | −5.20 | −0.85 |
| SF-539 | −5.77 | >−5 | −0.77 |
| SNB-19 | −5.2 | >−5 | −0.20 |
| SNB-75 | −4.97 | −5.50 | 0.53 |
| U251 | −5.4 | −5.10 | −0.30 |
| Prostate | | | |
| PC-3 | −5.6 | −5.30 | −0.30 |
| DU-145 | −5.02 | >−5 | −0.02 |
| Melanoma | | | |
| LOX IMVI | −5.47 | −5.10 | −0.37 |
| MALME-3M | | −5.20 | |
| MI4 | −5.26 | >−5 | −0.26 |
| SK-MEL-2 | −5.02 | −5.20 | 0.18 |
| SK-MEL-28 | −4.67 | −5.10 | 0.43 |
| SK-MEL-5 | −6.43 | −5.70 | −0.73 |
| UACC-257 | −5.13 | −5.10 | −0.03 |
| UACC-62 | −5.11 | −5.30 | 0.19 |
| Ovarian | | | |
| IGROVI | −4.88 | −5.30 | 0.42 |
| OVCAR-3 | −4.83 | −5.10 | 0.27 |
| OVCAR-4 | −5.15 | −5.50 | 0.35 |
| OVCAR-5 | −5.28 | >−5 | −0.28 |
| OVCAR-8 | −4.77 | −5.10 | 0.33 |
| SK-OV-3 | −4.3 | −5.10 | 0.80 |
| Renal | | | |
| 786-0 | −5.46 | −5.20 | −0.26 |
| A498 | −6.38 | >−5 | −1.38 |
| ACHN | −5.94 | −5.50 | −0.44 |
| CAKI-1 | −5.7 | −5.40 | −0.30 |
| RXF-393 | | −5.30 | |
| SN12C | −5.59 | −5.10 | −0.49 |
| TK-10 | −7.03 | >−5 | −2.03 |
| UO-31 | −4.85 | −5.60 | 0.75 |
| Breast | | | |
| MCF7 | −5.4 | −5.20 | −0.20 |
| NCI/ADR-RES | −4.74 | >−5 | |
| MDA-MB-231/ATCC | −5.69 | −5.20 | −0.49 |
| MDA-MB-435 | −7.66 | −5.10 | −2.56 |
| MDA-N | | −5.10 | |
| BT-549 | −4.71 | −5.10 | 0.39 |
| T-47D | −5.02 | −5.20 | 0.18 |
| HS 578T | −5.18 | −5.2 | 0.02 |

Example 9

Formula 405 where X is ——O——

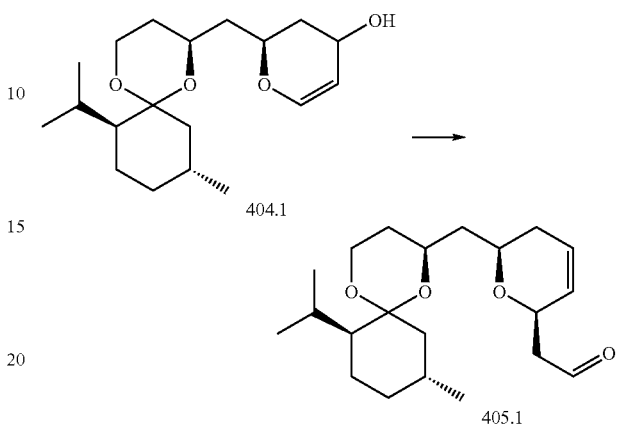

In an oven dried argon purged 100 mL round-bottom flask charged with a magnetic stir bar was added a solution of 482 mg (1.49 mmol, 1.0 eq) of the compound of Formula 404.1 in 31 mL of isobutylvinyl ether. 237 mg (0.744 mmol, 0.5 eq) of Hg(II) diacetate was added in one portion at room temperature [rt]. The reaction was run at rt for 48 hrs. The reaction was diluted with EtOAc and washed with sat. NaHCO$_3$ and brine. The combined organic layers were dried over MgSO$_4$, filtered and concentrated. Rapid flash chromatography using 15% ethyl acetate, 85% petroleum ether plus 1% triethyl amine yielded crude vinylated pyran. This was carried on immediately.

In an oven-dried argon-purged 250 mL round-bottom flask charged with a magnetic stir bar was added a solution of 480 mg (1.37 mmol, 1.0 eq) of the vinylated pyran in 26 mL of degassed, (via bubbling argon gas through), 99%+ anhydrous decane (Aldrich). The reaction vessel was lowered into a preheated 155° C. oil bath. The reaction was heated for 3 hrs at this temperature under an argon atmosphere. It was then removed from the oil bath and cooled to rt. It was allowed to sit overnight under an argon atmosphere. The whole reaction was loaded onto a column using petroleum ether to assist in the transfer. The column was then eluted with 10% ethyl acetate 90% petroleum ether, to yield 431 mg (83% over two steps) of the title compound of Formula 405, [6-(7-isopropyl-10-methyl-1,5-dioxa-spiro[5.5]undec-2-ylmethyl)-5,6-dihydro-2H-pyran-2-yl]-acetaldehyde, as a clear colorless oil.

Example 10

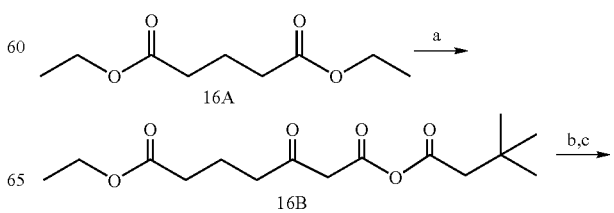

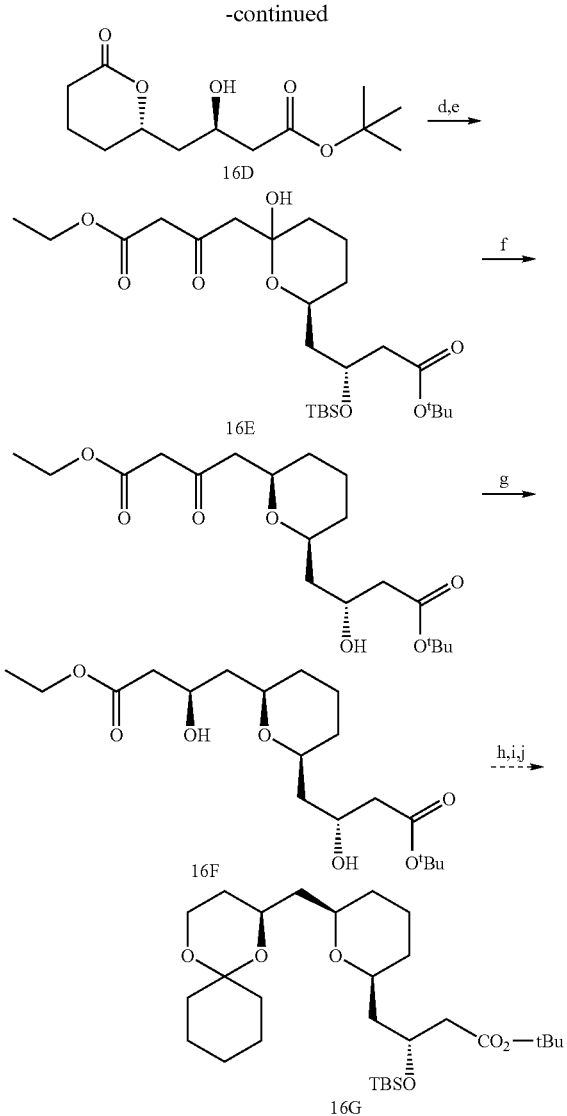

Conditions:
(a) (i) t-Butylacetoacetate, NaH, THF, 0° C. (ii) n-BuLi, (1.5 M in Hexanes), 0° C. (iii) 1, THF, -78° C.->-30° C. (65%)
(b) R-BinapRuBr₂, H₂ (20 atm), EtOH, 70° C.
(c) TsOH, Toulene, -10° C. (35% total two steps)
(d) TBS-OTf, 2,6-lutidine, DMAP, DCM (72%)
(e) (i) Ethylacetoacetate, NaH, THF, 0° C. (ii) n-BuLi, (1.5M in Hexanes), 0° C. (iii) Ester, THF, -78° C.->-30° C. (75%)
(f) 1% TFA, TES, DCM, -20° C. (90%)
(g) R-BinapRuBr₂, H₂ (1 atm), EtOH, 75° C.
(h) NaBH₄, MeOH
(i) Cyclohexanone, TsOH, Tol.
(j) TBS-OTf, 2,6-lutidine, DMAP, DCM

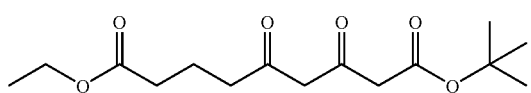

Procedure:

6.38 g of freshly distilled diisopropyl amine was combined with 100 ml of dry THF and cooled to −78° C. 40.7 mL of 1.55 M n-BuLi in Hexanes was then added slowly. After 10 minutes at −78° C., the solution was warmed to 0° C. for 15 minutes then re-cooled to −78° C. To this solution of lithium diusopropylamide [LDA] at −78° C. was added 5 g of tert-butylacetoacetate slowly. After 10 minutes at −78° C., the solution was warmed to 0° C. for 40 minutes. The bright yellow solution of dianion was then cooled to −78° C. and 2.97 g of diethylglutarate was added in 5 mL of dry THF in one portion. After 30 minutes at −78° C., the reaction was quenched by the addition of 140 mL of 1 N HCl in water. The reaction was then partitioned between the aqueous layer and 200 mL of ether. The ether was removed in vacuo and the residue purified via flash chromatography (25% Ether: Pentane—Rf=0.3) to give 65% product.

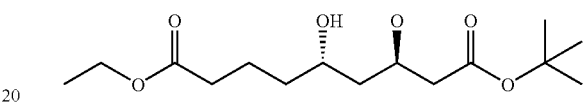

Procedure:

A 2-neck flask with 2 gas flow adaptors was charged with 21 mg of COD-RuBis-2-methylallyl complex and 50 mg of (S)-BINAP. To this was added 4mL of degassed acetone (Argon purge for 20 min.) and 12 mg of HBr (24 μL of 49% soln) in 0.4 mL degassed MeOH (as above). The solution became red-orange with a red precipitate. After 30 minutes, the solvents were carefully remove in vacuo (air sensitive!) to yield a tan powder that was used directly. To the crude (S)-BINAP-RuBr₂ was added 1 g of 3,5-dioxo-nonanedioic acid 1-tert-butyl ester 9-ethyl ester in 10 mL EtOH. The solution was stirred rapidly and the suspension transferred to a Parr Bomb apparatus under Argon blanket. The bomb was sealed and pressurized to 20 atmospheres for 3 cycles then left at 20 atmospheres and heated to 75° C. with stirring. After 6 hours, the reaction appeared complete by TLC and the product isolated by Flash Chromatography (Rf=0.2 in 1:1 Ethyl Acetate:Pentane) to yield 442 mg of product that was recrystallized in Ethyl Acetate:Pentane to yield 320 mg product.

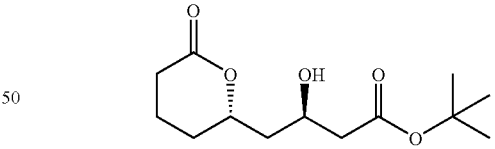

Procedure:

126 mg of 3,5-dihydroxy-nonanedioic acid 1-tert-butyl ester 9-ethyl ester was dissolved in 16 mL of dry toluene then cooled to −10° C. in an acetone/ice bath. To this was added 4 mg of Tosic Acid. After 8 hours at −10° C., the S.M. appeared consumed. The reaction was quenched with saturated sodium bicarbonate solution and partitioned between ethyl acetate and saturated sodium bicarbonate solution. The ethyl acetate was removed in vacuo and the residue purified via flash chromatography (1:1 Ethyl Acetate:Pentane-→1.5:1 Ethyl Acetate:Pentane Rf=0.3 in 1.5:1 E.A.:Pentane). Yield=75%

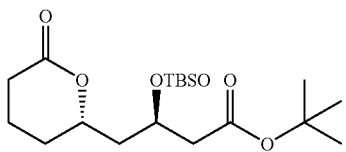

Procedure:

29 mg of 3-hydroxy-4-(6-oxo-tetrahydro-pyran-2-yl)-butyric acid tert-butyl ester was dissolved in 3 mL of dichloromethane and cooled to 0° C. To this was added 24 mg of dry 2,6-lutidine. 60 mg of TBS triflate was added followed by 50 mg of DMAP. The solution was allowed to warm to r.t. and stirred overnight. The reaction was then partitioned between ethyl acetate and saturated bicarbonate solution. The ethyl acetate was removed in vacuo and the residue purified via flash chromatography (15% ethyl acetate:pentane Rf=0.3) to yield the TBS ether in 72% yield.

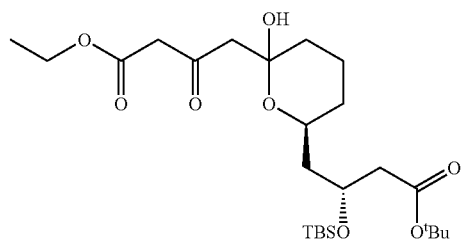

Procedure:

To 190 mg of NaH (95%) in 80 mL of dry THF was added 1.05 g of ethyl acetoacetate in 15 mL of dry THF at 0° C. After 10 minutes, 5.4 mL of 1.5 M n-BuLi in Hexanes was added. After 10 additional minutes, 1% of the solution (~1 mL) was taken and cooled to −78° C. in a dry flask. To this was added 15 mg of 3-(tert-butyl-dimethyl-silanyloxy)-4-(6-oxo-tetrahydro-pyran-2-yl)-butyric acid tert-butyl ester in 1 mL of dry THF. After 30 minutes, the reaction was quenched with 1N HCl and partitioned into ethyl acetate. The ethyl acetate was removed in vacuo and the residue purified by flash chromatography (30% ethyl acetate:pentane Rf=streak~0.3).

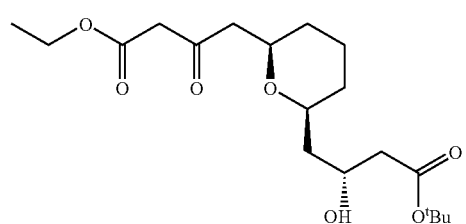

Procedure:

5 mg of 3-(tert-butyl-dimethyl-silanyloxy)-4-[6-(3-ethoxycarbonyl-2-oxo-propyl)-6-hydroxy-tetrahydro-pyran-2-yl]-butyric acid tert-butyl ester was dissolved in 1 mL of dichloromethane and cooled to −78° C. To this was added 100 μL of TES and 50 μL of TFA. The solution was allowed to slowly warm to 0° C., at which time a lower slightly lower Rf spot cleanly formed (Rf=0.2 in 30% E.A.:Pentane). The reaction was quenched with saturated bicarbonate solution and extracted into ethyl acetate. The product was then purified via flash chromatography to yield the syn tetrahydropyran in 90% without the TBS ether.

Example 11

Compound and synthetic step references in this example correspond to the following two schemes (as opposed to the reaction schemes and formula numbers employed previously in the specification).

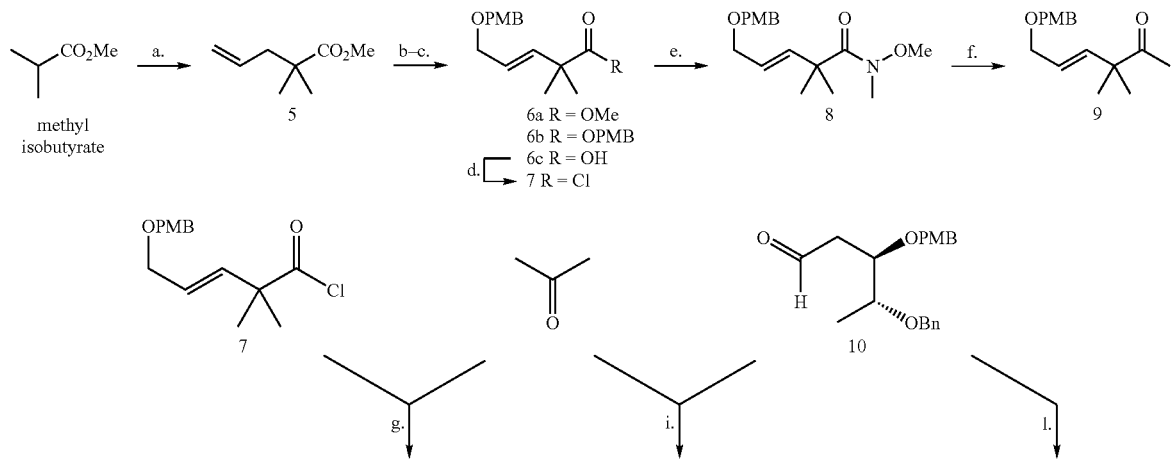

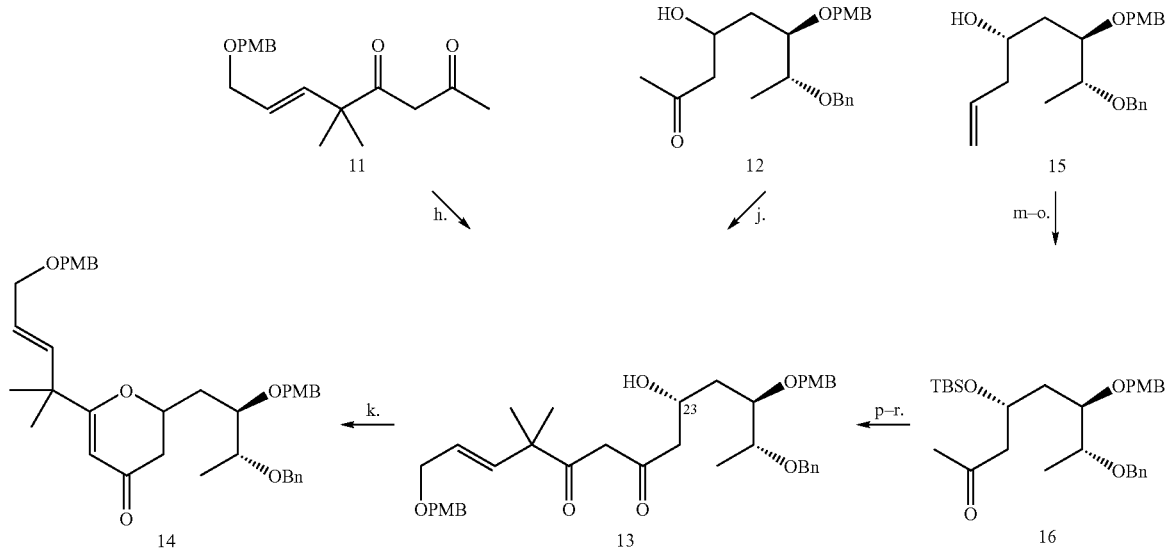

(a) LDA, THF, allyl Br, -78° C., 90%;
(b) NBS, benzoyl peroxide, CCl₄, reflux, 72%;
(c) NaH, PMBOH, THF, 35° C., NH₄OH quench gives 6a, b, 74%; aq. quench gives 6c, 74%;
(d) NaH, (COCl)₂, Et₂O;
(e) (MeO)NHMe·HCl, PhMgBr, -20° C., then 6a, b, 90%;
(f) MeLi, THF, -20° C., 99%;
(g) acetone, LDA, THF, -78° C., 77%;
(h) LDA, THF, -78° C. then 11, 65%, 58% ds;
(i) acetone, LDA, THF, -78° C., 87%, 81% ds;
(j) LDA, THF, -78° C. then 7, 61%;
(k) TsOH, 4 Å sieves, PhCH₃, 83%;
(l) (-)-MeOB(Ipc)₂, allyl MgBr, Et₂O, -78° C., 66%, 83% ds;
(m) NaH, TBSCl, DMAP, CH₂Cl₂, reflux, 86%;
(n) OsO₄, NMO, 2:1 THF/H₂O;
(o) NaIO₄, 2:1 THF/H₂O, 85% over 2 steps;
(p) 9, LDA, THF, -78° C., 96%;
(q) TPAP, NMO, CH₂Cl₂, 4 Å sieves, 55%;
(r) HF·pyridine, pyridine, THF, 70%.

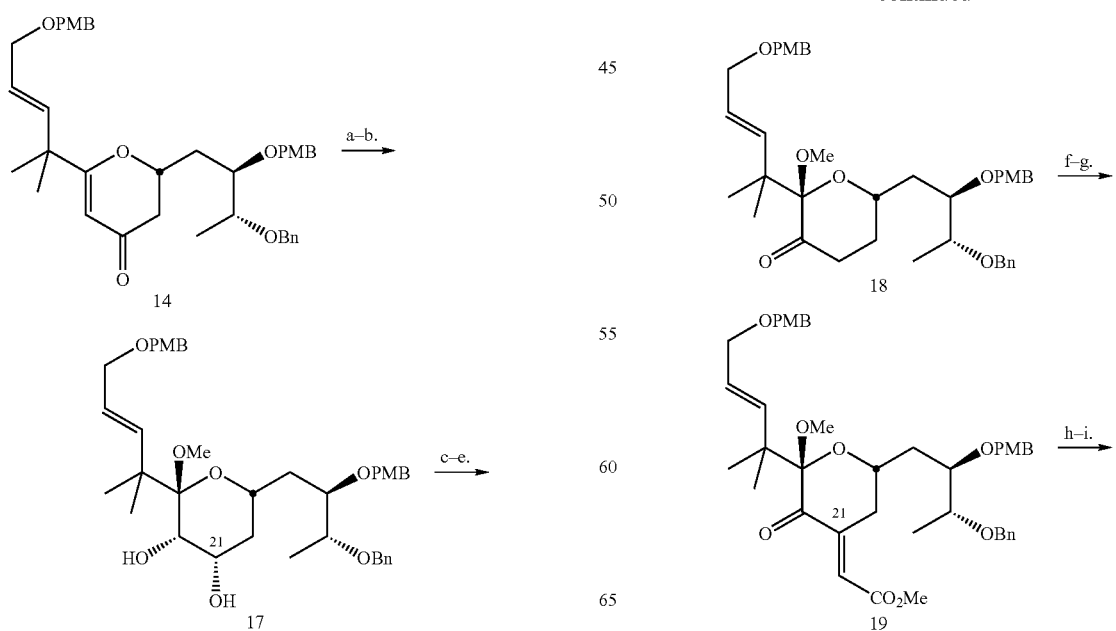

-continued

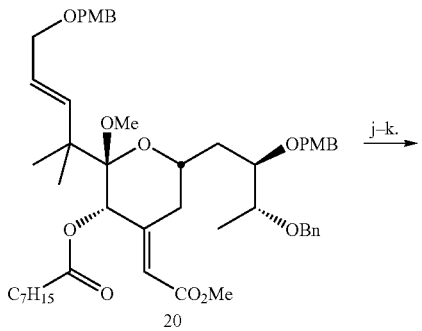
20

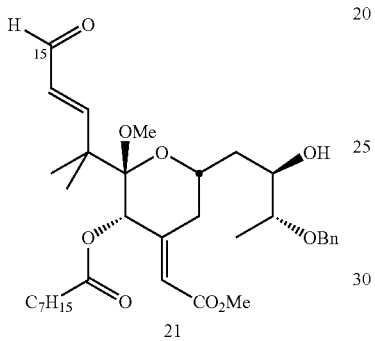
21

(a) NaBH$_4$, CeCl$_3$•7 H$_2$O, MeOH, -20° C.;
(b) mCPBA, NaHCO$_3$, MeOH, 0° C., 71% for 2 steps;
(c) BzCl, DMAP, CH$_2$Cl$_2$, 0° C.;
(d) Dess-Martin periodinane, CH$_2$Cl$_2$, 89% for 2 steps;
(e) SmI$_2$, -78° C., THF/MeOH, 87%;
(f) LDA, OHCCO$_2$Me, THF, -78° C., 88%;
(g) ClSO$_2$Me, Et$_3$N, CH$_2$Cl$_2$, -10° C., then DBU, THF, 81%;
(h) NaBH$_4$, CeCl$_3$•7 H$_2$O, MeOH, -20° C.,
(i) C$_7$H$_{15}$CO$_2$H, 2,4,6-trichlorobenzoyl chloride, NEt$_3$, PhCH$_3$, 86% for 2 steps;
(j) DDQ, wet CH$_2$Cl$_2$; (k) MnO$_2$, CH$_2$Cl$_2$, 42% for 2 steps.

5

To a stirred solution of diisopropylamine (16.82 ml, 120 mmol) in THF (50 ml) was added n-butyllithium (48 ml, 2.5 M in hexane) dropwise at -78° C. The mixture was stirred at 0° C. for 30 min, cooled again to -78° C., and treated with methyl isobutyrate (22.5 ml, 109 mmol) slowly over 10 min. The reaction mixture was stirred for 1.5 hours at -78° C. and 1 hour at -40° C. After addition of allyl bromide (11.8 ml, 135 mmol) dissolved in THF (25 ml) the mixture was allowed to warm up to room temperature [rt]overnight. The solution was evaporated without aqueous workup. The formed solid LiBr was removed by chromatographic filtration on silica gel with ether/pentane (1:1). Fractional distillation gave 5 (12.77 g, 90%) at bp=135→150° C. as colorless liquid.

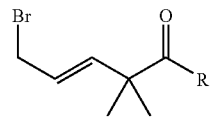
26

To a stirred solution of 5 (14.22 g, 101 mmol) in CCl$_4$ (80 ml) was added N-bromosuccinimide (20 g, 112 mmol) and dibenzoylperoxide (80 mg, 0.33 mmol) in a single portion. The reaction mixture was heated at reflux for 2 hours using an preheated oil bath (105° C.). After cooling to rt, the mixture was filtered and the residue was washed with CCl$_4$. The solvent was removed in vacuo and the crude material purified using flash chromatography on silica gel with EtOAc/hexane (9/1) yielding the desired allylic bromide 26 (8.34 g, 74%) as yellow oil.

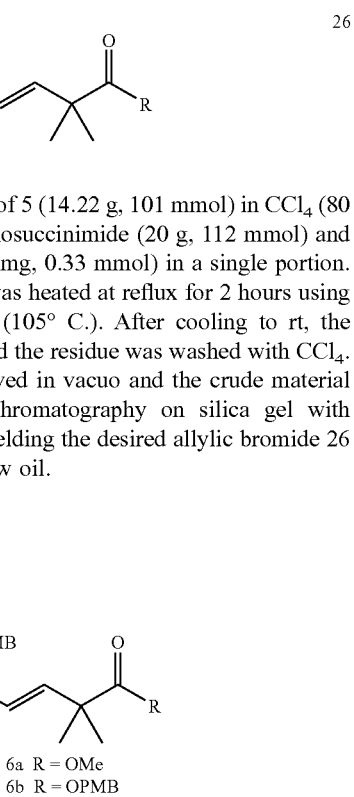

6a R = OMe
6b R = OPMB
6c R = OH

To a suspension of sodium hydride (1.83 g, 45.8 mmol; 60% in mineral oil) in 100 ml anhydrous THF was added a solution of p-methoxy benzylalcohol (5.75 g, 41.6 mmol) in THF (25 ml) slowly over 15 minutes at 0° C. The mixture was stirred at rt for 45 minutes before a solution of the previously prepared allylic bromide (2.3 g, 10.4 mmol) in 30 ml THF was added over 15 min. The reaction mixture was warmed to 35° C. for 6 h. The reaction was cooled to rt and quenched with water carefully. The aqueous layer was extracted with Et$_2$O (2×), then neutralized with 2N HCl, and again extracted with EtOAc (4×). The combined organic layers were dried over MgSO$_4$ and concentrated in vacuo. Purification of the residue on silica gel (EtOAc/hexane 33%–80%) afforded 6b (2.03 g, 74%) as yellow oil.

Alternatively the reaction can be quenched with saturated NH$_4$Cl solution. The aqueous layer was then extracted with Et$_2$O (3×) and the combined layers were dried over MgSO$_4$ and concentrated in vacuo. The resulting oil was purified by flash chromatography (EtOAc 20%) to provide a mixture of 6a & 6b, the methyl and p-methoxybenzyl esters.

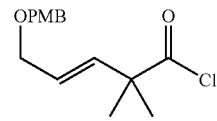
7

To a stirred solution of acid 6c (133 mg, 0.5 mmol) in anhydrous Et₂O (6 ml) and cooled to 0° C., was added sodium hydride (240 mg, 6.0 mmol; 60% in mineral oil) in a single portion. The mixture was stirred for 30 minutes at 0° C. and then oxalyl chloride (0.26 ml, 3.0 mmol) was added in a single portion. The resulting mixture was allowed to warm to rt and stirring was continued for 2 h. The mixture was then concentrated in vacuo and the resulting oil used without further purification.

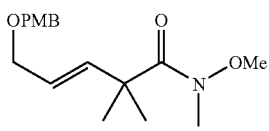

8

To a stirred solution of methyl and p-methoxybenzyl esters 6a and 6b (6.56 g, 23.55 mmol) in THF (20 ml), was added N,O-dimethylhydroxylamine hydrochloride (3.68 g, 37.7 mmol), followed by dropwise addition of phenylmagnesium bromide (2M in THF, 18.25 ml, 36.5 mmol) at −20° C. To the reaction mixture was subsequently added phenylmagnesium bromide (18.25 ml, 36.5 mmol) over 45 min. Stirring was continued for 1 hour at −10° C. The reaction was quenched with saturated NH₄Cl and diluted with Et₂O. The aqueous layer was extracted with EtOAc (3×) and the combined organics were dried over MgSO₄ and concentrated in vacuo. The resulting oil was purified by flash chromatography (EtOAc/hexane 1/3) to provide Weinreb amide 8 (6.54 g, 90%) as colorless oil.

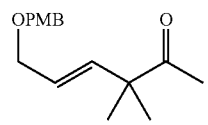

9

A solution of Weinreb amide 8 (5.82 g, 18.1 mmol) in THF (100 ml) was cooled to −78° C. then treated with methyllithium (1.4 M in Et₂O, 17.47 ml, 24.5 mmol). Stirring was continued for 1 hour at −78° C., and the reaction was quenched with saturated NH₄Cl, and diluted with Et₂O. The aqueous layer was extracted with EtOAc (3×) and the combined organics were dried over MgSO₄ and concentrated in vacuo. The resulting oil was purified by flash chromatography (EtOAc/hexane 1/4) to provide methyl ketone 9 (4.89 g, 99%) as a colorless oil.

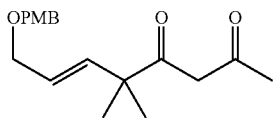

11

To a stirred solution of diisopropylamine (0.21 ml, 1.5 mmol) in THF (3 ml) was added n-butyllithium (0.93 ml, 1.6 M in hexane) dropwise at −78° C. The mixture was allowed to warm to 0° C. and stirred for 30 min, then cooled again to −78° C., and a solution of acetone (0.11 ml, 1.5 mmol) in THF (1 ml) was added dropwise. The acetone used was dried over 4 Å molecular sieves for several days and was dried again over 4 Å molecular sieves in THF solution immediately prior to use. After stirring for 20 minutes, the mixture was treated with a solution of acid chloride 7 (0.5 mmol) in 2 ml THF and stirring was continued at −78° C. for 1 h. The reaction was quenched with saturated NH₄Cl and warmed up to rt and diluted with Et₂O. The aequeous layer was extracted with EtOAc (3×) and the combined organic layers were dried over MgSO₄ and concentrated in vacuo. Purification of the residue by flash chromatography on silica gel (EtOAc/hexane 1/2) yielded β-diketone 11 (117 mg, 77%) as an orange oil.

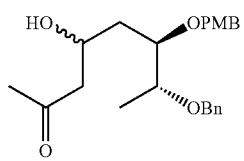

12

To a stirred solution of diisopropylamine (0.21 ml, 1.5 mmol) in THF (3 ml) was added n-butyllithium (0.93 ml, 1.6 M in hexane) dropwise at −78° C. The mixture was warmed to 0° C. and stirred for 30 minutes, then cooled again to −78° C., and treated with a solution of acetone (0.11 ml, 1.5 mmol) in THF (1 ml). The acetone used was dried over 4 Å molecular sieves for several days and was dried again over 4 Å molecular sieves in THF solution immediately prior to use. After recooling to −78° C. and stirring for 20 minutes, aldehyde 10 (164 mg, 0.5 mmol) was added dropwise and stirring was continued for 15 minutes. The reaction was quenched by addition of saturated NH₄Cl and the mixture was warmed to rt and diluted with Et₂O. The mixture was diluted with Et₂O and the layers separated. The aqueous layer was then extracted with EtOAc (3×). The combined organics were washed with brine, dried over MgSO₄, and concentrated in vacuo. Flash chromatography on silica gel (EtOAc/hexane 1/2) provided 12 (169 mg, 87%). The diastereoselectivity was determined to be 81%, favoring the desired isomer, after coupling with acid chloride 7 and cyclization to pyranone 14.

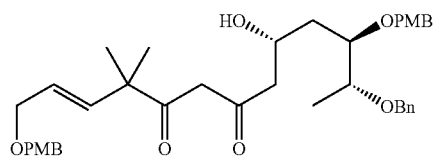

13

From 11: To a stirred solution of diisopropylamine (1.19 ml, 8.48 mmol) in THF (13 ml) was added n-butyllithium (4.08 ml, 8.16 mmol, 2.0 M in hexane) dropwise at −78° C. The mixture was warmed to 0° C. and stirred for 30 minutes, then a solution of β-diketone 11 (2.30 g, 8.77 mmol) in THF (13 ml) was added slowly over 10 minutes. After stirring for 1 hour at 0° C., the mixture was cooled to −78° C. and aldeyde 2 (1.21 g, 3.69 mmol) was added in a single portion. Stirring was continued for 30 minutes at −78° C. and the reaction mixture was then quenched with saturated NH₄Cl solution, allowed to warm to rt, and diluted with Et₂O. The mixture was extracted with EtOAc (3×) and the combined organics were dried over MgSO₄ and concentrated in vacuo. Flash chromatography on silica gel (EtOAc/hexane 1/2) afforded the aldol 13 (1.51 g, 65%) as a orange oil. The ratio of the two diastereomers was determined after cyclization to pyranone 7, and was 1.45:1 favoring the desired isomer.

From 12: To a stirred solution of diisopropylamine (0.46 µL, 0.204 mmol) in THF (0.5 ml) was added n-butyllithium (0.128 ml, 0.204 mmol, 1.6M in hexanes) dropwise at −78° C. The mixture was warmed to 0° C. and stirred for 30 min, then cooled again to −78° C., and treated with a solution of β-hydroxy ketone 12 (42.0 mg, 0.0662 mmol) in THF, (1 ml) dropwise. After stirring for 20 minutes at −78° C. the mixture was treated with a solution of acid chloride 7 (0.5 ml, ~0.20 mmol, prepared from 0.5 mmol acid 6c dissolved in 1 ml THF) and stirring was continued at −78° C. for 30 min. The reaction was quenched with $H_2O$, warmed up to rt by stirring vigorously for 30 min, and diluted with $Et_2O$. The aequeous layer was extracted with EtOAc (3×) and the combined organic layers were dried over $MgSO_4$ and concentrated in vacuo. Purification of the residue by flash chromatography yielded 13 (41.9 mg, 61%).

From 28: To distilled pyridine (1.3 ml, 16.8 mmol) in a high density polyethylene (HDPE) vial at −78° C. was added dropwise over 10 minutes a solution of 70% HF.pyridine (0.5 ml, ~17.5 mmol HF, ~4.4 mmol pyridine) to form a nearly equimolar solution of HF.pyridine. This solution was stored at −20° C. until needed.

To a solution of the previously prepared C23 OTBS β-diketone 28 (0.025 g, 0.033 mmol) in dry THF (2 ml) in a HDPE vial was rapidly added the HF-pyridine solution prepared above (0.25 ml) in a single portion. The resulting solution was layered with argon, sealed and stirred vigorously for 7 days at rt. The vial was unsealed, and the reaction quenched with saturated aqueous $NaHCO_3$ (1 ml). The reaction was diluted with ethyl acetate, the layers separated, and the aqueous phase extracted 3 times with ethyl acetate. The combined organic fractions were pooled, dried over $MgSO_4$ and concentrated under reduced pressure. The resulting oil was subjected to flash chromatography in 30% ethyl acetate/hexanes, which yielded -diketo alcohol 13 (0.015 g, 0.051 mmol, 70%) as a colorless oil.

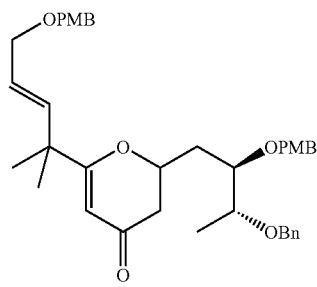

14

To a stirred solution of 13 (1.28 g, 2.02 mmol) in toluene (30 ml) was added p-toluene sulfonic acid (0.060 g, 0.0003 mmol) in a single portion followed by addition of 4 Å molecular sieves (1.5 g). After stirring at rt for 10 hours, the reaction was quenched with pyridine (2.0 ml, 24.7 mmol) and filtered. The resulting solution was concentrated under reduced pressure, then redissolved in dietyhl ether. This was washed with saturated $NaHCO_3$ and dried over $MgSO_4$ before the solvent was removed under reduced pressure. The resulting oil was subjected to flash chromatography in 30% ethyl acetate in hexanes, which was increased to 70% as the product began to elute from the column. This yielded 1.00 g (1.63 mmol, 81%) of 14 as a 1.54:1 mixture of diastereomers at C23 which were separable after a second chromatographic step in which 300 g of silica gel were used per 1 g of the pure diastereomers, and the material was eluted again using 30% ethyl acetate in hexanes.

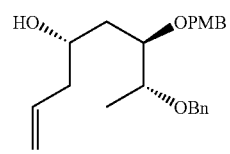

15

In a glove bag, under positive Ar pressure, 0.9834 g (3.11 mmole) methoxy diisopinylborane was weighed into a dried flask. Dry diethyl ether (8.4 ml) was added, and the resulting solution cooled to −78° C. To this solution was added dropwise over 5 minutes a 1M solution of allyl magnesium bromide (2.8 ml, 2.8 mmol), after which the solution was allowed to come to rt over 1 hour. A portion (6.2 ml, 2.06 mmole) of the resulting borane reagent was added to a stirred solution of the aldehyde 10 (0.6546 g, 2.0 mmol) in diethyl ether (5 ml) at −78° C. over 15 minutes. The reaction was stirred at −78° C. for 1 hour, and then allowed to warm to rt over 1 hour. The resulting boronate was then cleaved by addition of 10 ml of 15% NaOH and 2 ml 30% $H_2O_2$. This mixture was stirred for 30 minutes, and the layers were separated. The aqueous layer was then extracted 4 times with diethyl ether. The combined organic phases were dried over $MgSO_4$ and concentrated under reduced pressure. The resultant oil was subjected to flash chromatography in 15% ethyl acetate/hexanes produced 15 (0.4723 g, 1.28 mmol, 64%) as a clear oil.

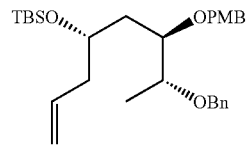

27

To a stirred solution of 15 (3.39 g, 9.19 mmol) in dry $CH_2Cl_2$ (80 ml) was added a 60% dispersion of NaH in mineral oil (0.551 g, 13.79 mmol) in a single portion, and the resulting solution was stirred at rt for 1 h. To this was added dimethyl aminopyridine (0.061 g, 0.5 mmol), followed by t-butyl dimethylsilyl chloride (2.216 g, 14.70 mmol). The solution was then refluxed for 16 h, after which the solution was cooled to rt and quenched with 10 ml of a saturated solution of aqueous ammonium chloride. The layers were separated, and the aqueous phase extracted 3 times with ethyl acetate. The combined organic phases were dried over $MgSO_4$ and concentrated under reduced pressure. The resultant oil was subjected to flash chromatography in 7.5% ethyl acetate/hexanes, yielding the TBS protected allyl alcohol 27 (3.833 g, 7.90 mmol, 86%) as a clear oil.

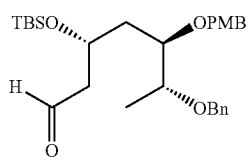

16

To a stirred solution of the previously prepared TBS allyl alcohol 27 (0.035 g, 0.072 mmol) in 2:1 THF/water (3 ml) was added N-methyl morpholine N-oxide (0.0092 g, 0.079 mmol) in one portion, followed by the rapid addition of a 2.5% solution of osmium tetroxide in isopropanol (0.090 ml, 0.07 mmol), again in one portion. The resultant solution was stirred 6 hours at rt before being stopped by the addition of excess solid sodium sulfite. The reaction mixture was then diluted with brine and ethyl acetate. The layers were separated, and the aqueous phase extracted three times with ethyl acetate. The combined organic phases were concentrated under reduced pressure. The resultant oil was redissolved in 3 ml 2:1 tetrahydrofuran/water, to which was added sodium periodate (0.052 g, 0.243 mmol). The reaction mixture was stirred 6 hours at rt before being diluted with water and ethyl acetate. The layers were separated, and the aqueous phase extracted three times with ethyl acetate, and the combined organic phases concentrated under reduced pressure. The resultant yellow oil was subjected to flash chromatography in 10% ethyl acetate/hexanes, and yielded aldehyde 16 (0.0297 g, 0.061 mmol, 85% over 2 steps) as a clear oil.

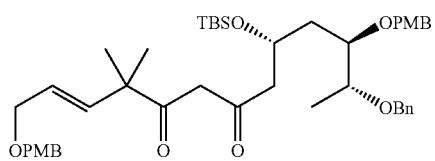

28

To a stirred solution of diisopropyl amine (0.352 ml, 2.51 mmol) in dry THF (25 ml) at −78° C. was added dropwise a 2.5M solution of nBuLi in hexanes (0.956 ml, 2.39 mmol). The solution was stirred for 30 minutes at 0° C. and then cooled to −78° C. A solution of methyl ketone 9 (0.592 g, 2.26 mmol) in dry THF (5 ml) was cannulated slowly into the reaction mixture over 10 minutes. The resulting solution was stirred at −78° C. for 30 minutes, warmed to rt for 2 minutes, then recooled to −78° C., after which a solution of aldehyde 16 (1.0 g, 2.05 mmol) in dry THF (3 ml) was slowly cannulated into the reaction mixture over 10 minutes. This was stirred at −78° C. for 15 minutes, then quenched with a saturated solution of aqueous ammonium chloride (25 ml). The reaction was then diluted with ethyl acetate, and the layers separated. The aqueous phase was extracted 3 times with ethyl acetate, and the combined organic phases dried with MgSO₄ and concentrated under reduced pressure. The resulting oil was subjected to flash chromatography in 10% ethyl acetate in hexanes, which was increased to 20% as the product began to elute from the column. This yielded 1.48 g (1.97 mmol, 96%) of an inconsequential mixture of diastereomers which were carried through to the next reaction.

To a stirred solution of the diastereomeric mixture of β-keto alcohols (0.1103 g, 0.147 mmol) in dry CH₂Cl₂ was added N-methyl morpholine N-oxide (0.1418 g, 1.207 mmol) and approximately 0.1 g powdered 4 Å molecular sieves. Tetrapropyl ammonium perruthenate (0.0131 g, 0.037 mmol) was added and the mixture stirred for 30 minutes. The reaction mixture was then filtered through a short plug of silica with copious quantities of ethyl acetate. The resulting solution was concentrated under reduced pressure and subjected to flash chromatography using 15% ethyl acetate in hexanes. This yielded 0.0513 g (0.069 mmol, 47%) of the desired β-diketone 28.

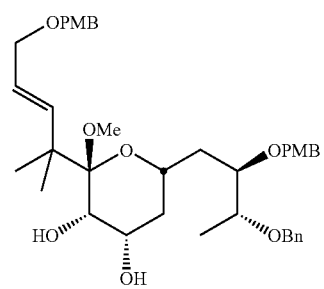

17

To a solution of pyranone 14 (0.205 g, 0.333 mmol) and cerium chloride heptahydrate (0.030 g, 0.082 mmol) in 5.5 ml methanol was added solid NaBH₄ (0.012 g, 0.33 mmol) in a single portion at −20° C. The reaction mixture was stirred for 1 hour at −20° C. and monitored by tlc. A second portion of NaBH₄ (0.012 g, 0.33 mmol) was added during this period when the reaction appeared stalled. The reaction was then quenched with 20 ml saturated aqueous NaCl, and the mixture brought to rt, filtered through a pad of Celite® and the layers separated. The separated aqueous layer was extracted four times with ethyl acetate, and the combined organics were dried over Na₂SO₄ and concentrated under reduced pressure to afford the crude allylic alcohol. This moderately stable oil was reacted further without purification.

The crude allylic alcohol was dissolved in 6 ml CH₂Cl₂/MeOH (2:1) and cooled to 0° C. before being treated with solid NaHCO₃ (0.042 g, 0.5 mmol). Purified m-chloroperoxybenzoic acid (0.046 g, 0.370 mmol) was added in a single portion and the reaction mixture was stirred for 30 minutes, then warmed to rt over a period of 15 minutes. The reaction was quenched with triethylamine (4.0 ml), stirred well for 20 minutes, diluted with 40 ml diethyl ether, and filtered through a pad of Celite®. The filtrate was concentrated under reduced pressure and the resulting oil purified using flash chromatography using (EtOAc/hexane 1/1) to give diol 17 (0.158 g, 0.238 mmol, 71%) as a colorless oil.

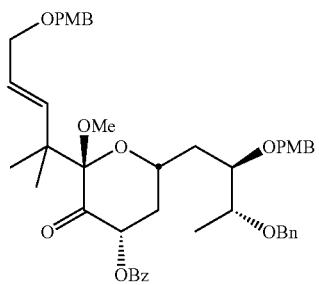

29

A solution of diol 17 (118 mg, 0.178 mmol) and 4-dimethylaminopyridine (77 mg, 0.62 mmol) in $CH_2Cl_2$ (3.2 ml) was cooled to –10° C. and treated with benzoyl chloride (27 µl, 0.23 mmol) dropwise via syringe. The resulting mixture was stirred at –10° C. for 30 minutes, quenched with saturated $NaHCO_3$ and diluted with EtOAc (20 ml). The organic layer was washed with $H_2O$ and brine, dried over $Na_2SO_4$ and concentrated in vacuo to afford a crude mixture of C21 monobenzoate and 4-dimethylaminopyridine as a colorless paste, which was filtered over a plug of silica gel (EtOAc/hexane 1/2).

The filtrate was evaporated and taken up in 8 ml $CH_2Cl_2$ and treated with solid 1,1,1-triacetoxy-1,1-dihydro-1,2-benziodoxol-3(1H)-one (Dess-Martin periodinane, 113 mg, 0.267 mmol) at rt. The solution was stirred for 4 hours at rt after which a second portion (113 mg, 0.267 mmol) of DMP was added. The opaque white mixture was stirred for another 1.5 hours and quenched with 4 ml saturated $NaHCO_3/Na_2S_2O_3$. The layers were separated and the aquous phase was extracted with $CH_2Cl_2$ (2×). The combined organics were dried over $Na_2SO_4$ and concentrated in vacuo to provide a colorless semisolid. Flash chromatography on silica gel (EtOAc/hexane 1/3) gave the desired keto-pyranone 29 (121 mg, 89% from 17) as a colorless oil.

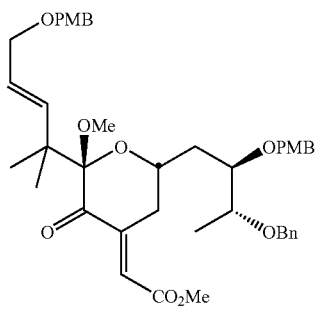

19

To a stirred solution of diisopropylamine (300 µl, 2.14 mmol) in THF (3.2 ml) was added n-butyllithium (1.25 ml, 1.6 M in hexanes, 2.00 mmol) dropwise at –78° C. The mixture was warmed to 0° C. and stirred for 30 min, then cooled again to –78° C., and a solution of ketone 18 (319 mg, 0.494 mmol) in 6.8 ml THF was added in a single portion. The solution was stirred for 30 minutes and treated with a solution of freshly distilled $OHCCO_2Me$ (88 mg, 0.74 mmol) in 5 ml THF, kept at –78° C. for 30 minutes and quenched with 3 ml saturated $NH_4Cl$. The reaction mixture was brought to rt and diluted with 200 ml EtOAc. The organic layer was washed with $H_2O$ (2×) and brine, dried over $Na_2SO_4$ and concentrated in vacuo. The crude residue was chromatographed on silica gel (EtOAc/hexanes 35/65) to afford the aldol product (319 mg, 88%) as an inconsequential mixture of diastereomers.

The isolated aldol product (303 mg, 0.412 mmol) and $Et_3N$ (340 µl, 2.50 mmol) were dissolved in anhydrous $CH_2Cl_2$ (15 ml) and cooled to –10° C. Methanesulfonylchloride (97 µl, 1.25 mmol) was added via syringe and the solution was stirred at –10° C. for 30 minutes and warmed to rt. 5 ml saturated $NaHCO_3$ were added and the reaction mixture was diluted with 100 ml EtOAc. The organic layer was washed with $H_2O$ and brine, dried over $Na_2SO_4$ and concentrated in vacuo. The residue was immediately dissolved in THF (20 ml) and treated with 1,8-diazabicyclo[5.4.0]undec-7-ene (DBU—75 µl, 0.5 mmol) dropwise at rt. The resulting bright yellow solution was stirred at rt for 20 minutes, treated with saturated $NH_4Cl$ and diluted with 150 ml EtOAc. The organic layer was washed with $H_2O$ and brine, dried over $Na_2SO_4$ and concentrated in vacuo to afford an orange residue which was chromatographed on silica gel (20% EtOAc/hexanes) to afford exocyclic methacrylate 30 (239 mg, 81%—unseparable mixture of E/Z isomers, ratio E/Z=7:1) as a yellow oil.

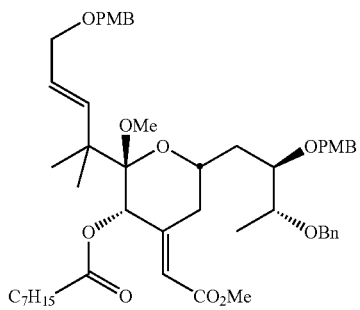

20

To a solution of enone 19 (205 mg, 0.286 mmol) and cerium chloride heptahydrate (52 mg, 0.15 mmol) in 11 ml methanol was added solid $NaBH_4$ (21 mg, 0.57 mmol) in a single portion at –30° C. Rapid gas evolution subsided after 3 minutes. After an additional –30 minutes at –30° C., the reaction mixture was poured directly onto a silica gel column and the product quickly eluted with EtOAc/hexanes (3/1) to afford the alcohol as colorless oil.

Octanoic acid (93 mg, 0.64 mmol) and $Et_3N$ (117 µl, 0.88 mmol) were dissolved in 8 ml toluene and treated with 2,4,6-trichlorobenzoylchloride (92 µl, 0.59 mmol) dropwise at rt. After 2.5 hours at rt, a toluene solution (5 ml) of freshly prepared alcohol was added gradually via syringe and stirring was continued for 1 h. The reaction mixture was quenched with 10 ml saturated $NaHCO_3$, diluted with EtOAc and washed successively with saturated $NH_4Cl$ and brine. The organics were dried over $Na_2SO_4$, the solvent was removed in vacuo, and the residue was chromatographed on silica gel (EtOAc/hexane 1/3) to provide octanoate 20 as an colorless oil (208 mg, 86% from 19).

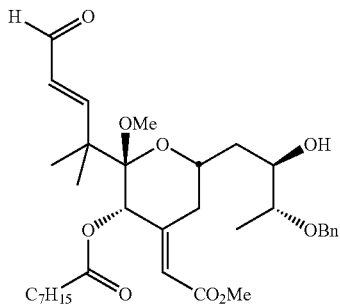

To a solution of 20 (2.0 mg, 0.0024 mmol) in 1 mL 1% aqueous CH$_2$Cl$_2$ was added solid 2,3-dichloro-5,6-dicyano-1,4-benzoquinone (DDQ, 1.2 mg, 0.0053 mmol) at 0° C. The reaction mixture was stirred for 30 minutes, then pipetted directly onto a plug of silica gel. The product was eluted with EtOAc/hexane (1/4) and the solvent was removed in vacuo to provide the crude diol (1.1 mg). This material was dissolved in anhydrous CH$_2$Cl$_2$ and treated with manganese (IV) oxide (0.4 mg, 0.0046 mmol) at 0° C. The reaction mixture was allowed to warm to rt and then pipetted directly onto a plug of silica gel. The product was eluted with EtOAc/hexane (1/3) and the solvent was removed in vacuo. Crude aldehyde 33 (0.64 mg, 42%) was obtained as a colorless oil.

Example 12

Compound and synthetic step references in this example correspond to the following scheme (as opposed to the reaction schemes and formula numbers employed previously in the specification).

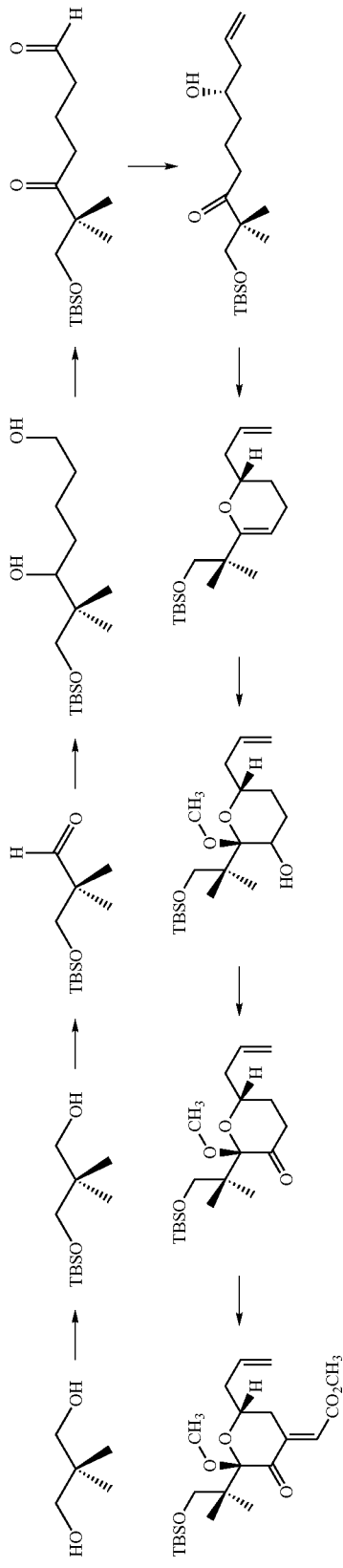
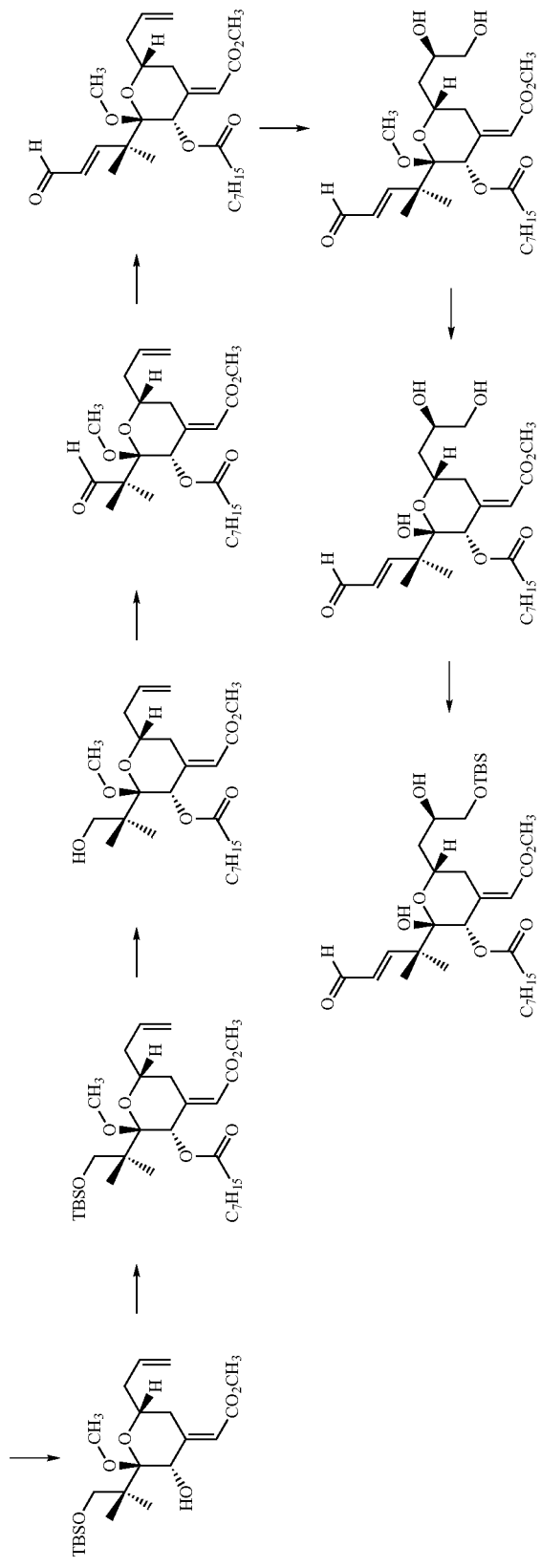

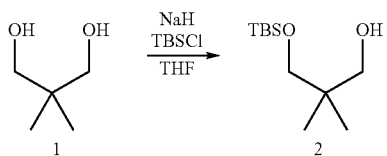

A 3-neck flask was charged with NaH (16 g, 60 wt % in mineral oil, 0.40 mol). The NaH was washed with Et$_2$O (3×40 mL). THF (800 mL) was added and the mixture stirred. To this suspension was added 2,2-dimethyl-1,3-propanediol 1 (40 g, 0.39 mol) in protions over 10 min. The resulting thick slurry was stirred at room temperature [rt] for 1 h. TBSCl (60.5 g, 0.40 mol) was added in one portion. The slurry thinned and was stirred at rt for 14 h. The reaction was diluted with MTBE (1.0 L) and washed with 10% aq. K$_2$CO$_3$ (700 mL, 300 mL) and brine (500 mL). The organic layer was dried over Na$_2$SO$_4$, filtered, and concentrated under reduced pressure to yield 88.4 g of a viscous liquid which was used without further purification.

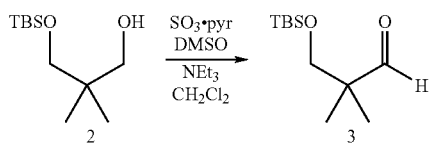

A solution of 2 (40 g, ca 0.18 mol) was stirred in CH$_2$Cl$_2$ (900 mL) and cooled in an ice bath to 4° C. To this solution was added NEt$_3$ (76 mL, 0.54 mol). A slurry of SO$_3$ pyr (44 g, 0.27 mol) in DMSO (100 mL) was added in two portions 5 min apart to keep T<10° C. The reaction was stirred for 2.5 h and the ice bath removed. Stirring was continued for 6.5 h and another portion of SO$_3$ pyr (10 g, 63 mmol) was added as a solid. The reaction was stirred for 9 h and diluted with CH$_2$Cl$_2$ (1.0 L). The resulting solution was washed with 1 N aq. HCl (2×500 mL), satd. aq. NaHCO$_3$ (500 mL), and brine (500 mL). The resulting organic layer was dried over Na$_2$SO$_4$, filtered, and concentrated under reduced pressure to 39.8 g of an orange liquid which was used without further purification.

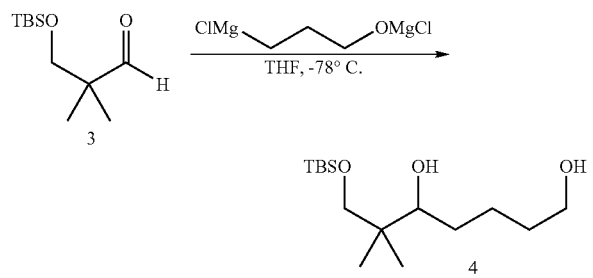

A solution of 4-chloro-1-butanol (23 mL, 0.23 mol) in THF (230 mL) was cooled to −78° C. A solution of MeMgCl (77 mL, 3.0 M in THF, 0.23 mol) was added dropwise via addition funnel over 30 min to keep T<−60° C. The reaction was let warm to −10° C. and Mg° (6.04 g, 0.251 mol) was added followed by BrCH$_2$CH$_2$Br (0.1 mL). The reaction was heated to reflux for 14.5 h. Heating was removed, THF (220 mL) was added, and the reaction was cooled to −78° C. A solution of 3 (39 g, ca 0.18 mol) in THF (100 mL) was added dropwise via addition funnel over 40 min to keep T<−60° C. The reaction was stirred 30 min at −78° C. and the cold bath removed. MTBE (500 mL) was added when the reaction reached −30° C. followed by aq. citric acid (87 g, 0.41 mol in 500 mL H$_2$O). The organic layer was collected and the aqueous layer was extracted with MTBE (200 mL). The combined organic layers were washed with brine (2×400 mL), dried over Na$_2$SO$_4$, filtered, and concentrated under reduced pressure to a light orange oil. The oil was dissolved in EtOAc and filtered through silica. The filtrate was concentrated under reduced pressure to yield 49.7 g of a light yellow oil which was used without further purification.

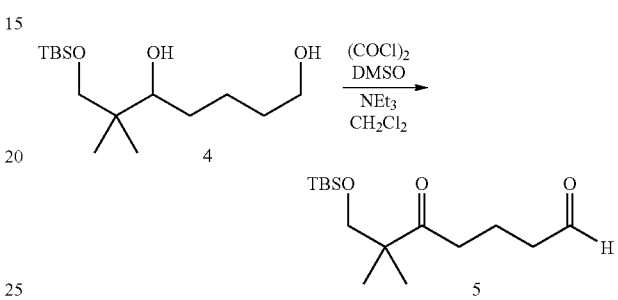

To a solution of CH$_2$Cl$_2$ (800 mL) was added (COCl)$_2$ (46.9 mL, 0.537 mol) and the resulting solution cooled to −78° C. DMSO (75.8 mL, 1.07 mol) was added dropwise via addition funnel over 15 min to keep T<−60° C. The resulting solution was stirred for 10 min. A solution of 4 (49.7 g, ca 0.179 mol) in CH$_2$Cl$_2$ (150 mL) was added dropwise via addition funnel over 25 min to keep T<−70 C. The resulting mixture was stirred 1 h at −78° C. and NEt$_3$ (250 mL, 1.79 mol) was added dropwise via addition funnel over 15 min to keep T<−60° C. The cold bath was removed and the reaction was allowed to warm to −30° C. and then poured into a mixture of H$_2$O (500 mL) and CH$_2$Cl$_2$ (800 mL). The resulting organic layer was collected and washed with H$_2$O (500 mL), satd. aq. NH$_4$Cl (2×400 mL), satd. aq. NaHCO$_3$ (500 mL), and brine (500 mL). The organic layer was then dried over Na$_2$SO$_4$, filtered, and concentrated under reduced pressure to a dark oil. Purification by flask chromatography on silica in 19:1→9:1 pet. ether:EtOAc yielded 27.81 g (54% based on 2,2-dimethyl-1,3-propanediol) of a straw yellow liquid.

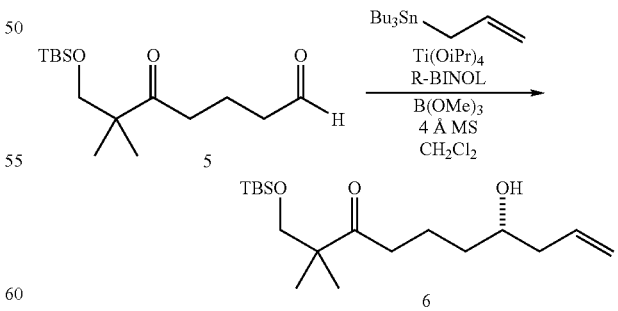

A 3-neck flask was charged with powdered 4 Å mol. sieves (47.5 g), CH$_2$Cl$_2$ (600 mL), and R-BINOL (3.6 g, 12.5 mmol). To this mixture was added Ti(OiPr)$_4$ (1.84 mL, 6.25 mmol). The resulting orange mixture was heated to reflux for 1 h, then cooled to rt in a water bath. A solution of 5 (36.0 g, 125 mmol) in CH$_2$Cl$_2$ (60 mL) was added followed by B(OMe)$_3$ (16.8 mL, 150 mmol) and Bu$_3$SnCH$_2$CHCH$_2$ (46.5 mL, 150 mmol). The resulting mixture was stirred at rt for 42 h, then filtered through celite into saturated aqueous NaHCO$_3$ (200 mL). The resulting mixture was stirred for 1 h. The organic layer was collected and the aqueous layer was extracted with CH$_2$Cl$_2$ (200 mL). The combined organic layers were dried over Na$_2$SO$_4$, filtered, and concentrated under reduced pressure to a thick orange oil. The residue was purified by flash chromatography on silica in 9:1→4:1 pet. ether:EtOAc to yield 29.03 g, (70%) of a yellow oil.

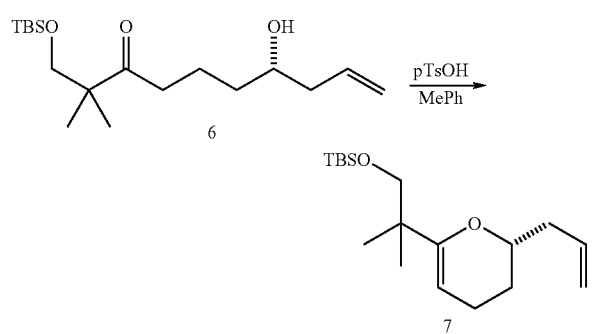

To a solution of 6 (28.8 g, 87.6 mmol) in MePh (500 mL) was added beaded 4 Å mol. sieves (50 g) and pTsOH (1.66 g, 8.76 mmol). The mixture was stirred at rt for 18 h then filtered through basic alumina (Brockman grade I, basic, 150 mesh) and the alumina washed with pet. ether. The filtrate was concentrated under reduced pressure to 23.2 g (85%) of a clear liquid.

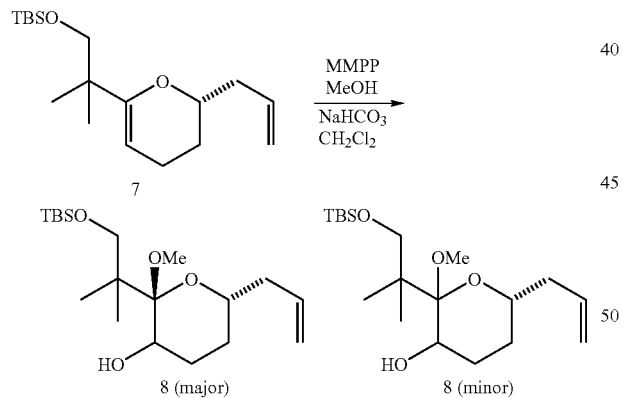

A mixture of 80% MMPP (25.7 g, 41.5 mmol), CH$_2$Cl$_2$ (245 mL), MeOH (122 mL), and NaHCO$_3$ (8.87 g) was stirred in an ice bath. A solution of 7 (21.5 g, 69.2 mmol) in CH$_2$Cl$_2$ (50 mL) was added dropwise via addition funnel over 10 min. The reaction was stirred for 10 min, and then poured into H$_2$O (200 mL). The organic layer was collected and the aqueous layer was extracted with CH$_2$Cl$_2$ (200 mL). The combined organic layers were dried over Na$_2$SO$_4$, filtered, and concentrated under reduced pressure to a thick oil which was purified by flash chromatography on silica in 19:1→9:1 pet. ether:EtOAc to yield 16.49 g (66%) of a clear oil.

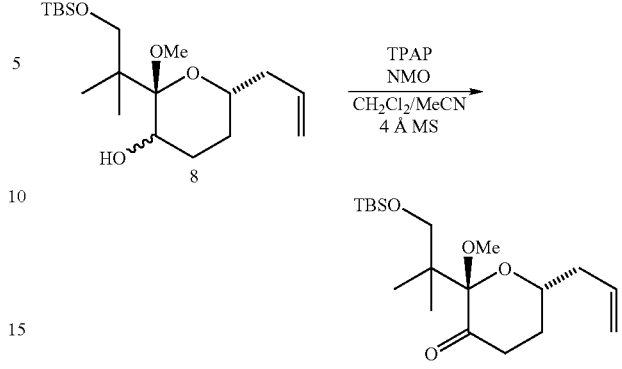

To an oven-dried flask was added the major diastereomer of 8 (5.3 g, 14.8 mmol) in 75 mL CH$_2$Cl$_2$. MeCN (12 mL) was added and the reaction was cooled in an ice bath. 7.6 g 4 Å molecular sieves was added, followed by NMO (2.6 g, 22.2 mmol) and TPAP (310 mg, 0.88 mmol). The reaction was stirred for 15 min. in an ice bath, then warmed to rt. Reaction stirred overnight. Additional 4 Å molecular sieves (1.05 g), NMO (1.0 g), and TPAP (120 mg) were added. After 5 hours of stirring, at rt, the reaction was filtered through celite, with a CH$_2$Cl$_2$ was. The filtrate was concentrated in vacuo and flashed through a plug of silica, eluting with CH$_2$Cl$_2$. The fractions containing product were concentrated in vacuo to yield 4.28 g (81%) of product.

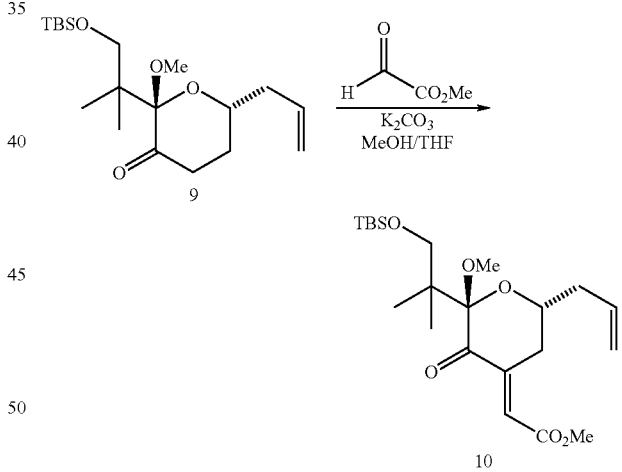

To a solution of 9 (1.72 g, 4.82 mmol) in MeOH (50 mL) was added K$_2$CO$_3$ (3.66 g, 26.5 mmol) and a solution of methyl glyoxylate (14.2 mL, ~1.7 M, 24 mmol) in THF. The resulting mixture was stirred at rt for 55 min and then poured into a mixture of satd. aq. NH$_4$Cl (200 mL) and Et$_2$O (100 mL). The organic layer was collected and the aqueous layer was extracted with Et$_2$O (100 mL). The combined organic layers were dried over MgSO$_4$, filtered, and concentrated under reduced pressure to an orange oil which was purified by flash chromatography on silica in 19:1 pet. ether:EtOAc to yield 1.50 g (72%) of a yellow oil which solidified on standing.

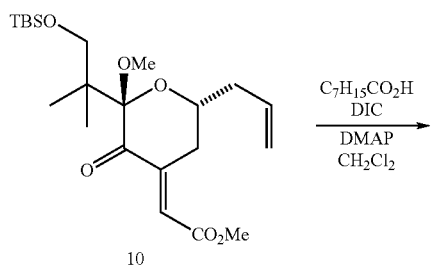

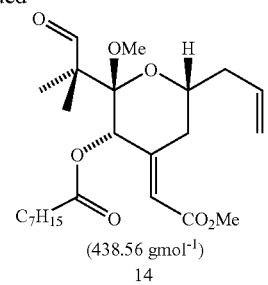

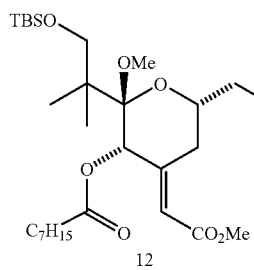

To an oven-dried flask was added 10 (3.29 g, 7.71 mmol) in MeOH (130 mL). CeCl$_3$.7H$_2$O (1.44 g, 3.86 mmol) was added and the reaction was stirred until the salts dissolved. The reaction was then cooled to −30° C., and NaBH$_4$ (580 mg, 15 mmol) was added. The reaction was stirred for 20 min at −30° C. The reaction was loaded directly onto a silica column (250 g) and eluted with 6:1 hexanes:EtOAc. The fractions containing product were combined and washed with H$_2$O (2×85 mL) and brine (3×85 mL). The organic layer was then dried over Na$_2$SO$_4$, filtered, and concentrated in vacuo to yield 3.49 g of crude product which was used directly in the next reaction.

The crude alcohol was dissolved in CH$_2$Cl$_2$ (75 mL) and DMAP (1.41 g, 11.5 mmol) was added. Octanoic acid (1.83 mL, 11.5 mmol) was then added, followed by DIC (1.81 mL, 11.6 mmol). The reaction was stirred at rt for 20 h. The reaction was then diluted with EtOAc and brine. The organic layer was collected and the aqueous layer was extracted with EtOAc (1×). The combined organic layers were washed with brine, dried over Na$_2$SO$_4$, filtered, and concentrated to 7.17 g of a solid/oil mixture. The crude material was purified via column chromatography (silica (300 g), hexanes:EtOAc, 19:1) to yield 3.98 g (93% over 2 steps) of pure product as a light yellow oil.

To a solution of TBS ether 12 (2.0 g, 3.61 mmol) in THF (36.1 mL) at rt was added 3.HF.Et$_3$N (6.0 mL, 36.1 mmol). The reaction mixture was stirred for 48 h and then diluted with ether (36 mL). The organic phase was washed with sat. aq. NaHCO$_3$ (2×20 mL) and brine (2×20 mL), dried over Na$_2$SO$_4$, and flashed through a plug of silica. The residue obtained after evaporation of solvent was carried forward without further purification. R$_f$=0.20 (hexane/ethyl acetate 4:1).

To a solution of the deprotected alcohol in CH$_2$Cl$_2$ (2.1 mL) and MeCN (2.1 mL), at rt, was added 4 Å molecular sieves (powder, 1.81 g) and NMO (1.06 g, 9.03 mmol). The mixture was cooled to 0° C. and TPAP (127 mg, 0.361 mmol) was added in one portion. The reaction mixture was stirred for 10 min. 0° C. and for 2 hrs. at rt. The reaction was filtered through celite, eluting with CH$_2$Cl$_2$, and concentrated in vacuo. The crude reaction mixture was then flashed through a plug of silica, also eluting with CH$_2$Cl$_2$, and then concentrated in vacuo. Purification via column chromatography (silica gel, 2.5% EtOAc/Petroleum Ether) revealed pure aldehyde 14 (1.20 g, 76% over 2 steps) as a yellow oil.

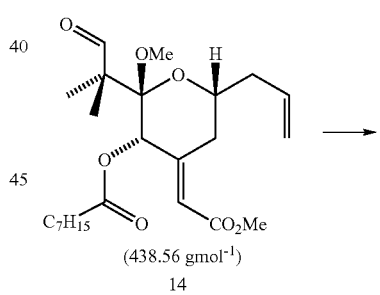

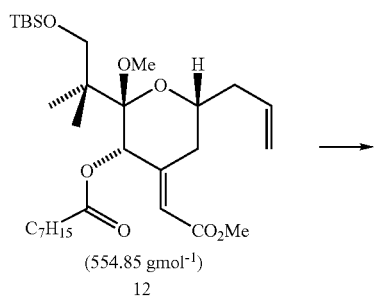

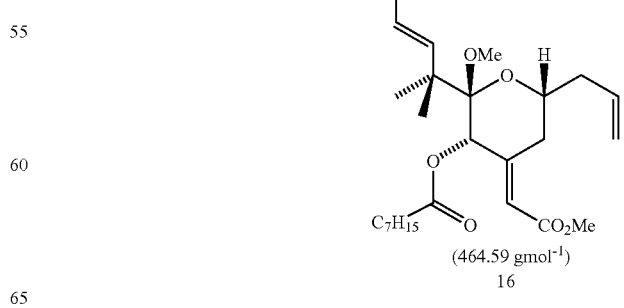

1-bromo-2-ethoxyethylene (690 μL, 6.5 mmol) was added to an oven-dried flask containing Et$_2$O (22 mL). The solution was cooled to −78° C., and t-BuLi (7.63 mL, 13 mmol, 1.7M in pentane) was added, dropwise. The reaction was stirred, at −78° C., for 30 min. Me$_2$Zn (3.35 mL, 6.7 mmol, 2.0M in toluene) was added, dropwise, and the reaction was stirred, at −78° C., for 30 min. A solution of aldehyde 14 (0.948 g, 2.2 mmol dissolved in Et$_2$O (22 mL, 0.11 mmol) was added dropwise, via syringe, and the reaction was stirred for 2 h at −78° C. The reaction was quenched with a 1.0 M solution of HCl (40 mL) and allowed to warm to rt. The mixture stirred vigorously for 19 h and was quenched with sat'd aq. NaHCO$_3$ (60 mL), diluted with EtOAc (35 mL) and H$_2$O (35 mL). The separated aqueous phase was extracted with EtOAc (3×60 mL) and the combined organic phases washed with brine (1×85 mL). The organic layer was dried (Na$_2$SO$_4$), filtered, and concentrated in vacuo. Purification via column chromatography (silica gel, Pet Ether→7% →10% EtOAc:Petroleum Ether) revealed pure enal 16 (905 mg, 90%) as a nearly colorless oil.

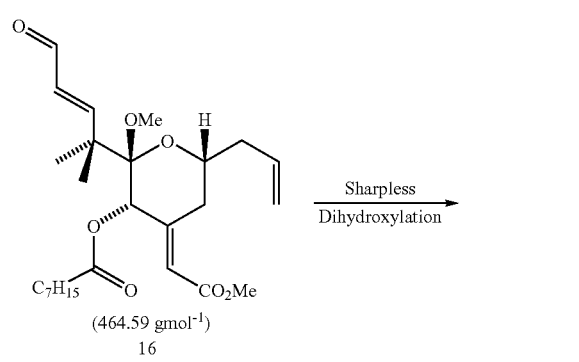

(464.59 gmol$^{-1}$)
16

Sharpless Dihydroxylation →

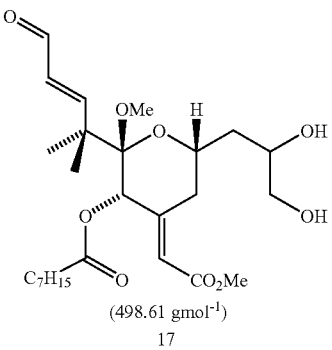

(498.61 gmol$^{-1}$)
17

Preparation of stock solution: K$_2$OsO$_2$(OH)$_4$ (2.0 mg, 0.0054 mmol), (DHQD)$_2$PYR (12.0 mg, 0.0136 mmol), K$_3$Fe(CN)$_6$ (1.34 g, 4.07 mmol), and K$_2$CO$_3$ (563 mg, 4.07 mmol) were combined in a round-bottom flask, to which was added 6.75 mL of H$_2$O and 6.75 mL of tBuOH. The two-phase system was vigorously stirred at rt for 2 h.

Enal 16 (300 mg, 0.646 mmol) was cooled to 0° C., and a 6.4 mL aliquot of the stock solution was added. The yellow-orange colored reaction mixture was stirred at 0–4° C. for 60 h (in cold room). After diluting with water (50 mL) the aqueous phase was extracted with ethyl acetate (3×250 mL). The combined organic phases were dried over MgSO$_4$, and then filtered. The solvents were removed in vacuo. Purification via column chromatography (silica gel, hexane/ethyl acetate 1:9) yielded diol 17 (233 mg, 72%) as a 2.5:1 inseparable mixture of diastereomers.

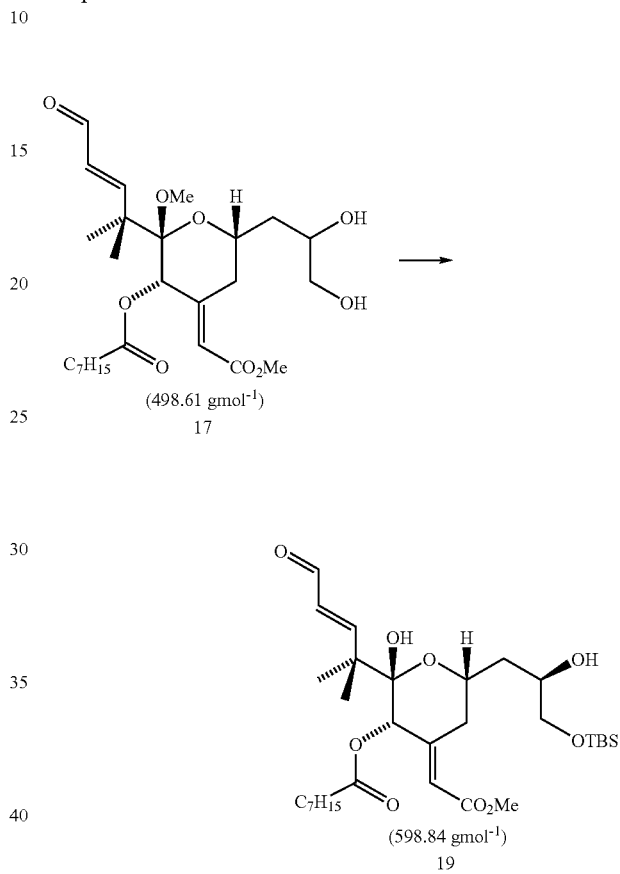

(498.61 gmol$^{-1}$)
17

(598.84 gmol$^{-1}$)
19

The diol (10 mg, 0.020 mmol) was taken up in a solution of MeCN:H$_2$O (960 μL, 240 μL), and transferred to an oven-dried flask. pTsOH (38 mg, 0.200 mmol) was added as 0.22M solution in MeCN:H$_2$O (730 μL, 180 μL). The reaction was stirred overnight, at rt, and then quenched with sat. aq. NaHCO$_3$ (~6 mL). The aqueous phase was extracted with EtOAc (×3). The combined organic layers were dried over Na$_2$SO$_4$, filtered, and concentrated in vacuo. The crude product was carried forward without further purification.

A 0.5M stock solution of 1:3 TBSCl:imidazole was prepared by dissolving TBSCl (754 mg, 5.0 mmol) and imidazole (1.02 g, 15.0 mmol) in CH$_2$Cl$_2$ (10.0 mL). A total of 9 eq. of this stock solution were added to the reaction over 6 hrs. (added in 3 eq. aliquots, 2 hrs. apart). Reaction was quenched with sat. aq. NH$_4$Cl and the aqueous phase was extracted with EtOAc (×3 mL). The combined organic phases were dried over Na$_2$SO$_4$, filtered, and concentrated in vacuo. Purification via column chromatography (silica gel, Hexanes:EtOAc, 75:25) revealed pure product (5.6 mg, 47% over 2 steps).

Example 13
Compound and synthetic step references in this example correspond to the following scheme (as opposed to the reaction schemes and formula numbers employed previously in the specification).
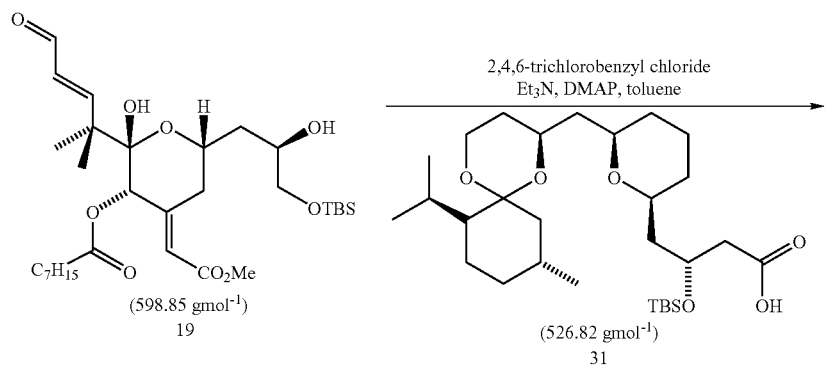
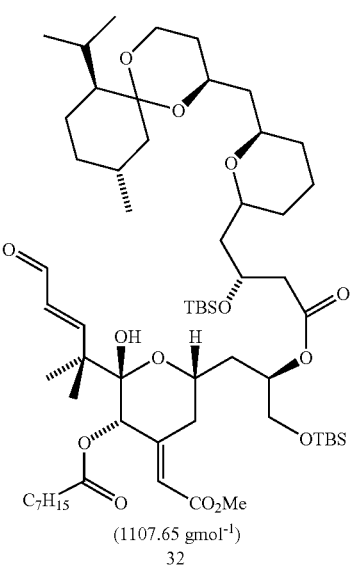

To a solution of acid 31 (28 mg, 0.05 mmol) in toluene (1.1 mL) was added NEt$_3$ (14 μL, 0.1 mmol) and 2,4,6-trichlorobenzoyl chloride (8.3 μL, 0.05 mmol) at rt and the mixture was stirred for 1 h. To this reaction mixture was added a solution of the alcohol 19 (15 mg, 0.025 mmol) and DMAP (15 mg, 0.125 mmol) in toluene (1.1 mL) at rt. The reaction mixture was stirred for 1 h and then directly poured onto a column (silica gel, hexane/ethyl acetate 85:15) and diluted with this solvent mixture to afford 24 mg (87%) of ester 32 as a colorless oil.

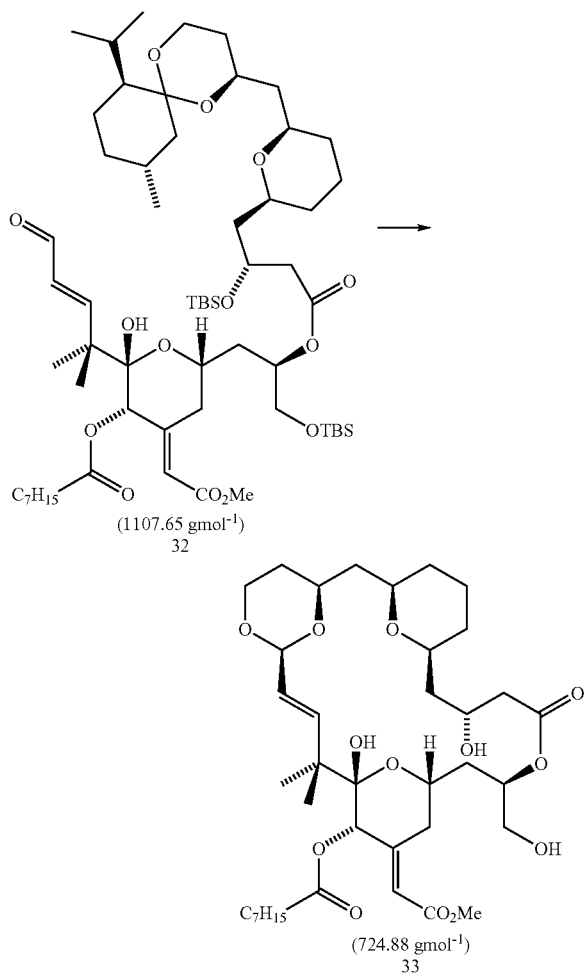

To a solution of aldehyde 32 (20 mg, 0.018 mmol) in THF (5 mL) at rt in a plastic vial was added 70% HF/pyridine (968 μL, excess) dropwise and the yellow reaction mixture was stirred for 1.5 h. The reaction was quenched by addition of sat. aq. NaHCO$_3$ solution (12.5 mL) and H$_2$O (7.5 mL). The biphasic mixture was extracted with ethyl acetate (4×12 mL). The combined organic phases werde dried over Na$_2$SO$_4$. After filtration and evacuation of solvents the residue was purified by column chromatography (silica gel, hexane/ethyl acetate 1:4) to yield 11 mg (82%) of Formula 33 as a white solid.

DOCUMENTS CITED BY REFERENCE

Alkatib, A., Exp. Hematol. 21:61–65 (1993).
Aprahamian et al., J. Biomed. Mat. Res. 21:965–977 (1986).
Berkow, R. L. et al., Biochem. Biophys. Res. Commun. 131:1109–1116 (1985).
Blumberg et al., WO97/34598 (1997) (corresponding to U.S. Pat. No. 6,060,505).
Boyd, M. R., "Status of the NCI preclinical antitumor drug discovery screen" in Cancer: Principles and Practice of Oncology Updates, DeVita et al., eds, pp. 1–12 (1989).
DeVries, D. J., et al., Biochem. Pharmacol. 37:4069–4073 (1998).
Emmanuel et al., Stain. Tech. 62:401–409 (1987).
Evans, D. A.; et al., Angew. Chem. Int. Ed. 37:2354–2359 (1998).
Evans, D. A.; et al., Angew. J. Am. Chem. Soc. 121:7540–7552 (1999).
Friendenstein et al., Exp. Hematol. 10:217–227 (1982).
Gennaro, A. R., Ed., Remington's Pharmaceutical Sciences, 18th Ed., Mack Publishing Co., Easton, Pa. (1990).
Grever, M. R., et al. Seminars Oncol. 19:622 (1992).
Harada et al. J. Am. Chem. Soc. 115:7665–7674 (1993).
Hardman, J. G., et al. (eds), Goodman & Gilmans's The Pharmacological Basis of Therapeutics, Ninth Edition, McGraw-Hill, New York, N.Y., Chapter 51 (1996).
Hornung, R. L., et al., Cancer Res. 52:101–107 (1992).
Irie, K., et al., J. Am. Chem. Soc. 120:9159 (1998).
Kageyama, M., et al., J. Am. Chem. Soc. 112:7407–7408 (1990).
Katzung, B. G. (Editor), Basic & Clinical Pharmacology, Seventh Ed., Appleton & Lange, Stamford, Conn., 1998, Chapter 55.
Kraft, A. S., et al., Proc. Natl. Acad. Sci. USA 83:1334–1338 (1986).
Kraft, A. S., et al., Cancer Chemother. Pharmacol. 37:271–278 (1996).
Lind, D. S., et al., Surgical Oncol.-Oxford 2:273–282 (1993).
Maki, A., et al., Anti-Cancer Drugs 6:392–397 (1995).
Masamune, S., Pure Appl. Chem 60:1587–1596 (1988a).
Masamune, S., Chimica 42:210–211 (1988b).
Mochly-Rosen, D., and Koshland Jr., D. E., J. Biol. Chem. 262:2291–2297 (1986).
Mohammad, R. M., et al., Leukemia Res. 19:667–673 (1995).
Mohammad, R. M., et al., Leukemia 10:130–137 (1996).
Mohammad, R. M., et al., Clin. Cancer Res. 4:1337–1343 (1998).
Monks, A., et al., J. Natl. Cancer Inst., 83:757–766 (1991).
Pettit, G. R., et al., J. Am. Chem. Soc. 104:6846–6848 (1982).
Pettit, G. R. J. Nat. Prod. 59:812–821 (1996), and references cited therein.
Ramsdell, J., et al., J. Biol. Chem. 261:7073–7080 (1986).
Scheid, C., et al., Cancer Inmunol. Immunother. 39:223–230 (1994).
Schuchter, L. M., et al., Cancer Res. 51:682–687 (1991).
Spitaler, M., et al., Biochem. Pharmacol. 56:861–869 (1998).
Still, C., et al., J. Org. Chem. 43:2923 (1978).
Szallasi, Z., et al., Cancer Res. 56:2105–2111 (1996), and references cited therein.
Tanaka, Y., et al., J. Biochem. 99:257–261 (1986).
Theisen, P. D., et al. J. Org. Chem. 53:2374–2378 (1998).
Uchida et al., J. Biomed. Mat. Res. 21:1–10 (1987).
Wender, P. A., et al., Proc. Natl. Acad. Sci. U.S.A. 92:239 (1995).
Wender, P. A., et al., J. Am. Chem. Soc. 120:4534–4535 (1998a).

Wender, P. A., et al., Proc. Natl. Acad. Sci. U.S.A. 95:6624–6629 (1998b).

Wender, P. A., et al., Tetrahedron Letters 39:8625–8628 (1998c).

Wilson, J. D., et al. (Editors), Harrison's Principles of Internal Medicine, Twelfth Ed., 1991, Chapters 300–310.

Although the invention has been described with respect to specific embodiments and examples, it will be appreciated that various changes and modifications may be made without departing from the spirit of the invention.

What is claimed is:

1. A compound having the structure represented by a formula:

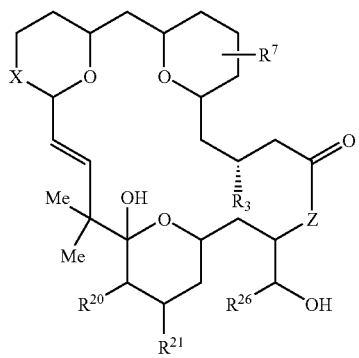

wherein:

$R^3$ is H', or OH;

$R^7$ is absent or represents from 1 to 4 substituents on the ring to which it is attached, independently selected from: lower alkyl, hydroxyl, amino, alkoxyl, alkylamino, =O, acylainino and acyloxy;

$R^{20}$ is H, OH, or -T-U—V—R' where:

T is —O—, —S—, —N(H)— or —N(Me)-;

U is absent or is —C(O)—, —C(S)—, —S(O)— or —S(O)$_2$—; and

V is absent or is —O—, —S—, —N(H)— or —N(Me)-, provided that V is absent when U is absent;

$R^{21}$ is =CR$^3$R$^b$ or $R^{21}$ represents independent moieties R$^6$ and R$^d$ where:

R$^a$ and R$^b$ are independently H, CO$_2$R', CONR$^a$R$^d$ or R';

R$^c$ and R$^d$ are independently H, alkyl, alkenyl, alkynyl or (CH$_2$)$_p$CO$_2$R';

$R^{26}$ is H, OH or R';

R' is independently selected from: H, C$_1$–C$_{10}$ alkyl, naphthyl, anthracyl, phenanthryl, alkenyl, alkynyl, heteroaryl, aralkyl and heteroaralkyl;

X is —CH$_2$—, —O—, —S— or —N(R$^e$)— where R$^e$ is COH, CO$_2$R' or SO$_2$R', Z is —O— or —N(H)—; p is 1, 2 or 3;

or a pharmaceutically acceptable salt thereof, excluding the compounds of Formula 1998a where $R^3$ is H or OH and where $R^{20}$ is —O—C(O)—CH$_3$, or —O—C(O)—(CH$_2$)$_6$—CH$_3$

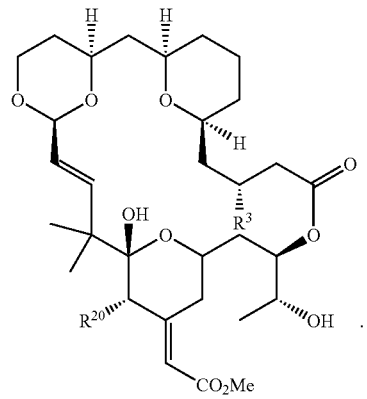

1998a

2. The compound or salt of claim 1 where:

$R^7$ is absent;

$R^{20}$ is H, OH, or -T-U—V—R';

wherein T is —O—, U is —C(O)—, V is absent, and R' is C$_1$–C$_{10}$ alkyl or alkenyl, $R^{21}$ is =CHCO$_2$-lower alkyl;

$R^{26}$ is H or C$_1$–C$_6$ alkyl; and

X is —CH$_2$— or —O—.

3. The compound or salt of claim 2 where:

$R^3$ is OH;

$R^{20}$ is H, OH, or

-T-U—V—R'; wherein T is —O—, U is —C(O)—, V is absent, and R' is C$_1$–C$_{10}$ alkyl or alkenyl.

4. The compound or salt of claim 3 where $R^{26}$ is H.

5. The compound of any one of claims 2 or 3 wherein R' is ethyl, isopropyl, cyclopropyl, 2-butyl or cyclopentyl.

6. The compound of claims 1, wherein R' is ethyl, isopropyl, cyclopropyl, 2-butyl or cyclopentyl.

7. The compound of any one of claims 2 or 3, wherein R' is 2-pentenyl, 2,4-pentadienyl, 2-octenyl, 2,4,6-octatrienyl.

8. The compound of any one of claims 2 or 3, wherein R' is

CH$_3$—CH$_2$—CH$_2$—CH=CH—CH=CH—.

9. The compound of claim 1, wherein R' is 2-pentenyl, 2,4-pentadienyl, 2-octenyl, 2,4,6-octatrienyl.

10. The compound of claim 1, wherein R' is CH$_3$—CH$_2$—CH$_2$—CH=CH—CH=CH—.

11. The compound of claim 1, having the stereochemical configuration represented by the formula:

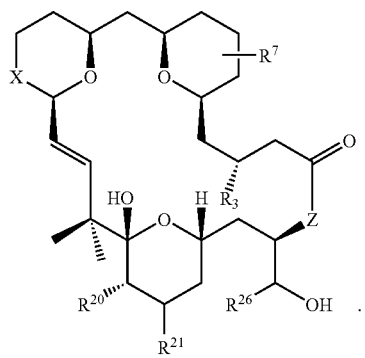

Formula II

12. The compound of claim 1, having the stereochemical configuration represented by the formula:

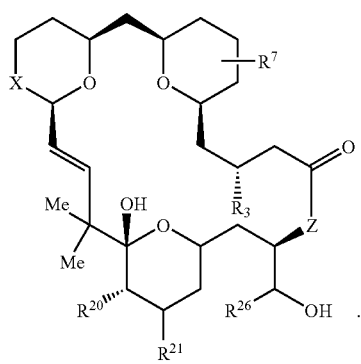

Formula II-B

13. A compound having the structure represented by a formula of the group:

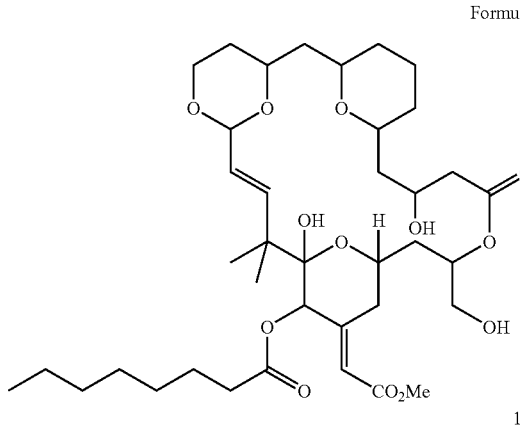

Formula IIa

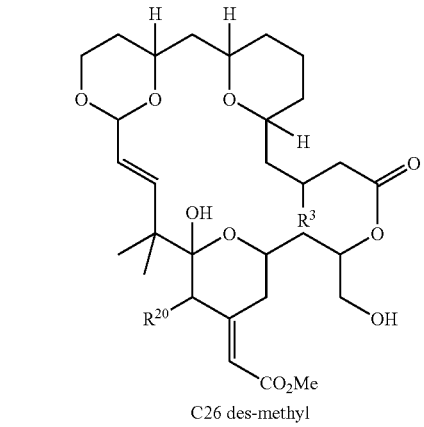

C26 des-methyl wherein:
R³ is H, or OH;
R²⁰ is H, OH, or -T—U—V—R' where:
   T is —O—, —S—, —N(H)— or —N(Me)-;
   U is absent or is —O—, —C(S)—, —S(O)— or —S(O)₂—; and V is absent or is —O—, —S—, —N(H)— or —N(Me)-, provided that V is absent when U is absent;
R' is independently selected from: H, alkyl, alkenyl, alkynyl, aryl, heteroaryl, aralkyl and heteroaralkyl;
or a pharmaceutically acceptable salt thereof.

14. A compound of claim 1 having one or more of the stereochemical configurations represented by the corresponding formula of the group:

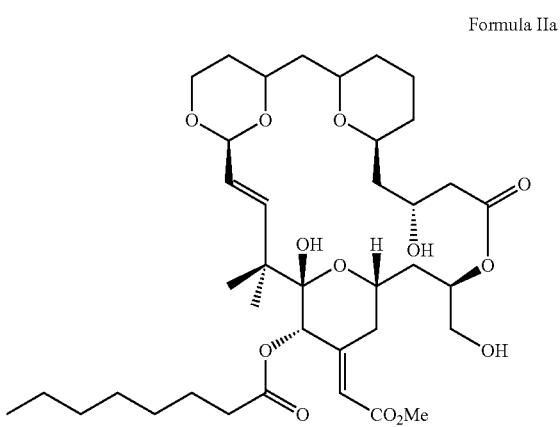

Formula IIa

1998a

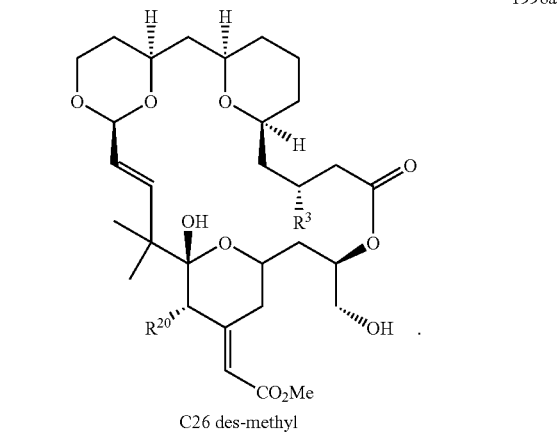

C26 des-methyl

15. The compound or salt of any of claim 13 or 14 where:
R²⁰ is H, OH or -T-U—V—R'
   wherein T is —O—, U is —C(O)—, V is absent, and R' is alkyl or alkenyl.

16. The compound or salt of claim 15 where:
R³ is OH;
R²⁰ is H, OH, or
-T-U—V—R';
   wherein T is —O—, U is —C(O)—, V is absent, and R' is alkyl or alkenyl.

17. The compound of claim 13 or 14, wherein R' is ethyl, isopropyl, cyclopropyl, 2-butyl or cyclopentyl.

18. The compound of claim 13 or 14, wherein R' is 2-pentenyl, 2,4-pentadienyl, 2-octenyl, 2,4,6-octatrienyl.

19. The compound of claim 13 or 14, wherein R' is CH₃—CH₂—CH₂CH═CH—CH═CH—.

* * * * *

UNITED STATES PATENT AND TRADEMARK OFFICE
CERTIFICATE OF CORRECTION

| | | |
|---|---|---|
| PATENT NO. | : 7,256,286 B2 | Page 1 of 1 |
| APPLICATION NO. | : 10/366776 | |
| DATED | : August 14, 2007 | |
| INVENTOR(S) | : Wender et al. | |

It is certified that error appears in the above-identified patent and that said Letters Patent is hereby corrected as shown below:

Column 1:

• Please replace lines 18-20 with:

--This invention was made with Government support under contract CA031845 awarded by the National Institutes of Health. The Government has certain rights in this invention.--

Signed and Sealed this
Nineteenth Day of April, 2011

David J. Kappos
*Director of the United States Patent and Trademark Office*